United States Patent
Biftu et al.

(10) Patent No.: US 10,519,115 B2
(45) Date of Patent: *Dec. 31, 2019

(54) ANTIDIABETIC TRICYCLIC COMPOUNDS

(71) Applicant: Merck Sharp & Dohme Corp., Rahway, NJ (US)

(72) Inventors: Tesfaye Biftu, Freehold, NJ (US); Purakkattle Biju, Westwood, MA (US); Steven L. Colletti, Princeton, NJ (US); Qun Dang, Westfield, NJ (US); Pawan Dhondi, Elizabeth, NJ (US); Candido Gude, Staten Island, NY (US); Hubert Josien, Jersey City, NJ (US); Nam Fung Kar, Brooklyn, NY (US); Anilkumar G. Nair, Edison, NJ (US); Ravi P. Nargund, East Brunswick, NJ (US); De-Yi Yang, Morris Plains, NJ (US); Cheng Zhu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/032,191

(22) PCT Filed: Nov. 10, 2014

(86) PCT No.: PCT/US2014/064722
§ 371 (c)(1),
(2) Date: Apr. 26, 2016

(87) PCT Pub. No.: WO2015/073342
PCT Pub. Date: May 21, 2015

(65) Prior Publication Data
US 2016/0257652 A1 Sep. 8, 2016

Related U.S. Application Data

(60) Provisional application No. 62/042,442, filed on Aug. 27, 2014, provisional application No. 61/904,673, filed on Nov. 15, 2013.

(51) Int. Cl.
| | |
|---|---|
| *C07D 221/16* | (2006.01) |
| *A61K 31/435* | (2006.01) |
| *C07D 401/12* | (2006.01) |
| *C07D 487/04* | (2006.01) |
| *C07D 487/10* | (2006.01) |
| *A61K 9/20* | (2006.01) |
| *A61K 31/444* | (2006.01) |
| *A61K 31/4545* | (2006.01) |
| *A61K 45/06* | (2006.01) |

(52) U.S. Cl.
CPC .............. *C07D 221/16* (2013.01); *A61K 9/20* (2013.01); *A61K 31/435* (2013.01); *A61K 31/444* (2013.01); *A61K 31/4545* (2013.01); *A61K 45/06* (2013.01); *C07D 401/12* (2013.01); *C07D 487/04* (2013.01); *C07D 487/10* (2013.01)

(58) Field of Classification Search
CPC ... A61K 31/444; A61K 31/335; C07D 221/16
See application file for complete search history.

(56) References Cited

U.S. PATENT DOCUMENTS

| | | | |
|---|---|---|---|
| 6,312,662 | B1 | 11/2001 | Erion et al. |
| 6,489,476 | B1 | 12/2002 | Dang et al. |
| 2005/0148643 | A1 | 7/2005 | Rui et al. |
| 2007/0213364 | A1 | 9/2007 | Yasuma et al. |

(Continued)

FOREIGN PATENT DOCUMENTS

| | | |
|---|---|---|
| CN | 103012343 A | 4/2013 |
| DE | 3316095 A1 | 5/1983 |

(Continued)

OTHER PUBLICATIONS

Briscoe, C. P. et al., The Orphan G Protein-coupled Receptor GPR40 is Activated by Medium and Long Chain Fatty Acids, The Journal of Biological Chemistry, 2003, 11303-11311, No. 13, 278.

(Continued)

*Primary Examiner* — Kaipeen E Yang
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

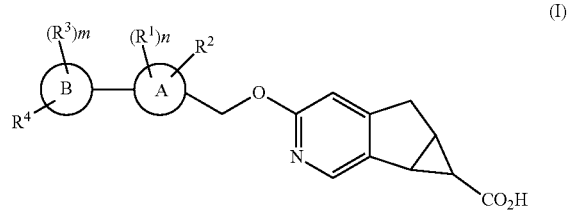

21 Claims, No Drawings

(56) References Cited

U.S. PATENT DOCUMENTS

| | | |
|---|---|---|
| 2007/0244155 A1 | 10/2007 | Sharma et al. |
| 2007/0265332 A1 | 11/2007 | Ge et al. |
| 2010/0216694 A1 | 8/2010 | Liang et al. |
| 2012/0004187 A1 | 1/2012 | Keil et al. |
| 2014/0045746 A1 | 2/2014 | Hagmann et al. |

FOREIGN PATENT DOCUMENTS

| | | | |
|---|---|---|---|
| EP | 0120403 A2 | 10/1984 | |
| EP | 0126030 A2 | 11/1984 | |
| EP | 0128862 A2 | 12/1984 | |
| EP | 0129506 B1 | 12/1984 | |
| GB | 2498976 A | 7/2013 | |
| GB | 2498968 A | 8/2013 | |
| JP | 6298731 | 10/1994 | |
| WO | WO9307124 A1 | 4/1993 | |
| WO | WO1995029897 A1 | 11/1995 | |
| WO | WO1998039342 A1 | 9/1998 | |
| WO | WO1998039343 A1 | 9/1998 | |
| WO | WO2000003997 A1 | 1/2000 | |
| WO | WO2000014095 A1 | 3/2000 | |
| WO | WO2001053272 A1 | 7/2001 | |
| WO | WO2001053291 A1 | 7/2001 | |
| WO | WO2002040019 A1 | 5/2002 | |
| WO | WO2002092575 A1 | 11/2002 | |
| WO | WO2003018061 A1 | 3/2003 | |
| WO | WO2004022551 A1 | 3/2004 | |
| WO | WO2004041266 A1 | 5/2004 | |
| WO | WO2005002520 A2 | 1/2005 | |
| WO | WO2005018672 A1 | 3/2005 | |
| WO | WO2005051373 A1 | 6/2005 | |
| WO | WO2005051890 A1 | 6/2005 | |
| WO | WO2005063729 A1 | 7/2005 | |
| WO | WO2005086661 A2 | 9/2005 | |
| WO | WO2005087710 A1 | 9/2005 | |
| WO | WO2006038738 A1 | 4/2006 | |
| WO | WO2006083612 A1 | 8/2006 | |
| WO | WO2006083781 A1 | 8/2006 | |
| WO | WO2006094209 A2 | 9/2006 | |
| WO | WO2006127503 A2 | 11/2006 | |
| WO | WO2007013689 A1 | 2/2007 | |
| WO | WO2007033002 A1 | 3/2007 | |
| WO | WO2007106469 A2 | 9/2007 | |
| WO | WO2007123225 A1 | 11/2007 | |
| WO | WO2007136572 A2 | 11/2007 | |
| WO | WO2007136573 A2 | 11/2007 | |
| WO | WO2008001931 A2 | 1/2008 | |
| WO | WO2008030520 A1 | 3/2008 | |
| WO | WO2008030618 A1 | 3/2008 | |
| WO | WO2008054674 A2 | 5/2008 | |
| WO | WO2008054675 A2 | 5/2008 | |
| WO | WO2008066097 A1 | 6/2008 | |
| WO | WO2008130514 A1 | 10/2008 | |
| WO | WO2009048527 A1 | 4/2009 | |
| WO | WO2009058237 A1 | 5/2009 | |
| WO | WO2009111056 A1 | 9/2009 | |
| WO | WO2010004347 A1 | 1/2010 | |
| WO | WO2010036613 A1 | 4/2010 | |
| WO | WO2010045258 A2 | 4/2010 | |
| WO | WO2010047982 A1 | 4/2010 | |
| WO | WO2010051176 A1 | 5/2010 | |
| WO | WO2010051206 A1 | 5/2010 | |
| WO | WO2010085522 A1 | 7/2010 | |
| WO | WO2010085525 A1 | 7/2010 | |
| WO | WO2010085528 A1 | 7/2010 | |
| WO | WO2010091176 A1 | 8/2010 | |
| WO | WO2010143733 A1 | 12/2010 | |
| WO | WO2012072691 A1 | 6/2012 | |
| WO | WO2013122028 A1 | 8/2013 | |
| WO | WO2013122029 A1 | 8/2013 | |
| WO | WO2013130370 A2 | 9/2013 | |
| WO | WO2014019186 A1 | 2/2014 | |
| WO | WO2014022528 A1 | 2/2014 | |
| WO | WO 2014022528 A1 * | 2/2014 | ........... C07D 401/14 |
| WO | WO 2015051496 A1 * | 4/2015 | ........... C07D 221/16 |
| WO | WO2015073342 A1 | 5/2015 | |

OTHER PUBLICATIONS

Brown, S. P. et al., Discovery of AM-1638: A Potent and Orally Bioavailable GPR40/FFA1 Full Agonist, American Chemical Society, 2012, p. 726-730, vol. 3.

Bushweller, J. H. et al., Synthesis of CIS- and Trans-1-Methylcyclohexane-1,4-Diols and Their 4-Hemisuccinate Esters, Synthetic Communications, 1989, p. 745-754, vol. 19, No. 5&6.

Houze, J. B. et al., AMG 837: A potent, orally bioavailable GPR40 agonist, Bioorganic & Medicinal Chemistry Letters, 2012, p. 1267-1270, vol. 22.

Internationl Search Report—PCT/US2014/064722—dated Nov. 10, 2014.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS ONE, 2011, p. 1-10, vol. 6, No. 11.

Luo, J. et al., A Potent Class of GPR40 Full Agonist Engages the EnteroInsular Axis to Promote Glucose Control in Rodents, PLOS ONE, 2012, p. 6-12, vol. 7, Issue 10.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

* cited by examiner

ANTIDIABETIC TRICYCLIC COMPOUNDS

CROSS-REFERENCE TO RELATED APPLICATIONS

This application is a U.S. National Phase application under 35 U.S.C. § 371 of PCT Application PCT/US14/064722 filed Nov. 10, 2014, which claims priority from and the benefit of US Provisional Application U.S. Ser. No. 62/042,442 filed Aug. 27, 2014, and US Provisional Application U.S. Ser. No. 61/904,673 filed Nov. 15, 2013.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglitide); and (5) inhibitors of incretin hormone degradation (DPP-4 inhibitors, such as sitagliptin, alogliptin, vildagliptin, linagliptin, denagliptin, and saxagliptin).

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., Nature, 422: 173 (2003); Briscoe, C. P. et al., J. Biol. Chem., 278: 11303 (2003); Kotarsky, K. et al., Biochem. Biophys. Res. Comm., 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion.

There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. Nos. 6,312,662; 6,489,476; US 2005/0148643; DE 3 316 095; JP 6 298 731; EP 0 126 030; EP 0 128 862; EP 0 129 506; and EP 0 120 403.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/072691, WO 2013/122028, WO2013/122029, and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

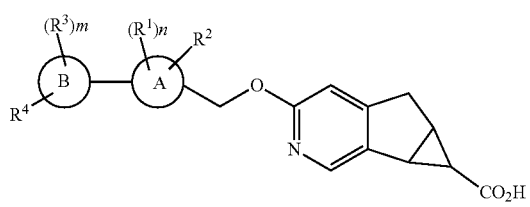

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

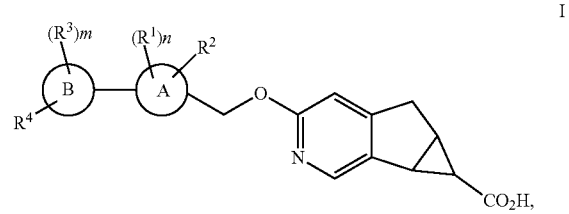

or a pharmaceutically acceptable salt thereof; wherein
A is phenyl;
B is selected from the group consisting of:
  (1) phenyl, and
  (2) pyridyl;
$R^1$ is selected from the group consisting of:
  (1) halogen,
  (2) —CN,
  (3) —$C_{1-6}$alkyl,
  (4) —$(CH_2)_r$—$OC_{3-6}$alkyl,
  (5) —$(CH_2)_r$—$C_{3-6}$cycloalkyl, and
  (6) —$(CH_2)_r$—O—$(CH_2)$—$C_{3-6}$cycloalkyl,
wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl;
$R^2$ is halogen;
each $R^3$ when present is independently selected from the group consisting of:

(1) halogen,
(2) —CN,
(3) —$C_{1-6}$alkyl, and
(4) —$(CH_2)_u$—$C_{3-6}$cycloalkyl,
wherein each $CH_2$, $C_{1-6}$alkyl and $C_{3-6}$cycloalkyl is unsubstituted or substituted with one to three substituents selected from halogen;
$R^4$ is selected from the group consisting of:
(1) —$(CH_2)_p C_{3-6}$cycloalkyl,
(2) —$O(CH_2)_p C_{3-6}$cycloalkyl,
(3) —$(CH_2)_p$—$C_{2-10}$cycloheteroalkyl,
(4) —$O(CH_2)_p$—$C_{2-10}$cycloheteroalkyl,
(5) aryl, and
(6) heteroaryl,
wherein $R^4$ is unsubstituted or substituted with one, two, three, four or five substituents selected from $R^5$;
$R^5$ is selected from the group consisting of:
(1) —$(CH_2)_s$halogen,
(2) —$C_{1-6}$alkyl,
(3) —$(CH_2)_s$—O—$C_{1-6}$alkyl,
(4) —$(CH_2)_s$OH,
(5) —$(CH_2)_s$CN,
(6) —$(CH_2)_s SO_2 C_{1-6}$alkyl,
(7) —$(CH_2)_s SO_2$—$(CH_2)_t$—$C_{3-6}$cycloalkyl,
(8) —$CF_3$,
(9) —$OCHF_2$,
(10) —$OCF_3$,
(11) —$SCH_3$,
(12) —$NH_2$,
(13) oxo,
(14) —$NHSO_2 C_{1-6}$alkyl,
(15) —$NHCOC_{1-6}$alkyl,
(16) —$NH(C_{1-6}$alkyl), and
(17) —$N(C_{1-6}$alkyl$)_2$,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH;
m is 0, 1, 2 or 3;
n is 1 or 2;
p is 0, 1, 2, 3 or 4;
r is 0, 1, 2 or 3;
s is 0, 1, 2 or 3;
t is 0, 1, 2 or 3;
u is 0, 1, 2 or 3;
v is 0, 1, 2 or 3; and
w is 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is phenyl. In a class of this embodiment, A is phenyl, wherein phenyl is substituted with one or two substituents selected from $R^1$, and wherein phenyl is substituted with one substituent selected from $R^2$. In another class of this embodiment, A is phenyl, wherein phenyl is substituted with two substituents selected from $R^1$, and wherein phenyl is substituted with one substituent selected from $R^2$.

In another class of this embodiment, A is phenyl, wherein phenyl is substituted with one substituent selected from $R^1$, and wherein phenyl is substituted with one substituent selected from $R^2$.

In another embodiment of the present invention, A is

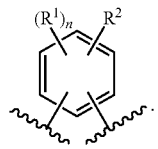

In another embodiment of the present invention, A is

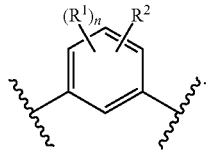

In another embodiment of the present invention, A is

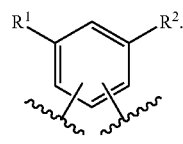

In another embodiment of the present invention, A is

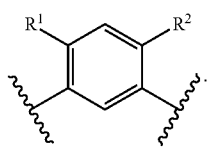

In another embodiment of the present invention, B is selected from the group consisting of: phenyl and pyridyl.

In another embodiment of the present invention, B is selected from phenyl and pyridyl, wherein phenyl and pyridyl are substituted with $R^4$, and are unsubstituted or substituted with one, two or three substituents selected from $R^3$. In a class of this embodiment of the present invention, B is selected from phenyl and pyridyl, wherein phenyl and pyridyl are substituted with $R^4$, and are unsubstituted or substituted with one or two substituents selected from $R^3$. In another class of this embodiment of the present invention, B is selected from phenyl and pyridyl, wherein phenyl and pyridyl are substituted with $R^4$, and are unsubstituted or substituted with one substituent selected from $R^3$. In another class of this embodiment of the present invention, B is selected from phenyl and pyridyl.

In another embodiment of the present invention, B is pyridyl, wherein pyridyl is substituted with $R^4$, and is unsubstituted or substituted with one, two or three substituents selected from $R^3$. In a class of this embodiment of the present invention, B is pyridyl, wherein pyridyl is substituted with $R^4$, and is unsubstituted or substituted with one or two substituents selected from $R^3$. In another class of this embodiment of the present invention, B is pyridyl, wherein pyridyl is substituted with $R^4$, and is unsubstituted or substituted with one substituent selected from $R^3$. In another class of this embodiment of the present invention, B is pyridyl.

In another embodiment of the present invention, B is phenyl, wherein phenyl is substituted with $R^4$, and is unsubstituted or substituted with one, two or three substituents selected from $R^3$. In a class of this embodiment of the present invention, B is phenyl, wherein phenyl is substituted with $R^4$, and is unsubstituted or substituted with one or two substituents selected from $R^3$. In another class of this embodiment of the present invention, B is phenyl, wherein phenyl is substituted with $R^4$, and is unsubstituted or substituted with one substituent selected from $R^3$. In another class of this embodiment of the present invention, B is phenyl.

In another embodiment of the present invention, each $R^1$ is independently selected from the group consisting of: halogen, —CN, —$C_{1-6}$alkyl, —$(CH_2)_r$—$OC_{1-6}$alkyl, —$(CH_2)_r$—$C_{3-6}$cycloalkyl, and —$(CH_2)_r$—O—$(CH_2)_r$—$C_{3-6}$cycloalkyl, wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl. In a class of this embodiment, $R^1$ is selected from the group consisting of: —CN, —$C_{1-6}$alkyl, —$(CH_2)_r$—$OC_{1-6}$alkyl, —$(CH_2)_r$—$C_{3-6}$cycloalkyl, and —$(CH_2)_r$—O—$(CH_2)_r$—$C_{3-6}$cycloalkyl, wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl.

In another embodiment of the present invention, $R^1$ is selected from the group consisting of: halogen, —CN, —$C_{1-6}$alkyl and —$(CH_2)_r$—$C_{3-6}$cycloalkyl, wherein each $CH_2$, —$C_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl. In a class of this embodiment, $R^1$ is selected from the group consisting of: —CN, —$C_{1-6}$alkyl and —$(CH_2)_r$—$C_{3-6}$cycloalkyl, wherein each $CH_2$, —$C_{1-6}$alkyl and $C_{3-6}$cycloalkyl is unsubstituted or substituted with one to four substituents selected from halogen, and —$C_{1-6}$alkyl.

In another embodiment of the present invention, $R^1$ is selected from the group consisting of: halogen, —CN, —$C_{1-6}$alkyl and —$C_{3-6}$cycloalkyl, wherein each —$C_{1-6}$alkyl and —$C_{3-6}$cycloalkyl is unsubstituted or substituted with one to four substituents selected from halogen, and —$C_{1-6}$alkyl. In a class of this embodiment, $R^1$ is selected from the group consisting of: —CN, —$C_{1-6}$alkyl and —$C_{3-6}$cycloalkyl, wherein each —$C_{1-6}$alkyl and —$C_{3-6}$cycloalkyl is unsubstituted or substituted with one to four substituents selected from halogen and —$C_{1-6}$alkyl.

In another embodiment of the present invention, $R^1$ is selected from the group consisting of: halogen, —CN, —$C_{1-6}$alkyl and —$C_{3-6}$cycloalkyl, wherein each —$C_{1-6}$alkyl and —$C_{3-6}$cycloalkyl is unsubstituted or substituted with one to four substituents selected from halogen. In a class of this embodiment, $R^1$ is selected from the group consisting of: —CN, —$C_{1-6}$alkyl and —$C_{3-6}$cycloalkyl, wherein each —$C_{1-6}$alkyl and —$C_{3-6}$cycloalkyl is unsubstituted or substituted with one to four substituents selected from halogen. In another class of this embodiment, $R^1$ is selected from the group consisting of: —CN, —$CF_3$ and cyclopropyl. In another class of this embodiment, $R^1$ is selected from the group consisting of: F, —CN, —$C_{1-6}$alkyl and —$C_{3-6}$cycloalkyl, wherein each —$C_{1-6}$alkyl and —$C_{3-6}$cycloalkyl is unsubstituted or substituted with one to four substituents selected from halogen. In another class of this embodiment, $R^1$ is selected from the group consisting of: F, —CN, —$CF_3$ and cyclopropyl.

In another embodiment of the present invention, $R^1$ is selected from the group consisting of: halogen, —CN, —$C_{1-6}$alkyl, and —$(CH_2)_r$—$OC_{1-6}$alkyl, wherein each $CH_2$, —$C_{1-6}$alkyl and —$OC_{1-6}$alkyl is unsubstituted or substituted with one to four substituents selected from halogen, and —$C_{1-6}$alkyl. In a class of this embodiment, $R^1$ is selected from the group consisting of: —CN, —$C_{1-6}$alkyl, and —$(CH_2)_r$—$OC_{1-6}$alkyl, wherein each $CH_2$, —$C_{1-6}$alkyl and —$OC_{1-6}$alkyl is unsubstituted or substituted with one to four substituents selected from halogen, and —$C_{1-6}$alkyl.

In another embodiment of the present invention, $R^1$ is selected from the group consisting of: halogen, —CN and —$C_{1-6}$alkyl, wherein each —$C_{1-6}$alkyl is unsubstituted or substituted with one to four substituents selected from halogen, and —$C_{1-6}$alkyl. In a class of this embodiment, $R^1$ is selected from the group consisting of: —CN and —$C_{1-6}$alkyl, wherein each —$C_{1-6}$alkyl is unsubstituted or substituted with one to four substituents selected from halogen and —$C_{1-6}$alkyl. In another class of this embodiment, $R^1$ is selected from the group consisting of: —CN and —$C_{1-6}$alkyl, wherein each —$C_{1-6}$alkyl is unsubstituted or substituted with one to four substituents selected from halogen.

In another embodiment of the present invention, $R^1$ is selected from the group consisting of: halogen, —CN, and —$C_{1-6}$alkyl, wherein each —$C_{1-6}$alkyl is unsubstituted or substituted with one to four substituents selected from halogen. In a class of this embodiment, $R^1$ is selected from the group consisting of: —CN, and —$C_{1-6}$alkyl, wherein each —$C_{1-6}$alkyl is unsubstituted or substituted with one to four substituents selected from halogen.

In another embodiment of the present invention, $R^1$ is selected from the group consisting of: F, —CN, and —$CF_3$. In a class of this embodiment, $R^1$ is selected from the group consisting of: —CN, and —$CF_3$. In a class of this embodiment, $R^1$ is selected from the group consisting of: F and —$CF_3$.

In another embodiment of the present invention, $R^1$ is selected from the group consisting of: halogen, and —$C_{1-6}$alkyl, wherein each —$C_{1-6}$alkyl is unsubstituted or substituted with one to four substituents selected from halogen, and —$C_{1-6}$alkyl.

In another embodiment of the present invention, $R^1$ is halogen. In a class of this embodiment, $R^1$ is selected from F and Cl. In another class of this embodiment, $R^1$ is Cl. In another class of this embodiment, $R^1$ is F.

In another embodiment of the present invention, $R^1$ is —CN.

In another embodiment of the present invention, $R^1$ is —$C_{1-6}$alkyl, wherein each —$C_{1-6}$alkyl is unsubstituted or substituted with one to four substituents selected from halogen, and —$C_{1-6}$alkyl.

In another embodiment of the present invention, $R^1$ is —$C_{1-6}$alkyl, wherein each —$C_{1-6}$alkyl is unsubstituted or substituted with one to four substituents selected from halogen. In a class of this embodiment, —$C_{1-6}$alkyl is unsubstituted or substituted with one to four substituents selected from Cl and F. In another class of this embodiment, —$C_{1-6}$alkyl is unsubstituted or substituted with one to four substituents selected from Cl. In another class of this embodiment, —$C_{1-6}$alkyl is unsubstituted or substituted with one to four substituents selected from F.

In another embodiment of the present invention, $R^1$ is —$C_{1-6}$alkyl, wherein each —$C_{1-6}$alkyl is substituted with one, two or three substituents selected from halogen. In a class of this embodiment, $R^1$ is —$C_{1-6}$alkyl, wherein —$C_{1-6}$alkyl is unsubstituted or substituted with one, two or three substituents selected from Cl and F. In another class of this embodiment, $R^1$ is —$C_{1-6}$alkyl, wherein —$C_{1-6}$alkyl is unsubstituted or substituted with one, two or three substituents selected from Cl. In another class of this embodiment, $R^1$ is —$C_{1-6}$alkyl, wherein —$C_{1-6}$alkyl is unsubstituted or substituted with one, two or three substituents selected from F.

In another class of this embodiment, $R^1$ is —$C_{1-6}$alkyl, wherein —$C_{1-6}$alkyl is substituted with one, two or three substituents selected from Cl and F. In another class of this embodiment, $R^1$ is —$C_{1-6}$alkyl, wherein —$C_{1-6}$alkyl is substituted with one, two or three substituents selected from Cl. In another class of this embodiment, $R^1$ is —$C_{1-6}$alkyl, wherein —$C_{1-6}$alkyl is substituted with one, two or three substituents selected from F.

In another embodiment of the present invention, $R^1$ is —$CF_3$ or —$CHF_2$. In another embodiment of the present invention, $R^1$ is —$CHF_2$. In another embodiment of the present invention, $R^1$ is —$CF_3$.

In another embodiment of the present invention, $R^2$ is halogen.

In another embodiment of the present invention, $R^2$ is selected from: Br, I, F and Cl. In another embodiment of the present invention, $R^2$ is selected from F and Cl. In another embodiment of the present invention, $R^2$ is F. In another embodiment of the present invention, $R^2$ is Cl.

In another embodiment of the present invention, each $R^3$ when present is independently selected from the group consisting of: halogen, —CN, —$C_{1-6}$alkyl and —$(CH_2)_u$—$C_{3-6}$cycloalkyl, wherein each $CH_2$, $C_{1-6}$alkyl and $C_{3-6}$cycloalkyl is unsubstituted or substituted with one to three substituents selected from halogen.

In another embodiment of the present invention, each $R^3$ when present is independently selected from the group consisting of: halogen, —CN, —$C_{1-6}$alkyl, and —$C_{3-6}$cycloalkyl, wherein each $C_{1-6}$alkyl and $C_{3-6}$cycloalkyl is unsubstituted or substituted with one to three substituents selected from halogen. In a class of this embodiment, each $C_{1-6}$alkyl is unsubstituted or substituted with one to three substituents selected from Cl and F. In another class of this embodiment, each $C_{1-6}$alkyl is unsubstituted or substituted with one to three substituents selected from Cl. In another class of this embodiment, each $C_{1-6}$alkyl is unsubstituted or substituted with one to three substituents selected from F.

In another embodiment of the present invention, each $R^3$ when present is independently selected from the group consisting of: halogen, —CN and —$C_{1-6}$alkyl, wherein each $C_{1-6}$alkyl is unsubstituted or substituted with one to three substituents selected from halogen. In a class of this embodiment, each $C_{1-6}$alkyl is unsubstituted or substituted with one to three substituents selected from Cl and F. In another class of this embodiment, each $C_{1-6}$alkyl is unsubstituted or substituted with one to three substituents selected from Cl. In another class of this embodiment, each $C_{1-6}$alkyl is unsubstituted or substituted with one to three substituents selected from F.

In another embodiment of the present invention, each $R^3$ when present is independently selected from the group consisting of: halogen, and —$C_{1-6}$alkyl, wherein each $C_{1-6}$alkyl is unsubstituted or substituted with one to three substituents selected from halogen. In a class of this embodiment, each $C_{1-6}$alkyl is unsubstituted or substituted with one to three substituents selected from Cl and F. In another class of this embodiment, each $C_{1-6}$alkyl is unsubstituted or substituted with one to three substituents selected from Cl. In another class of this embodiment, each $C_{1-6}$alkyl is unsubstituted or substituted with one to three substituents selected from F.

In another embodiment of the present invention, each $R^3$ when present is independently selected from the group consisting of: F, Cl, —$CF_3$, —$CHF_2$, and —$CH_3$. In another embodiment of the present invention, each $R^3$ is independently selected from the group consisting of: F, Cl, —$CF_3$, —$CHF_2$, and —$CH_3$.

In another embodiment of the present invention, each $R^3$ when present is independently selected from the group consisting of: F, —$CF_3$, —$CHF_2$, and —$CH_3$. In another embodiment of the present invention, each $R^3$ is independently selected from the group consisting of: F, —$CF_3$, —$CHF_2$, and —$CH_3$.

In another embodiment of the present invention, each $R^3$ when present is independently selected from the group consisting of: F, Cl and —$CH_3$. In another embodiment of the present invention, each $R^3$ when present is independently selected from the group consisting of: F and —$CH_3$.

In another embodiment of the present invention, each $R^3$ when present is independently selected from the group consisting of: Cl, F and —$CF_3$. In another embodiment of the present invention, each $R^3$ when present is independently selected from the group consisting of: F and —$CF_3$.

In another embodiment of the present invention, $R^3$ is halogen. In a class of this embodiment, $R^3$ is selected from Cl and F. In another class of this embodiment, $R^3$ is Cl. In another class of this embodiment, $R^3$ is F.

In another embodiment of the present invention, $R^3$ is —$C_{1-6}$alkyl, wherein $C_{1-6}$alkyl is unsubstituted or substituted with one to three substituents selected from halogen. In a class of this embodiment, $C_{1-6}$alkyl is unsubstituted or substituted with one to three substituents selected from Cl and F. In another class of this embodiment, $C_{1-6}$alkyl is unsubstituted or substituted with one to three substituents selected from Cl. In another class of this embodiment, $C_{1-6}$alkyl is unsubstituted or substituted with one to three substituents selected from F.

In another embodiment of the present invention, $R^3$ is —$C_{1-6}$alkyl.

In another embodiment of the present invention, $R^3$ is —$CF_3$.

In another embodiment of the present invention, $R^3$ is —$CHF_2$.

In another embodiment of the present invention, $R^3$ is —$CH_3$.

In another embodiment of the present invention, $R^3$ is absent.

In another embodiment of the present invention, $R^4$ is selected from the group consisting of: —$(CH_2)_pC_{3-6}$cycloalkyl, —$O(CH_2)_pC_{3-6}$cycloalkyl, —$(CH_2)_p$—$C_{2-10}$cycloheteroalkyl, —$O(CH_2)_p$—$C_{2-10}$cycloheteroalkyl, aryl and heteroaryl, wherein each $R^4$ is unsubstituted or substituted with one, two, three, four or five substituents selected from $R^5$.

In another embodiment of the present invention, $R^4$ is selected from the group consisting of: —$(CH_2)_pC_{3-6}$cycloalkyl, —$(CH_2)_p$—$C_{2-10}$cycloheteroalkyl, aryl and heteroaryl, wherein each $R^4$ is unsubstituted or substituted with one, two, three, four or five substituents selected from $R^5$. In a class of this embodiment, each $R^4$ is unsubstituted or substituted with one, two or three substituents selected from $R^5$. In another class of this embodiment, each $R^4$ is unsubstituted or substituted with one or two substituents selected from $R^5$.

In another embodiment of the present invention, $R^4$ is selected from the group consisting of: —$(CH_2)_pC_{3-6}$cycloalkyl, —$C_{2-10}$cycloheteroalkyl, aryl and heteroaryl, wherein $R^4$ is unsubstituted or substituted with one, two, three, four or five substituents selected from $R^5$. In a class of this embodiment, each $R^4$ is unsubstituted or substituted with one, two or three substituents selected from $R^5$. In another class of this embodiment, each $R^4$ is unsubstituted or substituted with one or two substituents selected from $R^5$.

In another embodiment of the present invention, $R^4$ is selected from the group consisting of: —$O(CH_2)_pC_{3-6}$cycloalkyl, aryl and heteroaryl, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —O-cyclobutyl, —O—$CH_2$-cyclobutyl, —O—$CH_2$-cyclopentyl, —O-cyclohexyl, 2,6-diazospiro[3,3]heptan-2yl, piperidine, phenyl, tetrazole, triazole, and pyrrolo[3,4-c]pyrazole, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —O—$CH_2$-cyclobutyl, —O-cyclohexyl, 2,6-diazospiro[3,3]heptan-2yl, piperidine, phenyl, tetrazole, and pyrrolo[3,4-c]pyrazole, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —$O(CH_2)_pC_{3-6}$cycloalkyl, —$C_{2-8}$cycloheteroalkyl and aryl, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —O—$CH_2$-cyclobutyl, —O-cyclohexyl, 2,6-diazospiro[3,3]heptan-2yl, piperidine, and phenyl, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —O-cyclohexyl, 2,6-diazospiro[3,3]heptan-2yl, piperidine, and phenyl, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —$O(CH_2)_pC_{3-6}$cycloalkyl, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —O—$CH_2$-cyclobutyl, and —O-cyclohexyl, wherein each cyclobutyl and cyclohexyl is unsubstituted or substituted with one, two, three, four or five substituents selected from $R^5$. In a class of this embodiment, each cyclobutyl and cyclohexyl is unsubstituted or substituted with one, two or three substituents selected from $R^5$. In another class of this embodiment, each cyclobutyl and cyclohexyl is unsubstituted or substituted with one or two substituents selected from $R^5$.

In another embodiment of the present invention, $R^4$ is —O-cyclohexyl, wherein cyclohexyl is unsubstituted or substituted with one, two, three, four or five substituents selected from $R^5$. In a class of this embodiment, cyclohexyl is unsubstituted or substituted with one, two or three substituents selected from $R^5$. In another class of this embodiment, cyclohexyl is unsubstituted or substituted with one or two substituents selected from $R^5$.

In another embodiment of the present invention, $R^4$ is selected from the group consisting of: —$(CH_2)_p$—$C_{2-10}$cycloheteroalkyl, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is selected from the group consisting of: —$C_{2-6}$cycloheteroalkyl, wherein cycloheteroalkyl is unsubstituted or substituted with one, two, three, four or five substituents selected from $R^5$. In a class of this embodiment, cycloheteroalkyl is unsubstituted or substituted with one, two or three substituents selected from $R^5$. In another class of this embodiment, cycloheteroalkyl is unsubstituted or substituted with one or two substituents selected from $R^5$.

In another embodiment of the present invention, $R^4$ is selected from the group consisting of: 2,6-diazospiro[3,3]heptan-2yl, and piperidine, wherein $R^4$ is unsubstituted or substituted with one, two, three, four or five substituents selected from $R^5$. In a class of this embodiment, $R^4$ is unsubstituted or substituted with one, two or three substituents selected from $R^5$. In another class of this embodiment, $R^4$ is unsubstituted or substituted with one or two substituents selected from $R^5$.

In another embodiment of the present invention, $R^4$ is aryl, wherein aryl is unsubstituted or substituted with one, two, three, four or five substituents selected from $R^5$. In a class of this embodiment, aryl is unsubstituted or substituted with one, two or three substituents selected from $R^5$. In another class of this embodiment, aryl is unsubstituted or substituted with one or two substituents selected from $R^5$.

In another embodiment of the present invention, $R^4$ is phenyl, wherein phenyl is unsubstituted or substituted with one, two, three, four or five substituents selected from $R^5$. In a class of this embodiment, phenyl is unsubstituted or substituted with one, two or three substituents selected from $R^5$. In another class of this embodiment, phenyl is unsubstituted or substituted with one or two substituents selected from $R^5$.

In another embodiment of the present invention, $R^4$ is selected from the group consisting of: —O(CH$_2$)$_p$C$_{3-6}$cycloalkyl, —C$_{2-8}$cycloheteroalkyl, aryl, and heteroaryl, wherein $R^4$ is unsubstituted or substituted with one, two, three, four or five substituents selected from $R^5$. In a class of this embodiment, $R^4$ is selected from the group consisting of: —O—CH$_2$-cyclobutyl, —O—cyclobutyl, —O-cyclohexyl, 2,6-diazospiro[3,3]heptan-2yl, piperidinyl, phenyl, and tetrazole, wherein $R^4$ is unsubstituted or substituted with one, two, three, four or five substituents selected from $R^5$.

In another embodiment of the present invention, $R^4$ is —O(CH$_2$)$_p$C$_{3-6}$cycloalkyl, wherein $R^4$ is unsubstituted or substituted with one, two, three, four or five substituents selected from $R^5$. In another embodiment of the present invention, $R^4$ is —O(CH$_2$)$_{0-1}$C$_{3-6}$cycloalkyl, wherein $R^4$ is unsubstituted or substituted with one, two, three, four or five substituents selected from $R^5$. In another embodiment of the present invention, $R^4$ is —O(CH$_2$)$_{0-1}$-cyclobutyl, wherein $R^4$ is unsubstituted or substituted with one, two, three, four or five substituents selected from $R^5$.

In another embodiment of the present invention, $R^4$ is selected from the group consisting of: —O—CH$_2$-cyclobutyl, and —O-cyclobutyl, wherein $R^4$ is unsubstituted or substituted with one, two, three, four or five substituents selected from $R^5$.

In another embodiment of the present invention, $R^4$ is —O—CH$_2$-cyclobutyl, wherein $R^4$ is unsubstituted or substituted with one, two, three, four or five substituents selected from $R^5$. In another embodiment of the present invention, $R^4$ is —O—CH$_2$-cyclobutyl, wherein $R^4$ is unsubstituted or substituted with one or two substituents selected from $R^5$.

In another embodiment of the present invention, $R^4$ is —O-cyclobutyl, wherein $R^4$ is unsubstituted or substituted with one, two, three, four or five substituents selected from $R^5$. In another embodiment of the present invention, $R^4$ is —O-cyclobutyl, wherein $R^4$ is unsubstituted or substituted with one substituent selected from $R^5$.

In another embodiment of the present invention, each $R^5$ is independently selected from the group consisting of: —(CH$_2$)$_s$halogen, —C$_{1-6}$alkyl, —(CH$_2$)$_s$—O—C$_{1-6}$alkyl, —(CH$_2$)$_s$OH, —(CH$_2$)$_s$CN, —(CH$_2$)$_s$SO$_2$C$_{1-6}$alkyl, —(CH$_2$)$_s$SO$_2$—(CH$_2$)$_t$—C$_{3-6}$cycloalkyl, —CF$_3$, —OCHF$_2$, —OCF$_3$, —SCH$_3$, —NH$_2$, oxo, —NHSO$_2$C$_{1-6}$alkyl, —NHCOC$_{1-6}$alkyl, —NH(C$_{1-6}$alkyl), and —N(C$_{1-6}$alkyl)$_2$, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH.

In another embodiment of the present invention, $R^5$ is selected from the group consisting of: —(CH$_2$)$_s$halogen, —C$_{1-6}$alkyl, —(CH$_2$)$_s$—O—C$_{1-6}$alkyl, —(CH$_2$)$_s$OH, —(CH$_2$)$_s$CN, —(CH$_2$)$_s$SO$_2$C$_{1-6}$alkyl, —(CH$_2$)$_s$SO$_2$—(CH$_2$)$_t$—C$_{3-6}$cycloalkyl, —CF$_3$, —OCHF$_2$, —OCF$_3$, —SCH$_3$, —NH$_2$, —NHSO$_2$C$_{1-6}$alkyl, —NHCOC$_{1-6}$alkyl, —NH(C$_{1-6}$alkyl), and —N(C$_{1-6}$alkyl)$_2$, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH.

In another embodiment of the present invention, $R^5$ is selected from the group consisting of: —(CH$_2$)$_s$halogen, —C$_{1-6}$alkyl, —(CH$_2$)$_s$—O—C$_{1-6}$alkyl, —(CH$_2$)$_s$OH, —(CH$_2$)$_s$CN, —(CH$_2$)$_s$SO$_2$C$_{1-6}$alkyl, —(CH$_2$)$_s$SO$_2$—(CH$_2$)$_t$—C$_{3-6}$cycloalkyl, —CF$_3$, —OCHF$_2$, —OCF$_3$, —SCH$_3$, —NH$_2$, —NHSO$_2$C$_{1-6}$alkyl, —NHCOC$_{1-6}$alkyl, —NH(C$_{1-6}$alkyl), and —N(C$_{1-6}$alkyl)$_2$, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH. In a class of this embodiment, each CH$_2$, C$_{1-6}$alkyl and C$_{3-6}$cycloalkyl is unsubstituted or substituted with one to three substituents selected from halogen, —CH$_3$, and —OH. In another class of this embodiment, each CH$_2$, C$_{1-6}$alkyl and C$_{3-6}$cycloalkyl is unsubstituted or substituted with one to three substituents selected from —CH$_3$, and —OH.

In another embodiment of the present invention, $R^5$ is selected from the group consisting of: —(CH$_2$)$_s$halogen, —C$_{1-6}$alkyl, —(CH$_2$)$_s$OH, —(CH$_2$)$_s$CN, —(CH$_2$)$_s$SO$_2$C$_{1-6}$alkyl, and —(CH$_2$)$_s$SO$_2$—(CH$_2$)$_t$—C$_{3-6}$cycloalkyl, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH. In a class of this embodiment, each CH$_2$, C$_{1-6}$alkyl and C$_{3-6}$cycloalkyl is unsubstituted or substituted with one to three substituents selected from halogen, —CH$_3$, and —OH. In another class of this embodiment, each CH$_2$, C$_{1-6}$alkyl and C$_{3-6}$cycloalkyl is unsubstituted or substituted with one to three substituents selected from —CH$_3$, and —OH.

In another embodiment of the present invention, $R^5$ is selected from the group consisting of: —(CH$_2$)$_s$halogen, —C$_{1-6}$alkyl, —(CH$_2$)$_s$OH, —(CH$_2$)$_s$CN, —(CH$_2$)$_s$SO$_2$C$_{1-6}$alkyl, and —(CH$_2$)$_s$SO$_2$—(CH$_2$)$_t$—C$_{3-6}$cycloalkyl, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH. In a class of this embodiment, each CH$_2$, C$_{1-6}$alkyl and C$_{3-6}$cycloalkyl is unsubstituted or substituted with one to three substituents selected from halogen, —CH$_3$, and —OH. In another class of this embodiment, each CH$_2$, C$_{1-6}$alkyl and C$_{3-6}$cycloalkyl is unsubstituted or substituted with one to three substituents selected from —CH$_3$, and —OH.

In another embodiment of the present invention, $R^5$ is selected from the group consisting of: halogen, —C$_{1-6}$alkyl, —(CH$_2$)$_s$OH, —CN, —SO$_2$C$_{1-6}$alkyl, and —SO$_2$—C$_{3-6}$cycloalkyl, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH. In a class of this embodiment, each CH$_2$, C$_{1-6}$alkyl and C$_{3-6}$cycloalkyl is unsubstituted or substituted with one to three substituents selected from halogen, —CH$_3$, and —OH. In another class of this embodiment, each CH$_2$, C$_{1-6}$alkyl and C$_{3-6}$cycloalkyl is unsubstituted or substituted with one to three substituents selected from —CH$_3$, and —OH.

In another embodiment of the present invention, $R^5$ is selected from the group consisting of: halogen, —C$_{1-6}$alkyl, —OH, —CN, —SO$_2$C$_{1-6}$alkyl, and —SO$_2$—C$_{3-6}$cycloalkyl, wherein each C$_{1-6}$alkyl and C$_{3-6}$cycloalkyl is unsubstituted or substituted with one to three substituents selected from halogen, C$_{1-6}$alkyl, and —(CH$_2$)$_w$OH. In a class of this embodiment, each C$_{1-6}$alkyl and C$_{3-6}$cycloalkyl is unsubstituted or substituted with one to three substituents selected from halogen, —CH$_3$, and —OH. In another class of this embodiment, each C$_{1-6}$alkyl and C$_{3-6}$cycloalkyl is unsubstituted or substituted with one to three substituents selected from —CH$_3$, and —OH.

In another embodiment of the present invention, $R^5$ is selected from the group consisting of: —(CH$_2$)$_s$halogen, —C$_{1-6}$alkyl, —(CH$_2$)$_s$OH, —(CH$_2$)$_s$SO$_2$C$_{1-6}$alkyl, and —(CH$_2$)$_s$SO$_2$—(CH$_2$)$_t$C$_{3-6}$cycloalkyl, wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH. In a class of this embodiment, each CH$_2$, C$_{1-6}$alkyl and C$_{3-6}$cycloalkyl is unsubstituted or substituted with one to three substituents selected from halogen, —CH$_3$, and —OH. In another class of this embodiment, each $CH_2$, $C_{1-6}$alkyl and $C_{3-6}$cycloalkyl is unsubstituted or substituted with one to three substituents selected from —$CH_3$, and —OH.

In another embodiment of the present invention, $R^5$ is selected from the group consisting of: halogen, —$C_{1-6}$alkyl, —OH, —$CH_2OH$, —$SO_2C_{1-6}$alkyl, and —$(CH_2)_sSO_2$—$C_{3-6}$cycloalkyl, wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_wOH$. In a class of this embodiment, each $CH_2$, $C_{1-6}$alkyl and $C_{3-6}$cycloalkyl is unsubstituted or substituted with one to three substituents selected from halogen, —$CH_3$, and —OH. In another class of this embodiment, each $CH_2$, $C_{1-6}$alkyl and $C_{3-6}$cycloalkyl is unsubstituted or substituted with one to three substituents selected from —$CH_3$, and —OH.

In another embodiment of the present invention, $R^5$ is selected from the group consisting of: halogen, —$C_{1-6}$alkyl, —OH, —$SO_2C_{1-6}$alkyl, and —$(CH_2)_sSO_2$—$C_{3-6}$cycloalkyl, wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_wOH$. In a class of this embodiment, each $CH_2$, $C_{1-6}$alkyl and $C_{3-6}$cycloalkyl is unsubstituted or substituted with one to three substituents selected from halogen, —$CH_3$, and —OH. In another class of this embodiment, each $CH_2$, $C_{1-6}$alkyl and $C_{3-6}$cycloalkyl is unsubstituted or substituted with one to three substituents selected from —$CH_3$, and —OH.

In another embodiment of the present invention, $R^5$ is selected from the group consisting of: halogen, —$C_{1-6}$alkyl, —OH, —$CH_2OH$, —$SO_2C_{1-6}$alkyl, and —$SO_2$—$C_{3-6}$cycloalkyl, wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_wOH$. In a class of this embodiment, each $CH_2$, $C_{1-6}$alkyl and $C_{3-6}$cycloalkyl is unsubstituted or substituted with one to three substituents selected from halogen, —$CH_3$, and —OH. In another class of this embodiment, each $CH_2$, $C_{1-6}$alkyl and $C_{3-6}$cycloalkyl is unsubstituted or substituted with one to three substituents selected from —$CH_3$, and —OH.

In another embodiment of the present invention, $R^5$ is selected from the group consisting of: halogen, —$C_{1-6}$alkyl, —OH, —$SO_2C_{1-6}$alkyl, and —$SO_2$—$C_{3-6}$cycloalkyl, wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_wOH$. In a class of this embodiment, each $CH_2$, $C_{1-6}$alkyl and $C_{3-6}$cycloalkyl is unsubstituted or substituted with one to three substituents selected from halogen, —$CH_3$, and —OH. In another class of this embodiment, each $CH_2$, $C_{1-6}$alkyl and $C_{3-6}$cycloalkyl is unsubstituted or substituted with one to three substituents selected from —$CH_3$, and —OH.

In another embodiment of the present invention, $R^5$ is selected from the group consisting of: Cl, F, —$CH_3$, —$CH_2C(CH_3)_2OH$, —$C(CH_3)(OH)CH_2OH$, —$C(CH_3)_2OH$, —OH, —$CH_2OH$, —$SO_2CH_3$, and —$SO_2$-cyclopropyl, wherein each $R^5$ is unsubstituted or substituted with one to three substituents selected from halogen, $C_{1-6}$alkyl, and —$(CH_2)_wOH$. In a class of this embodiment, each $R^5$ is unsubstituted or substituted with one to three substituents selected from halogen, —$CH_3$, and —OH. In another class of this embodiment, each $R^5$ is unsubstituted or substituted with one to three substituents selected from —$CH_3$, and —OH.

In another embodiment of the present invention, $R^5$ is selected from the group consisting of: Cl, F, —$CH_3$, —$CH_2C(CH_3)_2OH$, —$C(CH_3)_2OH$, —OH, —$SO_2CH_3$, and —$SO_2$-cyclopropyl, wherein each $R^5$ is unsubstituted or substituted with one to three substituents selected from halogen, $C_{1-6}$alkyl, and —$(CH_2)_wOH$. In a class of this embodiment, each $R^5$ is unsubstituted or substituted with one to three substituents selected from halogen, —$CH_3$, and —OH. In another class of this embodiment, each $R^5$ is unsubstituted or substituted with one to three substituents selected from —$CH_3$, and —OH.

In another embodiment of the present invention, $R^5$ is selected from the group consisting of: Cl, F, —$CH_3$, —$C(CH_3)_2OH$, —OH, —$SO_2CH_3$, and —$SO_2$-cyclopropyl, wherein each $R^5$ is unsubstituted or substituted with one to three substituents selected from halogen, $C_{1-6}$alkyl, and —$(CH_2)_wOH$. In a class of this embodiment, each $R^5$ is unsubstituted or substituted with one to three substituents selected from halogen, —$CH_3$, and —OH. In another class of this embodiment, each $R^5$ is unsubstituted or substituted with one to three substituents selected from —$CH_3$, and OH.

In another embodiment of the present invention, m is 0, 1, 2 or 3. In another embodiment of the present invention, m is 0, 1 or 2. In another embodiment of the present invention, m is 0, 1 or 3. In another embodiment of the present invention, m is 0, 2 or 3. In another embodiment of the present invention, m is 0 or 2. In another embodiment of the present invention, m is 0 or 1. In another embodiment of the present invention, m is 0 or 3. In another embodiment of the present invention, m is 1, 2 or 3. In another embodiment of the present invention, m is 1 or 3. In another embodiment of the present invention, m is 1 or 2. In another embodiment of the present invention, m is 0. In another embodiment of the present invention, m is 1. In another embodiment of the present invention, m is 2. In another embodiment of the present invention, m is 3.

In another embodiment of the present invention, n is 1 or 2. In another embodiment of the present invention, n is 1. In another embodiment of the present invention, n is 2.

In another embodiment of the present invention, p is 0, 1, 2, 3 or 4. In another embodiment of the present invention, p is 0, 1, 2 or 3. In another embodiment of the present invention, p is 0, 1 or 2. In another embodiment of the present invention, p is 0, 1 or 3. In another embodiment of the present invention, p is 0, 2 or 3. In another embodiment of the present invention, p is 0 or 2. In another embodiment of the present invention, p is 0 or 1. In another embodiment of the present invention, p is 0 or 3. In another embodiment of the present invention, p is 1, 2 or 3. In another embodiment of the present invention, p is 1 or 3. In another embodiment of the present invention, p is 1 or 2. In another embodiment of the present invention, p is 2 or 3. In another embodiment of the present invention, p is 0. In another embodiment of the present invention, p is 1. In another embodiment of the present invention, p is 2. In another embodiment of the present invention, p is 3.

In another embodiment of the present invention, r is 0, 1, 2 or 3. In another embodiment of the present invention, r is 0, 1 or 2. In another embodiment of the present invention, r is 0, 1 or 3. In another embodiment of the present invention, r is 0, 2 or 3. In another embodiment of the present invention, r is 0 or 2. In another embodiment of the present invention, r is 0 or 1. In another embodiment of the present invention, r is 0 or 3. In another embodiment of the present invention, r is 1, 2 or 3. In another embodiment of the present invention, r is 1 or 3. In another embodiment of the present invention, r is 1 or 2. In another embodiment of the present invention, r is 2 or 3. In another embodiment of the present invention, r is 0. In another embodiment of the present invention, r is 1. In another embodiment of the present invention, r is 2. In another embodiment of the present invention, r is 3.

In another embodiment of the present invention, s is 0, 1, 2 or 3. In another embodiment of the present invention, s is 0, 1 or 2. In another embodiment of the present invention, s is 0, 1 or 3. In another embodiment of the present invention, s is 0, 2 or 3. In another embodiment of the present invention, s is 0 or 2. In another embodiment of the present invention, s is 0 or 1. In another embodiment of the present invention, s is 0 or 3. In another embodiment of the present invention, s is 1, 2 or 3. In another embodiment of the present invention, s is 1 or 3. In another embodiment of the present invention, s is 1 or 2. In another embodiment of the present invention, s is 2 or 3. In another embodiment of the present invention, s is 0. In another embodiment of the present invention, s is 1. In another embodiment of the present invention, s is 2. In another embodiment of the present invention, s is 3.

In another embodiment of the present invention, t is 0, 1, 2 or 3. In another embodiment of the present invention, t is 0, 1 or 2. In another embodiment of the present invention, t is 0, 1 or 3. In another embodiment of the present invention, t is 0, 2 or 3. In another embodiment of the present invention, t is 0 or 2. In another embodiment of the present invention, t is 0 or 1. In another embodiment of the present invention, t is 0 or 3. In another embodiment of the present invention, t is 1, 2 or 3. In another embodiment of the present invention, t is 1 or 3. In another embodiment of the present invention, t is 1 or 2. In another embodiment of the present invention, t is 2 or 3. In another embodiment of the present invention, t is 0. In another embodiment of the present invention, t is 1. In another embodiment of the present invention, t is 2. In another embodiment of the present invention, t is 3.

In another embodiment of the present invention, u is 0, 1, 2 or 3. In another embodiment of the present invention, u is 0, 1 or 2. In another embodiment of the present invention, u is 0, 1 or 3. In another embodiment of the present invention, u is 0, 2 or 3. In another embodiment of the present invention, u is 0 or 2. In another embodiment of the present invention, u is 0 or 1. In another embodiment of the present invention, u is 0 or 3. In another embodiment of the present invention, u is 1, 2 or 3. In another embodiment of the present invention, u is 1 or 3. In another embodiment of the present invention, u is 1 or 2. In another embodiment of the present invention, u is 2 or 3. In another embodiment of the present invention, u is 0. In another embodiment of the present invention, u is 1. In another embodiment of the present invention, u is 2. In another embodiment of the present invention, u is 3.

In another embodiment of the present invention, v is 0, 1, 2 or 3. In another embodiment of the present invention, v is 0, 1 or 2. In another embodiment of the present invention, v is 0, 1 or 3. In another embodiment of the present invention, v is 0, 2 or 3. In another embodiment of the present invention, v is 0 or 2. In another embodiment of the present invention, v is 0 or 1. In another embodiment of the present invention, v is 0 or 3. In another embodiment of the present invention, v is 1, 2 or 3. In another embodiment of the present invention, v is 1 or 3. In another embodiment of the present invention, v is 1 or 2. In another embodiment of the present invention, v is 2 or 3. In another embodiment of the present invention, v is 0. In another embodiment of the present invention, v is 1. In another embodiment of the present invention, v is 2. In another embodiment of the present invention, v is 3.

In another embodiment of the present invention, w is 0, 1, 2 or 3. In another embodiment of the present invention, w is 0, 1 or 2. In another embodiment of the present invention, w is 0, 1 or 3. In another embodiment of the present invention, w is 0, 2 or 3. In another embodiment of the present invention, w is 0 or 2. In another embodiment of the present invention, w is 0 or 1. In another embodiment of the present invention, w is 0 or 3. In another embodiment of the present invention, w is 1, 2 or 3. In another embodiment of the present invention, w is 1 or 3. In another embodiment of the present invention, w is 1 or 2. In another embodiment of the present invention, w is 2 or 3. In another embodiment of the present invention, w is 0. In another embodiment of the present invention, w is 1. In another embodiment of the present invention, w is 2. In another embodiment of the present invention, w is 3.

In another embodiment of the present invention, the invention relates to compounds of structural formula Ia:

Ia wherein B is selected from: phenyl and pyridyl; or a pharmaceutically acceptable salt thereof.

In another embodiment of the present invention, the invention relates to compounds of structural formula Ib:

Ib wherein B is selected from: phenyl and pyridyl; or a pharmaceutically acceptable salt thereof.

In another embodiment of the present invention, the invention relates to compounds of structural formula Ic:

Ic wherein B is selected from: phenyl and pyridyl; or a pharmaceutically acceptable salt thereof.

In another embodiment of the present invention, the invention relates to compounds of structural formula Id:

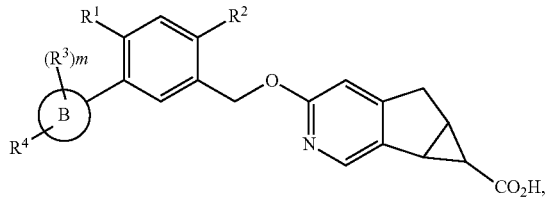

Id wherein B is selected from: phenyl and pyridyl; or a pharmaceutically acceptable salt thereof.

In another embodiment of the present invention, the invention relates to compounds of structural formula Ie:

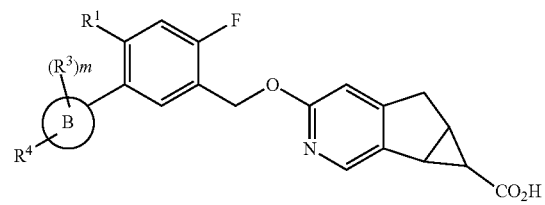

Ie wherein B is selected from: phenyl and pyridyl; or a pharmaceutically acceptable salt thereof.

In another embodiment of the present invention, the invention relates to compounds of structural formula Ig:

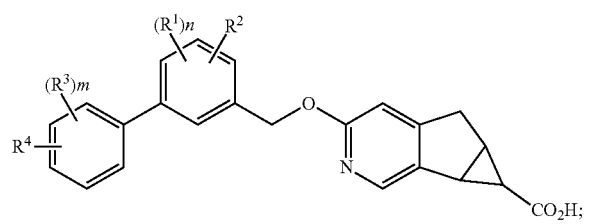

Ig or a pharmaceutically acceptable salt thereof.

In another embodiment of the present invention, the invention relates to compounds of structural formula Ih:

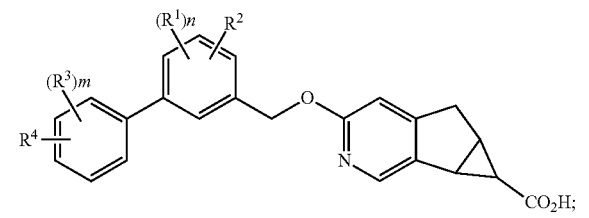

Ih or a pharmaceutically acceptable salt thereof.

In another embodiment of the present invention, the invention relates to compounds of structural formula Ii:

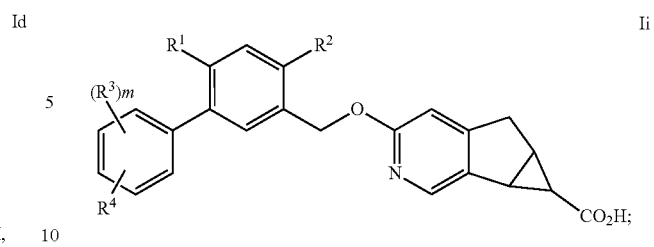

Ii or a pharmaceutically acceptable salt thereof.

In another embodiment of the present invention, the invention relates to compounds of structural formula Ij:

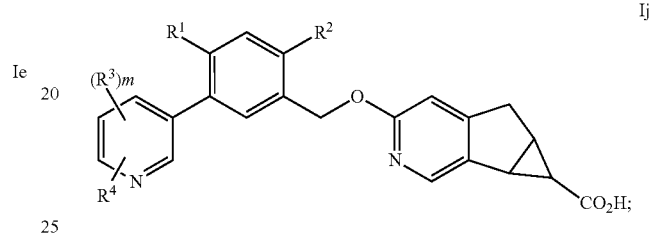

Ij or a pharmaceutically acceptable salt thereof.

The compound of structural formula I, includes the compounds of structural formulas Ia, Ib, Ic, Id, Ie, If, Ig, Ih, Ii and Ij, and pharmaceutically acceptable salts, hydrates and solvates thereof.

Another embodiment of the present invention relates to compounds of structural formula I wherein:
A is phenyl;
B is phenyl;
$R^1$ is selected from the group consisting of:
 (1) halogen,
 (2) —CN,
 (3) —$C_{1-6}$alkyl, and
 (4) —$(CH_2)_r$—$OC_{1-6}$alkyl,
 wherein each $CH_2$, —$C_{1-6}$alkyl and —$OC_{1-6}$alkyl is unsubstituted or substituted with one to four substituents selected from halogen, and —$C_{1-6}$alkyl;
$R^2$ is halogen;
each $R^3$ when present is independently selected from the group consisting of:
 (1) halogen, and
 (2) —$C_{1-6}$alkyl,
 wherein each $C_{1-6}$alkyl is unsubstituted or substituted with one to three substituents selected from halogen;
$R^4$ is selected from the group consisting of:
 (1) —$O(CH_2)_p C_{3-6}$cycloalkyl,
 (2) —$C_{2-6}$cycloheteroalkyl,
 (3) aryl, and
 (4) heteroaryl,
 wherein $R^4$ is unsubstituted or substituted with one, two, three, four or five substituents selected from $R^5$;
$R^5$ is selected from the group consisting of:
 (1) —$(CH_2)_s$halogen,
 (2) —$C_{1-6}$alkyl,
 (3) —$(CH_2)_s OH$,
 (4) —$(CH_2)_s CN$,
 (5) —$(CH_2)_s SO_2 C_{1-6}$alkyl, and
 (6) —$(CH_2)_s SO_2$—$(CH_2)_t$—$C_{3-6}$cycloalkyl,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w OH$;

m is 1;
n is 1;
p is 0, 1, 2, 3 or 4;
r is 0, 1, 2 or 3;
s is 0, 1, 2 or 3; and
t is 0, 1, 2 or 3;
or a pharmaceutically acceptable salt thereof.

Another embodiment of the present invention relates to compounds of structural formula I wherein:
A is phenyl;
B is phenyl;
$R^1$ is selected from the group consisting of:
  (1) halogen,
  (2) —CN,
  (3) —$C_{1-6}$alkyl, and
  (4) —$(CH_2)_r$—$OC_{1-6}$alkyl,
wherein each $CH_2$, —$C_{1-6}$alkyl and —$OC_{1-6}$alkyl is unsubstituted or substituted with one to four substituents selected from halogen, and —$C_{1-6}$alkyl;
$R^2$ is halogen;
each $R^3$ when present is independently selected from the group consisting of:
  (1) halogen, and
  (2) —$C_{1-6}$alkyl,
wherein each $C_{1-6}$alkyl is unsubstituted or substituted with one to three substituents selected from halogen;
$R^4$ is selected from the group consisting of:
  (1) —$O(CH_2)_pC_{3-6}$cycloalkyl,
  (2) —$C_{2-6}$cycloheteroalkyl,
  (3) aryl, and
  (4) heteroaryl,
wherein $R^4$ is unsubstituted or substituted with one, two, three, four or five substituents selected from $R^5$;
$R^5$ is selected from the group consisting of:
  (1) —$(CH_2)_s$halogen,
  (2) —$C_{1-6}$alkyl,
  (3) —$(CH_2)_s$OH,
  (4) —$(CH_2)_s$CN,
  (5) —$(CH_2)_sSO_2C_{1-6}$alkyl, and
  (6) —$(CH_2)_sSO_2$—$(CH_2)_t$—$C_{3-6}$cycloalkyl,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH;
m is 0, 1 or 2;
n is 1;
p is 0, 1, 2, 3 or 4;
r is 0, 1, 2 or 3;
s is 0, 1, 2 or 3; and
t is 0, 1, 2 or 3;
or a pharmaceutically acceptable salt thereof.

Another embodiment of the present invention relates to compounds of structural formula I wherein:
A is phenyl;
B is pyridyl;
$R^1$ is —$C_{1-6}$alkyl, unsubstituted or substituted with one to four substituents selected from halogen, and —$C_{1-6}$alkyl;
$R^2$ is halogen;
$R^3$ when present is —$C_{1-6}$alkyl, wherein each $C_{1-6}$alkyl is unsubstituted or substituted with one to three substituents selected from halogen;
$R^4$ is —$O(CH_2)_pC_{3-6}$cycloalkyl, wherein $R^4$ is unsubstituted or substituted with one, two, three, four or five substituents selected from $R^5$;
each $R^5$ is independently selected from the group consisting of:
  (1) —$C_{1-6}$alkyl, and
  (2) —$(CH_2)_s$OH,
  (3) —$(CH_2)_s$CN,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH;
m is 0, 1 or 2;
n is 1;
p is 0, 1, 2, 3 or 4;
s is 0, 1, 2 or 3; and
w is 0, 1, 2 or 3;
or a pharmaceutically acceptable salt thereof.

Another embodiment of the present invention relates to compounds of structural formula I wherein:
A is:

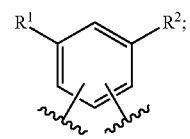

B is phenyl;
$R^1$ is selected from the group consisting of:
  (1) halogen,
  (2) —CN, and
  (3) —$C_{1-6}$alkyl,
wherein —$C_{1-6}$alkyl is unsubstituted or substituted with one to four substituents selected from halogen, and —$C_{1-6}$alkyl;
$R^2$ is halogen;
each $R^3$ when present is independently selected from the group consisting of:
  (1) halogen, and
  (2) —$C_{1-6}$alkyl,
wherein each $C_{1-6}$alkyl is unsubstituted or substituted with one to three substituents selected from halogen;
$R^4$ is selected from the group consisting of:
  (1) —$O(CH_2)_pC_{3-6}$cycloalkyl,
  (2) —$C_{2-8}$cycloheteroalkyl,
  (3) aryl, and
  (4) heteroaryl,
wherein $R^4$ is unsubstituted or substituted with one, two, three, four or five substituents selected from $R^5$;
each $R^5$ is independently selected from the group consisting of:
  (1) —$(CH_2)_s$halogen,
  (2) —$C_{1-6}$alkyl,
  (3) —$(CH_2)_s$OH,
  (4) —$(CH_2)_sSO_2C_{1-6}$alkyl, and
  (5) —$(CH_2)_sSO_2$—$(CH_2)_t$—$C_{3-6}$cycloalkyl,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH;
m is 0, 1 or 2;
p is 0, 1, 2, 3 or 4;
s is 0, 1, 2 or 3;
t is 0, 1, 2 or 3; and
w is 0, 1, 2 or 3;
or a pharmaceutically acceptable salt thereof.

Another embodiment of the present invention relates to compounds of structural formula I wherein:

A is:

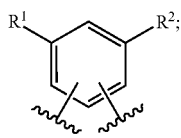

B is phenyl;
R¹ is selected from the group consisting of:
(1) halogen,
(2) —CN, and
(3) —$C_{1-6}$alkyl,
wherein each —$C_{1-6}$alkyl is unsubstituted or substituted with one to four substituents selected from halogen, and —$C_{1-6}$alkyl;
R² is halogen;
each R³ when present is independently selected from the group consisting of:
(1) halogen, and
(2) —$C_{1-6}$alkyl,
wherein each $C_{1-6}$alkyl is unsubstituted or substituted with one to three substituents selected from halogen;
R⁴ is selected from the group consisting of:
(1) —O(CH$_2$)$_p$C$_{3-6}$cycloalkyl,
(2) —C$_{2-8}$cycloheteroalkyl, and
(3) aryl,
wherein R⁴ is unsubstituted or substituted with one, two, three, four or five substituents selected from R⁵;
R⁵ is selected from the group consisting of:
(1) —(CH$_2$)$_s$halogen,
(2) —C$_{1-6}$alkyl,
(3) —(CH$_2$)$_s$OH,
(4) —(CH$_2$)$_s$SO$_2$C$_{1-6}$alkyl, and
(5) —(CH$_2$)$_s$SO$_2$—(CH$_2$)$_t$—C$_{3-6}$cycloalkyl,
wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH;
m is 1;
p is 0, 1, 2, 3 or 4;
s is 0, 1, 2 or 3;
t is 0, 1, 2 or 3; and
w is 0, 1, 2 or 3;
or a pharmaceutically acceptable salt thereof.

Another embodiment of the present invention relates to compounds of structural formula I wherein:
A is:

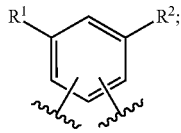

B is phenyl;
R¹ is selected from the group consisting of:
(1) halogen,
(2) —CN, and
(3) —$C_{1-6}$alkyl,
wherein each —$C_{1-6}$alkyl is unsubstituted or substituted with one to four substituents selected from halogen, and —$C_{1-6}$alkyl;
R² is halogen;
each R³ when present is independently selected from the group consisting of:
(1) halogen, and
(2) —$C_{1-6}$alkyl,
wherein each $C_{1-6}$alkyl is unsubstituted or substituted with one to three substituents selected from halogen;
R⁴ is selected from the group consisting of:
(1) —O(CH$_2$)$_p$C$_{3-6}$cycloalkyl,
(2) —C$_{2-8}$cycloheteroalkyl, and
(3) aryl,
wherein R⁴ is unsubstituted or substituted with one, two, three, four or five substituents selected from R⁵;
R⁵ is selected from the group consisting of:
(1) —(CH$_2$)$_s$halogen,
(2) —C$_{1-6}$alkyl,
(3) —(CH$_2$)$_s$OH,
(4) —(CH$_2$)$_s$SO$_2$C$_{1-6}$alkyl, and
(5) —(CH$_2$)$_s$SO$_2$—(CH$_2$)—C$_{3-6}$cycloalkyl,
wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH;
m is 0, 1 or 2;
p is 0, 1, 2, 3 or 4;
s is 0, 1, 2 or 3;
t is 0, 1, 2 or 3; and
w is 0, 1, 2 or 3;
or a pharmaceutically acceptable salt thereof.

Another embodiment of the present invention relates to compounds of structural formula I wherein:
A is

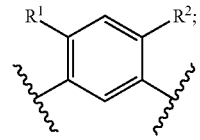

B is phenyl;
R¹ is selected from the group consisting of:
(1) halogen,
(2) —CN, and
(3) —$C_{1-6}$alkyl,
wherein —$C_{1-6}$alkyl is unsubstituted or substituted with one to four substituents selected from halogen, and —$C_{1-6}$alkyl;
R² is F;
each R³ is independently selected from the group consisting of:
(1) halogen, and
(2) —$C_{1-6}$alkyl,
wherein $C_{1-6}$alkyl is unsubstituted or substituted with one to three substituents selected from halogen;
R⁴ is selected from the group consisting of:
(1) —O—CH$_2$-cyclobutyl,
(2) —O-cyclobutyl,
(3) —O-cyclohexyl,
(4) 2,6-diazospiro[3,3]heptan-2yl,
(5) piperidine, and
(6) phenyl,
wherein R⁴ is unsubstituted or substituted with one, two, three, four or five substituents selected from R⁵;
each R⁵ is independently selected from the group consisting of:
(1) halogen,
(2) —$C_{1-6}$alkyl,
(3) —OH, (4) —SO₂C₁₋₆alkyl, and
(5) —SO₂—C₃₋₆cycloalkyl,
wherein each CH₂, C₁₋₆alkyl and C₃₋₆cycloalkyl is unsubstituted or substituted with one to three substituents selected from halogen, C₁₋₆alkyl, and —(CH₂)$_w$OH;
m is 0, 1 or 2; and
w is 0, 1, 2 or 3;
or a pharmaceutically acceptable salt thereof.

Another embodiment of the present invention relates to compounds of structural formula I wherein:
A is

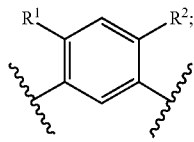

B is phenyl;
R¹ is selected from the group consisting of:
  (1) halogen,
  (2) —CN, and
  (3) —C₁₋₆alkyl,
wherein each —C₁₋₆alkyl is unsubstituted or substituted with one to four substituents selected from halogen, and —C₁₋₆alkyl;
R² is F;
each R³ when present is independently selected from the group consisting of:
  (1) halogen, and
  (2) —C₁₋₆alkyl,
wherein each C₁₋₆alkyl is unsubstituted or substituted with one to three substituents selected from halogen;
R⁴ is selected from the group consisting of:
  (1) —O—CH₂-cyclobutyl,
  (2) —O-cyclohexyl,
  (3) 2,6-diazospiro[3,3]heptan-2yl,
  (4) piperidine, and
  (5) phenyl,
wherein R⁴ is unsubstituted or substituted with one, two, three, four or five substituents selected from R⁵;
R⁵ is selected from the group consisting of:
  (1) halogen,
  (2) —C₁₋₆alkyl,
  (3) —OH,
  (4) —SO₂C₁₋₆alkyl, and
  (5) —SO₂—C₃₋₆cycloalkyl,
wherein each CH₂, C₁₋₆alkyl and C₃₋₆cycloalkyl is unsubstituted or substituted with one to three substituents selected from halogen, C₁₋₆alkyl, and —(CH₂)$_w$OH;
m is 1; and
w is 0, 1, 2 or 3;
or a pharmaceutically acceptable salt thereof.

Another embodiment of the present invention relates to compounds of structural formula I wherein:
A is

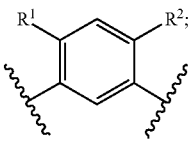

B is phenyl;
R¹ is selected from the group consisting of:
  (1) halogen,
  (2) —CN, and
  (3) —C₁₋₆alkyl,
wherein each —C₁₋₆alkyl is unsubstituted or substituted with one to four substituents selected from halogen, and —C₁₋₆alkyl;
R² is F;
each R³ when present is independently selected from the group consisting of:
  (1) halogen, and
  (2) —C₁₋₆alkyl,
wherein each C₁₋₆alkyl is unsubstituted or substituted with one to three substituents selected from halogen;
R⁴ is selected from the group consisting of:
  (1) —O—CH₂-cyclobutyl,
  (2) —O-cyclohexyl,
  (3) 2,6-diazospiro[3,3]heptan-2yl,
  (4) piperidine, and
  (5) phenyl,
wherein R⁴ is unsubstituted or substituted with one, two, three, four or five substituents selected from R⁵;
R⁵ is selected from the group consisting of:
  (1) halogen,
  (2) —C₁₋₆alkyl,
  (3) —OH,
  (4) —SO₂C₁₋₆alkyl, and
  (5) —SO₂—C₃₋₆cycloalkyl,
wherein each CH₂, C₁₋₆alkyl and C₃₋₆cycloalkyl is unsubstituted or substituted with one to three substituents selected from halogen, C₁₋₆alkyl, and —(CH₂)$_w$OH;
m is 0, 1 or 2; and
w is 0, 1, 2 or 3;
or a pharmaceutically acceptable salt thereof.

Illustrative, but non-limiting, examples of the compounds of the present invention that are useful as agonists of G-protein-coupled receptor 40 (GPR40) are the following compounds:

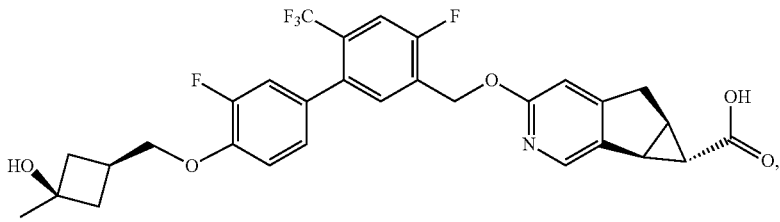

-continued
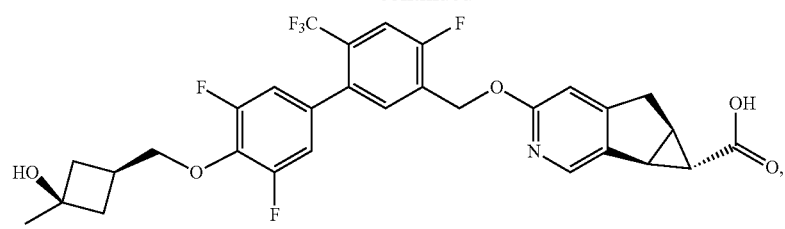
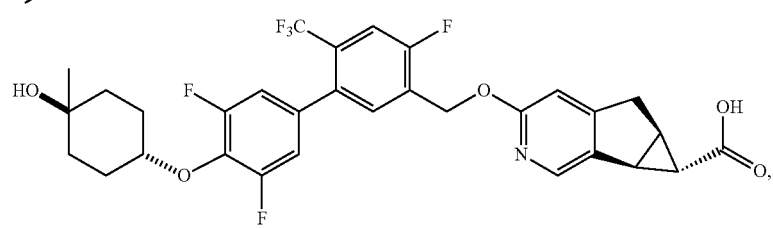
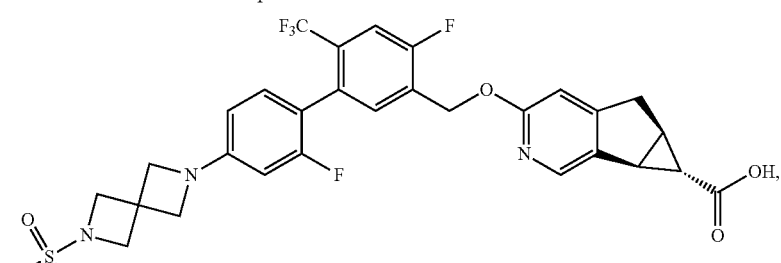
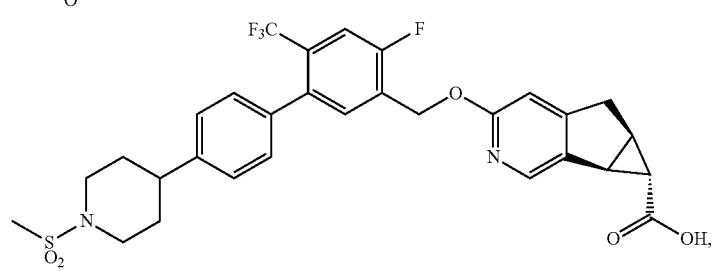
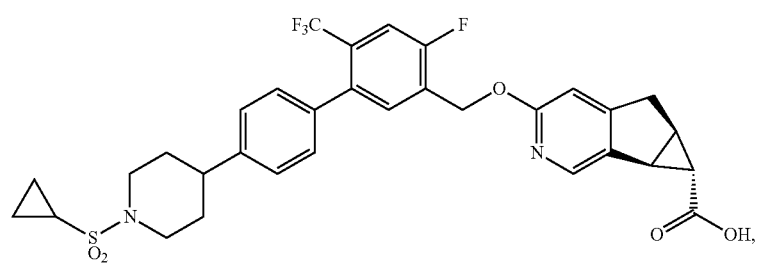
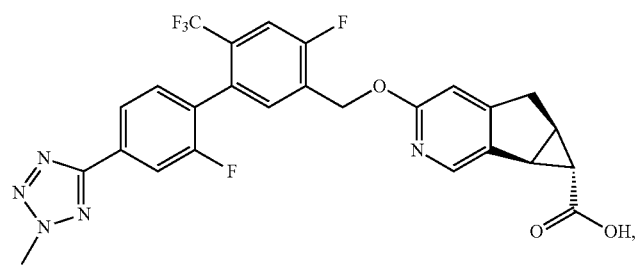

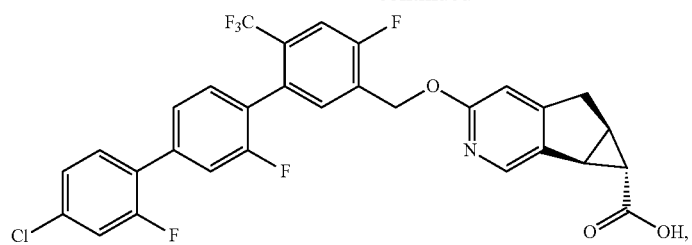
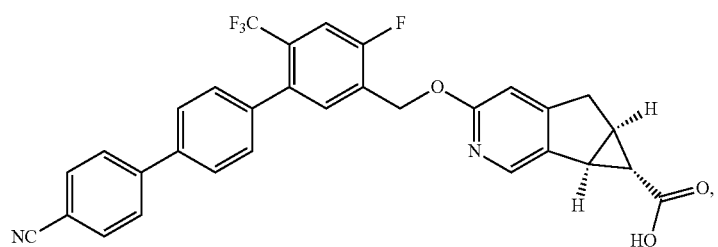
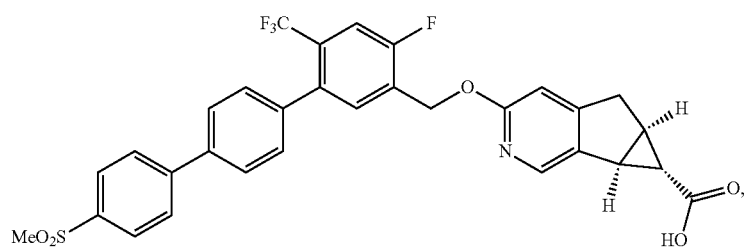
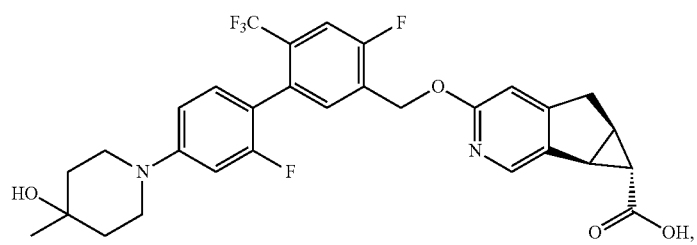
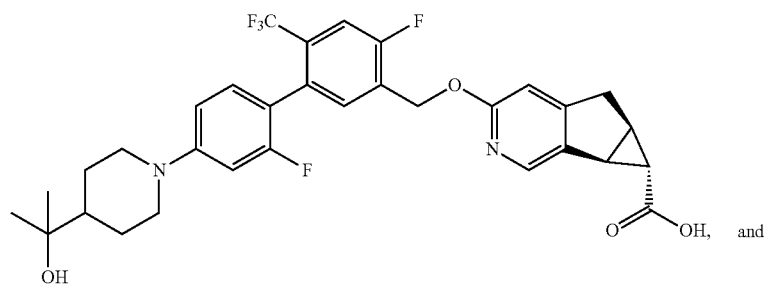

-continued

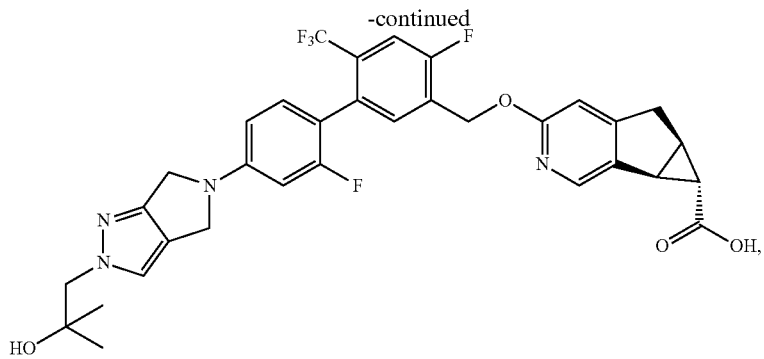

and pharmaceutically acceptable salts thereof.

In one embodiment of the present invention, the compounds of formula I have the absolute stereochemistry at the two stereogenic carbon centers as indicated in the compound of structural formula If:

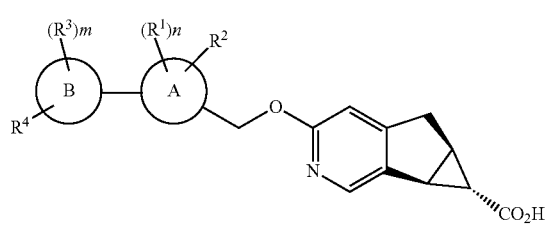

If and pharmaceutically acceptable salts thereof.

Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

DEFINITIONS

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclobutyl, cyclopentyl, cyclohexyl, cycloheptyl, and the like. In one embodiment of the present invention, cycloalkyl is selected from: cyclopropane, cyclobutane and cyclohexane. In another embodiment of the present invention, cycloalkyl is selected from: cyclobutane and cyclohexane. In another embodiment of the present invention, cycloalkyl is cyclopropane. In another embodiment of the present invention, cycloalkyl is cyclohexane.

"Cycloheteroalkyl" means a saturated or partly unsaturated non-aromatic monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). In one embodiment of the present invention, cycloheteroalkyl means a saturated or partly unsaturated non-aromatic monocyclic, bicyclic or bridged carbocyclic ring or ring system containing one or two ring heteroatoms selected from N, NH, S (including SO and $SO_2$) and O. Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1, 4:3, 6-dianhydromannitol, 1, 4:3, 6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is selected from: 2,6-diazospiro[3,3]heptan-2yl, and piperidine. In another embodiment of the present invention, cycloheteroalkyl is 2,6-diazospiro[3,3]heptan-2yl. In another embodiment of the present invention, cycloheteroalkyl is piperidine.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b) pyridyl, quinolyl, indolyl, isoquinolyl, quinazolinyl, dibenzofuranyl, and pyrrolo[3,4-c]pyrazole and the like. In one embodiment of the present invention, heteroaryl is selected from: pyridine, pyrimidine, thiazole, benzimidazole, benzthiazole, benzoxazole, and benzisoxazole. In another embodiment of the present invention, heteroaryl is tetrazole and pyrrolo[3,4-c]pyrazole. In another embodiment of the present invention, heteroaryl is tetrazole. In another embodiment of the present invention, heteroaryl is pyrrolo[3,4-c]pyrazole.

"Halogen" includes fluorine, chlorine, bromine and iodine. In another embodiment of the present invention, halogen includes fluorine, chlorine and iodine. In another embodiment of the present invention, halogen includes fluorine and chlorine. In another embodiment of the present invention, halogen is chlorine. In another embodiment of the present invention, halogen is fluorine.

"Me" represents methyl.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

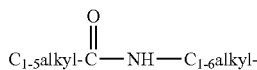

In choosing compounds of the present invention, one of ordinary skill in the art will recognize that the various substituents, i.e., $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods.

These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) hyperglycemia; (3) insulin resistance; (4) Metabolic Syndrome; (5) obesity; (6) hypercholesterolemia; (7) hypertriglyceridemia (elevated levels of triglyceride-rich-lipoproteins); (8) mixed or diabetic dyslipidemia; (9) low HDL cholesterol; (10) high LDL cholesterol; (11) hyperapo-B-liproteinemia; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammalian subject or patient in need of treatment. Other medical uses of the compounds of the present invention are described herein.

Certain compounds of the present invention of formula Id have the unexpected benefit of lower clearance in standard pharmacokinetic assays done in preclinical species, such as dogs and rats, compared to the compounds without one $R^2$ substituent selected from halogen, and without at least one $R^1$ substituent. Due to the lower clearance, these compounds of the present invention exhibit a longer half life (or a longer mean residence time), and may be useful for a once weekly dosing. In particular, certain compounds of the present invention of formula Id in which at least one $R^1$ substituent is selected from $CF_3$, CN and cyclopropyl have the unexpected benefit of lower clearance and a half life (or mean residence time) which is at least two times longer than the half life of the compounds without one $R^2$ substituent selected from halogen, and without at least one $R^1$ substituent selected from $CF_3$, CN and cyclopropyl on the A ring.

Certain compounds of the present invention of formula Id have the unexpected benefit of lower clearance in standard pharmacokinetic assays done in preclinical species, such as dogs and rats, compared to the compounds in which the phenyl ring is unsubstituted (i.e., there no $R^1$ and $R^2$ substituents on the phenyl ring). Due to the lower clearance, these formula Id compounds exhibit a longer half life (or a longer mean residence time).

In particular, certain compounds of the present invention of formula Id wherein $R^1$ is selected from $CF_3$, CN and cyclopropyl have the unexpected benefit of lower clearance and a longer half life (or a longer mean residence time) than the half life of the compounds in which the phenyl ring is unsubstituted (i.e., there no $R^1$ and $R^2$ substituents on the phenyl ring).

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (>140 mmHg/>90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome.

The terms "administration of" and or "administering a" compound should be understood to mean providing a compound of the invention or a prodrug of a compound of the invention to a human or other mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Additionally, in the treatment or prevention of conditions which require agonism of GPR40 receptor activity, an appropriate dosage level will generally be about 0.01 to 500 mg per kg patient body weight per week, which can be administered in single or multiple doses. Preferably, the dosage level will be about 0.1 to about 250 mg/kg per week; more preferably about 0.5 to about 100 mg/kg per week. A suitable dosage level may be about 0.01 to 250 mg/kg per week, about 0.05 to 100 mg/kg per week, or about 0.1 to 50 mg/kg per week. Within this range the dosage may be 0.05 to 0.5, 0.5 to 5 or 5 to 50 mg/kg per week. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may also be administered on a regimen of 1 to 4 times per week, preferably once or twice per week.

When treating or preventing diabetes mellitus and/or hyperglycemia or hypertriglyceridemia or other diseases for which compounds of the present invention are indicated, generally satisfactory results are obtained when the compounds of the present invention are administered at a weekly dosage of from about 0.1 mg to about 100 mg per kilogram of animal body weight, preferably given as a single weekly dose or in divided doses two to six times a week, or in sustained release form. For most large mammals, the total weekly dosage is from about 1.0 mg to about 1000 mg, preferably from about 1 mg to about 50 mg. In the case of a 70 kg adult human, the total weekly dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered separately or in the same pharmaceutical composition in combination with a compound of the formulas described herein include, but are not limited to:

(1) other dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe);

(11) HDL-raising drugs, (e.g., niacin and nicotinic acid receptor agonists, and extended-release versions thereof;

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, MR 1704, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, ertugliflozin, canagliflozin, BI-10773, PF-04971729, remogloflozin, TS-071, tofogliflozin, ipragliflozin, and LX-4211);

(27) inhibitors of acyl coenzyme A: diacylglycerol acyltransferase 1 and 2 (DGAT-1 and DGAT-2);

(28) inhibitors of fatty acid synthase;

(29) inhibitors of acyl coenzyme A: monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501.

Other suitable active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATI-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)-methoxy)-phenyl)iso, 5-(4-((3-(2-methyl-6-(3-hydroxypropoxy)pyridine-3-yl)-2-methylphenyl)methoxy)-phenyl)isothiazole-3-ol 1-oxide, and 5-[4-[[3-[4-(3-aminopropoxy)-2,6-dimethylphenyl]phenyl]-methoxy]phenyl]isothiazole-3-ol 1-oxide), and those disclosed in WO 11/078371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin, atorvastatin or rosuvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fabric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), 58921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as alacepril, benazepril; captopril; ceronapril, cilazapril; delapril; enalapril; fosinopril; imidapril; losinopril; moveltipril; quinapril; quinaprilat; ramipril; perindopril; perindropril; quanipril; spirapril; temocapril; trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists, which may be in free acid, free base, salt or prodrug form, such as candesartan, eprosartan, irbesartan, losartan, olmesartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), O1691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509,367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, 52367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552, 524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436, 272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) β11 HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, vildagliptin, P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/ TM30338 (7™ Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/ AC137 (Amylin); (59) Hoodia and trichocaulon extracts; (60) BVT74713 and other gut lipid appetite suppressants; (61) dopamine agonists such as bupropion (WELLBUTRIN/ GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, metformin, sibutramine, orlistat, Qnexa, topiramate, naltrexone, bupriopion, phentermine, and losartan, losartan with hydrochlorothiazide.

Specific ACC-1/2 inhibitors of use in combination with a compound of the present invention include: 1'-[(4,8-dimethoxyquinolin-2-yl)carbonyl]-6-(1H-tetrazol-5-yl)spiro [chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro [chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl) methoxy]pyridin-2(1H)-one, 4-[(5-chloropyridin-2-yl) methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from Januvia, 7-[(3R)-3-amino-4-(2,4,5-trifluorophenyl)butanoyl]-3-(trifluoromethyl)-5,6,7,8-tetrahydro-1,2,4-triazolo[4,3-a] pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d] pyrimidin-4(3H)-one, 2-ethyl-3-(4-{3-[(3S)-3-methylpiperidin-1-yl]propoxy}phenyl)pyrido[2,3-d] pyrimidin-4(3H)-one 2-methyl-3-(4-{3-[(3 S)-3-methylpiperidin-1-yl]propoxy}phenyl)pyrido[4,3-d] pyrimidin-4(3H)-one, 3-{4-[(1-cyclobutyl-4-piperidinyl) oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy] phenyl}-5-fluoro-2-methyl-4(3H)-quinazolinone, 3-{4-[(1-cyclobutylpiperidin-4-yl)oxy]phenyl}-7-fluoro-2-methyl-4 (3H)-quinazolinone, 3-{4-[(1-cyclobutylpiperidin-4-yl)oxy] phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy] phenyl}-2-ethylpyrido[4,3-d]pyrimidin-4(3H)-one, 6-methoxy-2-methyl-3-{4-[3-(1-piperidinyl)propoxy] phenyl}pyrido[3,4-d]pyrimidin-4(3H)-one, 6-methoxy-2-methyl-3-{4-[3-(1-pyrrolidinyl)propoxy]phenyl}pyrido[3, 4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3- methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2 S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl] carbonyl}-1-piperazinyl)-1-naphthoic acid; 3-(4-{[1-(3-ethoxyphenyl)-2-(2,4-difluorophenyl)-1H-imidazol-4-yl] carbonyl}-1-piperazinyl)-1-naphthoic acid; and 3-(4-{[1-(2, 3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5 S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl) ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b] pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b] pyridine-7,4'-piperidine]; 5) N-[(3R,4R)-3-({3-chloro-2-methyl-5-[1-methyl-1-(1-methyl-1H-1,2,4-triazol-5-yl) ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl) ethoxy)-3-(S)-(4-fluorophenyl)-4-(3-(5-oxo-1H,4H-1,2,4-triazolo)methyl)morpholine; aperpitant; CJ17493; GW597599; GW679769; R673; R067319; R1124; R1204; SSR146977; SSR240600; T-2328; and T2763.; or a pharmaceutically acceptable salts thereof.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The following Examples are provided to illustrate the invention and are not to be construed as limiting the invention in any manner. The scope of the invention is defined by the appended claims.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

List of Abbreviations

Ac is acetyl; ACN is acetonitrile; AcO is acetoxy; AcOH is acetic acid; AcONa is sodium acetate; Alk is alkyl; APCI is atmospheric pressure chemical ionization; $Ag_2CO_3$ is silver carbonate; aq or aq. is aqueous; Ar is aryl; br is broad; bu is butyl; t-BuOH is tert-butanol; ° C. is degrees celsius; $CH_2Cl_2$ is dichloromethane; $CCl_4$ is carbon tetrachloride; conc or conc. is concentrated; d is doublet; Celite is diatomaceous earth; DABCO is 1,4-diazabicyclo[2.2.2]-octane); DAST is (diethylamino)sulfur trifluoride; DCM is dichloromethane; DEA is diethyl amine: DIAD is diisopropyl azodicarboxylate; DMAP is 4-dimethylaminopyridine; DMF is N,N-dimethylformamide; DMSO is dimethylsulfoxide; dppf is 1,1'-bis(diphenyl-phosphino)ferrocene; ESI is electrospray ionization; EA or EtOAc is ethyl acetate; et is ethyl; EtOH is ethanol; $Et_3N$ is triethyl amine; g or gm is gram(s); h or hr or hrs is hour(s); HPLC is high pressure liquid chromatography; kg is kilogram(s); KHMDS is potassium hexamethyl disilazide; $K_2CO_3$ is potassium carbonate; $K_3PO_4$ is potassium carbonate; KOAc or AcOK is potassium acetate; L is liter; LiOH is lithium hydroxide; m is multiplet; mL or ml is milliliter; min or mins is minute(s); mol is mole(s); mmol is mmole(s); mg is milligram(s); mCPBA or MCPBA is meta-chloro-peroxybenzoic acid; me is methyl; MeCN is acetonitrile; MeOH is methyl alcohol; $MgSO_4$ is magnesium sulfate; MS is mass spectroscopy; MsCl or Ms-Cl is methane sulfonyl chloride or mesyl chloride; N is normal; NaOH is sodium hydroxide; $Na_2SO_4$ is sodium sulfate; NBS is N-bromo succinamide; NIS is N-iodo succinamide; NMP is 1-methyl-2-pyrrolidinone; NMO is N-methylmorpholine N-oxide; NMR is nuclear magnetic resonance spectroscopy; PE is petroleum ether; $Pd(dppf)Cl_2$ is [1,1'-bis(diphenylphosphino)ferrocene]-dichloro-palladium (II); $DTBPFPdCl_2$ or $Pd(dtbpf)Cl_2$ is [1,1'-bis(di-tert-butylphosphino)-ferrocene]dichloro-palladium (II); PMB is para-methoxybenzyl; PMBCl is para-methoxybenzyl chloride; $Pd(PPh_3)_4$ is tetrakis triphenyl phosphine palladium; prep. TLC or prep-TLC, or preparative TCL is preparative thin layer chromatography; rt or rt. or r.t. or RT is room temperature; s is singlet; SFC is super critical fluid chromatography; 2nd Generation Hoveyda-Grubbs Catalyst is (1,3-Bis-(2,4,6-trimethylphenyl)-2-imidazolidinyl-idene)dichloro(o-isopropoxyphenylmethylene)ruthenium; $2^{nd}$ Generation XPhos Precatalyst or Xphos precatalyst ($2^{nd}$ Generation) is Chloro(2-dicyclohexylphosphino-2',4',6'-triisopropyl-1,1'-biphenyl)[2-(2'-amino-1,1'-biphenyl)]palladium(II); t is triplet; TBAF is tetrabutyl ammonium fluoride; TBS is tert-butyldimethylsilyl; TEA is triethyl amine; THF istetrahydrofuran; TFA is trifluoroacetic acid; TLC is thin-layer chromatography; TMS-$N_3$ is trimethylsilyl azide; TsCl or TosCl is p-toluene sulfonyl chloride; $Pd_2(dba)_3$ is tris (dibenzylideneacetone) dipalladium(0); Xant-phos is 4,5-Bis(diphenylphosphino)-9,9-dimethylxanthene; Ruphos precatalyst is Methanesulfonato(2-dicyclohexylphosphino-2'-6'-di-i-propoxy-1,1'-biphenyl)(2-amino-1,1'-biphenyl-2-yl)palladium(II), and DTAD is Di-tert-butyl diazene-1,2-dicarboxylate.

Several methods for preparing the compounds of this invention are illustrated in the following Schemes and Examples. All temperatures are degrees Celsius unless otherwise noted. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products.

SCHEME 1

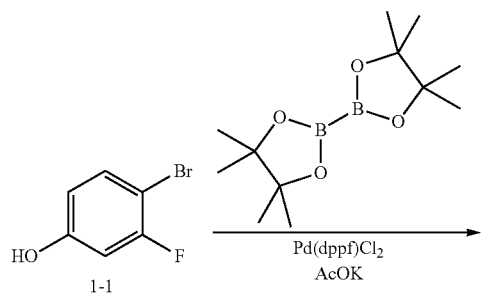

-continued
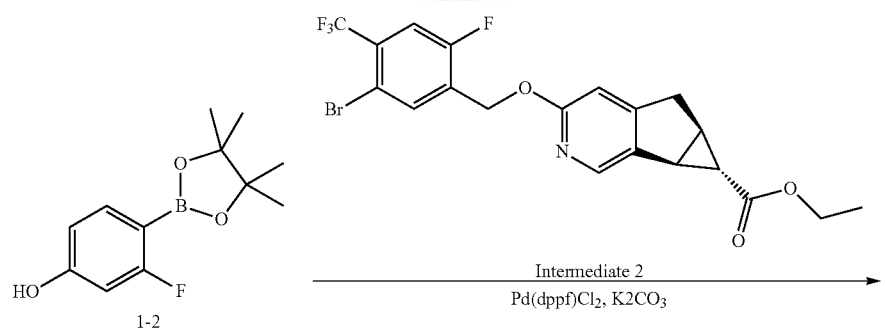
1-2
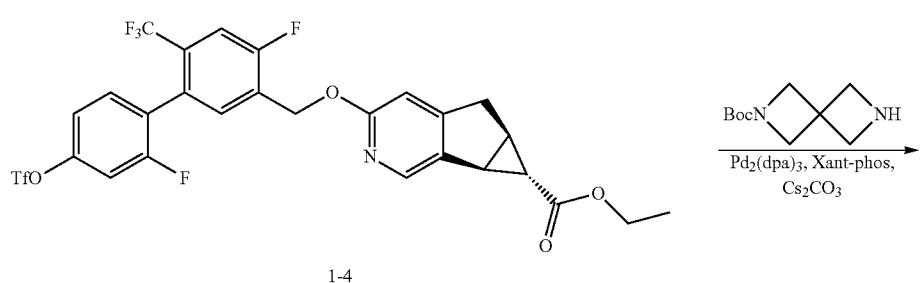
1-3
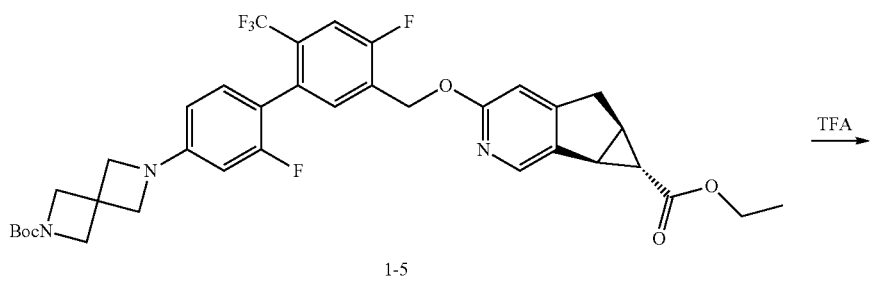
1-4
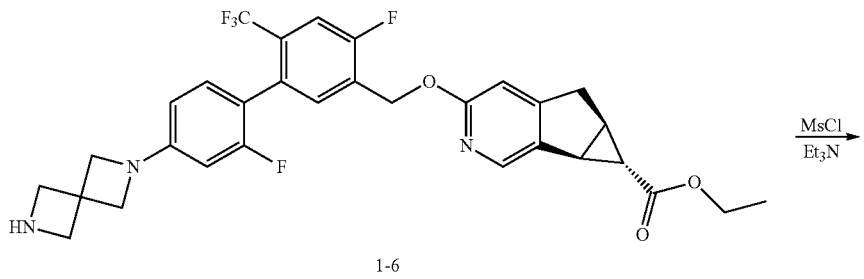
1-5
1-6

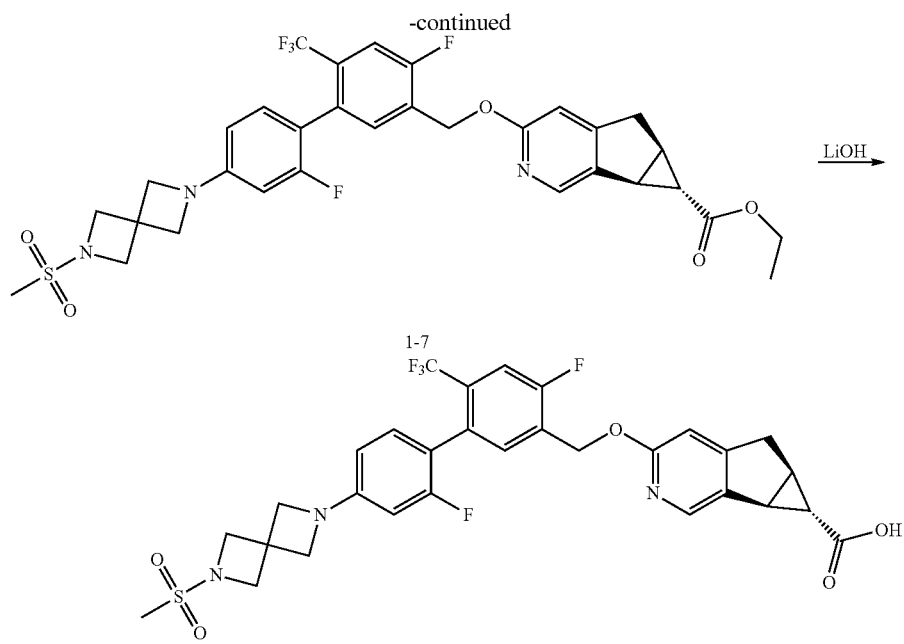

EXAMPLE 4

Scheme 1 describes the synthesis of Example 4. Commercially available 4-bromo-3-fluorophenol 1-1 was converted to boronic ester 1-2 and then coupled with Intermediate 2, both catalyzed by PdCl₂(dppf). After triflate formation, C—N coupling with tert-butyl 2,6-diazaspiro[3.3]heptane-2-carboxylate afforded 1-5. The Boc protecting group of 1-5 was removed to afford the corresponding amine 1-6 which was subsequently treated with MsCl and triethylamine to afford the sulfoamide 1-7. Treatment of 1-7 with lithium hydroxide at ambient temperature gave the final desired carboxylic acid.

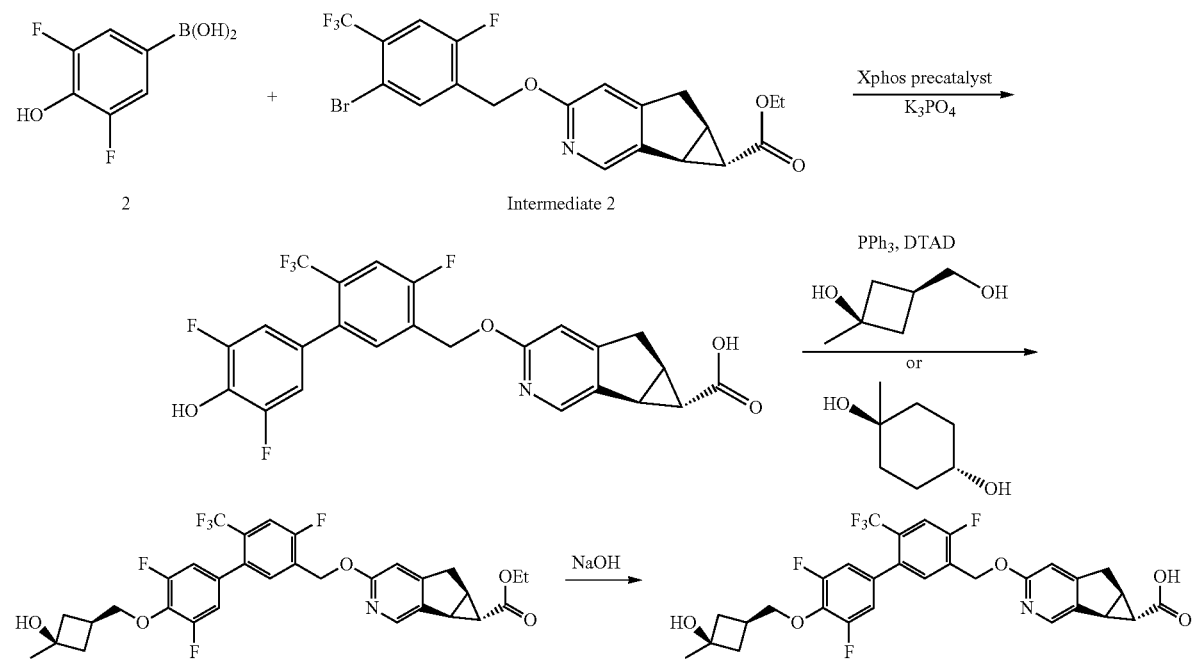

63

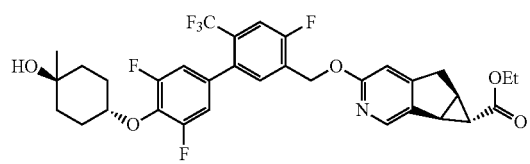

-continued

64

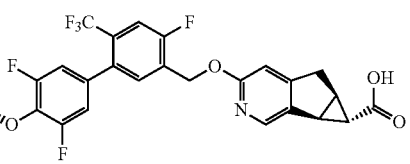

EXAMPLE 3

Scheme 2 illustrates the preparation of Examples 2 and 3. Commercially available (3,5-difluoro-4-hydroxyphenyl)boronic acid was coupled with Intermediate 2 to afford the biaryl phenol. The cross-coupling reaction was performed with Xphos precatalyst in the presence of aqueous $K_3PO_4$, under an inert nitrogen atmosphere. Then a Mitsunobu reaction with alcohol afforded the ether. The alcohols are either known in the literature (Synthetic Communications, 1989, 19, 745-54) or readily prepared by methods commonly known to those skilled in the art. Finally, base hydrolysis afforded the carboxylic acid final product.

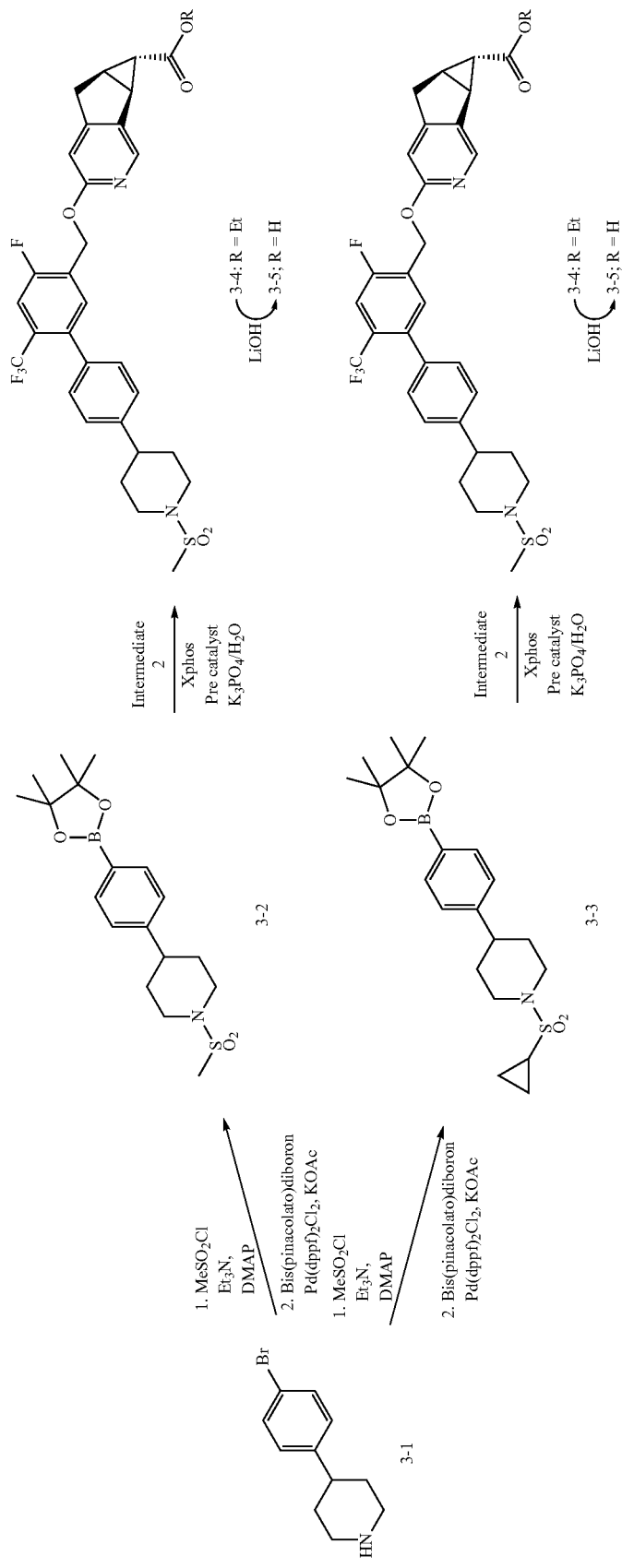

Examples 5 and 6 were synthesized as outlined in Scheme 3, the amino group in 4-(4'-bromophenyl)piperidine (3-1) is substituted by a corresponding alkyl sulfonyl chloride under basic conditions. The N-sulfonylated bromo derivatives were further reacted with bis(pinacolato)diboron using Pd(dppf)Cl$_2$ as catalyst to afford corresponding boronate esters (3-2 and 3-3). These boronate intermediates were coupled with the bromo derivative Intermediate 2 using 2$^{nd}$ generation XPHOS precatalyst as the reagent to afford advanced ester intermediates, (3-4 and 3-6), which under basic hydrolysis with LiOH yielded desired acids (3-5 and 3-7).

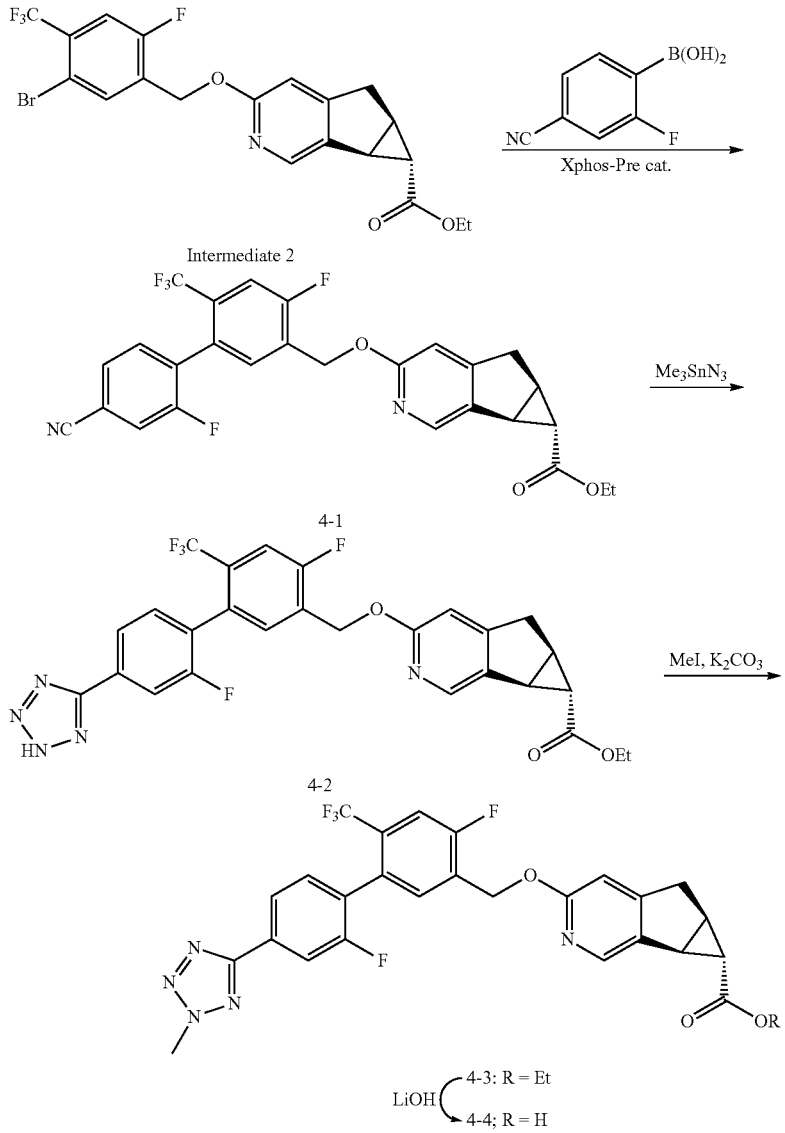

SCHEME 4

Example 7 was made as outlined in Scheme 4. The bromo derivative Intermediate 2 was coupled with 4-cyano-2-fluorophenylboronic acid pinacol ester using 2$^{nd}$ generation XPHOS pre catalyst as the reagent to afford cyano intermediate (4-1). This cyano intermediate was treated with azidotrimethyltin under thermal conditions to afford the addition product tetrazole derivative (4-2). Alkylation of the tetrazole derivative with methyl iodide in presence of K$_2$CO$_3$ as base yielded the 2-methyl-2H-tetrazol-5-yl derivative (4-3) as the major product, further treatment under basic hydrolysis conditions with LiOH yielded the desired acid (4-4).

SCHEME 5
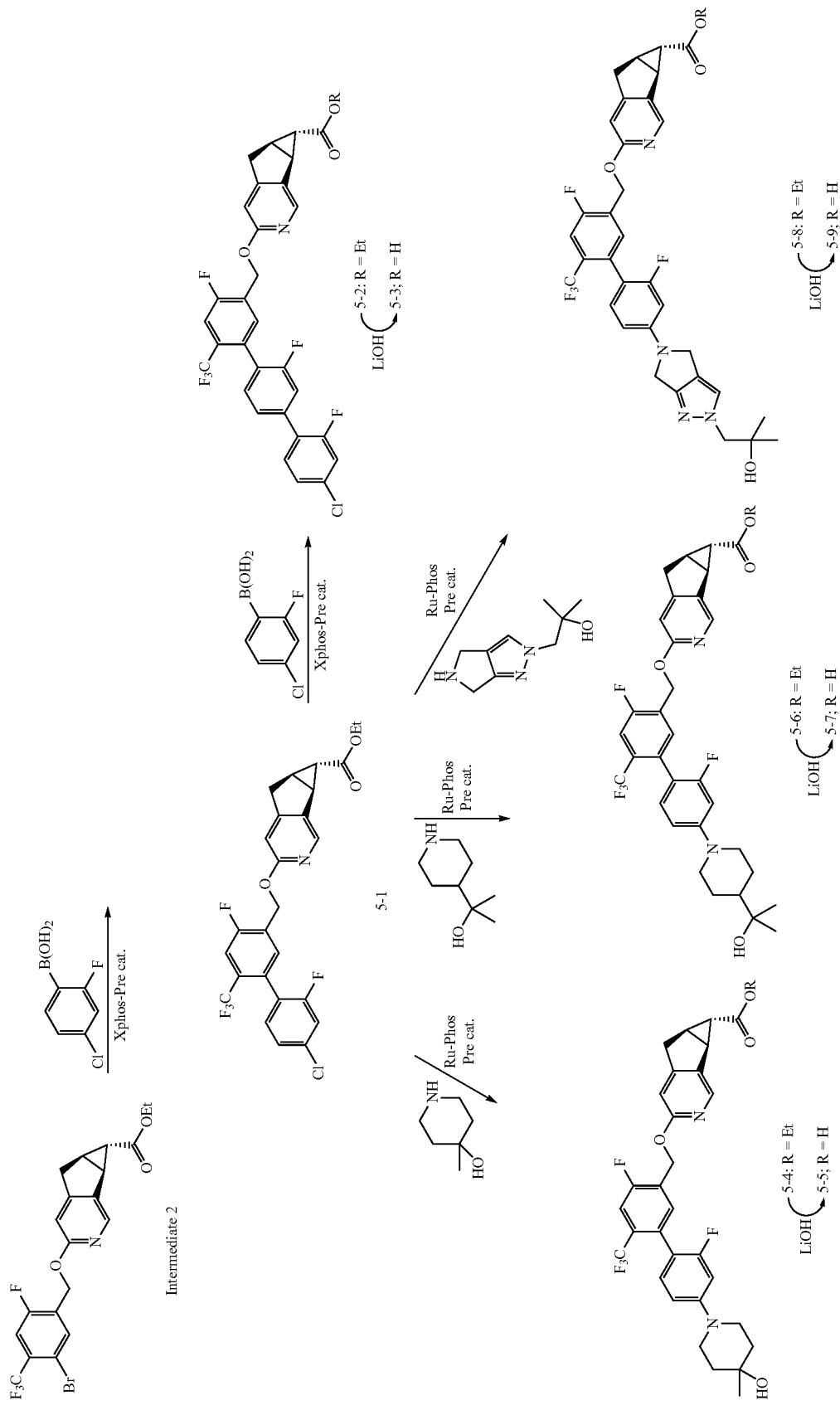

Examples 8, 11, 12 and 13 were made as outlined in Scheme 5. The bromo derivative Intermediate 2 was coupled with 4-chloro-2-fluorophenylboronic acid using $2^{nd}$ generation XPHOS pre catalyst as the reagent to afford chloro intermediate (5-1). This chloro intermediate under similar under similar reaction conditions afforded the corresponding N-arylated intermediates (5-6) and (5-8) respectively. Treatment of the N-arylated intermediates (5-4), (5-6) and (5-8) under basic hydrolysis conditions with LiOH yielded the desired acids (5-5), (5-7) and (5-9) respectively.

SCHEME 6

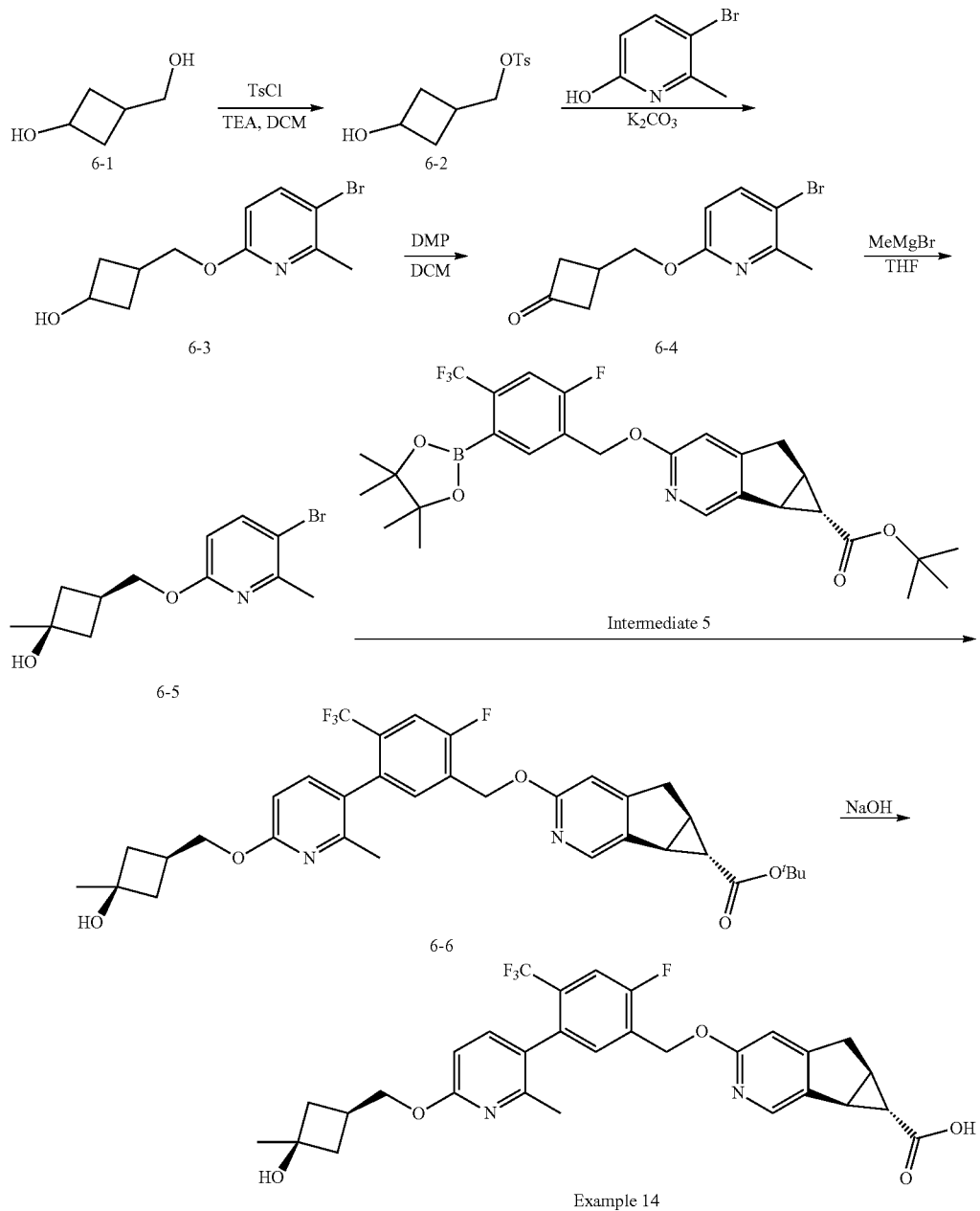

reaction conditions with another portion of 4-chloro-2-fluorophenylboronic acid afforded the tri phenyl derivative (5-2). Further treatment under basic hydrolysis conditions with LiOH yielded the desired acid (5-3). Treatment of the chloro derivative 5-1 with 4-methylpiperidin-4-ol HCl using $3^{rd}$ Generation RuPhos-pre catalyst as the reagent afforded N-arylated product (5-4). Treatment chloro derivative 5-1 with 2-(piperidin-4-yl)propan-2-ol and 1-(5,6-dihydropyrrolo[3,4-c]pyrazol-2(4H)-yl)-2-methylpropan-2-ol TFA Example 14 was prepared as shown in Scheme 6. Commercially available 3-(hydroxymethyl)cyclobutanol 6-1 was converted to mono-tosylate 6-2 and then coupled with 5-bromo-6-methylpyridin-2-ol to give the bromide 6-3. Oxidation by Dess-Martin's periodinane afforded 3-(((5-bromo-6-methylpyridin-2-yl)oxy)methyl)cyclobutanone 6-4. Treatment of ketone 6-4 with methylmagnesium bromide afforded cis-isomer (1s,3s)-3-(((5-bromo-6-methylpyridin-2-yl)oxy)methyl)-1-methylcyclobutanol 6-5, which was coupled with Intermediate 5 to give (5aR,6S,6aS)-tert-butyl 3-((2-fluoro-5-(6-(((1s,3s)-3-hydroxy-3-methylcyclobutyl)-methoxy)-2-methylpyridin-3-yl)-4-(trifluoromethyl)benzyl)oxy)-5,5a,6,6a-tetrahydrocyclo-propa[4,5]-cyclopenta[1,2-c]pyridine-6-carboxylate 6-6. Hydrolysis of 6-6 with sodium hydroxide gave the carboxylic acid (Example 14).
SCHEME 7
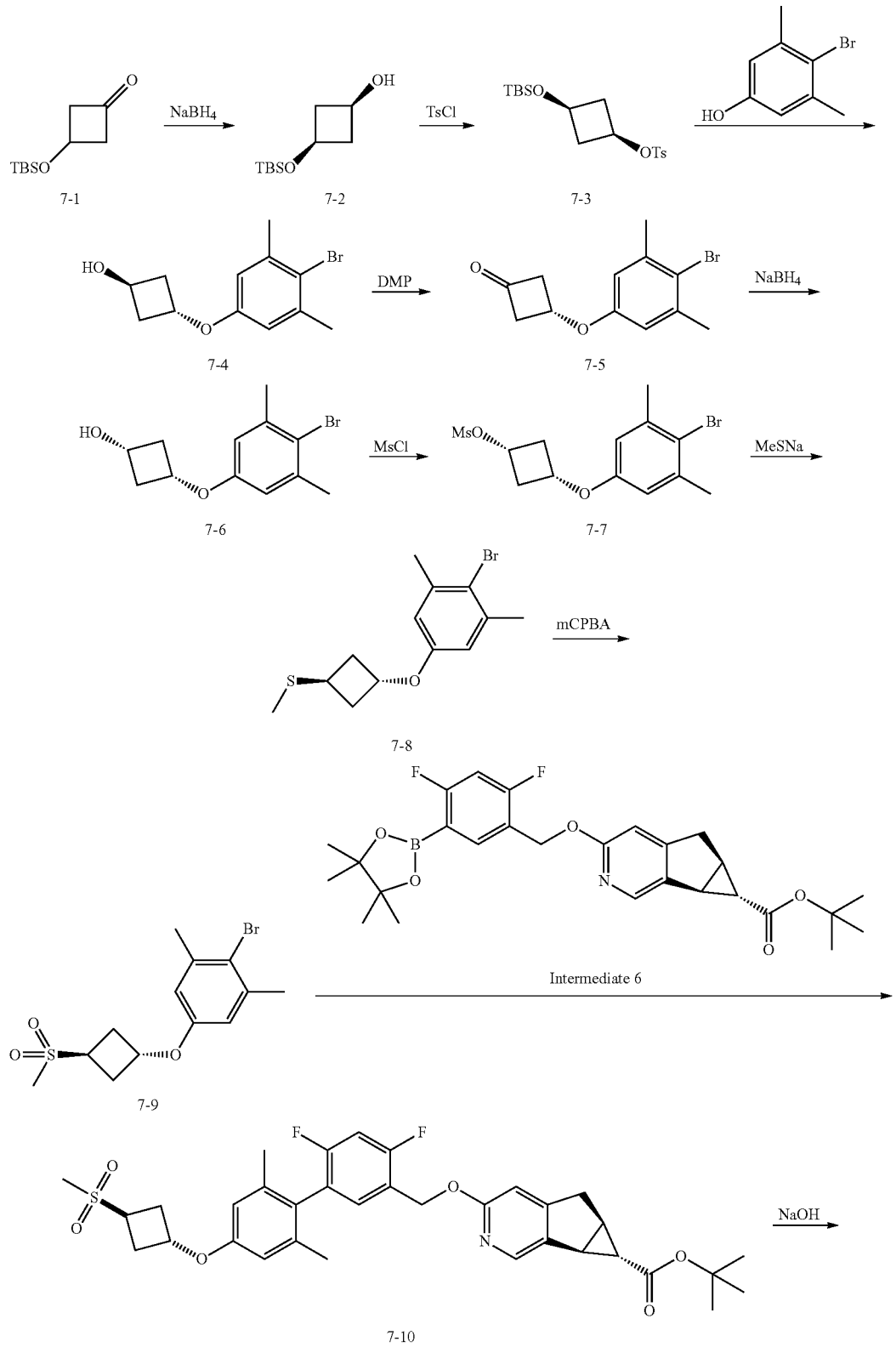

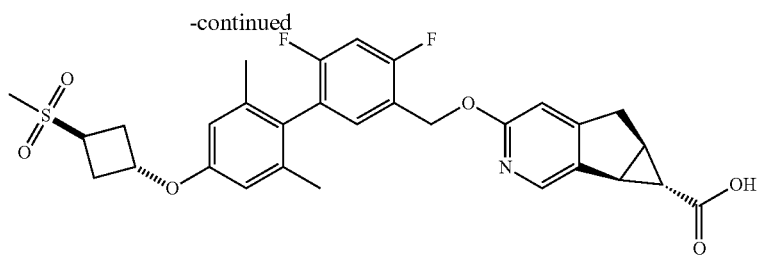

Example 15

Example 15 was made as shown in Scheme 7. Commercially available 3-((tert-butyldimethylsilyl)oxy)cyclobutanone 7-1 was reduced with NaBH₄, and then treated with TsCl to give the toslyate 7-3. Reaction of 7-3 with 4-bromo-3,5-dimethylphenol in the presence of Cs₂CO₃ afforded compound 7-4, which was oxidized with Dess-Martin's periodinane and reduced with NaBH₄ to give the cis-cyclobutyl alcohol 7-6. Alcohol 7-6 was then converted to the mesylate, followed by treatment with sodium methanethiolate, and oxidization by mCPBA to give the sulfone 7-9. Suzuki coupling of sulfone 7-9 with Intermediate 6, followed by hydrolysis gave the carboxylic acid (Example 15).

SCHEME 8

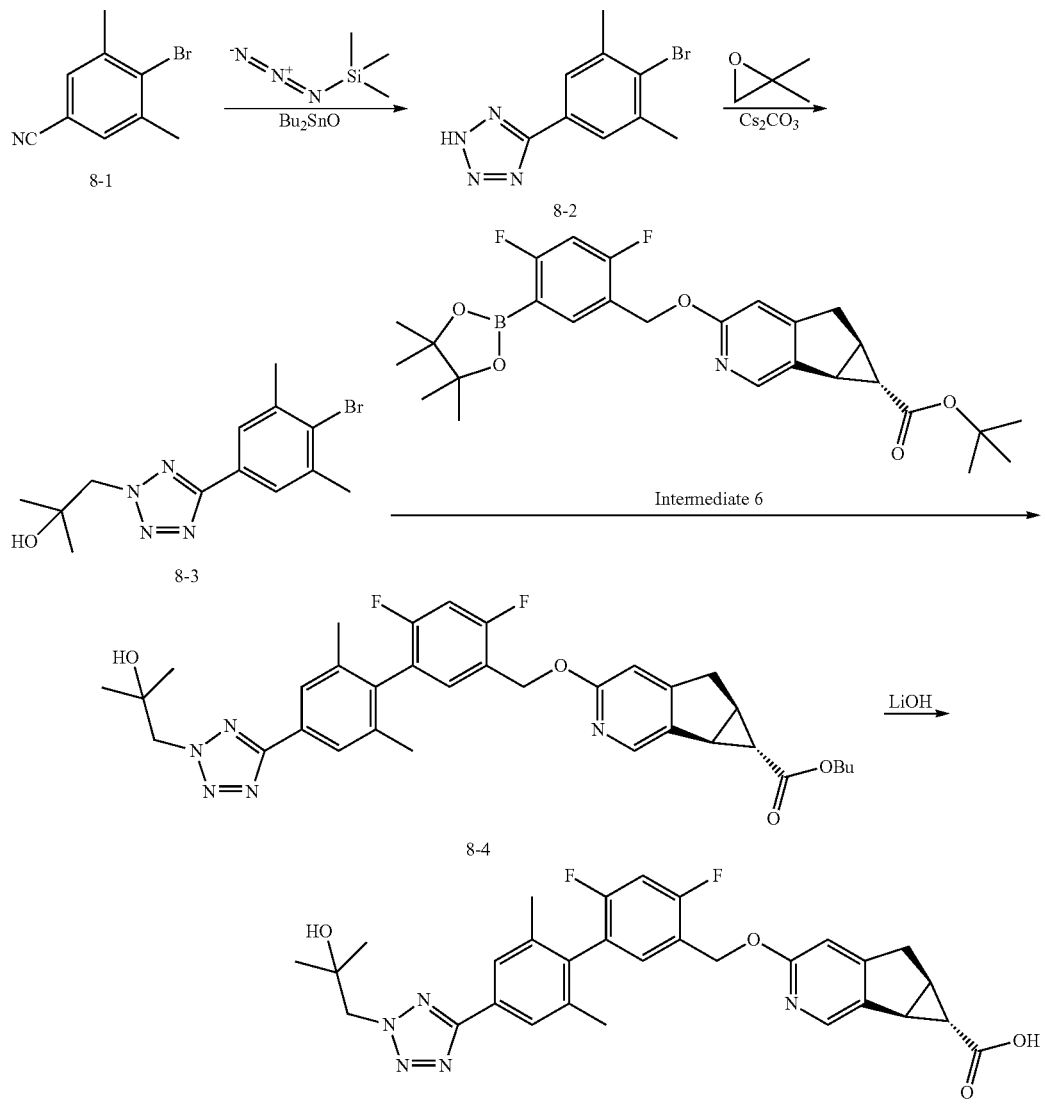

EXAMPLE 16

Example 16 was prepared as shown in Scheme 8. Commercially available 4-bromo-3,5-dimethylbenzonitrile 8-1 was converted to tetrazole 8-2, which was then treated with 2,2-dimethyloxirane to give alcohol 8-3. Suzuki coupling of alcohol 8-3 with Intermediate 6 afforded 8-4. Treatment of 8-4 with lithium hydroxide at ambient temperature gave the carboxylic acid (Example 16).

was hydrolyzed to amide 9-2, followed by treatment with N,N-dimethylformamide dimethyl acetal and then cyclization with hydrazine hydrate to give triazole 9-4. Reaction of triazole 9-4 with 2, 2-dimethyloxirane under basic conditions afforded tertiary alcohol 9-5, which was coupled with Intermediate 6 to afford 9-6. Finally hydrolysis with lithium

SCHEME 9

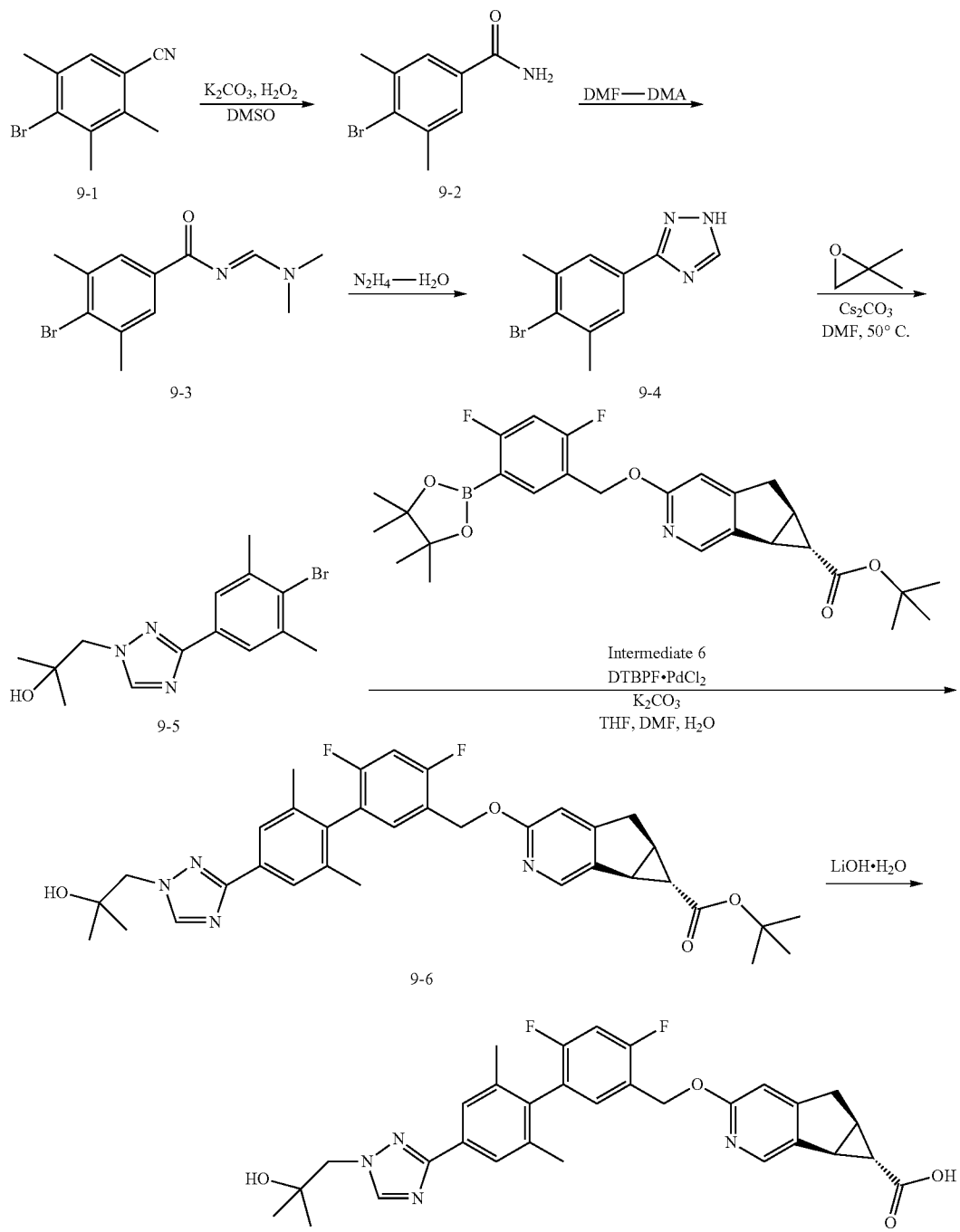

Scheme 9 describes the synthesis of Example 17. Commercially available 4-bromo-3, 5-dimethylbenzonitrile 9-1 hydroxide gave the final carboxylic acid product (Example 17).

SCHEME 10

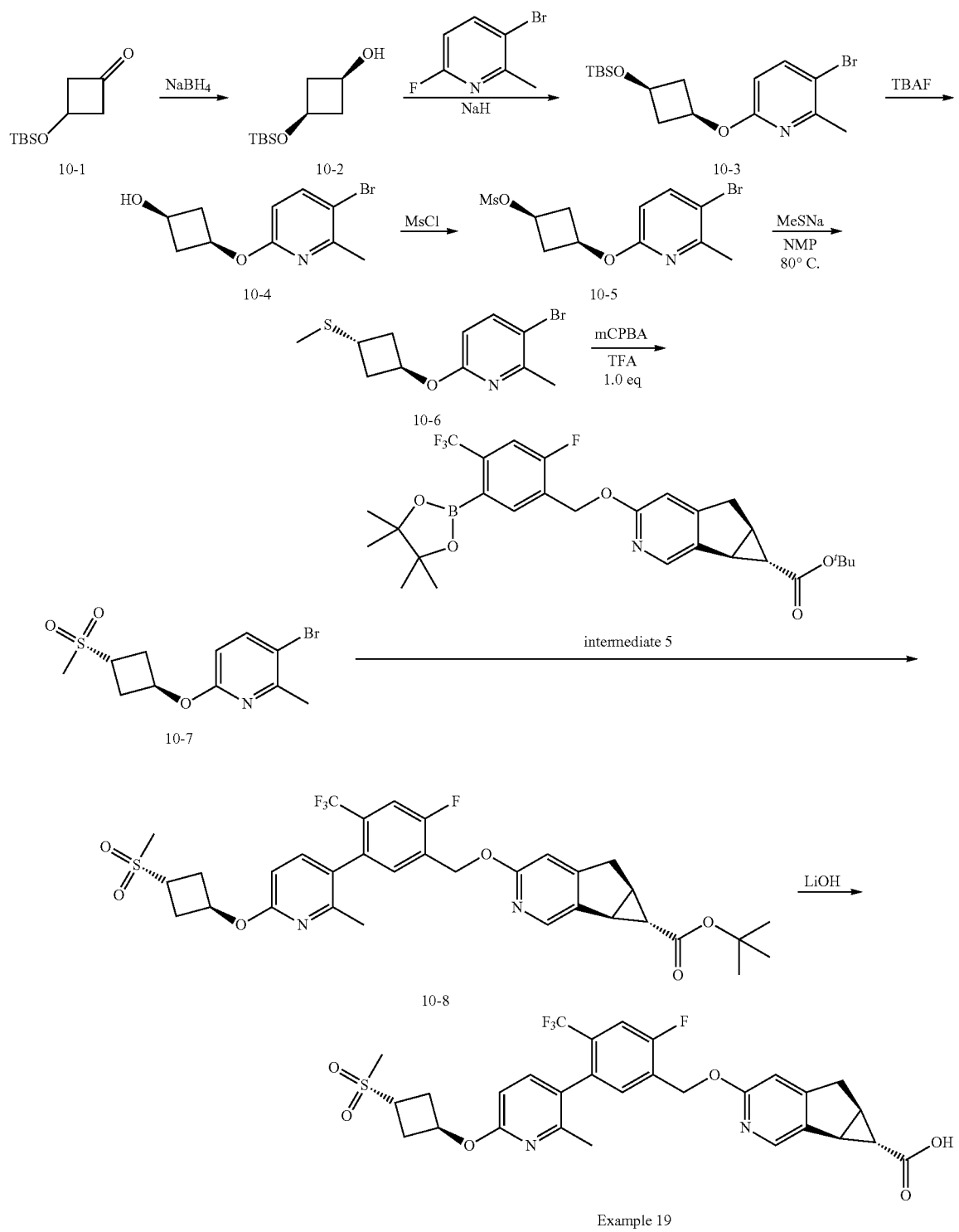

Example 19

Scheme 10 describes the synthesis of Example 19. Commercially available 3-((tert-butyldimethylsilyl)oxy)cyclobutanone 10-1 was reduced by NaBH$_4$ to give cis 10-2. The coupling of 10-2 with 3-bromo-6-fluoro-2-methylpyridine under basic condition and the following de-TBS reaction afforded alcohol 10-4, which was then converted to mesylate 10-5. Treatment with sodium methanethiolate and oxidation by m-CPBA gave 3-bromo-2-methyl-6-((1s,3s)-3-(methylsulfonyl)cyclobutoxy)pyridine 10-7. Suzuki coupling with Intermediate 5 and hydrolysis gave the final carboxylic acid product (Example 19).

SCHEME 11
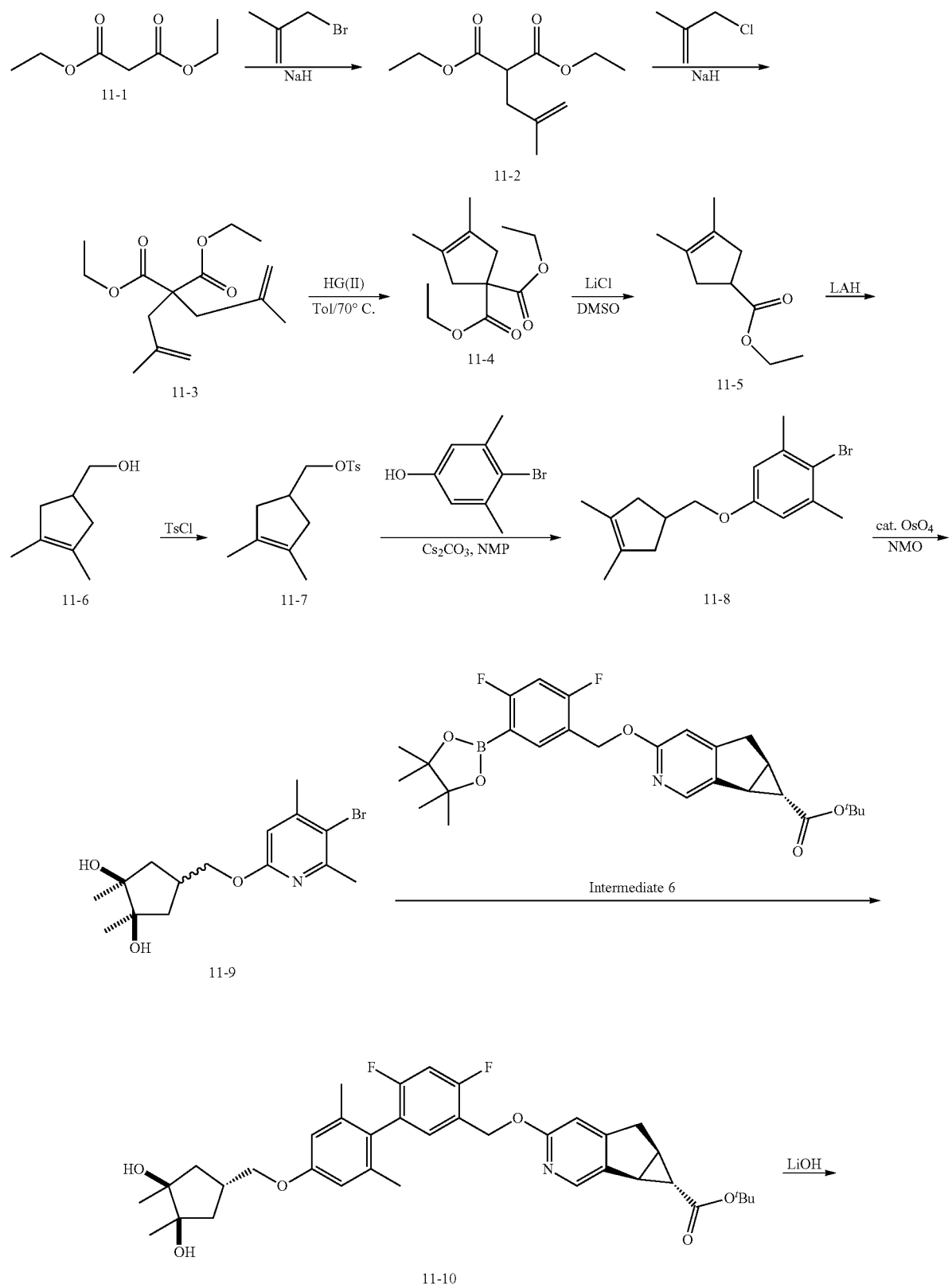

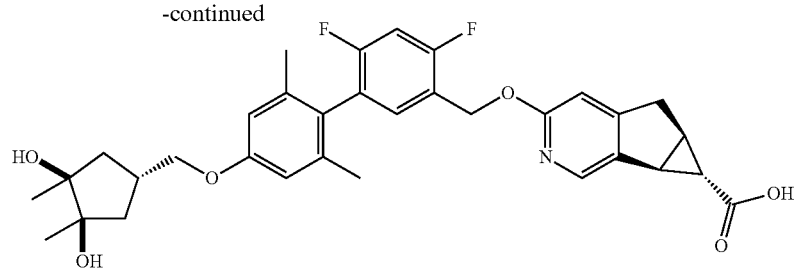

EXAMPLE 20

Scheme 11 describes the synthesis of Example 20. Commercially available diethyl malonate 11-1 was coupled with 3-bromo-2-methylprop-1-ene twice to give diethyl 2,2-bis(2-methylallyl)malonate 11-3. After cyclization of 11-3 with 2nd Generation Hoveyda-Grubbs Catalyst, decarboxylation of 11-4 afforded ethyl 3,4-dimethylcyclopent-3-enecarboxylate 11-5. The following reduction by LiAlH$_4$ afforded alcohol 11-6 which was converted to tosylate 11-7. Alkylation, followed by dihydroxylation by OsO$_4$ gave (1R,2S)-4-((4-bromo-3,5-dimethyl-phenoxy)methyl)-1,2-dimethyl-cyclopentane-1,2-diol 11-9. Suzuki coupling with Intermediate 6 and hydrolysis gave the final product (Example 20).

SCHEME 12

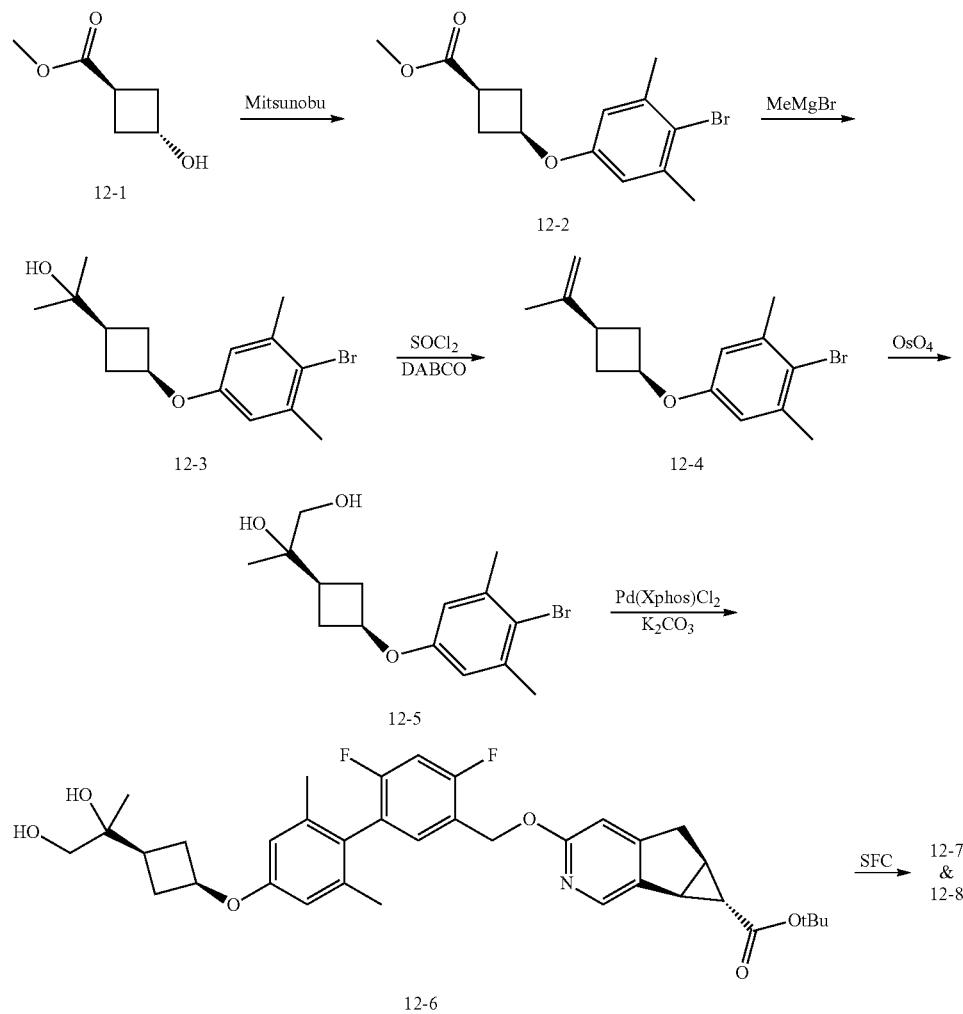

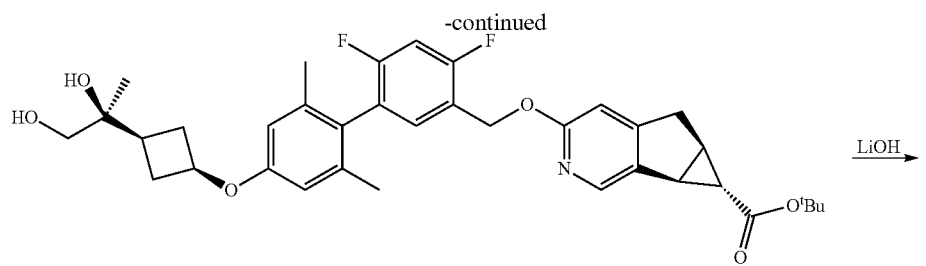

12-7

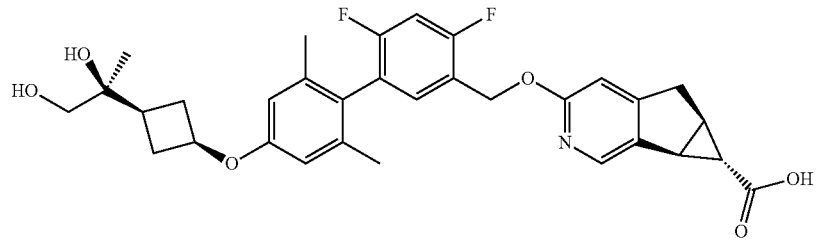

EXAMPLE 21

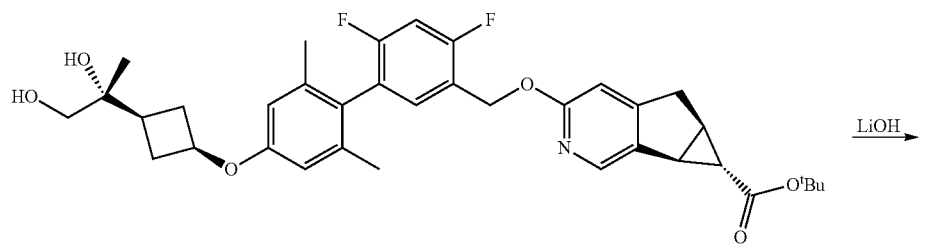

12-8

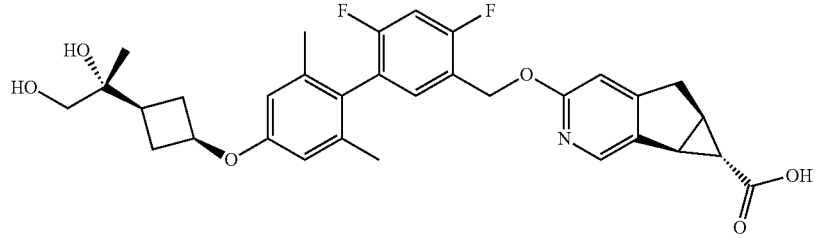

EXAMPLE 22

Scheme 12 describes the synthesis of Example 21 and 22. The Mitsunobu reaction of commercially available 4-bromo-3,5-dimethylphenol with trans-methyl 3-hydroxy-cyclobutanecarboxylate 12-1 afforded methyl 3-(4-bromo-3,5-dimethylphenoxy)-cyclobutanecarboxylate 12-2, followed by treatment with methyl magnesium bromide to give alcohol 12-3. Elimination of water molecular by treatment with SOCl₂ and DABCO afforded alkene 12-4, followed by treatment with osmium(VIII) oxide to yield diol 12-5. Suzuki coupling with Intermediate 6 afforded diastereomeric mixture 12-6 which was separated by SFC to give two diastereomers 12-7 & 12-8. Treatment of esters 12-7 & 12-8 with lithium hydroxide gave the carboxylic acids Example 21 and 22.

SCHEME 13

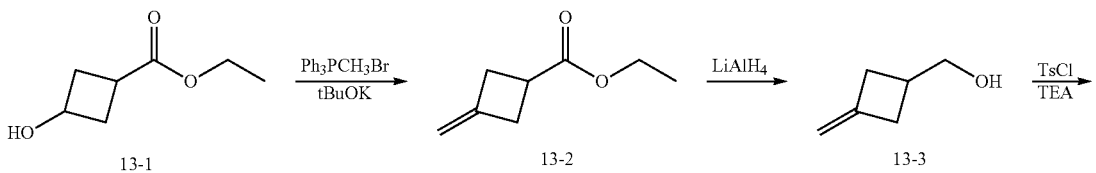

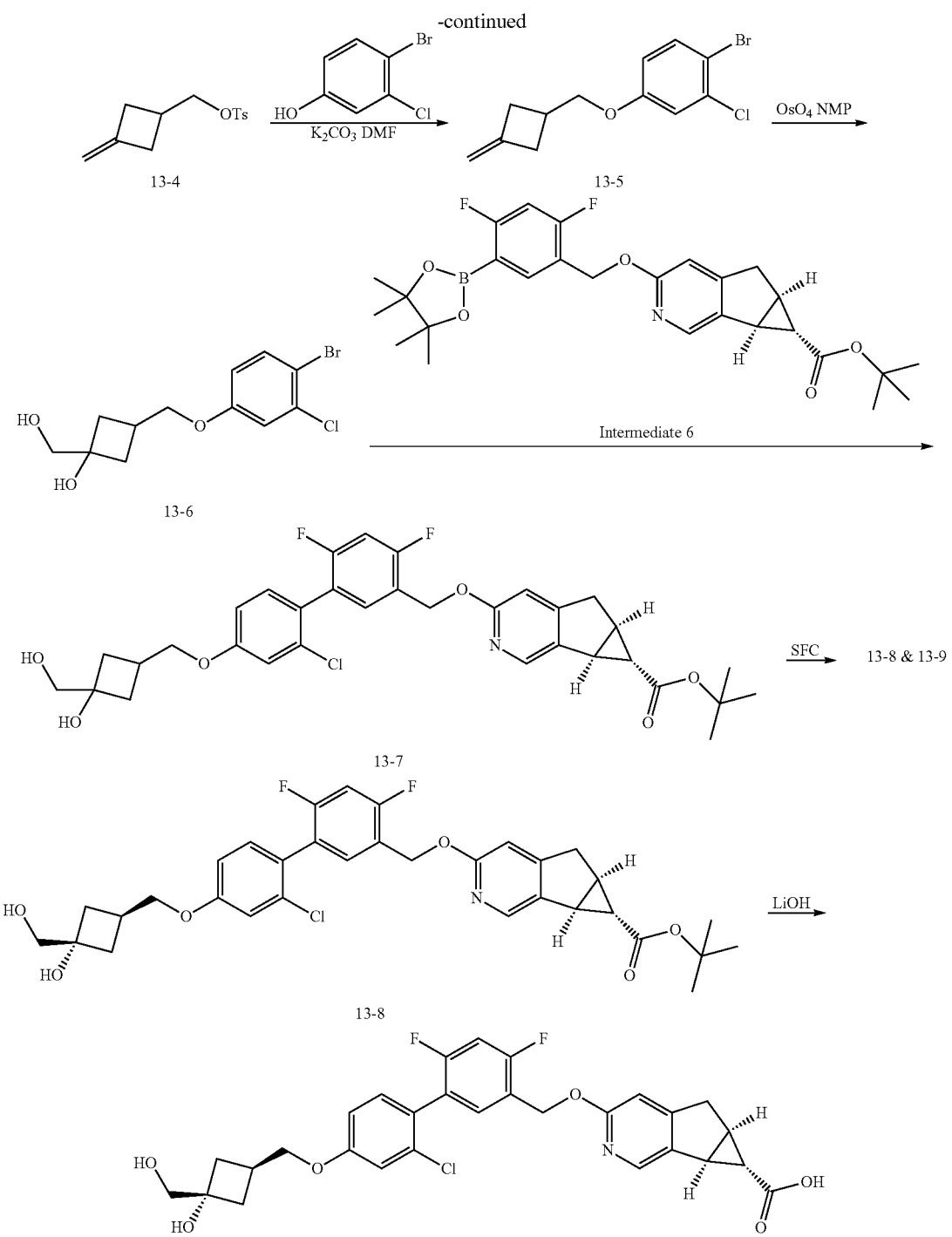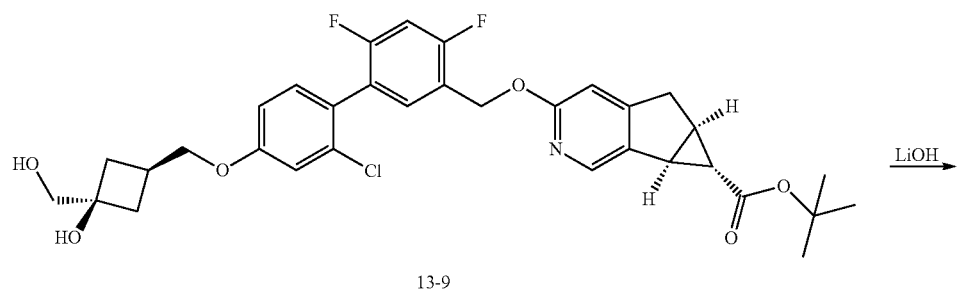

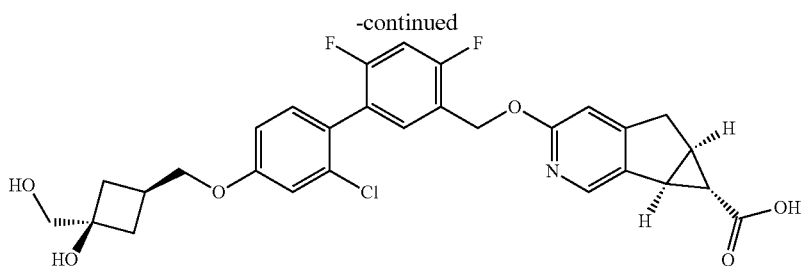

EXAMPLE 24

Scheme 13 describes the synthesis of Example 23 and Example 24. Commercially available ethyl 3-oxocyclobutanecarboxylate 13-1 was converted to alkene 13-2 via a Wittig reaction and the resulting ester was reduced to alcohol 13-3. The SN2 reaction between tosylate 13-4 and 4-bromo-3-chlorophenol gave 13-5, followed by treatment with osmium(VIII) oxide to yield diol 13-6. The following Suzuki coupling with Intermediate 6 afforded diastereomeric mixture 13-7, which was separated by SFC to give two diastereomers 13-8 & 13-9. Treatment of esters 13-8 & 13-9 with lithium hydroxide gave carboxylic acids Example 23 and 24 respectively.

SCHEME 14

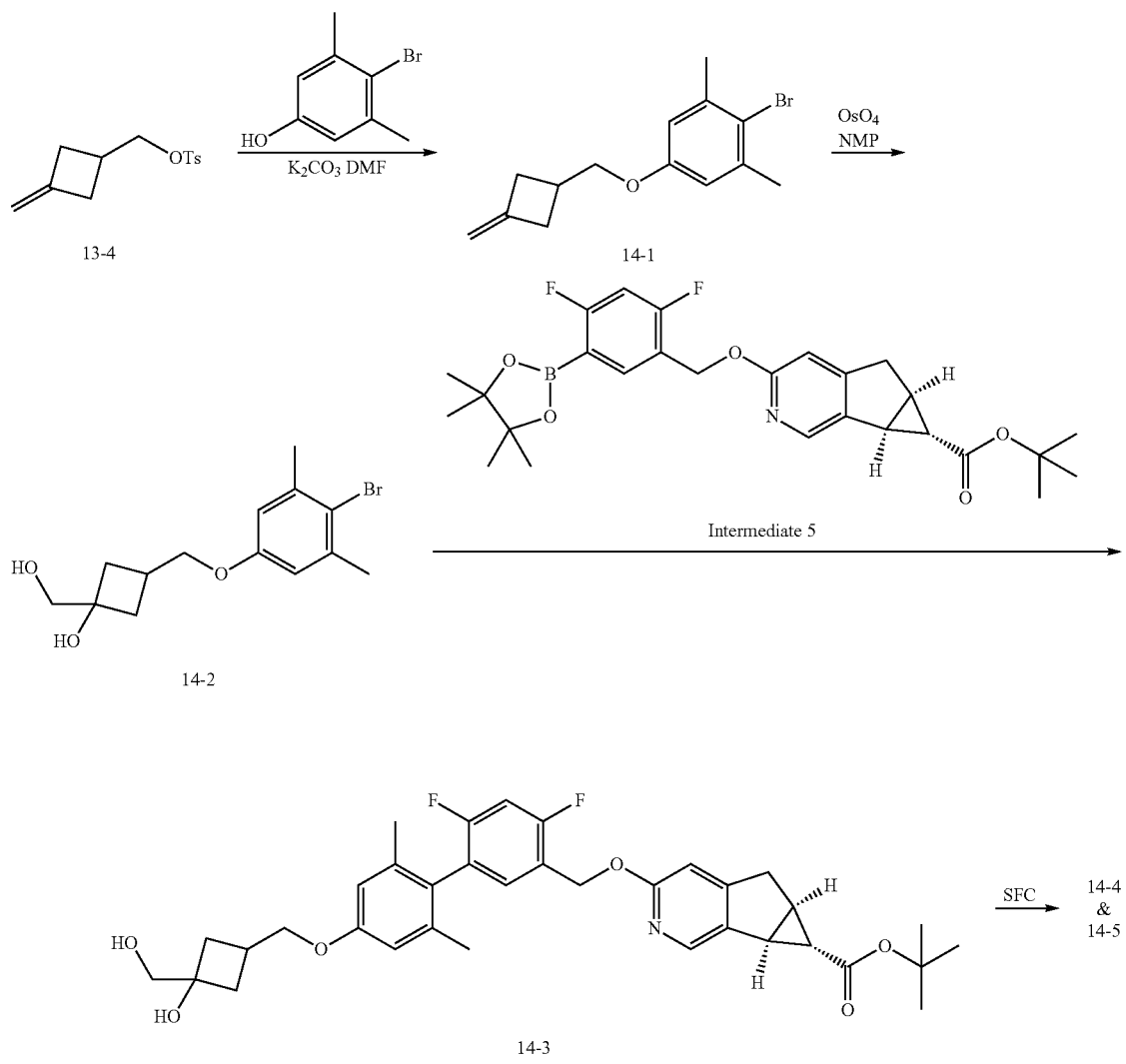

-continued

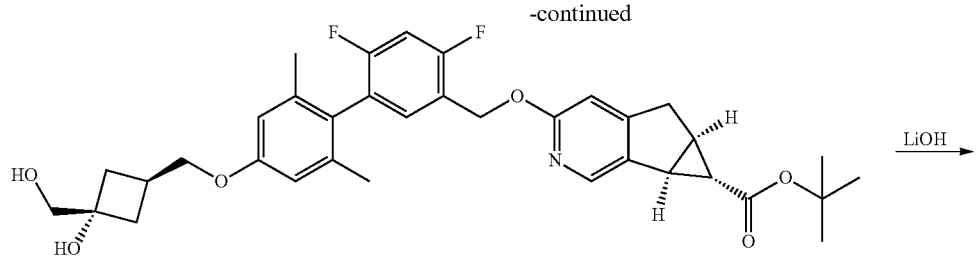

14-4

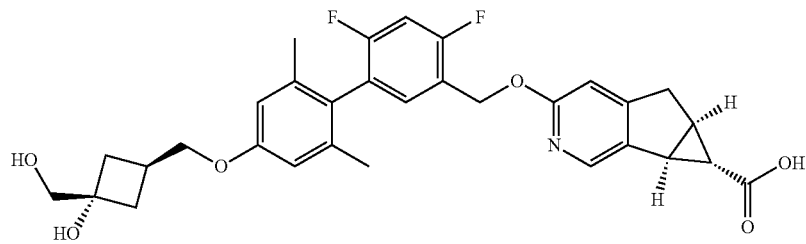

EXAMPLE 25

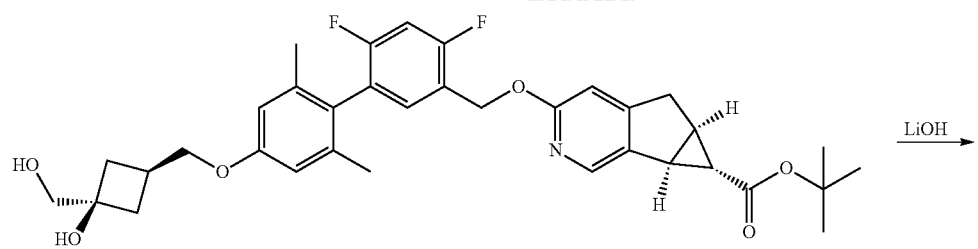

14-5

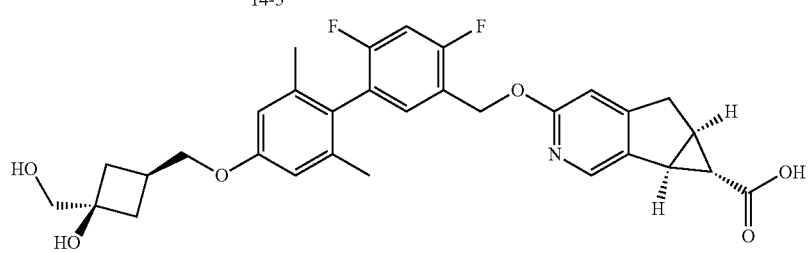

EXAMPLE 26

Scheme 14 describes the synthesis of Example 25 and Example 26. Commercially available ethyl 4-bromo-3,5-dimethylphenol was coupled with tosylate 13-4 (Scheme 13) to give alkene 14-1, which was treated with osmium(VIII) oxide to yield diol 14-2. Suzuki coupling with Intermediate 6 afforded diastereomeric mixture 14-3 which was separated by SFC to give two diastereomers 14-4 & 14-5. Treatment of esters 14-4 & 14-5 with lithium hydroxide gave the carboxylic acids Example 25 and 26 respectively.

Intermediate 1

4-Hydroxy-1,1a,6,6a-tetrahydro-3-aza-cyclopropa[a]indene-1-carboxylic acid ethyl ester

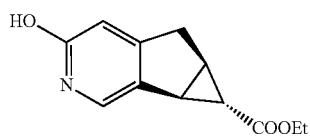 [SMILES: CCOC(=O)[C@H]1[C@@H]2Cc3cc(O)ncc3[C@@H]21]

Step A. (4-Bromo-pyridin-2-yl)-bis-(4-methoxy-benzyl)-amine

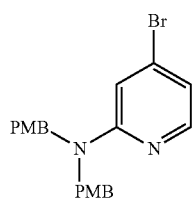

To a suspension of sodium hydride (60% in oil, 93 g, 2.32 mol) in DMF (1.8 L), was added 2-amino-4-bromopyridine (100 g, 0.58 mol) in DMF (500 mL) slowly at 0° C. Then the resulting mixture was allowed to stir at r.t. for 0.5 h under N₂ protection. PMBCl (227 g, 1.45 mol) was added to the reaction mixture and the reaction was maintained at 0-10° C. After addition, the mixture was allowed to stir at r.t. for 2 h. Then the mixture was poured into ice water carefully. The resulting solid precipitate was collected and washed with PE (150 mL×3), and the filtrate was concentrated to afford the title compound. $^1$HNMR (400 MHz, CDCl$_3$) δ: 7.99 (d, 1H, J=2.4 Hz), 7.12 (d, 4H, J=4.0 Hz), 6.84 (d, 4H, J=4.0 Hz), 6.71 (d, 1H, J=2.4 Hz), 6.64 (s, 1H), 4.66 (s, 4H), 3.79 (s, 6H).

Step B. (4-Bromo-5-iodo-pyridin-2-yl)-bis-(4-methoxy-benzyl)-amine

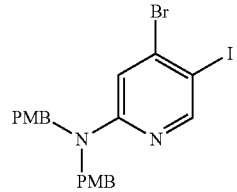

To a stirred solution of product from Step A (140 g, 0.34 mol) in DMF (2.8 L), was added NIS (115 g, 0.51 mmol) in several portions. The resulting mixture was heated to 40° C. and stirred for 24 h. The mixture was cooled and poured into ice water and stirred constantly. The resulting solid precipitate was collected and washed with PE (100 mL×3). The filtrate was concentrated under vacuum to afford the title compound. $^1$HNMR (400 MHz, CDCl$_3$) δ: 8.40 (s, 1H), 7.09 (d, 4H, J=4.0 Hz), 6.84-6.80 (m, 5H), 4.62 (s, 4H), 3.78 (s, 6H).

Step C. (4-Bromo-5-vinyl-pyridin-2-yl)-bis-(4-methoxy-benzyl)-amine

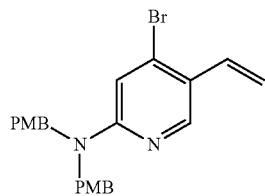

To a stirred solution of product from Step B (144 g, 267 mmol) in toluene (2 L), was added tributyl (vinyl) tin (85 g, 267 mmol), Pd(PPh$_3$)$_4$ (15.4 g, 13.4 mmol), KF (31 g, 534 mmol). The resulting mixture was heated to reflux for 18 h under N$_2$. The mixture was then cooled and KF (300 mL, 2 mol/L) was added. The reaction mixture was stirred for 20 minutes, and then filtered. The filtrate was separated, and the resulting organic layer was collected and evaporated under vacuum to give the crude product, which was purified by column chromatography on silica gel (eluting with PE:EA=20:1) to give the title compound. $^1$HNMR (400 MHz, CDCl$_3$) δ: 8.36 (s, 1H), 7.13 (d, 4H, J=4.0 Hz), 6.86-6.82 (m, 5H), 6.68 (s, 1H), 5.59 (d, 1H, J=8.0 Hz), 5.17 (d, 1H, J=6.4 Hz), 4.67 (s, 4H), 3.78 (s, 6H).

Step D. (4-Allyl-5-vinyl-pyridin-2-yl)-bis-(4-methoxy-benzyl)-amine

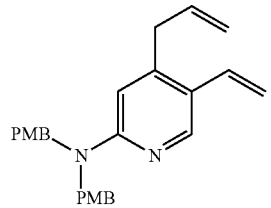

To a stirred solution of the product from Step C (90 g, 205 mmol) in THF (2 L), was added Cs$_2$CO$_3$ (134 g, 410 mmol), Pd(dppf)Cl$_2$ (7.5 g, 10.3 mmol), and allyltributyltin (136 g, 410 mmol). The resulting mixture was heated to reflux for 18 h under N$_2$. Then the mixture was cooled, and KF (300 mL, 2 mol/L) was added. The reaction mixture was stirred for 20 minutes. The mixture was filtered and the filtrate was separated. The resulting organic layer was collected and evaporated under vacuum to give the crude product, which was purified by chromatography over silica gel (eluting with PE:EA=30:1) to give the title compound. $^1$HNMR (400 MHz, CDCl$_3$) δ: 8.34 (s, 1H), 7.14 (d, 4H, J=4.0 Hz), 6.83 (d, 4H, J=4.0 Hz), 6.75 (dd, 1H, J=11.2 and 17.6 Hz), 6.29 (s, 1H), 5.86-5.79 (m, 1H), 5.53 (d, 2H, J=8.0 Hz), 5.14-4.96 (m, 3H), 4.69 (s, 4H), 3.79 (s, 6H), 3.27 (d, 2H, J=4.0 Hz). MS (ESI) m/e (M+H$^+$): 440.1

Step E: Bis-(4-methoxy-benzyl)-(5H-[2]pyrindin-3-yl)-amine

To a stirred solution of the product from Step D (55 g, 138 mmol) in DCM (700 mL), was added Grubbs reagent (II) (3.5 g, 4.14 mmol) in one portion. Then the resulting mixture was heated to reflux for 3 h under N$_2$. The mixture was then cooled and used in the next step directly. MS (ESI) m/e (M+H$^+$): 373.2.

Step F: 4-[Bis-(4-methoxy-benzyl)-amino]-1,1a,6,6a-tetrahydro-3-aza-cyclopropa[a]-indene-1-carboxylic acid ethyl ester

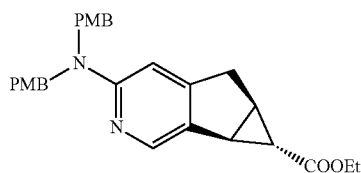

To a stirred solution of the product from Step E (52 g, 138 mmol) in DCM (0.7 L), was added Rh(OAc)$_2$ (1.6 g, 6.9 mmol) in one portion and the mixture was stirred for 15 minutes. Then ethyl diazoacetate (126 g, 1.1 mol) was added slowly to the mixture under gentle reflux conditions over 3 h. The resulting mixture was allowed to stir at r.t for 1 h. The reaction mixture was evaporated under vacuum to give the crude product, which was purified by column chromatography over silica gel (PE:EA=10:1) to give a cis-isomeric mixture of title compound as a racemate. The racemic mixture was separated by chiral column chromatography (eluting with PE:EA) to give the title compound. $^1$HNMR (400 MHz, CD$_3$OD) δ: 8.01 (s, 1H), 7.08 (d, 4H, J=4.0 Hz), 6.81. (d, 4H, J=4.0 Hz), 6.45 (s, 1H), 4.63 (s, 4H), 4.07 (dd, 2H, J=7.2 and 14.4 Hz), 3.74 (s, 6H), 3.13 (dd, 1H, J=6.0 and 12.0 Hz), 2.89 (d, 1H, J=8.0 Hz), 2.84 (d, 1H, J=2.4 Hz), 2.33-2.30 (m, 1H), 1.28-1.15 (m, 4H). MS (ESI) m/e (M+H$^+$): 459.1.

Step G: 4-Amino-1,1a,6,6a-tetrahydro-3-aza-cyclopropa[a]indene-1-carboxylic acid ethyl ester

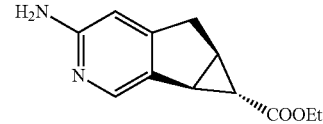 [SMILES: CCOC(=O)[C@H]1[C@@H]2Cc3cc(N)ncc3[C@@H]21]

To a stirred solution of product from Step F (19 g, 41.4 mmol) in DCM (130 mL), was added TFA (130 mL) in one portion. Then the resulting mixture was stirred at r.t overnight. LCMS showed reagent was consumed completely. The mixture was evaporated under vacuo to give the title compound, which was used in the next step directly. MS (ESI) m/e (M+H$^+$): 219.1.

Step H: 4-Hydroxy-1,1a,6,6a-tetrahydro-3-aza-cyclopropa[a]indene-1-carboxylic acid ethyl ester

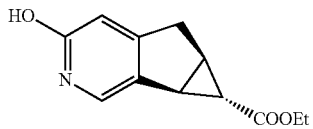 [SMILES: CCOC(=O)[C@H]1[C@@H]2Cc3cc(O)ncc3[C@@H]21]

To a stirred solution of product from Step G (23 g, crude) in H$_2$SO$_4$ (200 mL, 15%), was added NaNO$_2$ (14.4 g, 209 mmol) in portions at 0° C. Then the resulting mixture was allowed to stir at r.t for 2 h. LCMS showed reagent was consumed. The mixture was filtered, the solid filtered was purified by column (DCM:MeOH=20:1), the filtrate was basified with 2N NaOH to pH=5-6, then aqueous NaHCO$_3$ was added to adjust the pH=7, then extracted with DCM (300 mL×3), washed with brine, dried over Na$_2$SO$_4$, concentrated to afford the title compound. $^1$HNMR (400 MHz, CDCl$_3$) δ: 12.52 (s, 1H), 7.28 (s, 1H), 6.38. (s, 1H), 4.14 (dd, 2H, J=7.2 and 14.4 Hz), 3.18 (dd, 1H, J=6.0 and 12.0 Hz), 2.94 (d, 1H, J=8.8 Hz), 2.77 (dd, 1H, J=2.4 and 6.4 Hz), 2.43-2.39 (m, 1H), 1.28-1.25 (m, 4H). MS (ESI) m/e (M+H$^+$): 220 (M+H$^+$).

Intermediate 2

(5aR,6S,6aS)-ethyl 3-((5-bromo-2-fluoro-4-(trifluoromethyl)benzyl)oxy)-5,5a,6,6a-tetrahydrocyclopropa[4,5]cyclopenta[1,2-c]pyridine-6-carboxylate

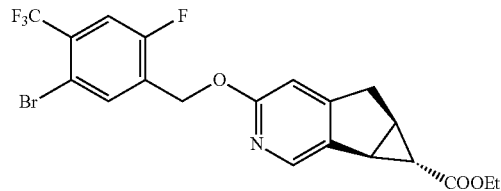 [SMILES: CCOC(=O)[C@H]1[C@@H]2Cc3cc(OCc4cc(Br)c(C(F)(F)F)cc4F)ncc3[C@@H]21]

Step A: methyl 2-fluoro-4-(trifluoromethyl)benzoate

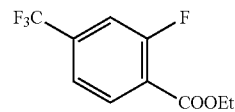

To a mixture of 1-bromo-2-fluoro-4-(trifluoromethyl)benzene (5.0 g, 0.02 mol) in EtOH (10 mL) was added Pd(dppf)Cl$_2$ (1.46 g, 0.2 mmol) and AcONa (3.37 g, 0.041 mol), and the resulting mixture was stirred at 80° C. under an atmosphere of CO (50 psi) for 8 hours. The mixture was then filtrated and the filtrate was partitioned with ethyl acetate and water. The aqueous layer was separated and extracted with ethyl acetate twice. The combined organic layers were washed with brine, dried over anhydrous Na$_2$SO$_4$ and concentrated in vacuo. The resulting residue was purified by column chromatography on silica gel (eluting with PE:EA=10:1) to give the title compound. $^1$H NMR (400 MHz, CDCl$_3$) δ: 8.04-8.08 (t, 1H, J=7.6 Hz), 7.49-7.47 (d, 1H, J=8.0 Hz), 7.43-7.40 (d, 1H, J=10.4 Hz), 4.44-4.40 (q, 2H, J=7.2 Hz), 1.43-1.38 (t, 3H, J=7.2 Hz).

Step B: ethyl 2-fluoro-5-nitro-4-(trifluoromethyl)benzoate

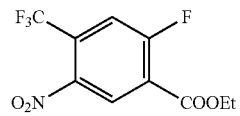

To a stirred solution of the product from Step A (120 g, 0.51 mol) in concentrated H$_2$SO$_4$ (0.5 L), was added dropwise fuming HNO$_3$ (50 ml) at 0° C. The resulting mixture was stirred at 25° C. for 1 h, then cooled and poured into ice water and stirred. The solid that precipitated was collected and washed with PE (100 mL×3). The filtrate was concentrated under vacuum to afford the title compound. $^1$HNMR (400 MHz, CDCl$_3$) δ: 8.54-8.45 (d, 1H, J=6.8 Hz), 7.63-7.60 (d, 1H, J=10.4 Hz), 4.48-4.43 (q, 2H, J=7.2 Hz), 1.55-1.39 (t, 3H, J=7.2 Hz).

Step C: ethyl 5-amino-2-fluoro-4-(trifluoromethyl)benzoate

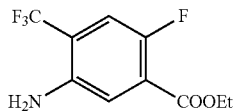

To a solution of the product from Step B (80 g, 0.28 mol) in MeOH (1 L) was added Pd/C (8 g). The mixture was degassed via vacuum and purged with H₂ several times, then the mixture was stirred under a H₂ balloon for 16 hours at room temperature. The mixture was filtered; and the filtrate was concentrated to give the title compound. MS (ESI) m/e (M+H⁺): 273.1, 293.2.

Step D: ethyl 5-bromo-2-fluoro-4-(trifluoromethyl)benzoate

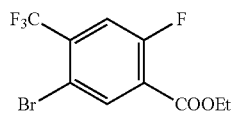

To a stirred solution of the product from Step C (60 g, 0.24 mol) in ACN (600 mL), was added CuBr₂ (59 g, 0.26 mol) and isopentyl nitrite (36 g, 0.31 mol). The resulting mixture was stirred at 25° C. for 18 h under N₂. The mixture was then cooled and filtered, and the filtrate was separated. The organic layer was collected and evaporated under vacuum to give a crude product, which was purified by column chromatography over silica gel (eluting with PE:EA=30:1) to give the title compound. $^1$HNMR (400 MHz, CDCl₃) δ: 8.24-8.05 (d, 1H, J=6.8 Hz), 7.53-7.50 (d, 1H, J=10.4 Hz), 4.48-4.43 (q, 2H, J=7.2 Hz), 1.45-1.39 (t, 3H, J=7.2 Hz).

Step E: 5-bromo-2-fluoro-4-(trifluoromethyl)benzoic acid

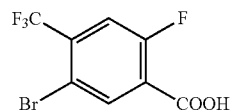

To a solution of the product from Step D (17.5 g, 55.7 mmol) in EtOH/H₂O (200/20 mL) was added LiOH (12 g, 0.28 mol). The reaction mixture was stirred at room temperature for 18 h. Then HCl (2 mol/L) was added to the reaction to adjust the pH to 5. The reaction mixture was concentrated under vacuum to remove the EtOH, and the remaining mixture was extracted with EtOAc (50 mL×3). The combined organic layers were concentrated to afford the title compound.

Step F: (5-bromo-2-fluoro-4-(trifluoromethyl)phenyl)methanol

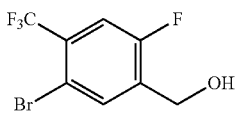

To a solution of the product from Step E (17.08 g, 59.7 mmol) in THF (170 mL) was added BH₃(Me₂S) (18 mL) at 0° C. The reaction was stirred at 17-19° C. for 18 h. Then the reaction was quenched with MeOH at 0° C. The reaction mixture was concentrated and the resulting crude residue was purified by chromatography over silica gel (eluting with PE:EA=5:1) to give the title compound.

Step G: 5-bromo-2-fluoro-4-(trifluoromethyl)benzyl methanesulfonate

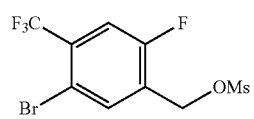 [SMILES: CS(=O)(=O)OCc1cc(Br)c(C(F)(F)F)cc1F]

To a solution of the product from Step F (4 g, 14.65 mmol) in DCM (20 ml) was added TEA (2.22 g, 22 mmol). The reaction mixture was cooled in an ice bath, then MsCl (1.5 g, 22 mmol) was added dropwise to the reaction. The reaction was stirred at 0° C. for 20 min, then water (30 mL) was added to the reaction mixture at 0° C. The resulting mixture was extracted with DCM (10 mL×3). The combined organic layers was dried over Na₂SO₄ and concentrated under vacuum to give the title compound.

Step H: (5aR,6S,6aS)-ethyl 3-((5-bromo-2-fluoro-4-(trifluoromethyl)benzyl)oxy)-5,5a,6,6a-tetrahydrocyclopropa[4,5]cyclopenta[1,2-c]pyridine-6-carboxylate

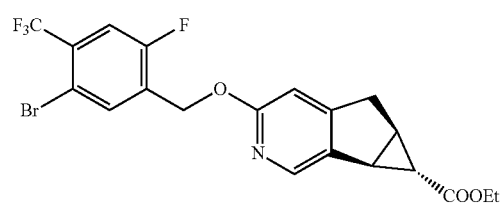 [SMILES: CCOC(=O)[C@H]1[C@@H]2Cc3cc(OCc4cc(Br)c(C(F)(F)F)cc4F)ncc3[C@@H]21]

To a solution of the product from Step G (5 g crude) in toluene (50 ml) were added Intermediate 1 (3.1 g, 14.1 mmol) and Ag₂CO₃ (11.66 g, 42.3 mmol). The reaction was stirred at 100° C. for 18 h. Then the reaction mixture was cooled to room temperature and filtered. The filtrate was concentrated in vacuo and the crude was purified by chromatography over silica gel (eluting with PE:EA=10:1) to give the title compound. $^1$HNMR (400 MHz, MeOH-d₄) δ: 8.05 (s, 1H), 7.81 (d, J=6.7 Hz, 1H), 7.39 (d, J=9.8 Hz, 1H), 6.64 (s, 1H), 5.41 (s, 2H), 4.13 (q, J=7.0 Hz, 2H), 3.23 (dd, J=6.3, 18.4 Hz, 1H), 3.00 (d, J=18.4 Hz, 1H), 2.91 (d, J=5.1 Hz, 1H), 2.48-2.40 (m, 1H), 1.25 (t, J=7.2 Hz, 3H), 1.22 (d, J=3.1 Hz, 1H). MS (ESI) m/e (M+H⁺): 474, 476.

Intermediate 3

5aR,6S,6aS)-ethyl 3-((2-fluoro-5-(4,4,5,5-tetramethyl-1,3,2-dioxaborolan-2-yl)-4-(trifluoromethyl)benzyl)oxy)-5,5a,6,6a-tetrahydrocyclopropa[4,5]cyclopenta[1,2-c]pyridine-6-carboxylate

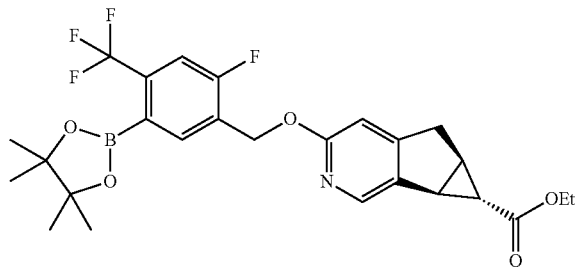 [SMILES: CCOC(=O)[C@H]1[C@@H]2Cc3cc(OCc4cc(B5OC(C)(C)C(C)(C)O5)c(C(F)(F)F)cc4F)ncc3[C@@H]21]

Bis(pinacolato)diboron (0.803 g, 3.16 mmol), potassium acetate (0.414 g, 4.22 mmol), Pd(dppf)Cl$_2$ (0.154 g, 0.211 mmol), and Intermediate 5 (1.00 g, 2.11 mmol) were dissolved in DMF (0.8 mL) and dioxane (2.5 mL), then placed in a sealed tube and heated in a microwave oven at 150° C. for 30 min. The reaction mixture was cooled and the solvent was evaporated under reduced pressure. The resulting residue was purified by column chromatography on silica gel (eluting with PE:EA=5:1) to give the title compound as a colorless gum. $^1$HNMR (400 MHz, CDCl$_3$) δ: 8.12-8.05 (m, 1H), 7.94-7.87 (m, 1H), 7.44-7.36 (m, 1H), 6.66-6.61 (m, 1H), 5.41 (s, 2H), 4.20-4.12 (m, 2H), 3.28-3.19 (m, 1H), 3.06-2.90 (m, 2H), 2.51-2.41 (m, 1H), 1.36 (s, 12H), 1.28 (t, J=6.3 Hz, 3H), 1.24-1.21 (m, 1H).

Intermediate 4

(5aR,6S,6aS)-tert-butyl 3-hydroxy-5,5a,6,6a-tetrahydrocyclopropa[4,5]cyclopenta[1,2-c]pyridine-6-carboxylate

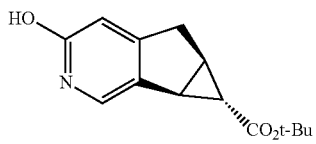 [SMILES: CC(C)(C)OC(=O)[C@H]1[C@@H]2Cc3cc(O)ncc3[C@@H]21]

Step A: (E)-methyl 5-(3-(tert-butoxy)-3-oxoprop-1-en-1-yl)-2-chloroisonicotinate

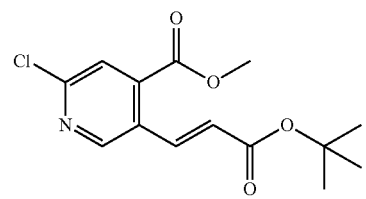 [SMILES: COC(=O)c1cc(Cl)ncc1/C=C/C(=O)OC(C)(C)C]

To a solution of 5-bromo-2-chloroisonicotinic acid (Combi-Blocks, 100 g, 423 mmol) in THF (200 mL) and toluene (800 mL) was added DMF (1.6 mL, 21.15 mmol). To the resulting slurry was added slowly oxalyl chloride (47 mL, 529 mmol). The reaction was stirred over the weekend at room temperature. Then MeOH (100 mL) was added slowly while cooling in a water bath. After 2 h at room temperature, aqueous K$_2$HPO$_4$ (1 M, 423 mL, 423 mmol) was added slowly while cooling in a water bath. The layers were separated and the aqueous layer was extracted with toluene (1×250 mL). The combined organic layers were filtered through Solka-Floc™ cellulose, then washed with water (1×200 mL), dried over MgSO$_4$ and concentrated in vacuo to give the crude methyl ester intermediate. To the methyl ester intermediate in toluene (2 L) was added chloro[tris(2-methylphenyl)phosphine] [2-(2'-amino-1,1'-biphenyl)]palladium(II) (2.6 g, 4.23 mmol, 1%) and N,N-dicyclohexylmethylamine (226 mL, 1057 mmol). The reaction was degassed for 1 h, then t-butyl acrylate was added in a single portion and the reaction mixture was heated to 80° C. overnight. Then additional chloro[tris(2-methylphenyl)phosphine] [2-(2'-amino-1,1'-biphenyl)]palladium(II) (1.3 g, 2.12 mmol, 0.5%) was added and the reaction was heated at 80° C. for 3 h. The reaction mixture was then cooled to room temperature and quenched with water (500 mL). The organic layer was separated, washed with saturated brine (1×500 ml), then filtered through a plug of silica gel (150 g) and rinsed with 20% EtOAc in hexanes. The filtrate was concentrated in vacuo to give a crude oil, which was recrystallized from EtOAc in hexane (1:1) at −10° C. to provide the title compound. MS (ESI) m/e (M+H$^+$): 242.2.

Step B: (E)-5-(3-(tert-butoxy)-3-oxoprop-1-en-1-yl)-2-chloroisonicotinic acid

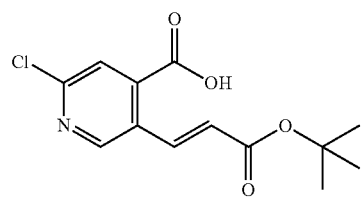 [SMILES: CC(C)(C)OC(=O)/C=C/c1cnc(Cl)cc1C(=O)O]

To a solution of (E)-methyl 5-(3-(tert-butoxy)-3-oxoprop-1-en-1-yl)-2-chloroisonicotinate (1 g, 3.36 mmol) in THF (10 ml) was added a solution of lithium hydroxide hydrate (0.155 g, 3.69 mmol) in water (2 ml), and the reaction was stirred overnight at room temperature. The reaction was then concentrated in vacuo and the resulting residue was diluted with 5 mL water, and slowly acidified with ice-cold 1N HCl solution (4.03 mL). The resulting white solid was filtered and dried under high vacuum to provide the title compound. MS (ESI) m/e (M+H$^+$): 284.2.

Step C: (E)-tert-butyl 3-(6-chloro-4-((E)-2-chloro-2-hydrazonoacetyl)pyridin-3-yl)acrylate

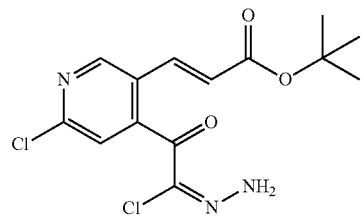 [SMILES: CC(C)(C)OC(=O)/C=C/c1cnc(Cl)cc1C(=O)/C(Cl)=N\N]

DMF (25 µl, 0.323 mmol) was added to a suspension of (E)-5-(3-(tert-butoxy)-3-oxoprop-1-en-1-yl)-2-chloroisonicotinic acid (1.73 g, 6.10 mmol) in dichloromethane (55 mL) and the reaction mixture was stirred at room temperature for 1 hour. The reaction mixture was then concentrated in vacuo, and co-evaporated with 1,2-dichloroethane. DCM (24 ml) was added to the resulting residue, and the resulting solution was added to a solution of (isocyanoimino)triphenyl-phosphorane (2.77 g, 9.15 mmol) in DCM (14 mL) over 10 min. The reaction mixture was stirred at room temperature for 2 hours. Then water (6.6 ml, 366 mmol) was added and the mixture was stirred at room temperature overnight. Then the organic layer was separated, dried over MgSO$_4$ and concentrated in vacuo to provide a residue, which was purified by column chromatography over silica gel (eluting with EtOAc: hexanes=0:100 to 30:70) to give the title compound. MS (ESI) m/e (M+H$^+$): 344, 346, 348.

Step D: (E)-tert-butyl 3-(6-chloro-4-(2-diazoacetyl)pyridin-3-yl)acrylate

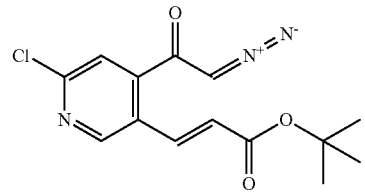 [SMILES: CC(C)(C)OC(=O)/C=C/c1cnc(Cl)cc1C(=O)C=[N+]=[N-]]

Anhydrous zinc bromide (325 mg, 1.443 mmol) was added to a solution of compound (E)-tert-butyl 3-(6-chloro-4-((E)-2-chloro-2-hydrazonoacetyl)pyridin-3-yl)acrylate (2.09 g, 6.07 mmol) in DCM (20 ml), followed by the dropwise addition of diisopropylethylamine (1.2 ml, 8.42 mmol). The reaction was stirred at room temperature for 1 hour, and then diluted with EtOAc. The organic layer was washed with 1% ethylenediamine tetraacetic acid tetrasodium salt, dried over anhydrous MgSO$_4$, and concentrated in vacuo. The resulting crude residue was purified by column chromatography over silica gel (eluting with EtOAc: hexanes=0:100 to 30:70) to give the title compound. MS (ESI) m/e (M+H$^+$): 308, 310.

Step E: (5aR,6R,6aS)-tert-butyl 3-chloro-5-oxo-5,5a,6,6a-tetrahydrocyclopropa-[4,5]cyclopenta-[1,2-c]pyridine-6-carboxylate

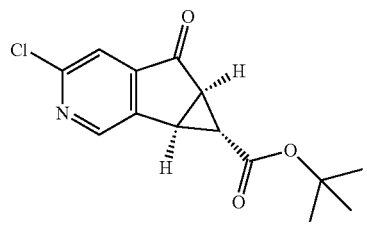 [SMILES: CC(C)(C)OC(=O)[C@H]1[C@@H]2C(=O)c3cc(Cl)ncc3[C@H]12]

A solution of 2,2-bis((S)-4-phenyl-4,5-dihydrooxazol-2-yl)acetonitrile (5.17 mg, 0.016 mmol), copper(I)trifluoromethanesulfonate toluene complex (3.36 mg, 6.50 µmol) and 2,6-di-tert-butylpyridine (29.2 µl, 0.130 mmol) in THF (1 mL) was warmed to 25° C., then (E)-tert-butyl 3-(6-chloro-4-(2-diazoacetyl)pyridin-3-yl)acrylate (400 mg, 1.300 mmol) in THF (3 mL) was added dropwise over 5 min. After 2.5 hours, the reaction mixture was diluted with EtOAc (3 mL) and MTBE (3 mL), washed with 0.5 M aqueous citric acid (6 mL), and concentrated in vacuo to provide a residue. The residue was purified by chromatography over silica gel (eluting with EtOAc:hexanes=0:100 to 30:70) to provide the title compound. The ee was upgraded to 95% by dissolution in EtOAc (6 mL/g) and removal of the racemate by filtration. MS (ESI) m/e (M+H$^+$): 267.1.

Step F: (5aR,6S,6aS)-tert-butyl 3-chloro-5,5a,6,6a-tetrahydrocyclo-propa[4,5]-cyclopenta[1,2-c]pyridine-6-carboxylate

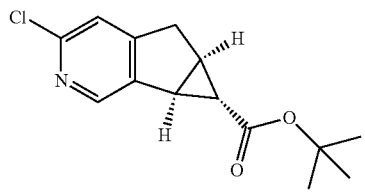 [SMILES: CC(C)(C)OC(=O)[C@H]1[C@@H]2Cc3cc(Cl)ncc3[C@@H]21]

Sodium borohydride (1.6 mg, 0.071 mmol) was added to a solution of (5aR,6R,6aS)-tert-butyl 3-chloro-5-oxo-5,5a,6,6a-tetrahydrocyclopropa[4,5]cyclopenta-[1,2-c]pyridine-6-carboxylate (20 mg, 0.071 mmol) in MeOH (0.4 mL) at 0° C. After 30 minutes, the reaction was quenched with saturated aqueous NH$_4$Cl and concentrated in vacuo. The resulting residue was re-dissolved in MTBE and washed once with water. The organic layer was separated, dried over MgSO$_4$ and concentrated in vacuo to give the alcohol intermediate. The alcohol intermediate was dissolved in THF (400 µL) and treated with trifluoroacetic anhydride (2 equiv, 0.142 mmol) for 30 minutes. The reaction was then cooled to 0° C., and concentrated aqueous HCl (5 equiv, 0.355 mmol) was added, followed by the portionwise addition of zinc dust (9.3 mg, 0.142 mmol) over 5 minutes. After stirring for 15 minutes, the reaction was diluted with water and extracted with MTBE twice. The combined organic layers were dried over MgSO$_4$ and concentrated in vacuo to give a residue, which was purified by column chromatography over silica gel (eluting with EtOAc:hexanes=10:90 to 20:80) to provide the title compound. $^1$H NMR (400 MHz, CDCl$_3$): δ 8.27 (s, 1H), 7.05 (s, 1H), 3.18 (dd, J=6.35 Hz, 12.2 Hz, 1H), 2.97 (d, J=18.5 Hz, 1H), 2.83 (d, J=6.35 Hz, 1H), 2.37 (m, 1H), 1.39 (s, 9H), 1.09 (br.s, 1H). MS (ESI) m/e (M+H$^+$): 280.1.

Step G: (5aR,6S,6aS)-tert-butyl 3-(2-(trimethylsilyl)ethoxy)-5,5a,6,6a-tetrahydrocyclopropa[4,5]cyclopenta[1,2-c]pyridine-6-carboxylate

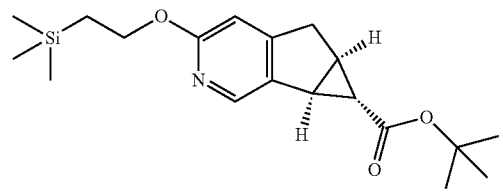 [SMILES: CC(C)(C)OC(=O)[C@H]1[C@@H]2Cc3cc(OCC[Si](C)(C)C)ncc3[C@@H]21]

To (5aR,6S,6aS)-tert-butyl 3-chloro-5,5a,6,6a-tetrahydrocyclopropa[4,5]cyclopenta[1,2-c]pyridine-6-carboxylate (0.5 g, 1.882 mmol), cesium carbonate (1.533 g, 4.70 mmol), and BrettPhos™ Precat (0.075 g, 0.094 mmol) in a vial under nitrogen was added toluene (5 ml) and water (0.102 ml, 5.64 mmol). The reaction was degassed with bubbling nitrogen for 5 min, then 2-(Trimethylsilyl)ethanol (0.405 ml, 2.82 mmol) was added and the reaction was stirred at 80° C. for 16 hours. Then water (10 mL) and EtOAc (30 ml) were added and the aqueous layer was separated and extracted with EtOAc twice. The organic layers were combined and washed with brine, dried over anhydrous $Na_2SO_4$, filtered, and concentrated in vacuo to give the title compound, which was used in the next step without further purification.

Step H: (5aR,6S,6aS)-tert-butyl 3-hydroxy-5,5a,6,6a-tetrahydrocyclopropa[4,5]-cyclopenta[1,2-c]pyridine-6-carboxylate

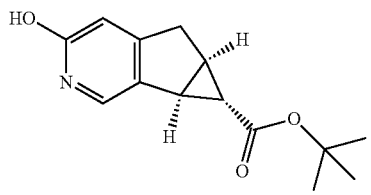 [SMILES: CC(C)(C)OC(=O)[C@H]1[C@@H]2Cc3cc(O)ncc3[C@@H]21]

To a solution of (5aR,6S,6aS)-tert-butyl 3-(2-(trimethylsilyl)ethoxy)-5,5a,6,6a-tetrahydrocyclopropa[4,5]cyclopenta[1,2-c]pyridine-6-carboxylate (200 mg, 0.575 mmol) in acetonitrile (5 ml) was added water (5 ml), followed by phosphoric acid (0.146 ml, 2.014 mmol). The reaction was stirred at room temperature for 19.5 h, then concentrated in vacuo. The resulting residue was diluted with water and extracted with dichloromethane. The combined organic layers were washed with brine, dried over $Na_2SO_4$, filtered, and the solvent was evaporated in vacuo to give the title compound. $^1$H NMR (400 MHz, CD3CL): δ: ppm 7.26 (s, 1H), 6.38 (s, 1H), 3.14-3.24 (m, J=18.39, 6.26 Hz, 1H), 2.95-2.91 (m, 1H), 2.70-2.69 (d, J=5.1 Hz, 1H), 2.32-2.31 (m, 1H), 0.83 (br. s., 1H). MS (ESI) m/e (M+H$^+$): 248.1.

Intermediate 5

(5aR,6S,6aS)-tert-butyl 3-((2-fluoro-5-(4,4,5,5-tetramethyl-1,3,2-dioxaborolan-2-yl)-4-trifluoromethyl)benzyl)oxy)-5,5a,6,6a-tetrahydrocyclopropa[4,5]cyclopenta[1,2-c]pyridine-6-carboxylate

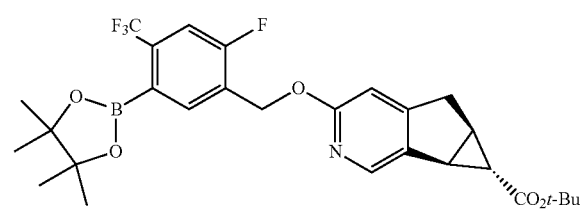 [SMILES: CC(C)(C)OC(=O)[C@H]1[C@@H]2Cc3cc(OCc4cc(B5OC(C)(C)C(C)(C)O5)c(C(F)(F)F)cc4F)ncc3[C@@H]21]

Intermediate 5 was prepared according to a procedure similar to the procedure of Intermediate 3 starting from the appropriate starting materials and using the appropriate reagents. $^1$H NMR (400 MHz, CDCl$_3$) δ: 8.03-8.12 (m, 1H), 7.81-7.93 (m, J=7.43 Hz, 1H), 7.31-7.44 (m, J=10.17 Hz, 1H), 6.51-6.65 (m, 1H), 5.38 (s, 2H), 3.14-3.24 (m, J=18.39, 6.26 Hz, 1H), 2.93-3.05 (m, J=18.39 Hz, 1H), 2.80-2.88 (m, J=5.09 Hz, 1H), 2.30-2.43 (m, 1H), 1.57 (s, 6H), 1.34 (s, 12H), 1.12 (br. s., 1H). MS (ESI) m/e (M+H$^+$): 549.8.

Intermediate 6

(5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate

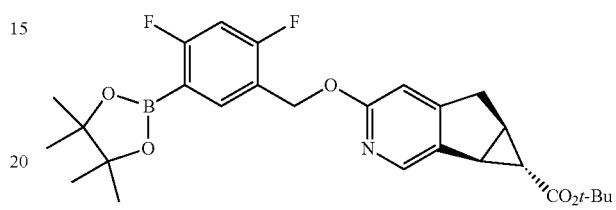

Step A: 5-Bromo-2,4-difluoro-benzoic acid

To a stirred solution of 2,4-difluorobenzoic acid (40 g, 0.26 mol) in concentrated $H_2SO_4$/TFA (1:5, 600 mL) at 0° C. was added NBS (45 g, 0.26 mmol) in portions. The resulting mixture was heated at 60° C. overnight, then the reaction was cooled to room temperature and most of the TFA was removed by evaporation. The resulting residue was carefully partitioned between EtOAc and water. The aqueous layer was separated and extracted with EtOAc twice. The combined organic layers were washed with brine, dried over anhydrous $Na_2SO_4$, and concentrated to give the crude product. The crude product was suspended in water and PE. The resulting solid was collected by filtration, and then re-crystallized from ethanol to give the title compound. $^1$H NMR (400 MHz, CDCl$_3$) δ: 7.02 (dd, J=9.78, 8.61 Hz, 1H), 8.28 (t, J=7.63 Hz, 1H).

Step B: (5-Bromo-2,4-difluoro-phenyl)-methanol

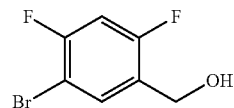

To a solution of 5-bromo-2,4-difluoro-benzoic acid (45.2 g, 190 mmol) in anhydrous THF (500 mL) cooled in an ice-bath was added $(CH_3)_2S.BH_3$ (57 mL, 570 mmol). The resulting mixture was allowed to stir at room temperature overnight. Then methanol (500 mL) was carefully added to quench the reaction, and the mixture was stirred at 60° C. for 1 h. The mixture was acidified with HCl (1N) to pH-5 and extracted with EtOAc twice. The combined organic layers were washed with brine, dried over anhydrous $Na_2SO_4$ and concentrated. The resulting residue was purified via silica gel chromatography (PE/EtOAc=8/1) to give the title compound. $^1$H NMR (400 MHz, $CDCl_3$) δ: 4.77 (br. s., 2H), 6.95 (t, J=8.78 Hz, 1H), 7.71 (t, J=7.53 Hz, 1H).

Step C:
1-Bromo-5-bromomethyl-2,4-difluoro-benzene

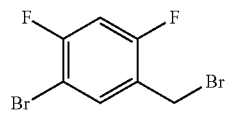

To a solution of (5-bromo-2,4-difluoro-phenyl)-methanol (35.2 g, 158 mmol) in anhydrous DCM (800 mL) cooled in an ice-bath was added $PBr_3$ (42.7 g, 157.8 mmol) dropwise. The reaction mixture was stirred at 0° C. for 1 h and at room temperature for 3 h. Then the reaction was quenched with water, and the aqueous layer was extracted by DCM twice. The combined organic layers were washed with brine, dried over anhydrous $Na_2SO_4$ and concentrated. The resulting residue was purified by column chromatography on silica gel (PE/EtOAc=50/1) to afford the title compound. $^1$H NMR (400 MHz, $CDCl_3$) δ: 4.43 (s, 2H), 6.92 (s, 1H), 7.60 (t, J=7.43 Hz, 1H).

Step D: (5aR,6S,6aS)-tert-butyl 3-((5-bromo-2,4-difluorobenzyl)oxy)-5,5a,6,6a-tetrahydrocyclopropa[4,5]cyclopenta[1,2-c]pyridine-6-carboxylate

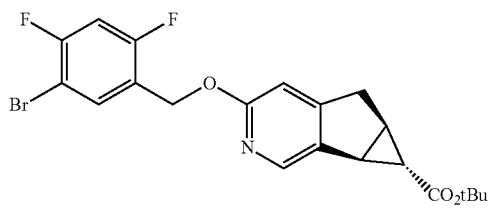 [SMILES: CC(C)(C)OC(=O)[C@H]1[C@@H]2Cc3cc(OCc4cc(Br)c(F)cc4F)ncc3[C@@H]21]

A mixture of 1-bromo-5-bromomethyl-2,4-difluoro-benzene (26.3 g, 77.4 mmol), Intermediate 4 (19.1 g, 77.4 mmol) and $Ag_2CO_3$ (64 g, 232 mmol) in dry toluene (600 mL) was heated at 110° C. for 12 h under a $N_2$ atmosphere. Then the reaction mixture was cooled to room temperature and diluted with DCM (500 mL), and the resulting precipitate was filtered off. The filtrate was concentrated and the resulting residue was purified by column chromatography on silica gel (PE/EtOAc=10/1 to 5/1) to give the title compound. $^1$H NMR (400 MHz, $CDCl_3$) δ: 1.16 (br. s., 1H), 1.47 (s, 9H), 1.57 (s, 1H), 2.37-2.41 (m, 1H), 2.87 (d, J=5.09 Hz, 1H), 2.98-3.03 (m, 1H), 3.22 (dd, J=18.39, 6.26 Hz, 1H), 5.35 (s, 2H) 6.61 (s, 1H), 6.92 (t, J=8.80 Hz, 1H), 7.67-7.74 (m, 1H), 8.09 (s, 1H). MS (ESI) m/e (M+H$^+$): 452.3/454.3.

Step E: (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate

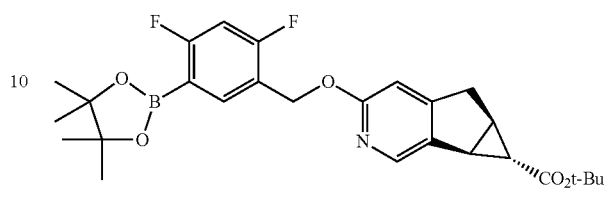

A mixture of (5aR,6S,6aS)-tert-butyl 3-((5-bromo-2,4-difluorobenzyl)oxy)-5,5a,6,6a-tetrahydrocyclopropa[4,5]cyclopenta[1,2-c]pyridine-6-carboxylate (3.0 g, 7.07 mmol), boronate 4,4,4',4',5,5,5',5'-octamethyl-2,2'-bi(1,3,2-dioxaborolane) (2.69 g, 10.6 mmol), KOAc (1.39 g, 14.14 mmol), and Pd(dppf)$Cl_2$ (517 mg, 0.71 mmol) in anhydrous DMF (2 mL)/anhydrous dioxane (6 mL) was charged in a sealed tube under a $N_2$ atmosphere and heated at 150° C. under microwave irradiation for 30 min. The mixture was then cooled to room temperature and diluted with EtOAc (50 mL). The organic layer was separated, washed with water and brine, dried over anhydrous $Na_2SO_4$ and concentrated. The resulting residue was purified by column chromatography on silica gel (PE/EtOAc=3/1) to give the title compound. MS (ESI) m/e (M+H$^+$): 500.2

Example 1

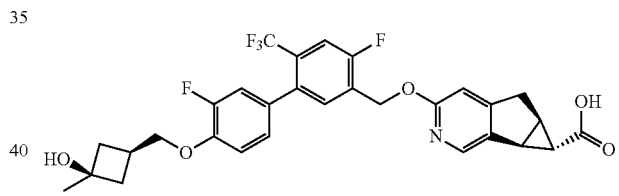

(5aR,6S,6aS)-3-{[3',4-difluoro-4'-(((1s,3s)-3-hydroxy-3-methylcyclobutyl)methoxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylic acid

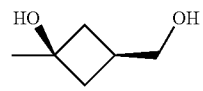

Step A:
(1s,3s)-3-(hydroxymethyl)-1-methylcyclobutanol

To a solution of (1s,3s)-3-hydroxy-3-methylcyclobutanecarboxylic acid (2.00 g, 15.4 mmol) in THF (30 ml) at 0° C. was added borane-THF complex (30.7 ml, 30.7 mmol) dropwise. It was stirred at 0° C. for an hour and room temperature overnight. It was quenched with methanol (30 ml) at 0° C. The reaction mixture was concentrated under reduced pressure. The residue was purified by chromatography over silical gel (eluting with a gradient of hexanes: EtOAc 100:0 to 50:50, to give the title compound. ¹HNMR (500 MHz, CDCl₃) δ: 3.65 (t, 2H, J=5.1 Hz), 2.17-2.21 (m, 2H), 2.05-2.14 (m, 1H), 1.83-1.87 (m, 2H), 1.39 (s, 3H).

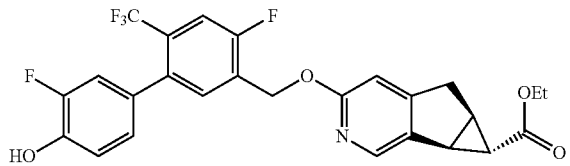 [SMILES: CCOC(=O)[C@H]1[C@@H]2Cc3cc(OCc4cc(-c5ccc(O)c(F)c5)c(C(F)(F)F)cc4F)ncc3[C@@H]21]

Step B: (5aR,6S,6aS)-ethyl 3-{[3',4-difluoro-4'-hydroxy-6-(trifluoromethyl)-[1,1'-biphenyl]-3-yl]methoxy}-5,5a,6,6a-tetrahydrocyclopropa[4,5]cyclopenta[1,2-c]pyridine-6-carboxylate A mixture of (5aR,6S,6aS)-ethyl 3-{[-bromo-2-fluoro-4-(trifluoromethyl)benzyl]oxy}-5,5a,6,6a-tetrahydrocyclopropa[4,5]cyclopenta[1,2-c]pyridine-6-carboxylate (400 mg, 0.844 mmol), (3-fluoro-4-hydroxyphenyl)boronic acid (198 mg, 1.27 mmol), and chloro(2-dicyclohexylphosphino-2',4',6'-triisopropyl-1,1'-biphenyl)[2-(2'-amino-1,1'-biphenyl)] palladium(II) (100 mg, 0.126 mmol) was degassed and purged with nitrogen three times. THF (4 ml) and 1M potassium phosphate tribasic (2.50 ml, 2.50 mmol) were added. The reaction mixture was stirred at 65° C. overnight. Then the reaction was cooled to room temperature and partitioned between EtOAc (2×20 ml) and water (20 ml). The combined organic layers were dried over MgSO₄, filtered, and the filtrate was concentrated under reduced pressure. The resulting residue was purified by chromatography over silica gel (eluting with a gradient of hexanes: EtOAc 100:0 to 80:20, to give the title compound. MS (ESI) m/e (M+H⁺): 506.1.

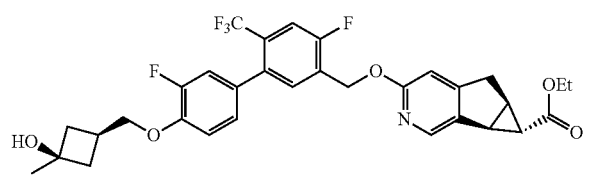 [SMILES: C[C@]1(O)C[C@@H](COc2ccc(-c3cc(COc4cc5c(cn4)[C@H]4[C@@H](C5)[C@@H]4C(=O)O)c(F)cc3C(F)(F)F)cc2F)C1]

Step C: (5aR,6S,6aS)-ethyl 3-{[3',4-difluoro-4'-(((1s,3s)-3-hydroxy-3-methylcyclobutyl) methoxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylate To a solution of (5aR,6S,6aS)-ethyl 3-{[3',4-difluoro-4'-hydroxy-6-(trifluoromethyl)-[1,1'-biphenyl]-3-yl]methoxy}-5,5a,6,6a-tetrahydrocyclopropa[4,5]cyclopenta[1,2-c]pyridine-6-carboxylate (202 mg, 0.400 mmol) in DCM (3 ml) at ambient temperature were added (1s,3s)-3-(hydroxymethyl)-1-methylcyclobutanol (46.4 mg, 0.400 mmol), di-tert-butyl diazene-1,2-dicarboxylate (101 mg, 0.440 mmol), and polymer-bound triphenylphosphine (393 mg, 1.20 mmol) (~3 mmol/g). The reaction mixture was stirred at room temperature overnight. It was filtered through Celite™. The filtrate was concentrated under reduced pressure. The resulting residue was purified by chromatography over silica gel (eluting with a gradient of hexanes:EtOAc 100:0 to 50:50) to give the title compound. MS (ESI) m/e (M+H⁺): 604.3.

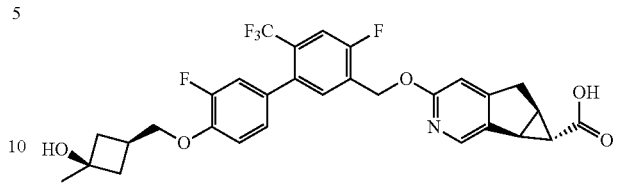

Step D: (5aR,6S,6aS)-3-{[3',4-difluoro-4'-(((1s,3s)-3-hydroxy-3-methylcyclobutyl) methoxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylic acid To a solution of (5aR,6S,6aS)-ethyl 3-{[3',4-difluoro-4'-(((1s,3s)-3-hydroxy-3-methylcyclo-butyl)methoxy)-6-(trifluoromethyl)-[1,1'-biphenyl]-3-yl]methoxy}-5,5a,6,6a-tetrahydro-cyclopropa[4,5]cyclopenta [1,2-c]pyridine-6-carboxylate (100 mg, 0.166 mmol) in THF (0.9 ml) at ambient temperature were added methanol (0.6 ml), water (0.6 ml), and 5 M NaOH (0.1 ml). The reaction mixture was stirred at room temperature for 3 hours, then neutralized with formic acid (0.1 ml), and evaporated under reduced pressure. The resulting residue was dissolved in DMSO (1 ml) and acetonitrile (1 ml), and purified by reverse-phase HPLC eluting with 60% acetonitrile in water (0.1% formic acid as a modifier) initially, grading to 70% acetonitrile in water. The desired fractions were collected and lyophilized to give the title compound. ¹H NMR (500 MHz, CD₃OD) δ: 8.05 (s, 1H), 7.53 (d, 1H, J=10.3 Hz), 7.47 (d, 1H, J=7.1 Hz), 7.10 (t, 1H, J=8.5 Hz), 6.97-7.03 (m, 2H), 6.70 (s, 1H), 5.45 (s, 2H), 4.07 (d, 2H, J=6.5 Hz), 3.23 (dd, 1H, J=19.3, 6.3 Hz), 3.03 (d, 1H, J=18.5 Hz), 2.89 (d, 1H, J=6.4 Hz), 2.39-2.42 (m, 1H), 2.31-2.37 (m, 1H), 2.17-2.21 (m, 2H), 1.94-1.99 (m, 2H), 1.37 (s, 3H), 1.12 (t, 1H, J=2.5 Hz). MS (ESI) m/e (M+H⁺): 576.2.

Example 2

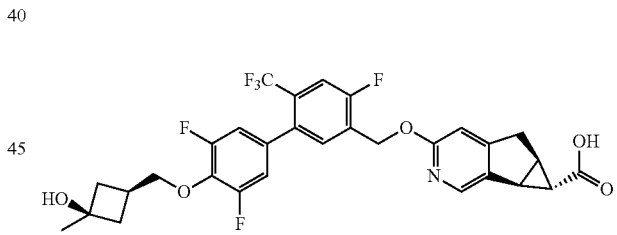

(5aR,6S,6aS)-3-{[3',4,5'-trifluoro-4'-(((1s,3s)-3-hydroxy-3-methylcyclobutyl)methoxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylic acid

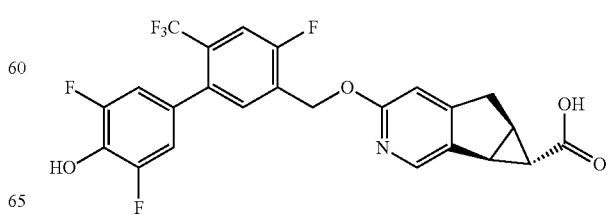

Step A: (5aR,6S,6aS)-ethyl 3-{[3',4,5'-trifluoro-4'-hydroxy-6-(trifluoromethyl)-[1,1'-biphenyl]-3-yl]methoxy}-5,5a,6,6a-tetrahydrocyclopropa[4,5]cyclopenta[1,2-c]pyridine-6-carboxylate A mixture of (5aR,6S,6aS)-ethyl 3-{[5-bromo-2-fluoro-4-(trifluoromethyl)-benzyl]oxy}-5,5a,6,6a-tetrahydrocyclopropa[4,5]cyclopenta[1,2-c]pyridine-6-carboxylate (850 mg, 1.79 mmol), (3,5-difluoro-4-hydroxyphenyl)boronic acid (468 mg, 2.69 mmol), and chloro(2-dicyclohexyl-phosphino-2',4',6'-triisopropyl-1,1'-biphenyl)[2-(2'-amino-1,1'-biphenyl)] palladium(II) (212 mg, 0.269 mmol) was degassed and purged with nitrogen three times. THF (12 ml) and 1M potassium phosphate tribasic (5.40 ml, 5.40 mmol) were added. The reaction mixture was stirred at 65° C. overnight, then cooled to room temperature, and partitioned between EtOAc (2×40 ml) and water (40 ml). The combined organic layers were dried over MgSO$_4$, and filtered. The filtrate was concentrated under reduced pressure. The resulting residue was purified by chromatography over silica gel (eluting with a gradient of hexanes:EtOAc 100:0 to 50:50, to give the title compound. MS (ESI) m/e (M+H$^+$): 524.1.

Step B: (5aR,6S,6aS)-ethyl 3-{[3',4,5'-trifluoro-4'-(((1s,3s)-3-hydroxy-3-methylcyclobutyl) methoxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylate To a solution of (5aR,6S,6aS)-ethyl 3-{[3',4,5'-trifluoro-4'-hydroxy-6-(trifluoromethyl)-[1,1'-biphenyl]-3-yl]methoxy}-5,5a,6,6a-tetrahydrocyclopropa-[4,5]cyclopenta[1,2-c]pyridine-6-carboxylate (830 mg, 1.59 mmol) in DCM (4 ml) and THF (4 ml) at ambient temperature were added (1s,3s)-3-(hydroxymethyl)-1-methylcyclobutanol (239 mg, 2.06 mmol), de-tert-butyl diazene-1,2-dicarboxylate (475 mg, 2.06 mmol), and polymer-bound triphenylphosphine (832 mg, 3.17 mmol) (~3 mmol/g). The reaction mixture was stirred at room temperature overnight, and then filtered through Celite™. The filtrate was concentrated under reduced pressure. The resulting residue was purified by chromatography over silica gel (eluting with a gradient of hexanes:EtOAc 100:0 to 50:50, to give the title compound. MS (ESI) m/e (M+H$^+$): 622.3.

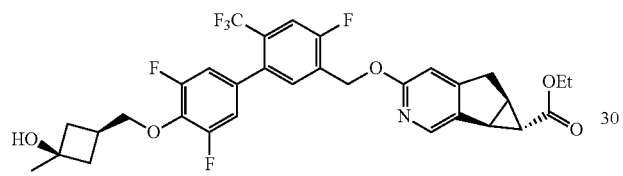

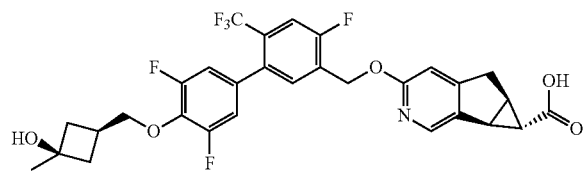 [SMILES: C[C@]1(O)C[C@@H](COc2c(F)cc(-c3cc(COc4cc5c(cn4)[C@H]4[C@@H](C5)[C@@H]4C(=O)O)c(F)cc3C(F)(F)F)cc2F)C1]

Step C: (5aR,6S,6aS)-3-{[3',4,5'-trifluoro-4'-(((1s,3s)-3-hydroxy-3-methylcyclobutyl) methoxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylic acid To a solution of (5aR,6S,6aS)-ethyl 3-{[3',4,5'-trifluoro-4'-(((1s,3s)-3-hydroxy-3-methylcyclobutyl) methoxy)-6-(trifluoromethyl)-[1,1'-biphenyl]-3-yl]methoxy}-5,5a,6,6a-tetrahydrocyclopropa[4,5] cyclopenta[1,2-c]pyridine-6-carboxylate (632 mg, 1.02 mmol) in THF (6 ml) at ambient temperature were added methanol (4 ml), water (4 ml), and 5 M NaOH (1 ml). The reaction mixture was stirred at room temperature for 3 hours, then neutralized with formic acid (0.5 ml), and evaporated under reduced pressure. The resulting residue was dissolved into DMSO (3 ml) and acetonitrile (3 ml), and purified by reverse-phase HPLC eluting with 60% acetonitrile in water (0.1% formic acid as a modifier) initially, grading to 70% acetonitrile in water. The desired fractions were collected and lyophilized to give the title compound. $^1$H NMR (500 MHz, CD$_3$OD) δ: 8.05 (s, 1H), 7.57 (d, 1H, J=8.3 Hz), 7.51 (d, 1H, J=7.0 Hz), 6.90-6.95 (m, 2H), 6.71 (s, 1H), 5.45 (s, 2H), 4.14 (d, 2H, J=6.5 Hz), 3.26 (dd, 1H, J=18.5, 6.3 Hz), 3.03 (d, 1H, J=18.5 Hz), 2.90 (dd, 1H, J=6.5, 2.0 Hz), 2.41 (td, 1H, J=6.4, 3.3 Hz), 2.25-2.31 (m, 1H), 2.12-2.16 (m, 2H), 1.92-1.98 (m, 2H), 1.35 (s, 3H), 1.13 (t, 1H, J=2.8 Hz). MS (ESI) m/e (M+H$^+$): 594.3.

Example 3

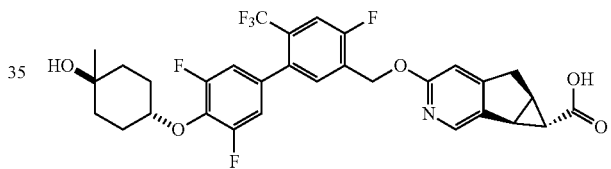

(5aR,6S,6aS)-3-{[3',4,5'-trifluoro-4'-(((1r,4r)-4-hydroxy-4-methylcyclohexyl)oxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylic acid

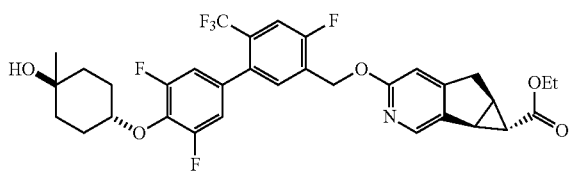 [SMILES: C[C@]1(O)CC[C@H](Oc2c(F)cc(-c3cc(COc4cc5c(cn4)[C@H]4[C@@H](C5)[C@@H]4C(=O)O)c(F)cc3C(F)(F)F)cc2F)CC1]

Step A: (5aR,6S,6aS)-ethyl 3-{[3',4,5'-trifluoro-4'-(((1r,4r)-4-hydroxy-4-methylcyclohexyl) oxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylate To a solution of (5aR,6S,6aS)-ethyl 3-{[3',4,5'-trifluoro-4'-hydroxy-6-(trifluoromethyl)-[1,1'-biphenyl]-3-yl]methoxy}-5,5a,6,6a-tetrahydrocyclopropa-[4,5]-cyclopenta[1,2-c]pyridine-6-carboxylate (400 mg, 0.764 mmol) in DCM (3 ml) and THF (3 ml) at ambient temperature were added (1s,4s)-1-methylcyclohexane-1,4-diol (129 mg, 0.993 mmol), di-tert-butyl diazene-1,2-dicarboxylate (229 mg, 0.993 mmol), and polymer-bound triphenylphosphine (401 mg, 1.53 mmol) (~3 mmol/g). The reaction mixture was stirred at room temperature overnight, then filtered through Celite™, and the filtrate was concentrated under reduced pressure. The resulting residue was purified by chromatography over silica gel (eluting with a gradient of hexanes: EtOAc 100:0 to 50:50, to give the title compound. MS (ESI) m/e (M+H$^+$): 636.5.

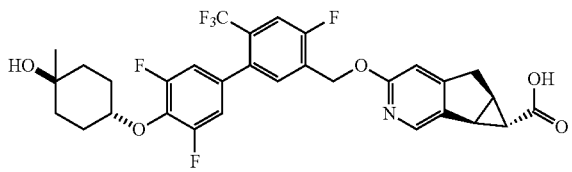 [SMILES: C[C@]1(O)CC[C@H](Oc2c(F)cc(-c3cc(COc4cc5c(cn4)[C@H]4[C@@H](C5)[C@@H]4C(=O)O)c(F)cc3C(F)(F)F)cc2F)CC1]

Step B: (5aR,6S,6aS)-3-{[3',4,5'-trifluoro-4'-(((1r,4r)-4-hydroxy-4-methylcyclohexyl)oxy)-6-(trifluoromethyl)-[1,1'-biphenyl]-3-yl]methoxy}-5,5a,6,6a-tetrahydrocyclopropa[4,5]cyclopenta[1,2-c]pyridine-6-carboxylic acid To a solution of (5aR,6S,6aS)-ethyl 3-{[3',4,5'-trifluoro-4'-(((1r,4r)-4-hydroxy-4-methyl-cyclohexyl)oxy)-6-(trifluoromethyl)-[1,1'-biphenyl]-3-yl]methoxy}-5,5a,6,6a-tetrahydro-cyclopropa[4,5]cyclopenta[1,2-c]pyridine-6-carboxylate (170 mg, 0.267 mmol) in THF (1 ml) at ambient temperature were added methanol (0.6 ml), water (0.6 ml), and 5 M NaOH (0.2 ml). The reaction mixture was stirred at room temperature for 3 hours, then neutralized with formic acid (0.1 ml), and evaporated under reduced pressure. The resulting residue was dissolved in DMSO (2 ml) and acetonitrile (2 ml), and purified by reverse-phase HPLC eluting with 60% acetonitrile in water (0.1% formic acid as a modifier) initially, grading to 70% acetonitrile in water. The desired fractions were collected and lyophilized to give the title compound. $^1$H NMR (500 MHz, CD$_3$OD) δ: 8.05 (s, 1H), 7.57 (d, 1H, J=10.2 Hz), 7.52 (d, 1H, J=6.8 Hz), 6.91-6.96 (m, 2H), 6.71 (s, 1H), 5.45 (s, 2H), 4.14 (s, 1H), 3.23 (dd, 1H, J=19.3, 6.3 Hz), 3.03 (d, 1H, J=18.5 Hz), 2.89 (d, 1H, J=6.4 Hz), 2.41 (td, 1H, J=6.4, 3.1 Hz), 1.93-1.99 (m, 2H), 1.83-1.89 (m, 2H), 1.77-1.81 (m, 2H), 1.45-1.52 (m, 2H), 1.25 (s, 3H), 1.12 (t, 1H, J=2.7 Hz). MS (ESI) m/e (M+H$^+$): 608.3.

Example 4

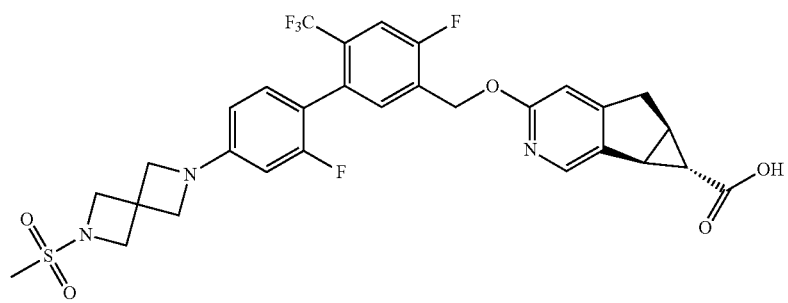 [SMILES: CS(=O)(=O)N1CC2(CN(c3ccc(-c4cc(COc5cc6c(cn5)[C@H]5[C@@H](C6)[C@@H]5C(=O)O)c(F)cc4C(F)(F)F)c(F)c3)C2)C1]

(5aR,6S,6aS)-3-((2',4-difluoro-4'-(6-(methylsulfonyl)-2,6-diazaspiro[3,3]heptan-2-yl)-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylic acid

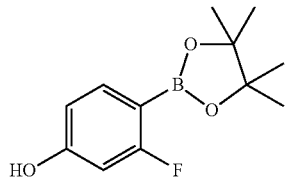 [SMILES: CC1(C)OB(c2ccc(O)cc2F)OC1(C)C]

Step A: 3-fluoro-4-(4,4,5,5-tetramethyl-1,3,2-dioxaborolan-2-yl)phenol

To a solution of 4-bromo-3-fluorophenol (1.00 g, 5.23 mmol, 1.0 eq) in dioxane (20 mL) was added AcOK (1.54 g, 15.7 mmol 3.0 eq), 4,4,4',4',5,5,5',5'-octamethyl-2,2'-bi(1,3,2-dioxaborolane) (1.46 g, 5.75 mmol, 1.1 eq) and PdCl$_2$(dppf) (382 mg, 0.523 mmol, 0.1 eq) at room temperature under nitrogen atmosphere. The mixture was heated up to 80° C. and stirred for 16 hours. After cooling to room temperature, the mixture was mixed with water (50 mL) and extracted with EtOAc (50 mL×3). The combined organic layers were dried over anhydrous Na$_2$SO$_4$, and filtered. The filtrate was evaporated in vacuo to give the crude product, which was purified by column silica gel chromatography eluting with PE:EtOAc=3:1 to give the title compound as a white oil. $^1$HNMR (400 MHz, CDCl$_3$) δ: 7.61 (t, J=7.6, 1H), 6.63-6.53 (m, 2H), 1.35 (s, 12H).

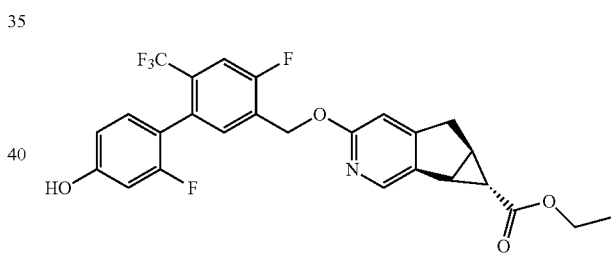

Step B: (5aR,6S,6aS)-ethyl 3-42',4-difluoro-4'-hydroxy-6-(trifluoromethyl)-[1,1'-biphenyl]-3-yl)methoxy)-5,5a,6,6a-tetrahydrocyclopropa[4,5]cyclopenta[1,2-c]pyridine-6-carboxylate To a solution of 3-fluoro-4-(4,4,5,5-tetramethyl-1,3,2-dioxaborolan-2-yl)phenol (100 mg, 0.420 mmol, 1.0 eq) in dioxane (2 mL) and H₂O (0.5 ml) was added K₂CO₃ (174 mg, 1.26 mmol, 3.0 eq), (5aR,6S,6aS)-ethyl 3-((5-bromo-2-fluoro-4-(trifluoromethyl)benzyl)oxy)-5,5a,6,6a-tetrahydro-cyclopropa[4,5]cyclopenta[1,2-c]pyridine-6-carboxylate (199 mg, 0.420 mmol, 1.0 eq) and PdCl₂(dppf) (30.7 mg, 0.042 mmol, 0.1 eq) at room temperature under nitrogen atmosphere. The mixture was heated up to 90° C. and stirred for 16 hours. After cooling to room temperature, the mixture was added water (50 mL) and extracted with EtOAc (50 mL×3). The combined organic layers were dried over anhydrous Na₂SO₄, and filtered. The filtrate was evaporated in vacuo to give the crude product, which was purified by preparative TLC (EtOAc:PE=1:1) to give the title compound as a white solid. ¹HNMR (400 MHz, CDCl₃) δ: 8.08 (s, 1H), 7.46 (d, J=9.6 Hz, 2H), 7.05 (t, J=8.0 Hz, 1H), 6.64-6.61 (m, 3H), 5.46 (s, 2H), 4.16 (q, J=6.8 Hz, 2H), 3.23 (dd, J=6.0 Hz&18.4 HZ, 1H), 3.01 (d, J=18.8 Hz, 1H), 2.94 (d, J=6.0 Hz, 1H), 2.48-2.44 (m, 1H), 1.29-1.23 (m, 4H). MS (ESI) m/e (M+H⁺): 506.1.

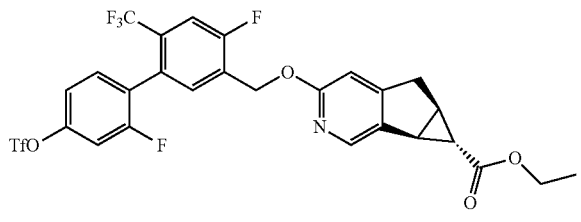 [SMILES: CCOC(=O)[C@H]1[C@@H]2Cc3cc(OCc4cc(-c5ccc(OS(=O)(=O)C(F)(F)F)cc5F)c(C(F)(F)F)cc4F)ncc3[C@@H]21]

Step C: (5aR,6S,6aS)-ethyl 3-((2',4-difluoro-6-(trifluoromethyl)-4'-(((trifluoromethyl)-sulfonyl)oxy)-[1,1'-biphenyl]-3-yl)methoxy)-5,5a,6,6a-tetrahydrocyclopropa[4,5]cyclopenta[1,2-c]pyridine-6-carboxylate To a solution of (5aR,6S,6aS)-ethyl 3-((2',4-difluoro-4'-hydroxy-6-(trifluoromethyl)-[1,1'-biphenyl]-3-yl)methoxy)-5,5a,6,6a-tetrahydrocyclopropa[4,5]cyclopenta-[1,2-c]pyridine-6-carboxylate (80.0 mg, 0.158 mmol, 1.0 eq), Et₃N (47.9 mg, 0.474 mmol, 3.0 eq) in DCM (2 ml) was added dropwise PhN(Tf)₂ (113 mg, 0.316 mmol, 2.0 eq) at 0° C. under nitrogen atmosphere. Then the mixture was warmed to room temperature and stirred for 16 hours. The mixture was added water (50 mL) and extracted with EtOAc (50 mL×3). The combined organic layers were dried over anhydrous Na₂SO₄, and filtered. The filtrate was evaporated in vacuo to give the crude product, which was purified by preparative TLC (EtOAc:PE=5:1) to give the title compound as a white solid. ¹HNMR (400 MHz, CDCl₃) δ: 8.07 (s, 1H), 7.51-7.48 (m, 2H), 7.37 (t, J=8.0, 1H), 7.16-7.12 (m, 2H), 6.65 (s, 1H), 5.49 (s, 2H), 4.16 (q, J=7.2 Hz, 2H), 3.23 (dd, J=6.0 Hz&18.0 HZ, 1H), 3.01 (d, J=18.0 Hz, 1H), 2.93 (d, J=6.0 Hz, 1H), 2.47-2.45 (m, 1H), 1.29-1.22 (m, 4H). MS (ESI) m/e (M+H⁺): 638.0.

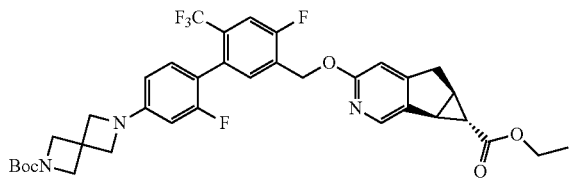 [SMILES: CCOC(=O)[C@H]1[C@@H]2Cc3cc(OCc4cc(-c5ccc(N6CC7(CN(C(=O)OC(C)(C)C)C7)C6)cc5F)c(C(F)(F)F)cc4F)ncc3[C@@H]21]

Step D: (5aR,6S,6aS)-ethyl 3-((4'-(6-tert-butoxycarbonyl)-2,6-diazaspiro[3.3]heptan-2-yl)-2',4-difluoro-6-(trifluoromethyl)-[1,1'-biphenyl]-3-yl)methoxy)-5,5a,6,6a-tetrahydrocyclopropa-[4,5]cyclopenta[1,2-c]pyridine-6-carboxylate To a solution of (5aR,6S,6aS)-ethyl 3-((2',4-difluoro-6-(trifluoromethyl)-4'-(((trifluoromethyl)-sulfonyl)oxy)-[1,1'-biphenyl]-3-yl)methoxy)-5,5a,6,6a-tetrahydrocyclopropa[4,5]cyclopenta[1,2-c]pyridine-6-carboxylate (70 mg, 0.110 mmol, 1.0 eq) in THF (2 mL) was added Xant-phos (12.7 mg, 0.022 mmol, 0.2 eq), tert-butyl 2,6-diazaspiro[3.3]heptane-2-carboxylate oxalic acid (47.5 mg, 0.165 mmol, 1.5 eq), Pd₂(dba)₃ (10.0 mg, 0.0110 mmol, 0.1 eq) and Cs₂CO₃ (107 mg, 0.330 mmol, 3.0 eq) at room temperature under nitrogen atmosphere. The mixture was heated up to 90° C. and stirred for 16 hours. After cooling to room temperature, the mixture was mixed with water (50 mL) and extracted with EtOAc (50 mL×3). The combined organic layers were dried over anhydrous Na₂SO₄, and filtered. The filtrate was evaporated in vacuo to give the crude product, which was purified by preparative TLC (EtOAc:PE=5:1) to give the title compound as a white solid. ¹HNMR (400 MHz, CDCl₃) δ: 8.07 (s, 1H), 7.46-7.43 (m, 2H), 7.03 (t, J=8.4 Hz, 1H), 6.61 (s, 1H), 6.23-6.16 (m, 2H), 5.46 (s, 2H), 4.16 (q, J=7.2 Hz, 2H), 3.22 (dd, J=6.8 Hz&18.4 HZ, 1H), 3.00 (d, J=18.4 Hz, 1H), 2.93 (d, J=6.8 Hz, 1H), 2.47-2.43 (m, 1H), 1.46 (s, 9H), 1.27-1.26 (m, 4H). MS (ESI) m/e (M+H+): 686.2.

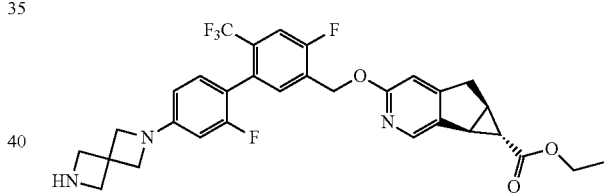

Step E: (5aR,6S,6aS)-ethyl 3-((2',4-difluoro-4'-(2,6-diazaspiro[3.3]heptan-2-yl)-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylate To a solution of (5aR,6S,6aS)-ethyl 3-((4'-(6-(tert-butoxycarbonyl)-2,6-diazaspiro[3.3]heptan-2-yl)-2',4-difluoro-6-(trifluoromethyl)-[1,1'-biphenyl]-3-yl)methoxy)-5,5a,6,6a-tetrahydro-cyclopropa[4,5]cyclopenta[1,2-c]pyridine-6-carboxylate (60 mg, 0.0875 mmol, 1.0 eq) in DCM (2.0 mL) was added TFA (0.5 ml) at room temperature under nitrogen atmosphere. Then the mixture was warmed to 40° C. and stirred for 2 hours. After cooling to room temperature, the mixture was added water (10 mL) and extracted with EtOAc (10 mL×3). The combined organic layers were dried over anhydrous Na₂SO₄, and filtered. The filtrate was evaporated in vacuo to give the crude product which was purified by preparative TLC (EtOAc:PE 1:1) to give the title compound as a white solid. MS (ESI) m/e (M+H⁺): 586.2.

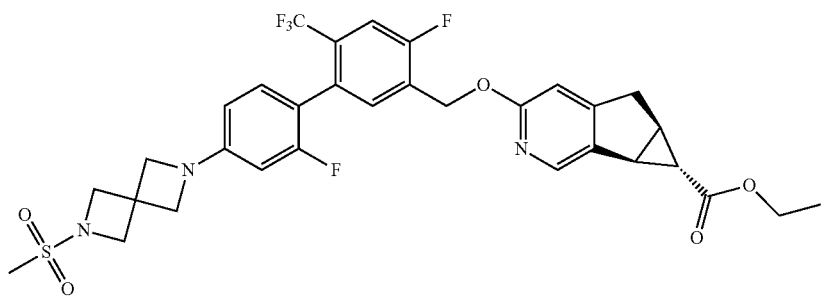 [SMILES: CCOC(=O)[C@H]1[C@@H]2Cc3cc(OCc4cc(-c5ccc(N6CC7(C6)CN(S(C)(=O)=O)C7)cc5F)c(C(F)(F)F)cc4F)ncc3[C@@H]21]

Step F: (5aR,6S,6aS)-ethyl 3-((2',4-difluoro-4'-(6-(methylsulfonyl)-2,6-diazaspiro[3.3]-heptan-2-yl)-6-(trifluoromethyl)-[1,1'-biphenyl]-3-yl)methoxy)-5,5a,6,6a-tetrahydrocyclopropa-[4,5]cyclopenta[1,2-c]pyridine-6-carboxylate To a solution of (5aR,6S,6aS)-ethyl 3-((2',4-difluoro-4'-(2,6-diazaspiro[3.3]heptan-2-yl)-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylate (20 mg, 0.0342 mmol, 1.0 eq), Et$_3$N (31.2 mg, 0.308 mmol, 9.0 eq) in DCM (2 ml) was added dropwise MsCl (11.8 mg, 0.103 mmol, 3.0 eq) at 0° C. under nitrogen atmosphere. Then the mixture was warmed to room temperature and stirred for 16 hours. The mixture was mixed with water (50 mL) and extracted with EtOAc (50 mL×3). The combined organic layers were dried over anhydrous Na$_2$SO$_4$, and filtered. The filtrate was evaporated in vacuo to give the crude product which was purified by preparative TLC (EtOAc:PE=5:1) to give the title compound as a white solid. $^1$HNMR (400 MHz, CDCl$_3$) δ: 8.07 (s, 1H), 7.45 (d, J=9.6 Hz, 2H), 7.04 (d, J=8.0 Hz, 1H), 6.61 (s, 1H), 6.24-6.17 (m, 2H), 5.46 (s, 2H), 4.16 (s, 4H), 4.05 (s, 4H), 3.31-3.28 (m, 1H), 3.10 (d, J=18.8 Hz, 1H), 2.97-2.95 (m, 1H), 2.49-2.46 (m, 1H), 1.20-1.19 (m, 1H). MS (EST) m/e (M+H$^+$): 664.1.

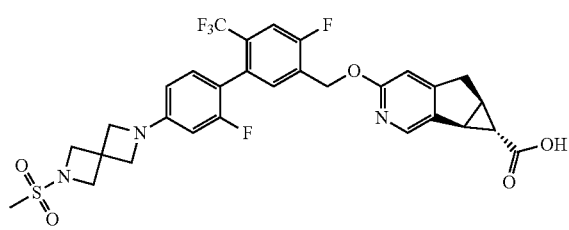 [SMILES: CS(=O)(=O)N1CC2(CN(c3ccc(-c4cc(COc5cc6c(cn5)[C@H]5[C@@H](C6)[C@@H]5C(=O)O)c(F)cc4C(F)(F)F)c(F)c3)C2)C1]

Step G: (5aR,6S,6aS)-3-((2',4-difluoro-4'-(6-(methylsulfonyl)-2,6-diazaspiro[3.3]heptan-2-yl)-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylic acid To a solution of (5aR,6S,6aS)-ethyl 3-((2',4-difluoro-4'-(6-(methylsulfonyl)-2,6-diazaspiro[3.3]heptan-2-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylate (15.0 mg, 0.0226 mmol, 1.0 eq) in THF (1.0 mL), MeOH (1.0 mL) and H$_2$O (1.0 mL) was added LiOH (5.40 mg, 0.226 mmol, 10.0 eq) at room temperature. The mixture was stirred at room temperature for 1 hour. Then the mixture was mixed with water (10 mL) and extracted with EtOAc (10 mL×3). The combined organic layers were dried over anhydrous Na$_2$SO$_4$, and filtered. The filtrate was evaporated in vacuo to give the crude product which was purified by reverse phase HPLC (Gilson 281, YMC Actus Triart C18 (15×30 mm 5 uM), water with 0.1% TFA/CH$_3$CN gradient) to give the title compound as a white solid. $^1$HNMR (400 MHz, CDCl$_3$) δ: 8.10 (s, 1H), 7.55 (d, J=10.4 Hz, 1H), 7.45 (d, J=6.8 Hz, 1H), 7.02 (t, J=8.4 Hz, 1H), 6.88 (s, 1H), 6.32-6.24 (m, 2H), 5.48 (s, 2H), 4.12 (s, 4H), 4.04 (s, 4H), 3.31-3.28 (m, 1H), 3.10 (d, J=18.8 Hz, 1H), 2.97-2.95 (m, 4H), 2.49-2.46 (m, 1H), 1.20-1.19 (m, 1H). MS (ESI) m/e (M+H$^+$): 636.2.

Example 5

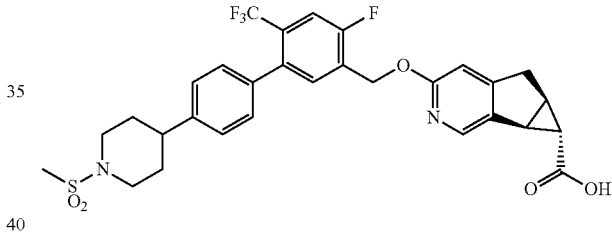

(5aR,6S,6aS)-3-((4-fluoro-4'-(1-(methylsulfonyl)piperidin-4-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

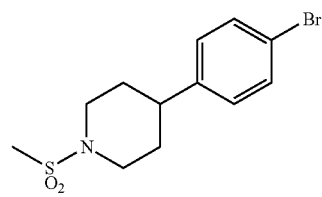 [SMILES: CS(=O)(=O)N1CCC(c2ccc(Br)cc2)CC1]

Step A:
4-(4-bromophenyl)-1-(methylsulfonyl)piperidine

To a solution of 4-(4'-bromophenyl)piperidine (1 g, 4.16 mmol) in DCM (40 mL) was added DMAP (0.051 g, 0.415 mmol), triethylamine (0.723 ml, 5.18 mmol), and methanesulfonyl chloride (0.357 mL, 4.58 mmol). The resulting solution was stirred at 20-24° C. for 1 hour. The reaction mixture was diluted with DCM and saturated NH$_4$Cl/water (1:1). The aqueous phase was separated and extracted twice with DCM. The combined organic layers were washed with brine, dried over Na$_2$SO$_4$, and concentrated under vacuum to give a title compound.

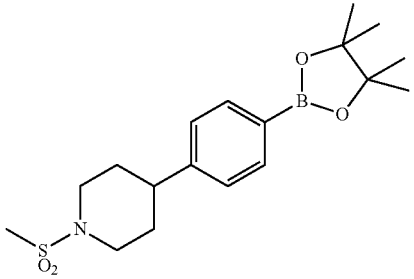

Step B: 1-(methylsulfonyl)-4-(4-(4,4,5,5-tetramethyl-1,3,2-dioxaborolan-2-yl)phenyl)piperidine The solution of crude product from Step A (1.33 g, 4.16 mmol), bis(pinacolato)diboron (2.11 g, 8.33 mmol), and potassium acetate (1.23 g, 12.49 mmol) in DMSO (17 mL) was sparged with N$_2$ for 15 minutes. Pd(dppf)Cl$_2$ (0.609 g, 0.833 mmol) was added to reaction. The resulting mixture was stirred at 80° C. overnight, then diluted with H$_2$O and EtOAc. The aqueous phase was separated and extracted with EtOAc twice. The combined organic layers were washed with brine, dried over Na$_2$SO$_4$, filtered, and concentrated under vacuum to give the crude product, which was purified by column chromatography (Biotage, 50 g silica column), eluting with hexane/EtOAc (80:20 to 20:80) to give the title compound.

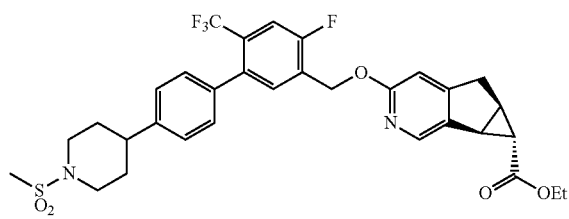 [SMILES: CCOC(=O)[C@H]1[C@@H]2Cc3cc(OCc4cc(-c5ccc(C6CCN(S(C)(=O)=O)CC6)cc5)c(C(F)(F)F)cc4F)ncc3[C@@H]21]

Step C: (5aR,6S,6aS)-ethyl 3-((4-fluoro-4'-(1-(methylsulfonyl)piperidin-4-yl)-6-(trifluoromethyl)-[1,1'-biphenyl]-3-yl)methoxy)-5,5a,6,6a tetrahydrocyclopropa[4,5]cyclopenta-[1,2-c]pyridine-6-carboxylate To a solution of Intermediate 2 (50 mg, 0.105 mmol) in THF (3.0 mL), 1-(methylsulfonyl)-4-(4-(4,4,5,5-tetramethyl-1,3,2-dioxaborolan-2-yl)phenyl)piperidine (50.1 mg, 0.137 mmol) was added and sparged with N$_2$ for 5 minutes. To this solution was added 2$^{nd}$ generation XPHOS precatalyst (8.3 mg, 0.011 mmol) and K$_3$PO$_4$/H$_2$O (0.211 mL, 1 mol/L). The resulting mixture was sparged with N$_2$ for 5 minutes and stirred at 65° C. for 5 h. The reaction mixture was partitioned between H$_2$O and EtOAc. The aqueous layer was extracted with EtOAc (5 mL×2). The combined organic layers were concentrated under vacuum and the resulting crude product was purified by chromatography over silica gel (eluting with hexane and EtOAc=100:0 to 30:70) to give the title compound. MS (ESI) m/e (M+H$^+$): 633.3.

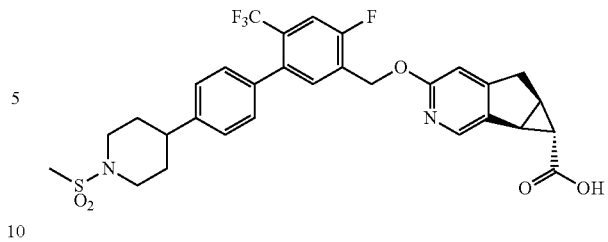

Step D: (5aR,6S,6aS)-3-((4-fluoro-4'-(1-(methylsulfonyl)piperidin-4-yl)-6-(trifluoromethyl)-[1,1'-biphenyl]-3-yl)methoxy)-5,5a,6,6a-tetrahydrocyclopropa[4,5]cyclopenta-[1,2-c]pyridine-6-carboxylic acid To a solution of product from Step C (60 mg, 0.095 mmol) in THF/EtOH/H$_2$O (0.5/0.5/0.5 mL) was added LiOH/H$_2$O (0.47 mL, 1 mol/L). The resulting solution was stirred at 20-24° C. for 15 h. After the reaction was finished, the reaction mixture was concentrated under vacuum. The resulting residue was re-dissolved in CH$_3$CN/H$_2$O/DMSO (2/1/1 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.06 (s, 1H), 7.53 (d, 1H, J=10.5 Hz), 7.45 (d, 1H, J=7.0 Hz), 7.31 (d, 2H, J=8.5 Hz), 7.22 (d, 2H, J=8.0 Hz), 6.71 (s, 1H), 5.47 (s, 2H), 3.88 (m, 2H), 3.27-3.22 (m, 1H), 3.04 (d, 1H), 2.93-2.86 (m, 6H), 2.77-2.72 (m, 1H), 2.45-2.42 (m, 1H), 2.01-1.99 (m, 2H), 1.88-1.79 (m, 2H), 1.14 (t, 1H, J=2.5 Hz). MS (ESI) m/e (M+H$^+$): 605.25.

Example 6

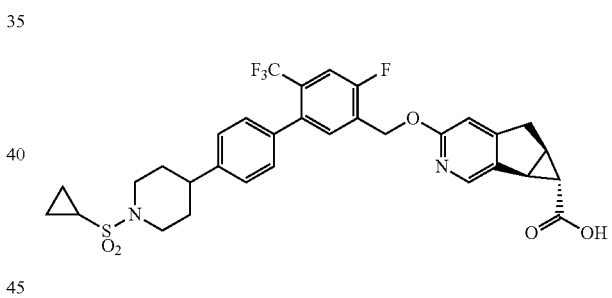

(5aR,6S,6aS)-3-((4'-(1-(cyclopropylsulfonyl)piperidin-4-yl)-4-fluoro-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

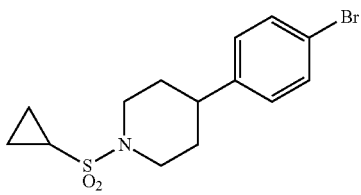 [SMILES: O=S(=O)(C1CC1)N1CCC(c2ccc(Br)cc2)CC1]

Step A: 4-(4-bromophenyl)-1-(cyclopropylsulfonyl)piperidine

To a solution of 4-(4'-bromophenyl)piperidine (1 g, 4.15 mmol) in DCM (40 mL) was added DMAP (0.051 g, 0.415 mmol), triethylamine (0.723 ml, 5.18 mmol), and cyclopropanesulfonyl chloride (0.644 g, 4.58 mmol). The resulting solution was stirred at 20-24° C. for 1 hour. The reaction mixture was diluted with DCM and saturated NH$_4$Cl/water (1:1). The aqueous phase was separated and extracted twice with DCM. The combined organic layers were washed with brine, dried over Na$_2$SO$_4$, and concentrated under vacuum to give a title compound.

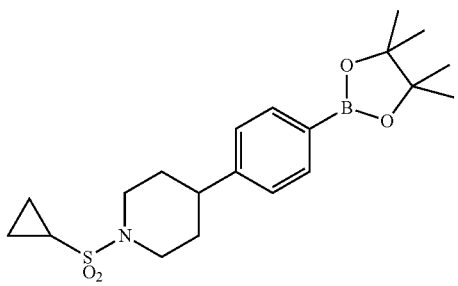 [SMILES: CC1(C)OB(c2ccc(C3CCN(S(=O)(=O)C4CC4)CC3)cc2)OC1(C)C]

Step B: 1-(cyclopropylsulfonyl)-4-(4-(4,4,5,5-tetramethyl-1,3,2-dioxaborolan-2-yl)phenyl)piperidine The solution of crude product from Step A (1.43 g, 4.15 mmol), bis(pinacolato)diboron (2.106 g, 8.29 mmol), and potassium acetate (1.221 g, 12.44 mmol) in DMSO (17 mL) was sparged with N$_2$ for 15 minutes. Then Pd(dppf)Cl$_2$ (0.607 g, 0.829 mmol) was added to above solution. The resulting mixture was stirred at 80° C. overnight. After the reaction was completed, the reaction mixture was diluted with H$_2$O and EtOAc. The aqueous phase was separated and extracted with EtOAc twice. The combined organic layers were washed with brine, dried over Na$_2$SO$_4$, filtered, and concentrated under vacuum to give the crude product, which was purified by column chromatography (Biotage 50 g column), eluting with hexane/EtOAc (80:20 to 20:80) to give the title compound.

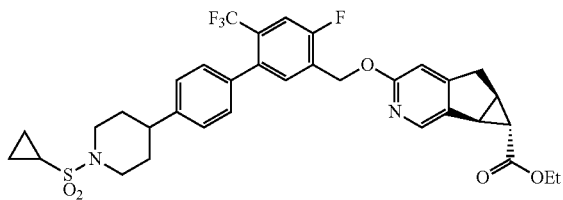 [SMILES: CCOC(=O)[C@H]1[C@@H]2Cc3cc(OCc4cc(-c5ccc(C6CCN(S(=O)(=O)C7CC7)CC6)cc5)c(C(F)(F)F)cc4F)ncc3[C@@H]21]

Step C: (5aR,6S,6aS)-ethyl 3-((4'-(1-(cyclopropylsulfonyl)piperidin-4-yl)-4-fluoro-6-(trifluoromethyl)-[1,1'-biphenyl]-3-yl)methoxy)-5,5a,6,6a-tetrahydrocyclopropa[4,5]cyclo-penta[1,2-c]pyridine-6-carboxylate To a solution of Intermediate 2 (50 mg, 0.105 mmol) in THF (1.0 mL) and crude product from Step B (49.5 mg, 0.127 mmol) was sparged with N$_2$ for 10 minutes. To this solution was added 2$^{nd}$ generation XPHOS precatalyst (8.3 mg, 0.011 mmol) and K$_3$PO$_3$/H$_2$O (0.211 mL, 1 mol/L). The resulting mixture was sparged with N$_2$ for 10 minutes and stirred at 66° C. for 7 h. The reaction mixture was then partitioned between H$_2$O and EtOAc. The aqueous phase was extracted with EtOAc (5 mL×2). The combined organic layers were concentrated under vacuum and the resulting crude product was purified by chromatography over silica gel, eluting with hexane and EtOAc (100:0 to 40:60) to give the title compound. MS (ESI) m/e (M+H$^+$): 659.

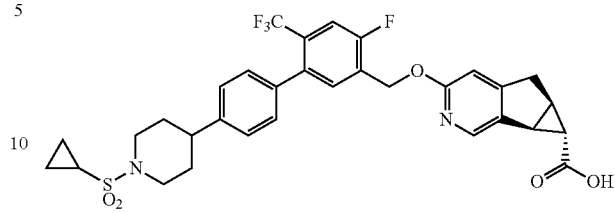

Step D: (5aR,6S,6aS)-3-((4'-(1-(cyclopropylsulfonyl)piperidin-4-yl)-4-fluoro-6-(trifluoromethyl)-[1,1'-biphenyl]-3-yl)methoxy)-5,5a,6,6atetrahydrocyclopropa[4,5]-cyclopenta[1,2-c]pyridine-6-carboxylic acid To a solution of product from Step C (70 mg, 0.105 mmol) in THF/EtOH/H$_2$O (1/1/1 mL) was added LiOH/H$_2$O (1.1 mL, 1 mol/L). The resulting solution was stirred at 20-24° C. for 18 h. After the reaction was finished, the reaction mixture was concentrated under vacuum. The resulting residue was re-dissolved in CH$_3$CN/H$_2$O/DMSO (2/1/1 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.05 (s, 1H), 7.53 (d, 1H, J=10.5 Hz), 7.44 (d, 1H, J=7.0 Hz), 7.30 (d, 2H, J=8.0 Hz), 7.21 (d, 2H, J=8.0 Hz), 6.69 (s, 1H), 5.45 (s, 2H), 3.88 (dd, 2H, J=10.0, 2.0 Hz), 3.26-3.21 (m, 1H), 3.04-2.99 (m, 3H), 2.90-2.88 (m, 1H), 2.77-2.72 (m, 1H), 2.54-2.49 (m, 1H), 2.42-2.39 (m, 1H), 1.99-1.96 (m, 2H), 1.86-1.77 (m, 2H), 1.13-1.01 (m, 5H). MS (ESI) m/e (M+H$^+$): 631.

Example 7

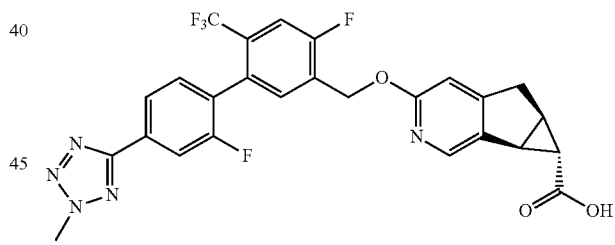

(5aR,6S,6aS)-3-((2',4-difluoro-4'-(2-methyl-2H-tetrazol-5-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

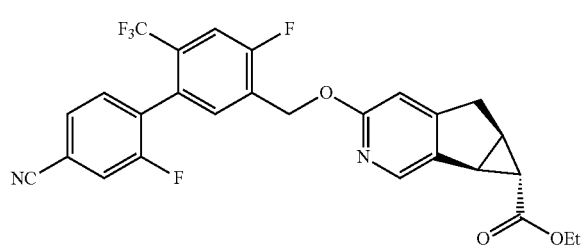 [SMILES: CCOC(=O)[C@H]1[C@@H]2Cc3cc(OCc4cc(-c5ccc(C#N)cc5F)c(C(F)(F)F)cc4F)ncc3[C@@H]21]

Step A: (5aR,6S,6aS)-ethyl 3-((4'-cyano-2',4-difluoro-6-(trifluoromethyl)-[1,1'-biphenyl]-3-yl)methoxy)-5,5a,6,6a-tetrahydrocyclopropa[4,5]cyclopenta[1,2-c]pyridine-6-carboxylate A solution of Intermediate 2 (200 mg, 0.422 mmol) and 4-cyano-2-fluorophenylboronic acid (156 mg, 0.633 mmol) in THF (4.2 mL) was sparged with $N_2$ for 10 minutes. To this solution was added $2^{nd}$ generation XPHOS precatalyst (33.2 mg, 0.042 mmol) and $K_3PO_4/H_2O$ (0.843 mL, 1 mol/L). The solution was sparged with $N_2$ for 10 minutes. The reaction mixture was stirred at 65° C. for 3 h. The reaction was partitioned between $H_2O$ and EtOAc (3×5 mL). The combined organic layers were concentrated and purified by silica gel chromatography (Biotage 25 g SNAP), eluting with hexane and EtOAc (100:0 to 50:50) to give the title compound. MS (ESI) m/e (M+H$^+$): 515.

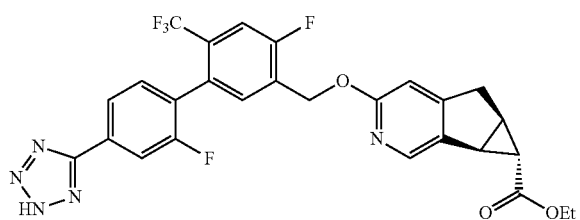 [SMILES: CCOC(=O)[C@H]1[C@@H]2Cc3cc(OCc4cc(-c5ccc(-c6nn[nH]n6)cc5F)c(C(F)(F)F)cc4F)ncc3[C@@H]21]

Step B: (5aR,6S,6aS)-ethyl 3-((2',4-difluoro-4'-(1H-tetrazol-5-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylate To a solution of product from Step A (50 mg, 0.097 mmol) in toluene (3 mL) was added azidotrimethyltin (80 mg, 0.389 mmol). The reaction mixture was stirred at 110° C. for 20 h. The reaction was partitioned between $H_2O$ and EtOAc (3×5 mL). The combined organic layers were concentrated and purified by silica gel chromatography (Biotage 25 g SNAP), eluting with hexane and EtOAc (100:0 to 50:50) to give the title compound. MS (ESI) m/e (M+H$^+$): 558.

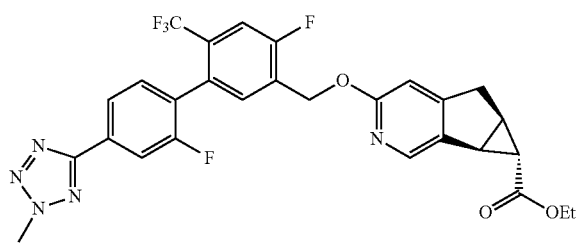 [SMILES: CCOC(=O)[C@H]1[C@@H]2Cc3cc(OCc4cc(-c5ccc(-c6nnn(C)n6)cc5F)c(C(F)(F)F)cc4F)ncc3[C@@H]21]

Step C: (5aR,6S,6aS)-ethyl 3-((2',4-difluoro-4'-(2-methyl-2H-tetrazol-5-yl)-6-(trifluoromethyl)-[1,1'-biphenyl]-3-yl)methoxy)-5,5a,6,6atetrahydrocyclopropa[4,5]-cyclopenta[1,2-c]pyridine-6-carboxylate To a solution of product from Step B (45.4 mg, 0.048 mmol) in DMF (1 mL) was added iodomethane (6.03 μL, 0.097 mmol) and potassium carbonate (13.39 mg, 0.097 mmol). The reaction mixture was stirred at 20-24° C. for 20 h. The product was detected by LCMS. The reaction was partitioned between $H_2O$ and EtOAc (5/5 mL). The organic phase was separated and washed with $H_2O$ (3×5 mL), brine, dried over $MgSO_4$, filtered, and concentrated under vacuum to give the title crude compound containing trace amount of regio isomer. MS (ESI) m/e (M+H$^+$): 572.

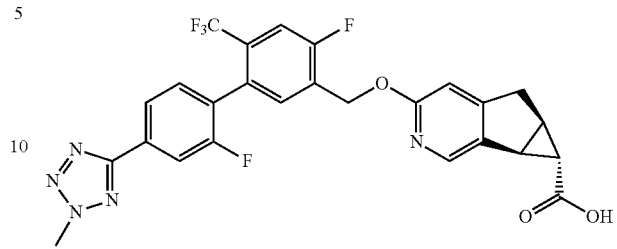

Step D: (5aR,6S,6aS)-3-((2',4-difluoro-4'-(2-methyl-2H-tetrazol-5-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid To a solution of product from Step C (27.7 mg, 0.048 mmol) in THF/EtOH/$H_2O$ (0.3/0.3/0.3 mL) was added LiOH/$H_2O$ (0.49 mL, 1 mol/L). The reaction mixture was stirred at 20-24° C. for 20 h. The reaction mixture was concentrated. The resulting residue was re-dissolved in $CH_3CN/H_2O$/DMSO (2/1/1 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.05 (s, 1H), 7.97 (dd, 1H J=8.0, 1.5 Hz), 7.88 (dd, 1H, J=10.0, 1.0 Hz), 7.63 (d, 1H, J=10.5 Hz), 7.56 (d, 1H, J=7.0 Hz), 7.41 (t, 1H, J=7.5 Hz), 6.70 (s, 1H), 5.48 (s, 2H), 4.44 (s, 3H), 3.23 (dd, 1H, J=18.5, 6.5 Hz), 3.02 (d, 1H, J=18.5 Hz), 2.91-2.89 (m, 1H), 2.43-2.39 (m, 1H), 1.13-1.12 (m, 1H). MS (ESI) m/e (M+H$^+$): 544.

Example 8

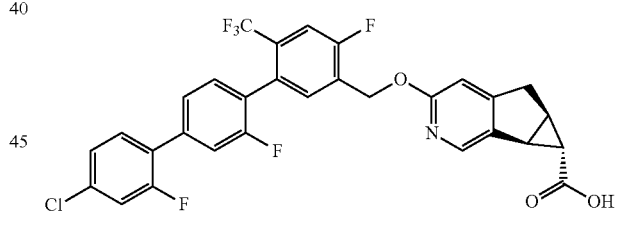

(5aR,6S,6aS)-3-((4''-chloro-2',2'',4-trifluoro-6-(trifluoromethyl)-[1,1':4',1''-terphenyl]-3-yl)methoxy)-5,5a,6,6a-tetrahydrocyclopropa[4,5]cyclopenta[1,2-c]pyridine-6-carboxylic acid

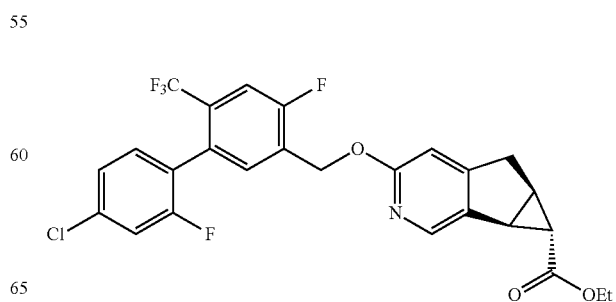

Step A: (5aR,6S,6aS)-ethyl 3-((4'-chloro-2',4-difluoro-6-(trifluoromethyl)-[1,1'-biphenyl]-3-yl)methoxy)-5,5a,6,6a-tetrahydrocyclopropa[4,5]cyclopenta[1,2-c]pyridine-6-carboxylate A solution of Intermediate 2 (500 mg, 1.054 mmol) and 4-chloro-2-fluorophenylboronic acid (276 mg, 1.581 mmol) in THF (10.5 mL) was sparged with $N_2$ for 10 minutes. To this solution was added $2^{nd}$ generation XPHOS pre catalyst (83 mg, 0.105 mmol) and $K_3PO_3/H_2O$ (2.1 mL, 1 mol/L). The solution was sparged with $N_2$ for 10 minutes. The reaction mixture was then stirred at 65° C. for 12 h. The reaction was partitioned between $H_2O$ and EtOAc (5/15 mL). The aqueous phase was separated and extracted with EtOAc (10 mL×2). The combined organic layers were washed with brine, dried over $MgSO_4$, concentrated and purified by column chromagraphy on silica gel, and eluting with hexane and EtOAc (100:0 to 60:40). The impure product fractions were collected and repurified by preparative HPLC (Reverse phase C-18) and eluting with $H_2O$ w/0.05% TFA and $CH_3CN$ w/0.05% TFA to give the title compound. MS (ESI) m/e (M+H$^+$): 524.

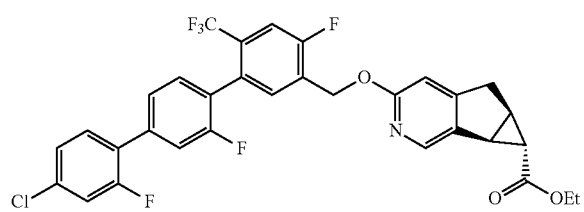 [SMILES: CCOC(=O)[C@H]1[C@@H]2Cc3cc(OCc4cc(-c5ccc(-c6ccc(Cl)cc6F)cc5F)c(C(F)(F)F)cc4F)ncc3[C@@H]21]

Step B: (5 aR,6S,6aS)-ethyl 3-((4''-chloro-2',2'',4-trifluoro-6-(trifluoromethyl)-[1,1':4',1''-terphenyl]-3-yl)methoxy)-5,5a,6,6a-tetrahydrocyclopropa[4,5]cyclopenta[1,2-c]pyridine-6-carboxylate A solution of the product from Step A, compound 5-1 of Scheme 5 (50 mg, 0.095 mmol) and 4-chloro-2-fluorophenylboronic acid (27.5 mg, 0.157 mmol) in dioxane (1 mL) was sparged with $N_2$ for 10 minutes. To this solution was added $2^{nd}$ generation XPHOS pre catalyst (11.26 mg, 0.014 mmol) and $K_3PO_3/H_2O$ (0.286 mL, 1 mol/L). The solution was sparged with $N_2$ for 10 minutes. The reaction mixture was then stirred at 80° C. for 30 h. Then the reaction was partitioned between $H_2O$ and EtOAc (3×5 mL). The aqueous phase was separated and extracted with EtOAc (5 mL×2). The combined organic layers were washed with brine, dried over $MgSO_4$, concentrated and purified by preparative HPLC (Reverse phase C-18) eluting with $H_2O$ w/0.05% TFA and $CH_3CN$ w/0.05% TFA to give the title compound. MS (ESI) m/e (M+H$^+$): 618.

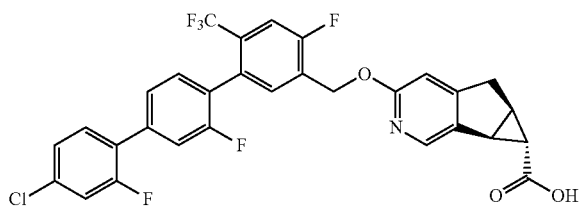 [SMILES: O=C(O)[C@H]1[C@@H]2Cc3cc(OCc4cc(-c5ccc(-c6ccc(Cl)cc6F)cc5F)c(C(F)(F)F)cc4F)ncc3[C@@H]21]

Step C: (5aR,6S,6aS)-3-((4''-chloro-2',2'',4-trifluoro-6-(trifluoromethyl)-[1,1':4',1''-terphenyl]-3-yl)methoxy)-5,5a,6,6a-tetrahydrocyclopropa[4,5]cyclopenta[1,2-c]pyridine-6-carboxylic acid To a solution of product from Step B (25 mg, 0.040 mmol) in THF/EtOH/$H_2O$ (0.3/0.3/0.3 mL) was added LiOH/$H_2O$ (0.41 mL, 1 mol/L). The reaction mixture was stirred at 20-24° C. for 20 h. The reaction mixture was concentrated. The resulting residue was re-dissolved in $CH_3CN/H_2O$/DMSO (1/0.5/0.5 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.05 (s, 1H), 7.63-7.53 (m, 3H), 7.43-7.30 (m, 5H), 6.71 (s, 1H), 5.48 (s, 2H), 3.22 (dd, 1H, J=18.5, 6.5 Hz), 3.01 (d, 1H, J=10.0 Hz), 2.86-2.85 (m, 1H), 2.39-2.36 (m, 1H), 1.10-1.08 (m, 1H). MS (ESI) m/e (M+H$^+$): 590.

The following Examples 9 and 10 was prepared in a similar manner to Example 8 using the appropriate intermediates and commercially available starting materials.

| Ex. No. | Structure | M.W. | Compound Name | LC/MS (ESI) observed [M + 1]+ |
|---|---|---|---|---|
| 9 | 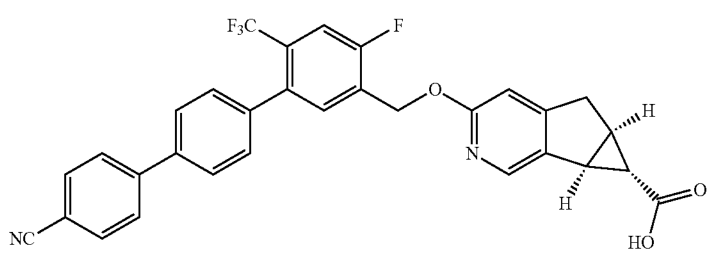 [SMILES: N#Cc1ccc(-c2ccc(-c3cc(COc4cc5c(cn4)[C@H]4[C@@H](C5)[C@@H]4C(=O)O)c(F)cc3C(F)(F)F)cc2)cc1] | 544 | (5aR,6S,6aS)-3-((4''-cyano-4-fluoro-6-(trifluoromethyl)-[1,1':4',1''-terphenyl]-3-yl)methoxy)-5,5a,6,6a-tetrahydrocyclopropa[4,5]cyclopenta[1,2-c]pyridine-6-carboxylic acid | 545 |

| Ex. No. | Structure | M.W. | Compound Name | LC/MS (ESI) observed [M + 1]+ |
|---|---|---|---|---|
| 10 | 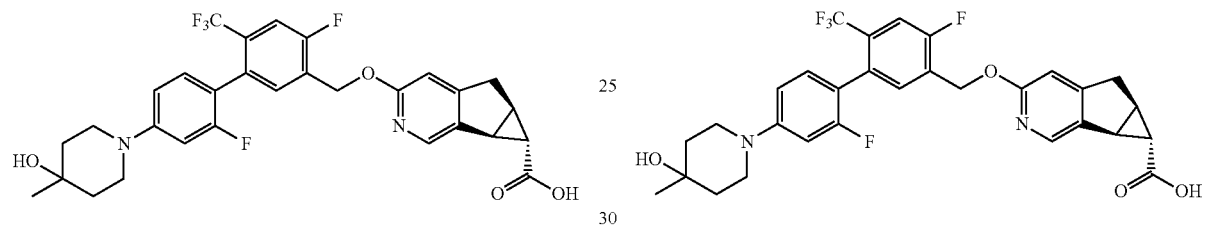 | 597 | (5aR,6S,6aS)-3-((4-fluoro-4''-(methylsulfonyl)-6-(trifluoromethyl)-[1,1';4',1''-terphenyl]-3-yl)methoxy)-5,5a,6,6a-tetrahydrocyclopropa[4,5]cyclpenta[1,2-c]pyridine-6-carboxylic acid | 598 |

Example 11

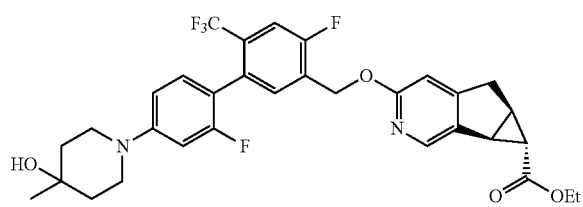 [SMILES: CCOC(=O)[C@H]1[C@@H]2Cc3cc(OCc4cc(-c5ccc(N6CCC(C)(O)CC6)cc5F)c(C(F)(F)F)cc4F)ncc3[C@@H]21]

(5aR,6S,6aS)-3-((2',4-difluoro-4'-(4-hydroxy-4-methylpiperidin-1-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid Step A: (5aR,6S,6aS)-ethyl 3-((2',4-difluoro-4'-(4-hydroxy-4-methylpiperidin-1-yl)-6-(trifluoromethyl)-[1,1'-biphenyl]-3-yl)methoxy)-5,5a,6,6atetrahydrocyclopropa[4,5]cyclopenta-[1,2-c]pyridine-6-carboxylate A solution of compound 5-1 of Scheme 5 (20 mg, 0.038 mmol), 4-methylpiperidin-4-ol HCl (11.58 mg, 0.076 mmol), 3$^{rd}$ Generation RuPhos-pre catalyst (3.19 mg, 3.82 μmol), cesium carbonate (37.3 mg, 0.115 mmol) were suspended in dioxane (1 ml) in a closed vial. The reaction was degassed and purged with nitrogen, then heated at 80° C. for 15 h. The reaction mixture was then partitioned between H$_2$O and EtOAc. The aqueous layer was extracted with EtOAc (5 mL×2). The combined organic layers were concentrated under vacuum and the resulting crude product was purified by chromatography over silica gel (eluting with hexane and EtOAc=100:0 to 20:80) to give the title compound. MS (ESI) m/e (M+H$^+$): 603.2

Step B: 5aR,6S,6aS)-3-((2',4-difluoro-4'-(4-hydroxy-4-methylpiperidin-1-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid To a solution of product from Step A (20 mg, 0.033 mmol) in THF/EtOH/H$_2$O (0.5/0.5/0.5 mL) was added LiOH/H$_2$O (0.17 mL, 1 mol/L). The resulting solution was stirred at 20-24° C. for 15 h, and then concentrated under vacuum. The resulting residue was re-dissolved in CH$_3$CN/H$_2$O/DMSO (2/1/1 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.05 (s, 1H), 7.52 (d, 1H, J=10.5 Hz), 7.43 (d, 1H, J=7.5 Hz), 7.02 (t, 1H, J=8.5 Hz), 6.78-6.76 (m, 1H), 6.72-6.69 (m, 2H), 5.45 (s, 2H), 3.43-3.38 (m, 2H), 3.27-3.21 (m, 3H), 3.03 (d, 1H), 2.91 (m, 1H), 2.43-2.40 (m, 1H), 1.72-1.69 (m, 4H), 1.26 (s, 3H), 1.14 (bs, 1H). MS (ESI) m/e (M+H$^+$): 575.25.

Example 12

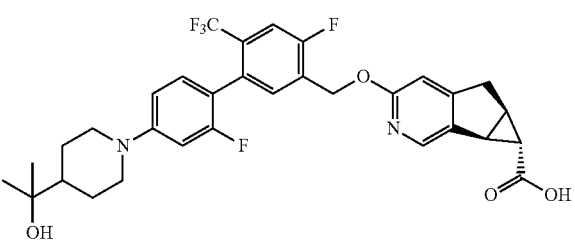 [SMILES: CC(C)(O)C1CCN(c2ccc(-c3cc(COc4cc5c(cn4)[C@H]4[C@@H](C5)[C@@H]4C(=O)O)c(F)cc3C(F)(F)F)c(F)c2)CC1]

(5aR,6S,6aS)-3-((2',4-difluoro-4'-(4-(2-hydroxypropan-2-yl)piperidin-1-yl)-6-(trifluoromethyl)-[1,1'-biphenyl]-3-yl)methoxy)-5,5a,6,6a-tetrahydrocyclopropa[4,5]cyclopenta[1,2-c]-pyridine-6-carboxylic acid

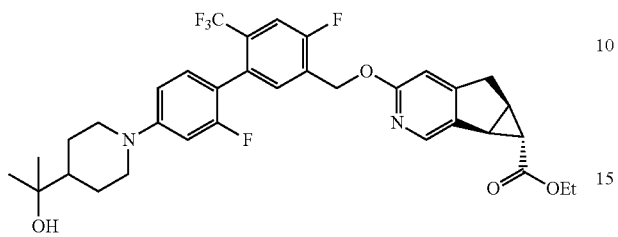

Step A: (5aR,6S,6aS)-ethyl 3-((2',4-difluoro-4'-(4-(2-hydroxypropan-2-yl)piperidin-1-yl)-6-(trifluoromethyl)-[1,1'-biphenyl]-3-yl)methoxy)-5,5a,6,6a-tetrahydrocyclopropa[4,5]cyclo-penta[1,2-c]pyridine-6-carboxylate A solution of compound 5-1 of Scheme 5 (50 mg, 0.095 mmol), 2-(piperidin-4-yl)propan-2-ol (27.3 mg, 0.19 mmol), 3rd Generation RuPhos-pre catalyst (8 mg, 9.5 μmol), cesium carbonate (93 mg, 0.29 mmol) were suspended in dioxane (2 ml) in a closed vial. The reaction was degassed and purged with nitrogen, then heated at 80° C. for 15 h. The reaction mixture was partitioned between H$_2$O and EtOAc. The aqueous layer was extracted with EtOAc (5 mL×2). The combined organic layers were concentrated under vacuum and the resulting crude product was purified by chromatography over silica gel (eluting with hexane and EtOAc=100:0 to 20:80) to give the title compound. MS (ESI) m/e (M+H$^+$): 631.3

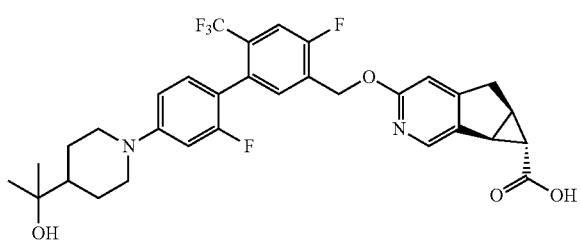 [SMILES: CC(C)(O)C1CCN(c2ccc(-c3cc(COc4cc5c(cn4)[C@H]4[C@@H](C5)[C@@H]4C(=O)O)c(F)cc3C(F)(F)F)c(F)c2)CC1]

Step B: (5aR,6S,6aS)-3-((2',4-difluoro-4'-(4-(2-hydroxypropan-2-yl)piperidin-1-yl)-6-(trifluoromethyl)-[1,1'-biphenyl]-3-yl)methoxy)-5,5a,6,6a-tetrahydrocyclopropa[4,5]cyclo penta[1,2-c]pyridine-6-carboxylic acid To a solution of product from Step A (45 mg, 0.07 mmol) in THF/EtOH/H$_2$O (0.5/0.5/0.5 mL) was added LiOH/H$_2$O (0.35 mL, 1 mol/L). The resulting solution was stirred at 20-24° C. for 15 h. After the reaction was finished, the reaction mixture was concentrated under vacuum. The resulting residue was re-dissolved in CH$_3$CN/H$_2$O/DMSO (2/1/1 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.05 (s, 1H), 7.52 (d, 1H, J=10.5 Hz), 7.43 (d, 1H, J=7.5 Hz), 7.02 (t, 1H, J=9 Hz), 6.78-6.76 (m, 1H), 6.71-6.68 (m, 2H), 5.45 (s, 2H), 3.85 (d, 2H, J=11.5 Hz), 3.27-3.21 (m, 1H), 3.03 (d, 1H), 2.91 (m, 1H), 2.69 (m, 2H), 2.42 (m, 1H), 1.88 (m, 2H), 1.46 (m, 3H), 1.18 (s, 6H), 1.13 (t, 1H, J=3 Hz). MS (ESI) m/e (M+H$^+$): 603.28.

Example 13

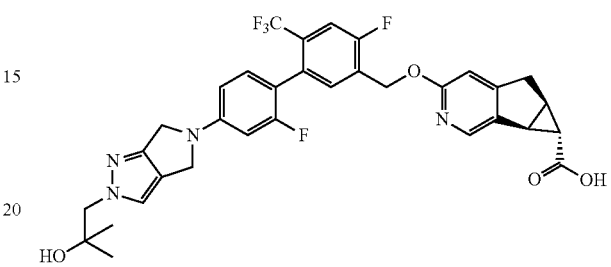

(5aR,6S,6aS)-3-((2',4-difluoro-4'-(2-(2-hydroxy-2-methylpropyl)pyrrolo[3,4-c]pyrazol-5(2H,4H,6H)-yl)-6-(trifluoromethyl)-[1,1'-biphenyl]-3-yl)methoxy)-5,5a,6,6a-tetrahydrocyclo-propa[4,5]cyclopenta[1,2-c]pyridine-6-carboxylic acid

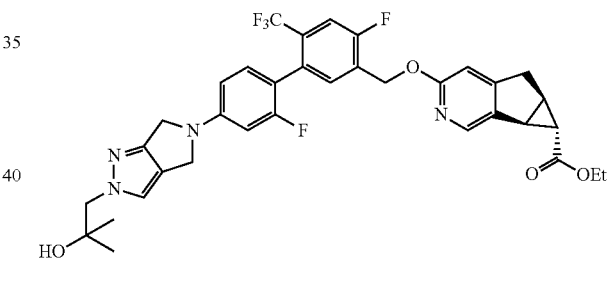

Step A: (5aR,6S,6aS)-ethyl-3-((2',4-difluoro-4'-(2-(2-hydroxy-2-methylpropyl)-pyrrolo[3,4-c]pyrazol-5(2H,4H,6H)-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylate A solution of compound 5-1 of Scheme 5 (20 mg, 0.038 mmol), 1-(5,6-dihydropyrrolo[3,4-c]pyrazol-2(4H)-yl)-2-methylpropan-2-ol, TFA (17 mg, 0.057 mmol), 3$^{rd}$ Generation RuPhos-pre catalyst (3.1 mg, 3.8 μmol), cesium carbonate (37.3 mg, 0.12 mmol) were suspended in dioxane (1 ml) in a closed vial. The reaction was degassed and purged with nitrogen, then heated at 80° C. for 15 h. The reaction mixture was partitioned between H$_2$O and EtOAc. The aqueous layer was extracted with EtOAc (5 mL×2). The combined organic layers were concentrated under vacuum and the resulting crude product was purified by chromatography over silica gel (eluting with hexane and EtOAc=100:0 to 20:80) to give the title compound. MS (ESI) m/e (M+H$^+$): 669.3.

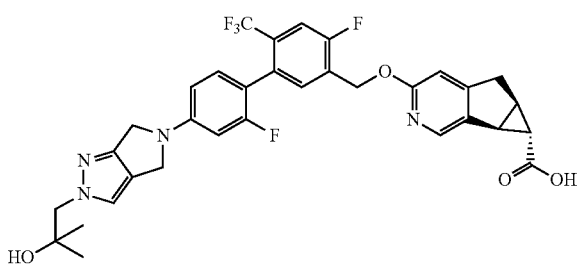

Step B: (5aR,6S,6aS)-3-((2',4-difluoro-4'-(2-(2-hydroxy-2-methylpropyl)pyrrolo[3,4-c]pyrazol-5(2H, 4H,6H)-yl)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid To a solution of product from Step A (17 mg, 0.025 mmol) in THF/EtOH/H$_2$O (0.5/0.5/0.5 mL) was added LiOH/H$_2$O (0.13 mL, 1 mol/L). The resulting solution was stirred at 20-24° C. for 5 h, and then concentrated under vacuum. The resulting residue was re-dissolved in CH$_3$CN/H$_2$O/DMSO (2/1/1 mL), acidified by adding formic acid to adjust pH to 5, and directly purified by preparative HPLC (over C18 column using a gradient of acetonitrile in water w/0.1% formic acid) to give the title compound. $^1$H NMR (500 MHz, MeOD-d$_4$): δ: 8.05 (s, 1H), 7.54-7.44 (m, 3H), 7.05 (t, 1H, J=8.5 Hz), 6.71 (s, 1H), 6.51-6.43 (m, 2H), 5.45 (s, 2H), 4.44 (s, 3H), 4.11 (s, 2H), 3.27-3.21 (m, 1H), 3.03 (d, 1H), 2.91 (m, 1H), 2.42 (m, 1H), 1.18 (s, 6H), 1.13 (t, 1H, J=3 Hz). MS (ESI) m/e (M+H$^+$): 641.3.

Example 14

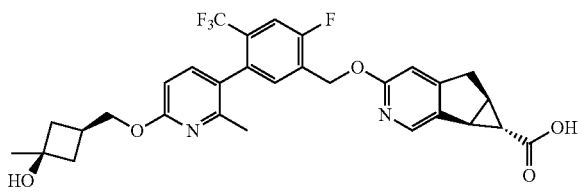 [SMILES: Cc1nc(OC[C@H]2C[C@@](C)(O)C2)ccc1-c1cc(COc2cc3c(cn2)[C@H]2[C@@H](C3)[C@@H]2C(=O)O)c(F)cc1C(F)(F)F]

(5 aR,6S,6aS)-3-((2-fluoro-5-(6-(((1s,3s)-3-hydroxy-3-methylcyclobutyl)methoxy)-2-methylpyridin-3-yl)-4-(trifluoromethyl)benzyl)oxy)-5,5a,6,6a-tetrahydrocyclopropa-[4,5]cyclopenta[1,2-c]pyridine-6-carboxylic acid

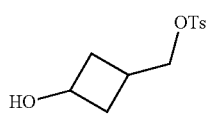

Step A: (3-hydroxycyclobutyl)methyl 4-methylbenzenesulfonate

To a mixture of triethylamine (111.0 g, 1.102 mol), DMAP (5.38 g, 44.1 mmol) and 3-(hydroxymethyl)-cyclobutanol (45 g, 441 mmol) in DCM (500 mL) at 0° C. was added 4-methylbenzene-1-sulfonyl chloride (76 g, 397 mmol). The reaction mixture was stirred at 25° C. for 16 h, then washed with water (150 mL×3) and brine (100 mL), dried over anhydrous Na$_2$SO$_4$, and concentrated in vacuo. The resulting residue was purified by column chromatography on silica gel, eluting with PE/EtOAc=1:1 to give the title compound. $^1$H NMR (400 MHz, CDCl$_3$) δ: 7.61-7.79 (m, 2H), 7.22-7.34 (m, 2H), 3.92 (dd, J=11.74, 6.65 Hz, 2H), 2.38 (s, 3H), 1.81-2.34 (m, 5H), 1.48-1.63 (m, 1H).

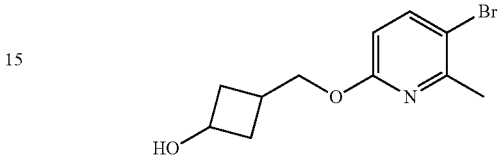

Step B: 3-(((5-bromo-6-methylpyridin-2-yl)oxy)methyl)cyclobutanol

A mixture of (3-hydroxycyclobutyl)methyl 4-methylbenzenesulfonate (10.0 g, 39.0 mmol), 5-bromo-6-methylpyridin-2-ol (8.80 g, 46.8 mmol) and K$_2$CO$_3$ (13.48 g, 98 mmol) in DMF (100 mL) was stirred at 100° C. for 16 h. Then the reaction mixture was cooled to room temperature and poured into water (300 mL). The resulting mixture was extracted with EtOAc (100 mL×3), and the combined organic layers were washed with brine (100 mL), dried over anhydrous MgSO$_4$, and filtered. The filtrate was concentrated in vacuo to give the crude product, which was purified by flash column chromatography on silica gel (PE:EtOAc=10:1 to 4:1) to give the title compound. $^1$H NMR (400 MHz, CDCl$_3$) δ: 7.59 (d, J=8.61 Hz, 1H), 6.43 (d, J=8.61 Hz, 1H), 4.21 (dd, J=9.39, 6.65 Hz, 2H), 2.42-2.56 (m, 4H), 2.06-2.36 (m, 3H), 1.70-1.91 (m, 2H). MS (ESI) m/e (M+H$^+$): 272.1/274.1

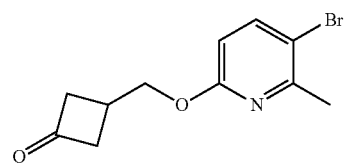

Step C: 3-(((5-bromo-6-methylpyridin-2-yl)oxy)methyl)cyclobutanone

To a solution of 3-(((5-bromo-6-methylpyridin-2-yl)oxy)methyl)cyclobutanol (6.5 g, 23.9 mmol) in CH$_2$Cl$_2$ (50 mL) was added Dess-Martin Periodinane (15.20 g, 35.8 mmol). The reaction mixture was stirred at 20° C. for 3 h, then poured into a cooled, stirred saturated solution of NaHCO$_3$/Na$_2$S$_2$O$_3$ (1:1, 150 mL). The resulting mixture was stirred vigorously for 30 min, then the aqueous layer was separated and extracted with DCM (50 mL×3). The combined organic layers were washed with brine (100 mL), dried over anhydrous MgSO$_4$ and filtered. The filtrate was concentrated to give a residue, which was purified by flash column chromatography on silica gel (PE:EtOAc=4:1) to give the title compound. $^1$H NMR (400 MHz, CDCl$_3$) δ: 7.62 (d, J=8.61 Hz, 1H), 6.46 (d, J=8.61 Hz, 1H), 4.41 (d, J=6.26 Hz, 2H), 3.15-3.25 (m, 2H), 2.94-3.03 (m, 2H), 2.82-2.92 (m, 1H), 2.52 (s, 3H). MS (ESI) m/e (M+H⁺): 270.0/272.0

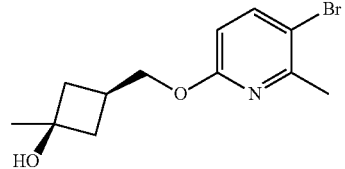 [SMILES: Cc1nc(OC[C@H]2C[C@@](C)(O)C2)ccc1Br]

Step D: (1s,3s)-3-(((5-bromo-6-methylpyridin-2-yl)oxy)methyl)-1-methylcyclobutanol To a solution of 3-(((5-bromo-6-methylpyridin-2-yl)oxy)methyl)cyclobutanone (5.1 g, 18.9 mmol) in THF (50 mL) at −78° C. under a nitrogen atmosphere was added methylmagnesium bromide (6.9 mL, 3M in ether, 20.6 mmol) dropwise. The mixture was warmed to 10° C. and stirred for 4 h, then saturated aqueous NH₄Cl (100 mL) was added to quench the reaction. The mixture was extracted with EtOAc (50 mL×3) and the combined organic layers were dried over anhydrous Na₂SO₄ and filtered. The filtrate was concentrated to give a residue, which was purified by flash column chromatography on silica gel (PE:EtOAc=4:1) to give the title compound. ¹H NMR (400 MHz, CDCl₃) δ: 7.60 (d, J=8.61 Hz, 1H), 6.44 (d, J=8.61 Hz, 1H), 4.23 (d, J=5.48 Hz, 2H), 2.52 (s, 3H), 2.17-2.27 (m, 2H), 1.90-2.06 (m, 2H), 1.40 (s, 3H). MS (ESI) m/e (M+H⁺): 286.0/288.0

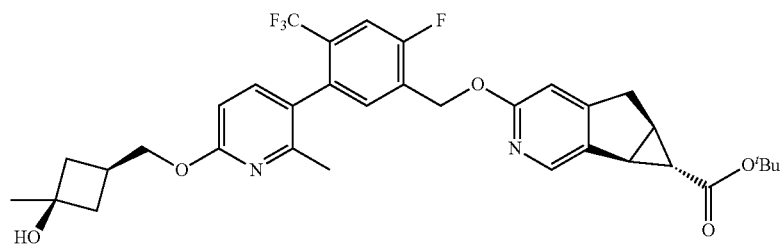 [SMILES: Cc1nc(OC[C@H]2C[C@@](C)(O)C2)ccc1-c1cc(COc2cc3c(cn2)[C@H]2[C@@H](C3)[C@@H]2C(=O)OC(C)(C)C)c(F)cc1C(F)(F)F]

Step E: (5aR,6S,6aS)-tert-butyl 3-((2-fluoro-5-(6-(((1s,3s)-3-hydroxy-3-methyl-cyclobutyl)methoxy)-2-methylpyridin-3-yl)-4-(trifluoromethyl)benzyl)oxy)-5,5a,6,6a-tetrahydrocyclopropa[4,5]cyclopenta[1,2-c]pyridine-6-carboxylate A mixture of Pd(dppf)Cl₂ (0.506 g, 0.692 mmol), K₂CO₃ (2.390 g, 17.29 mmol), (5aR,6S,6aS)-tert-butyl 3-((2-fluoro-5-(4,4,5,5-tetramethyl-1,3,2-dioxaborolan-2-yl)-4-(trifluoromethyl)-benzyl)oxy)-5,5a,6,6a-tetrahydrocyclopropa[4,5]cyclopenta[1,2-c]pyridine-6-carboxylate (3.8 g, 6.92 mmol), and (1s,3s)-3-(((5-bromo-6-methylpyridin-2-yl)oxy)methyl)-1-methylcyclobutanol (2.177 g, 7.61 mmol) in THF (15 ml)/water (6 mL) in a sealed tube under a N₂ atmosphere was irradiated by microwave to 100° C. for 30 min. After cooling to room temperature, the mixture was diluted with EtOAc (100 mL). The organic layer was separated, washed with water (30 mL) and brine (30 mL), dried over anhydrous Na₂SO₄ and concentrated in vacuo. The resulting residue was purified by column chromatography on silica gel eluting with PE:EA=3:1 to give the title compound. ¹H NMR (400 MHz, methanol-d₄) δ: 8.02 (s, 1H), 7.54-7.63 (m, 1H), 7.30-7.44 (m, 2H), 6.68 (s, 1H), 6.61 (d, J=8.22 Hz, 1H), 5.45 (d, J=3.52 Hz, 2H), 4.25 (d, J=6.26 Hz, 2H), 3.14-3.26 (m, 1H), 3.02 (s, 1H), 2.78-2.88 (m, 1H), 2.08-2.41 (m, 5H), 2.01 (s, 3H), 1.92-1.96 (m, 1H), 1.43 (s, 9H), 1.35 (s, 3H), 1.07 (br. s., 1H). MS (ESI) m/e (M+H⁺): 629.3

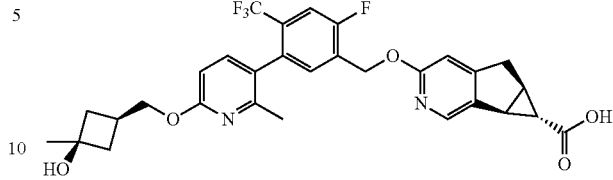

Step F: (5aR,6S,6aS)-3-((2-fluoro-5-(6-(((1s,3s)-3-hydroxy-3-methylcyclobutyl)-methoxy)-2-methyl-pyridin-3-yl)-4-(trifluoromethyl)benzyl)oxy)-5,5a,6,6a-tetrahydro-cyclopropa[4,5]cyclopenta[1,2-c]pyridine-6-carboxylic acid NaOH (0.445 g, 11.13 mmol) was added to a stirred mixture of (5aR,6S,6aS)-tert-butyl 3-((2-fluoro-5-(6-((3-hydroxy-3-methylcyclobutyl)methoxy)-2-methylpyridin-3-yl)-4-(trifluoro-methyl)benzyl)oxy)-5,5a,6,6a-tetrahydrocyclopropa[4,5]cyclopenta[1,2-c]pyridine-6-carboxylate (3.5 g, 5.57 mmol) in THF (10 mL)/water (10 mL)/MeOH (10 mL) The mixture was stirred at 50° C. for 2 h, then acidified with 2N HCl (aqueous, 30 mL) to pH=5, and extracted with ethyl acetate (3×100 mL). The combined organic layers were washed with brine (50 mL), dried with anhydrous Na₂SO₄ and concentrated under reduced pressure to give the crude product. The crude product was purified by flash silica gel chromatography (ISCO®; 40 g SepaFlash® Silica Flash Column, Eluent of 0~50% EtOAc/PE gradient @ 40 mL/min) to give the title compound. ¹H NMR (400 MHz, methanol-d₄) δ: 8.02 (s, 1H), 7.56 (d, J=10.17 Hz, 1H), 7.38 (d, J=6.65 Hz, 1H), 7.33 (d, J=8.61 Hz, 1H), 6.66 (s, 1H), 6.60 (d, J=8.61 Hz, 1H), 5.44 (d, J=3.13 Hz, 2H), 4.24 (d, J=6.26 Hz, 2H), 3.16-3.26 (m, 1H), 2.95-3.05 (m, 1H), 2.85-2.92 (m, 1H), 2.40 (d, J=3.13 Hz, 1H), 2.09-2.35 (m, 3H), 2.01 (d, J=1.96 Hz, 3H), 1.90-1.98 (m, 2H), 1.32-1.38 (m, 3H), 1.11 (d, J=2.35 Hz, 1H). MS (ESI) m/e (M+H⁺): 573.2.

Example 15

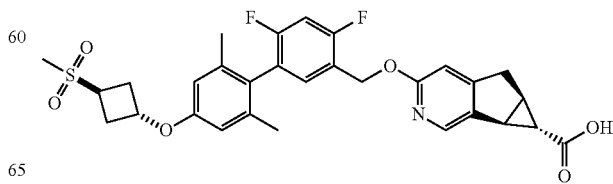

(5aR,6S,6aS)-3-((4,6-difluoro-2',6'-dimethyl-4'-(1r,3r)-3-(methylsulfonyl)cyclobutoxy)-[1,1'-biphenyl]-3-yl)methoxy)-5,5a,6,6a-tetrahydrocyclopropa[4,5]cyclopenta[1,2-c]pyridine-6-carboxylic acid

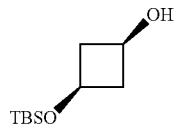

Step A:
cis-3-((tert-butyldimethylsilyl)oxy)cyclobutanol

To a solution of 3-((tert-butyldimethylsilyl)oxy)cyclobutanone (5.0 g, 24.7 mmol) in methanol (20 mL) at 0° C. was added NaBH₄ (1.04 g, 27.5 mmol) in portions. The resulting mixture was stirred at 0° C. for 1 h, then HCl (aqueous, 1M) was added to quench the reaction and the insoluble solids were filtered off. The filtrate was concentrated to give the title compound, which was used in the next step without purification.

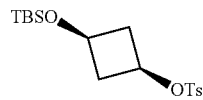 [SMILES: Cc1ccc(S(=O)(=O)O[C@H]2C[C@@H](O[Si](C)(C)C(C)(C)C)C2)cc1]

Step B:
cis-3-((tert-butyldimethylsilyl)oxy)cyclobutyl 4-methylbenzenesulfonate To a solution of cis-3-((tert-butyldimethylsilyl)oxy)cyclobutanol (5.00 g, 24.7 mmol), triethylamine (5.00 g, 49.4 mmol) in dry DCM (60 mL) at 0° C. was added 4-methyl-benzene-1-sulfonyl chloride (5.65 g, 29.7 mmol). The resulting mixture was stirred at 40° C. for 15 h, then cooled to rt and diluted with DCM (100 mL). The DCM layer was washed with brine (20 mL), dried over anhydrous Na₂SO₄ and concentrated in vacuo. The resulting residue was purified via silica gel chromatography (PE:EtOAc=5:1 Rf=0.4) to afford the title compound.

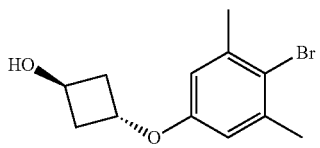

Step C:
trans-3-(4-bromo-3,5-dimethylphenoxy)cyclobutanol

A mixture of cis-3-((tert-butyldimethylsilyl)oxy)cyclobutyl 4-methylbenzenesulfonate (8.7 g, 24.4 mmol), 4-bromo-3,5-dimethylphenol (5.89 g, 29.3 mmol), and Cs₂CO₃ (11.93 g, 36.6 mmol) in dry 1-methyl-2-pyrrolidinone (60 mL) was stirred at 90° C. for 16 h. After cooling to room temperature, the mixture was diluted with EtOAc (100 mL). The organic layer was washed with water (30 mL) and brine (30 mL), dried over anhydrous Na₂SO₄ and concentrated in vacuo. The resulting residue was purified by column chromatography on silica gel (PE:EtOAc=5:1 Rf=0.43) to afford the title compound. ¹H NMR (400 MHz, CDCl₃) δ: 6.53 (s, 2H), 4.88-4.78 (m, 1H), 4.68-4.57 (m, 1H), 2.53-2.45 (m, 2H), 2.41 (dd, J=4.8, 6.8 Hz, 2H), 2.37 (s, 6H).

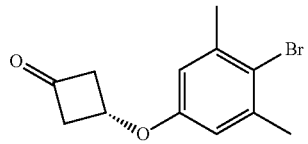

Step D:
3-(4-bromo-3,5-dimethylphenoxy)cyclobutanone

To a solution of trans-3-(4-bromo-3,5-dimethylphenoxy)cyclobutanol (2.5 g, 9.22 mmol) in DCM (20 mL) at 0° C. was added Dess-Martin Periodinane (5.87 g, 13.8 mmol). The reaction mixture was stirred at 15° C. for 16 h. The mixture was poured into a cooled and stirred saturated solution of NaHCO₃/Na₂S₂O₃ (1:1; 50 mL). The resulting mixture was stirred vigorously for 30 min, then the aqueous layers were separated and extracted with DCM (20 mL×2). The combined organic layers were washed with brine (30 mL), dried over anhydrous MgSO₄ and filtered. The filtrate was concentrated to give a residue, which was purified by flash column chromatography on silica gel, eluting with 0-25% EtOAc in hexanes, then 25% EtOAc in hexanes to give the title compound 3-(4-bromo-3,5-dimethylphenoxy)cyclobutanone. ¹H NMR (400 MHz, CDCl₃) δ: 6.61-6.56 (m, 2H), 4.98-4.85 (m, 1H), 3.54-3.40 (m, 2H), 3.30-3.15 (m, 2H), 2.37 (s, 6H)

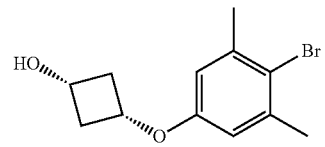

Step E:
cis-3-(4-bromo-3,5-dimethylphenoxy)cyclobutanol

To a solution of 3-(4-bromo-3,5-dimethylphenoxy)cyclobutanone (2.3 g, 8.55 mmol) in MeOH (20 mL) at 0° C. was added NaBH₄ (0.388 g, 10.26 mmol) in portions. The resulting mixture was stirred at 0° C. for 1 h. Then HCl (aqueous, 1M) was added to quench the reaction and the insoluble solids were filtered off. The filtrate was concentrated to give a residue, which was purified by silica gel column, eluting with 0-40% EtOAc in hexanes, then 40% EtOAc in hexanes to give the title compound. ¹H NMR (400 MHz, CDCl₃) δ: 6.56 (S, 2H), 4.14-4.29 (m, 1H), 4.04-4.07 (m, 1H), 2.90-2.94 (m, 2H), 2.06-2.11 (m, 2H), 2.34 (s, 6H).

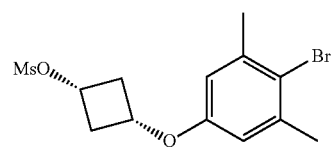 [SMILES: Cc1cc(O[C@H]2C[C@@H](OS(C)(=O)=O)C2)cc(C)c1Br]

Step F:
cis-3-(4-bromo-3,5-dimethylphenoxy)cyclobutyl methanesulfonate

To a solution of cis-3-(4-bromo-3,5-dimethylphenoxy)cyclobutanol (2.28 g, 8.41 mmol) in CH₂Cl₂ (40 mL) and Et₃N (1.75 ml, 12.61 mmol) at 0° C. was added MsCl (0.786 mL, 10.1 mmol). The reaction mixture was stirred at this temperature for 1 hour. Then the mixture was diluted with DCM (50 mL), washed with brine (15 mL), dried over anhydrous MgSO₄ and filtered. The filtrate was concentrated and the resulting residue was purified by silica gel column chromatography (PE/EtOAc=4/1) to give the title compound.

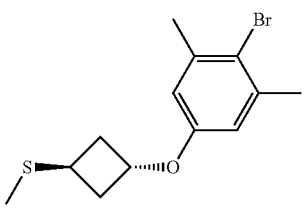

Step G: (trans-3-(4-bromo-3,5-dimethylphenoxy)cyclobutyl)(methyl)sulfane

A mixture of sodium methanethiolate (0.45 g, 6.44 mmol) and cis-3-(4-bromo-3,5-dimethyl-phenoxy)cyclobutyl methanesulfonate (1.5 g, 4.3 mmol) in NMP (20 mL) was placed in a sealed tube. The reaction mixture was irradiated in a microwave oven at 100° C. for 30 min. Then the mixture was cooled to rt and diluted with ethyl acetate (50 mL). The organic layer was washed with brine (8 mL), dried over anhydrous MgSO₄ and concentrated under reduced pressure. The resulting residue was purified by flash chromatography on silica gel, eluting with PE/EtOAc=20:1, to give the title compound.

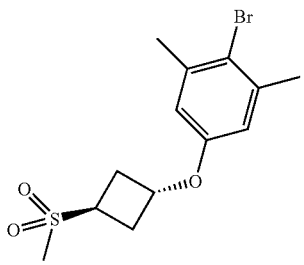 [SMILES: Cc1cc(O[C@H]2C[C@H](S(C)(=O)=O)C2)cc(C)c1Br]

Step H: 2-bromo-1,3-dimethyl-5-((1r,3r)-3-(methyl-sulfonyl)cyclobutoxy)benzene To a solution of (trans-3-(4-bromo-3,5-dimethylphenoxy)cyclobutyl)(methyl)sulfane (1.2 g, 3.98 mmol) in CH₂Cl₂ (10 mL) at 25° C. was added mCPBA (1.65 g, 9.56 mmol). The reaction mixture was stirred at 25° C. for 4. Then the reaction mixture was diluted with DCM (50 mL), washed with saturated NaHCO₃ twice, washed by brine, dried over anhydrous MgSO₄ and concentrated under reduced pressure. The resulting residue was purified by silica gel column, eluting with 0-50% EtOAc in hexanes, then 50% EtOAc in hexanes, to give the title compound. MS (ESI) m/e (M+H⁺): 333.1/335.1

Step I: (5 aR,6S,6 aS)-tert-butyl 3-((4,6-di fluoro-2',6'-dimethyl-4'-((1r,3r)-3-(methyl-sulfonyl)cyclobutoxy)-[1,1'-biphenyl]-3-yl)methoxy)-5,5a,6,6a-tetrahydro-cyclopropa-[4,5]cyclopenta[1,2-c]pyridine-6-carboxylate A mixture of 2-bromo-1,3-dimethyl-5-((1r,3r)-3-(methyl-sulfonyl)cyclobutoxy)benzene (800 mg, 2.40 mmol), K₂CO₃ (664 mg, 4.80 mmol), 1,1'-bis(di-tert-butylphosphino)ferrocene palladium dichloride (156.0 mg, 0.240 mmol) and (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclo-propa[4,5]cyclo-penta[1,2-c]pyridine-6-carboxylate (1319 mg, 2.64 mmol) in THF (6 mL)/water (2 mL) was irradiated by microwave to 100° C. for 30 min under a nitrogen atmosphere. After cooling to room temperature, the reaction mixture was diluted with EtOAc (50 mL). The organic layer was separated, washed with water (20 mL) and brine (20 mL), dried over anhydrous Na₂SO₄ and concentrated in vacuo. The resulting residue was purified by silica gel preparative TLC (PE:EtOAc=5:1, Rf=0.4) to give the title compound. MS (ESI) m/e (M+H⁺): 626.1

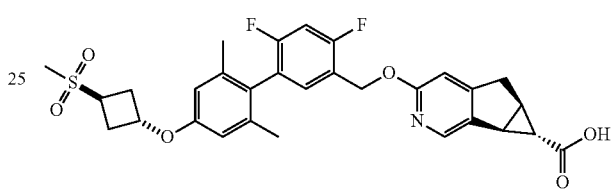

Step J: (5aR,6S,6aS)-3-((4,6-difluoro-2',6'-dimethyl-4'-((1r,3r)-3-(methylsulfonyl)-cyclobutoxy)-[1,1'-biphenyl]-3-yl)methoxy)-5,5a,6,6a-tetrahydrocyclopropa[4,5]-cyclopenta-[1,2-c]pyridine-6-carboxylic acid To a mixture of (5aR,6S,6aS)-tert-butyl 3-((4,6-difluoro-2',6'-dimethyl-4'-((1r,3r)-3-(methylsulfonyl)cyclobutoxy)-[1,1'-biphenyl]-3-yl)methoxy)-5,5a,6,6a-tetrahydrocyclopropa[4,5]cyclopenta[1,2-c]pyridine-6-carboxylate (976 mg, 1.56 mmol) in MeOH (3 mL) THF (3 mL)/water (3 mL) was added NaOH (437 mg, 10.9 mmol). The reaction mixture was stirred at room temperature for 12 h, then acidified with HCl (2 N) to pH=3, and extracted with ethyl acetate (2×10 mL). The combined organic layers were washed with water, brine, dried over Na₂SO₄ and concentrated in vacuo to afford the title compound. ¹H NMR (400 MHz, methanol-d₄) δ: 8.05 (s, 1H), 7.22 (t, J=8.22 Hz, 1H), 7.05 (t, J=9.59 Hz, 1H), 6.67 (s, 1H), 6.56 (s, 2H), 5.35 (s, 2H), 3.90-4.01 (m, 1H), 3.18-3.25 (m, 1H), 3.02 (d, J=18.39 Hz, 1H), 2.94 (s, 3H), 2.52-2.64 (m, 2H), 2.42 (d, J=3.13 Hz, 1H), 1.96-2.02 (m, 2H), 1.92 (s, 6H), 1.11 (br. s., 1H). MS (ESI) m/e (M+H⁺): 570.1

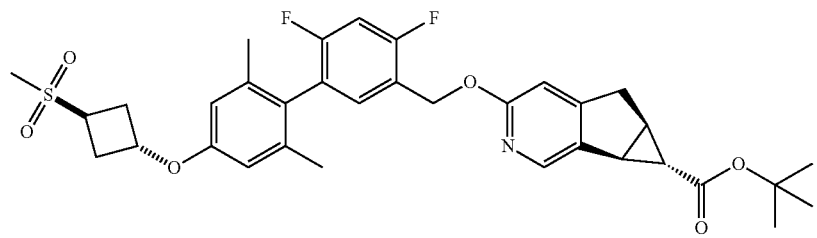 [SMILES: Cc1cc(O[C@H]2C[C@H](S(C)(=O)=O)C2)cc(C)c1-c1cc(COc2cc3c(cn2)[C@H]2[C@@H](C3)[C@@H]2C(=O)OC(C)(C)C)c(F)cc1F]

Example 16

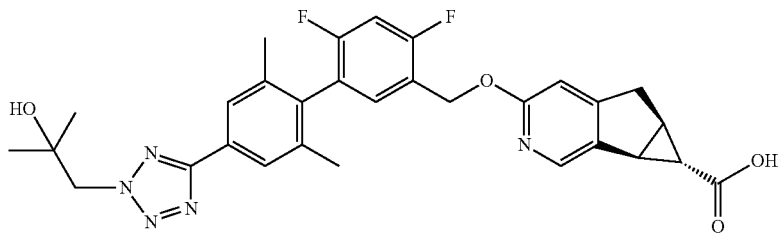 [SMILES: Cc1cc(-c2nnn(CC(C)(C)O)n2)cc(C)c1-c1cc(COc2cc3c(cn2)[C@H]2[C@@H](C3)[C@@H]2C(=O)O)c(F)cc1F]

(5aR,6S,6aS)-3-((4,6-difluoro-4'-(2-(2-hydroxy-2-methylpropyl)-2H-tetrazol-5-yl)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

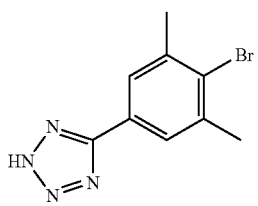

Step A: 5-(4-bromo-3,5-dimethylphenyl)-2H-tetrazole

To a solution of 4-bromo-3,5-dimethylbenzonitrile (2.30 g, 10.95 mmol) and trimethylsilyl azide (2.52 g, 21.9 mmol) in toluene (30 mL) was added dibutylstannanone (0.545 g, 2.19 mmol) under $N_2$. The mixture was stirred at 120° C. for 18 h. After cooling to rt, the reaction mixture was concentrated under reduce pressure. The resulting residue was dissolved in methanol and re-concentrated, and then partitioned between ethyl acetate (50 mL) and 10% sodium bicarbonate solution (30 mL). The organic layer was separated and extracted with 10% sodium bicarbonate solution (25 mL). The combined aqueous extracts were acidified to pH=5 with 10% hydrochloric acid solution and the resulting solid was collected by filtration. The filter cake was washed with water and dried to afford the title compound. $^1$H NMR (400 MHz, methanol-d4) δ: 7.77 (br s., 2H), 2.49 (br s., 6H)

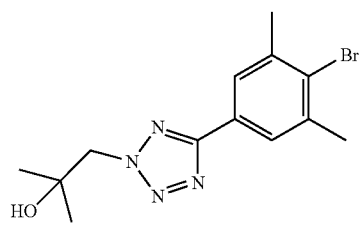 [SMILES: Cc1cc(-c2nnn(CC(C)(C)O)n2)cc(C)c1Br]

Step B: 1-(5-(4-bromo-3,5-dimethylphenyl)-2H-tetrazol-2-yl)-2-methylpropan-2-ol A mixture of 2, 2-dimethyloxirane (3.59 g, 49.8 mmol), $Cs_2CO_3$ (4.06 g, 12.45 mmol) and 5-(4-bromo-3,5-dimethylphenyl)-2H-tetrazole (2.1 g, 8.3 mmol) in DMF (20 mL) was heated at 100° C. for 16 h. Then the mixture was cooled to rt and partitioned between $H_2O$ (30 mL) and EtOAc (30 mL). The aqueous layer was separated and extracted with EtOAc (20 mL×2). The combined organic layers were washed with brine (20 mL), dried over anhydrous $Na_2SO_4$, and concentrated in vacuo to give a crude residue which was purified by flash chromatography on silica gel (0-30% EtOAc in petroleum ether) to give the title compound. $^1$H NMR (400 MHz, CDCl$_3$) δ: 7.84 (s, 2H), 4.66 (s, 2H), 2.48 (s, 6H), 1.29 (s, 6H). MS (ESI) m/e (M+H$^+$): 325.0.

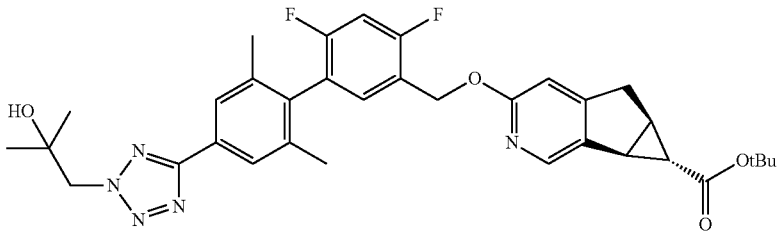 [SMILES: Cc1cc(-c2nnn(CC(C)(C)O)n2)cc(C)c1-c1cc(COc2cc3c(cn2)[C@H]2[C@@H](C3)[C@@H]2C(=O)OC(C)(C)C)c(F)cc1F]

Step C: (5aR,6S,6aS)-tert-butyl 3-((4,6-difluoro-4'-(2-(2-hydroxy-2-methylpropyl)-2H-tetrazol-5-yl)-2',6'-dimethyl-[1,1'-biphenyl]-3-yl)methoxy)-5,5a,6,6a-tetrahydro-cyclopropa-[4,5]cyclopenta[1,2-c]pyridine-6-carboxylate A mixture of 1-(5-(4-bromo-3,5-dimethylphenyl)-2H-tetrazol-2-yl)-2-methylpropan-2-ol (800 mg, 2.46 mmol), (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydro-cyclopropa[4,5]cyclopenta[1,2-c]pyridine-6-carboxylate (1228 mg, 2.460 mmol), $K_2CO_3$ (680 mg, 4.92 mmol), and [1,1'-bis(di-tert-butylphosphino)ferrocene]-dichloropalladium(II) (160 mg, 0.246 mmol) in THF (8 mL))/water (2 mL) was irradiated to 100° C. by microwave for 30 min under a nitrogen atmosphere. After cooling to room temperature, the mixture was diluted with EtOAc (50 mL). The organic layer was separated, washed with water (20 mL) and brine (20 mL), dried over anhydrous $Na_2SO_4$ and concentrated in vacuo. The resulting crude product was purified by column chromatography on silica gel $SiO_2$, eluting with PE/EtOAc=2:1 to give the title compound. $^1$H NMR (400 MHz, CDCl$_3$) δ: 8.05 (s, 1H), 7.91 (s, 2H), 7.24 (s, 1H), 6.94 (t, J=9.4 Hz, 1H), 6.57 (s, 1H), 5.39 (s, 2H), 4.67 (s, 2H), 3.17 (dd, J=6.3, 18.4 Hz, 1H), 2.96 (d, J=18.4 Hz, 1H), 2.88 (s, 1H), 2.83 (d, J=5.1 Hz, 1H), 2.40-2.29 (m, 2H), 2.09 (s, 6H), 1.44 (s, 9H), 1.28 (s, 7H), 1.10 (t, J=2.5 Hz, 1H). MS (ESI) m/e (M+H$^+$): 618.3

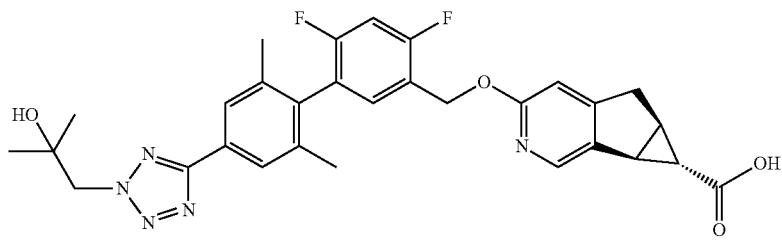 [SMILES: Cc1cc(-c2nnn(CC(C)(C)O)n2)cc(C)c1-c1cc(COc2cc3c(cn2)[C@H]2[C@@H](C3)[C@@H]2C(=O)O)c(F)cc1F]

Step D: (5aR,6S,6aS)-3-((4,6-difluoro-4'-(2-(2-hydroxy-2-methylpropyl)-2H-tetrazol-5-yl)-2',6'-dimethyl-[1,1'-biphenyl]-3-yl)methoxy)-5,5a,6,6a-tetrahydrocyclopropa[4,5]-cyclopenta[1,2-c]pyridine-6-carboxylic acid LiOH.H$_2$O (0.883 g, 21.05 mmol) was added to a stirred mixture of (5aR,6S,6aS)-tert-butyl 3-((4,6-difluoro-4'-(2-(2-hydroxy-2-methylpropyl)-2H-tetrazol-5-yl)-2',6'-dimethyl-[1,1'-biphenyl]-3-yl)methoxy)-5,5a,6,6a-tetrahydrocyclopropa-[4,5]cyclopenta[1,2-c]pyridine-6-carboxylate (1.3 g, 2.105 mmol) in MeOH (3 mL)/THF (3 mL)/water (3 mL). The mixture was stirred at 30° C. for 12 h, then was acidified with 2N HCl to pH=6, and extracted with ethyl acetate (2×20 mL). The combined organic layers were washed with brine (saturated, 15 mL), dried over anhydrous Na$_2$SO$_4$, and filtered. The filtrate was evaporated under reduced pressure to give the crude product. The crude product was purified by prep-HPLC (preparative HPLC on a GILSON 281 instrument fitted with a Phenomenex Gemini C18 250*21.2 mm*4 um using water and acetonitrile as the eluents. Mobile phase A: water (containing 0.01 mol/L TFA, v/v), mobile phase B: acetonitrile. Gradient: 40-70% B, 0-12 min; 100% B, 10.5-12.5 min; 5% B, 13-15 min) to give the title compound. $^1$H NMR (400 MHz, methanol-d$_4$) δ: 8.03 (s, 1H), 7.87 (s, 2H), 7.31 (t, J=8.2 Hz, 1H), 7.11 (t, J=9.8 Hz, 1H), 6.66 (s, 1H), 5.37 (s, 2H), 4.68 (s, 2H), 3.21 (dd, J=6.3, 18.8 Hz, 1H), 3.00 (d, J=18.8 Hz, 1H), 2.86 (d, J=4.7 Hz, 1H), 2.41-2.34 (m, 1H), 2.05 (s, 6H), 1.31 (s, 6H), 1.08 (brs., 1H). MS (ESI) m/e (M+H$^+$): 562.2.

Example 17

(5aR,6S,6aS)-3-((4,6-difluoro-4'-(1-(2-hydroxy-2-methylpropyl)-1H-1,2,4-triazol-3-yl)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

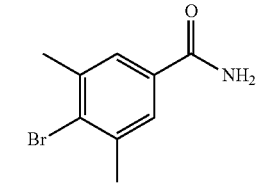

Step A: 4-bromo-3,5-dimethylbenzamide

To a solution of 4-bromo-3, 5-dimethylbenzonitrile (1.0 g, 4.8 mmol) in DMSO (10 ml) at 0° C. was added 35% H$_2$O$_2$ (0.542 mL, 6.19 mmol) and K$_2$CO$_3$ (1.32 g, 9.52 mmol). The resulting mixture was stirred at 20° C. for 2 hours and then poured into water (50 mL). The resulting solid was collected by filtration, then washed with water twice, dried in an oven to give the title compound. $^1$H NMR (400 MHz, CD$_3$OD) δ: 7.62 (s, 2H), 2.46 (s, 6H).

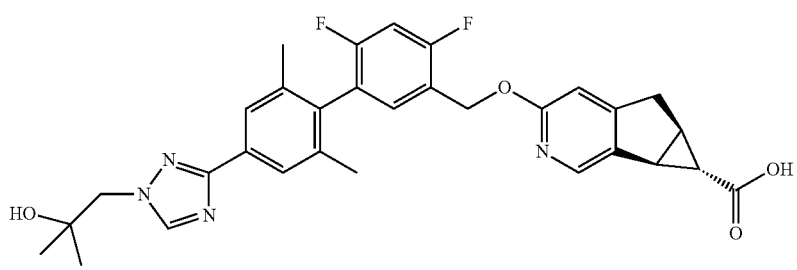 [SMILES: Cc1cc(-c2ncn(CC(C)(C)O)n2)cc(C)c1-c1cc(COc2cc3c(cn2)[C@H]2[C@@H](C3)[C@@H]2C(=O)O)c(F)cc1F]

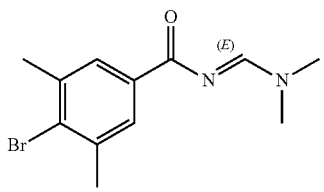

Step B: (E)-4-bromo-N-((dimethylamino)methylene)-3,5-dimethylbenzamide

A mixture of 4-bromo-3,5-dimethylbenzamide (1.0 g, 4.4 mmol) and dimethylformamide dimethyl acetal (1.76 mL, 13.2 mmol) was heated at 120° C. for 12 hours. Then the reaction mixture was cooled to 20° C. and petroleum ether (40 mL) was added. The resulting precipitate was collected by filtration and dried in an oven to afford the title compound, which was used directly in the next step without further purification. $^1$H NMR (400 MHz, CD$_3$OD) δ: 8.61 (s, 1H), 7.93 (s, 2H), 3.25 (d, J=4.7 Hz, 6H), 2.45 (s, 6H). ESI-MS m/z [M+H]$^+$: 283.1

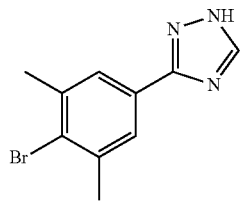

Step C: 3-(4-bromo-3,5-dimethylphenyl)-1H-1,2,4-triazole

To a suspension of (E)-4-bromo-N-((dimethylamino)methylene)-3,5-dimethylbenzamide (1.1 g, 3.9 mmol) in acetic acid (10 mL) at 0° C. was added hydrazine hydrate (0.583 g, 11.7 mmol). The resulting mixture was stirred at 20° C. for 2 hours, and then concentrated by evaporation. The resulting crude solid was washed with water twice and dried in an oven to give the title compound, which was used in next step without further purification. $^1$H NMR (400 MHz, CD$_3$OD) δ: 8.38 (br. s., 1H), 7.77 (s, 2H), 2.48 (s, 6H). ESI-MS m/z [M+H]$^+$: 251.9

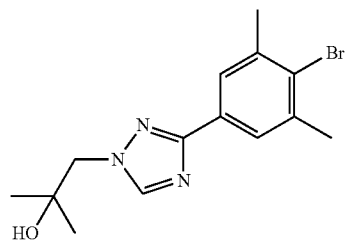 [SMILES: Cc1cc(-c2ncn(CC(C)(C)O)n2)cc(C)c1Br]

Step D: 1-(3-(4-bromo-3,5-dimethylphenyl)-1H-1,2,4-triazol-1-yl)-2-methylpropan-2-ol To a solution of 3-(4-bromo-3,5-dimethylphenyl)-1H-1,2,4-triazole (300 mg, 1.19 mmol) and Cs$_2$CO$_3$ (582 mg, 1.79 mmol) in DMF (3 mL) at room temperature was added 2,2-dimethyloxirane (858 mg, 11.9 mmol). The resulting solution was stirred at 50° C. for 12 h, then cooled to room temperature and water (20 mL) was added. The resulting aqueous phase was extracted with EtOAc (3×20 mL). The combined organic layers were washed with brine (20 mL), dried over Na$_2$SO$_4$ and concentrated in vacuo. The resulting residue was purified by reverse phase preparative HPLC (preparative HPLC on a EG instrument fitted with a Waters XSELECT C18 150*30 mm*5 um using water and acetonitrile as the eluents. Mobile phase A: water (containing 0.1% TFA, v/v), mobile phase B: acetonitrile. Gradient: 38-55% B, 13 min; 100% B, 2 min) to give the title compound. $^1$H NMR (400 MHz, CD$_3$OD) δ: 8.50 (s, 1H), 7.79 (s, 2H), 4.23 (s, 2H), 2.47 (s, 6H), 1.25 (s, 6H). ESI-MS m/z [M+H]$^+$: 324.0

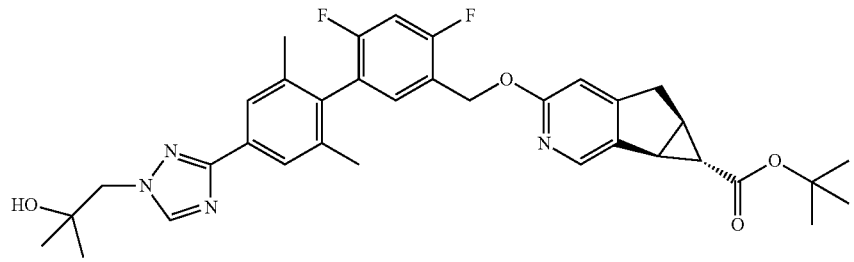 [SMILES: Cc1cc(-c2ncn(CC(C)(C)O)n2)cc(C)c1-c1cc(COc2cc3c(cn2)[C@H]2[C@@H](C3)[C@@H]2C(=O)OC(C)(C)C)c(F)cc1F]

Step E: (5aR,6S,6aS)-tert-butyl 3-((4,6-difluoro-4'-(1-(2-hydroxy-2-methylpropyl)-1H-1,2,4-triazol-3-yl)-2',6'-dimethyl-[1,1'-biphenyl]-3-yl)methoxy)-5,5a,6,6a-tetrahydrocyclo-propa[4,5]cyclopenta[1,2-c]pyridine-6-carboxylate A mixture of 1-(3-(4-bromo-3,5-dimethylphenyl)-1H-1,2,4-triazol-1-yl)-2-methylpropan-2-ol (50 mg, 0.15 mmol), (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate (92 mg, 0.19 mmol) and K$_2$CO$_3$ (63.9 mg, 0.463 mmol) in THF/H$_2$O (3:1, 4 mL) was added a catalytic amount of 2$^{nd}$ Generation XPhos Precatalyst (12.1 mg, 0.015 mmol) under N$_2$ protection. After the addition was complete, the mixture was stirred at 100° C. under microwave irradiation for 30 min under N$_2$ protection. After cooling to room temperature, the mixture was filtered with diatomaceous earth and the filtrate was diluted with ethyl acetate (20 mL). The organic layer was washed with water. The water layer was separated, and extracted with ethyl acetate (2×5 mL). The combined organic layers were washed with brine (10 mL), dried over anhydrous Na₂SO₄, filtered and the filtrate was concentrated. The resulting residue was purified by silica gel preparative TLC (PE:EtOAc=1:1) to give the title compound. ¹H NMR (400 MHz, CD₃OD) δ: 8.45 (s, 1H), 8.06 (s, 1H), 7.80 (s, 2H), 7.32 (t, J=8.2 Hz, 1H), 7.13 (t, J=9.6 Hz, 1H), 6.69 (s, 1H), 5.39 (s, 2H), 4.23 (s, 2H), 3.23 (dd, J=6.3, 18.8 Hz, 1H), 3.01 (d, J=18.4 Hz, 1H), 2.86 (d, J=4.7 Hz, 1H), 2.41-2.33 (m, 1H), 2.05 (s, 5H), 1.46 (s, 8H), 1.26 (s, 6H), 1.10 (d, J=2.7 Hz, 1H). ESI-MS m/z [M+H]⁺: 617.2

(5aR,6S,6aS)-3-((2-fluoro-5-(6-(2-(2-hydroxy-2-methylpropyl)pyrrolo[3,4-c]pyrazol-5(2H,4H,6H)-yl)-2-methylpyridin-3-yl)-4-(trifluoromethyl)benzyl)oxy)-5,5a,6,6a-tetrahydrocyclopropa[4,5]cyclopenta[1,2-c]pyridine-6-carboxylic acid

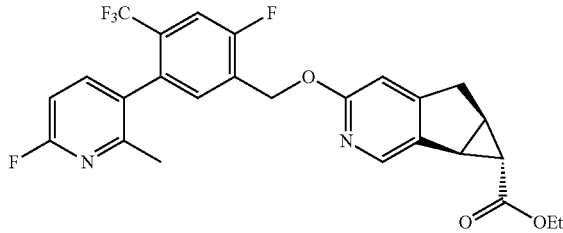

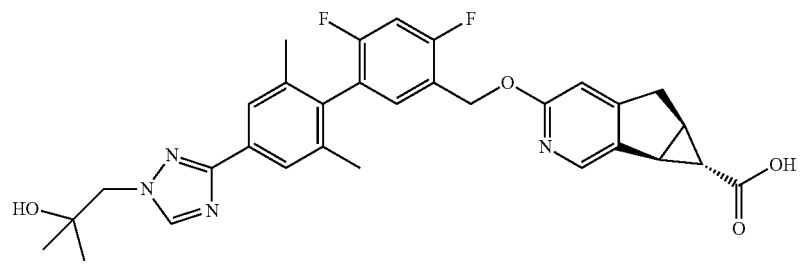 [SMILES: Cc1cc(-c2ncn(CC(C)(C)O)n2)cc(C)c1-c1cc(COc2cc3c(cn2)[C@H]2[C@@H](C3)[C@@H]2C(=O)O)c(F)cc1F]

Step F: (5aR,6S,6aS)-3-((4,6-difluoro-4'-(1-(2-hydroxy-2-methylpropyl)-1H-1,2,4-triazol-3-yl)-2',6'-dimethyl-[1,1'-biphenyl]-3-yl)methoxy)-5,5a,6,6a-tetrahydrocyclo-propa[4,5]cyclo-penta[1,2-c]pyridine-6-carboxylic acid Lithium hydroxide hydrate (64 mg, 1.6 mmol) was added to a stirred mixture of (5aR,6S,6aS)-tert-butyl 3-((4,6-difluoro-4'-(1-(2-hydroxy-2-methylpropyl)-1H-1,2,4-triazol-3-yl)-2',6'-dimethyl-[1,1'-biphenyl]-3-yl)methoxy)-5,5a,6,6a-tetrahydro-cyclopropa[4,5]cyclopenta[1,2-c]pyridine-6-carboxylate (100 mg, 0.162 mmol) in MeOH/THF/H₂O (1:1:1, 3 mL). The mixture was stirred at 23° C. for 2 h, then acidified with 2N HCl to pH=6, and extracted with ethyl acetate (2×20 mL). The combined organic layers were washed with brine (15 mL), dried over anhydrous Na₂SO₄, filtered and the filtrate was evaporated under reduced pressure. The resulting residue was purified by silica gel preparative TLC (DCM:MeOH=10:1) to give the title compound. ¹H NMR (400 MHz, CD₃OD) δ: 8.45 (s, 1H), 8.07 (s, 1H), 7.80 (s, 2H), 7.33 (t, J=8.0 Hz, 1H), 7.13 (t, J=9.8 Hz, 1H), 6.70 (s, 1H), 5.39 (s, 2H), 4.23 (s, 2H), 3.23 (d, J=6.3 Hz, 1H), 3.04 (d, J=18.8 Hz, 1H), 2.93 (d, J=5.1 Hz, 1H), 2.44 (d, J=3.1 Hz, 1H), 2.05 (s, 5H), 1.37-1.22 (m, 5H), 1.14 (br. s., 1H). ESI-MS m/z [M+H]⁺: 561.2

Step A: (5aR,6S,6aS)-ethyl 3-((2-fluoro-5-(6-fluoro-2-methylpyridin-3-yl)-4-trifluoromethyl)benzyl)oxy)-5,5a,6,6a-tetrahydrocyclopropa[4,5]cyclopenta[1,2-c]pyridine-6-carboxylate A solution of Intermediate 2, (5aR,6S,6aS)-ethyl 3-((5-bromo-2-fluoro-4-(trifluoromethyl)benzyl)oxy)-5,5a,6,6a-tetrahydrocyclopropa[4,5]cyclopenta[1,2-c]pyridine-6-carboxylate (300 mg, 0.633 mmol) and (6-fluoro-2-methylpyridin-3-yl)boronic acid (108 mg, 0.696 mmol) in THF (6 mL) was degassed and purged with N₂ for 5 minutes. To this solution was added 2ⁿᵈ Generation XPHOS Pre catalyst (49.8 mg, 0.063 mmol) and K₃PO₄/H₂O (1.26 mL, 1 mol/L). The reaction mixture was degassed, purged with N₂ for 5 minutes, and stirred at 65° C. for 3.5 h. Then reaction mixture was partitioned between H₂O and EtOAc (5/15 mL). The aqueous phase was separated and extracted with EtOAc (10 mL×2). The combined organic layers were washed with brine, dried over MgSO₄, concentrated and purified by column chromatography on silica gel, eluting with hexane and EtOAc (90:10 to 30:70) to give the title compound. MS (ESI) m/e (M+H+): 505

Example 18

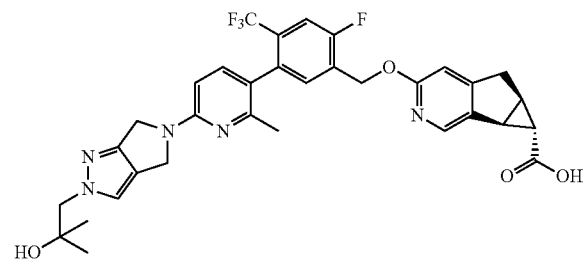 [SMILES: CCOC(=O)[C@H]1[C@@H]2Cc3cc(OCc4cc(-c5ccc(N6Cc7cn(CC(C)(C)O)nc7C6)nc5C)c(C(F)(F)F)cc4F)ncc3[C@@H]21]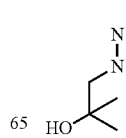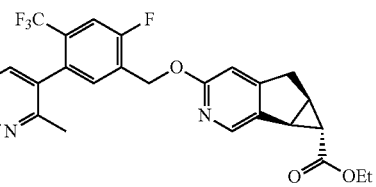

Step B: (5aR,6S,6aS)-ethyl 3-((2-fluoro-5-(6-(2-(2-hydroxy-2-methylpropyl)-pyrrolo[3,4-c]pyrazol-5(2H,4H,6H)-yl)-2-methylpyridin-3-yl)-4-(trifluoromethyl)benzyl)-oxy)-5,5a,6,6a-tetrahydrocyclopropa[4,5]cyclopenta[1,2-c]pyridine-6-carboxylate To a solution of (5aR,6S,6aS)-ethyl 3-((2-fluoro-5-(6-fluoro-2-methylpyridin-3-yl)-4-(trifluoromethyl)benzyl)-oxy)-5,5a,6,6a-tetrahydrocyclopropa[4,5]cyclopenta[1,2-c]pyridine-6-carboxylate (25 mg, 0.050 mmol) suspended in NMP (1 ml) in a microwave vial, were added 1-(5,6-dihydropyrrolo[3,4-c]pyrazol-2(4H)-yl)-2-methylpropan-2-ol 2TFA (40.6 mg, 0.099 mmol), and Hunig's Base (0.173 ml, 0.991 mmol). The reaction mixture was heated at 120° C. for 1 day, then worked up with EtOAc/H₂O, and extracted with EtOAc (3×). Combined organic layers were washed with brine (3×) and dried over MgSO₄, filtered, and concentrated. The resulting residue was purified by column chromatography on silica gel, eluting with hexane and EtOAc (100:0 to 20:80) normal phase using Silica ISCO 12 g (0-80% EtOAc/Hexane) to give the title compound. MS (ESI) m/e (M+H+): 666

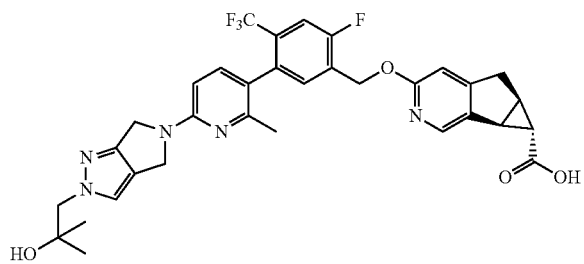 [SMILES: Cc1nc(N2Cc3cn(CC(C)(C)O)nc3C2)ccc1-c1cc(COc2cc3c(cn2)[C@H]2[C@@H](C3)[C@@H]2C(=O)O)c(F)cc1C(F)(F)F]

Step C: (5aR,6S,6aS)-3-((2-fluoro-5-(6-(2-(2-hydroxy-2-methylpropyl)pyrrolo[3,4-c]pyrazol-5(2H,4H,6H)-yl)-2-methylpyridin-3-yl)-4-(trifluoromethyl)benzyl)oxy)-5,5a,6,6a-tetrahydrocyclopropa[4,5]cyclopenta[1,2-c]pyridine-6-carboxylic acid To a solution of product from Step B (18 mg, 0.027 mmol) in THF/EtOH/H₂O (0.5/0.5/0.5 mL) was added LiOH/H₂O (0.135 mL, 1 mol/L). The reaction mixture was stirred at 20-24° C. for 3 h and then concentrated. The resulting residue was re-dissolved in CH₃CN/H₂O/DMSO (1/0.5/0.5 mL), acidified by adding formic acid to adjust the pH to 5, and directly purified via preparative HPLC (over C18 column using a gradient of acetonitrile in water w/0.1% formic acid) to give the title compound. $^1$H NMR (500 MHz, CD₃OD): δ: 8.05 (s, 1H), 7.56 (d, J=10.2 Hz, 1H), 7.49 (s, 1H), 7.38 (d, J=7.1 Hz, 1H), 7.26 (d, J=8.5 Hz, 1H), 6.70 (s, 1H), 6.44 (d, J=8.6 Hz, 1H), 5.43-5.50 (m, 2H), 4.59 (s, 4H), 4.10 (s, 2H), 3.27-3.21 (m, 1H), 3.03 (d, 1H), 2.90 (d, J=6.6 Hz, 1H), 2.42 (td, J=6.4, 3.2 Hz, 1H); 2.03 (d, J=2.1 Hz, 3H), 1.19 (s, 6H); 1.12 (s, 1H). MS (ESI) m/e (M+H+): 638

Example 19

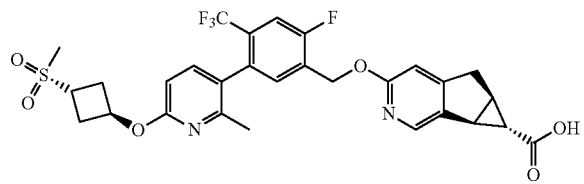

(5aR,6S,6aS)-3-((2-fluoro-5-(2-methyl-6-((1r,3r)-3-(methylsulfonyl)cyclobutoxy)pyridin-3-yl)-4-trifluoromethyl)benzyl)oxy)-5,5a,6,6a-tetrahydrocyclopropa[4,5]cyclopenta[1,2-c]pyridine-6-carboxylic acid

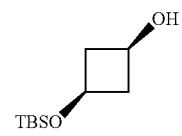 [SMILES: CC(C)(C)[Si](C)(C)O[C@H]1C[C@@H](O)C1]

Step A: (1s,3s)-3-((tert-butyldimethylsilyl)oxy)cyclobutanole

To a solution of 3-((tert-butyldimethylsilyl)oxy)cyclobutanone (5.0 g, 24.7 mmol) in methanol (20 mL) at 0° C. was added NaBH₄ (1.04 g, 27.5 mmol) portionwise. The reaction mixture was stirred at 0° C. for 1 hr. Then HCl (aq., 1M) was added slowly to quench the reaction and the insolubles was filtered off. The reaction mixture was then extracted with EtOAc (100 mL×3). The combined organic layers were washed with water, dried with anhydrous Na₂SO₄, filtered and the filtrate was evaporated under reduced pressure to give the title compound, which was used in the next step without purification.

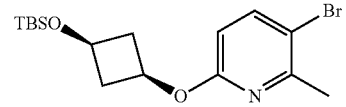 [SMILES: Cc1nc(O[C@H]2C[C@@H](O[Si](C)(C)C(C)(C)C)C2)ccc1Br]

Step B: 3-bromo-6-((1s,3s)-3-((tert-butyldimethylsilyl)oxy)cyclobutoxy)-2-methyl-pyridine NaH (1.189 g, 29.7 mmol, 60%) was added slowly to a solution of (1s,3s)-3-((tert-butyldimethylsilyl)oxy)cyclobutanol 4.01 g, 19.8 mmol) and 3-bromo-6-fluoro-2-methylpyridine (4.52 g, 23.8 mmol) in DMF (80 mL) at 0° C. The reaction mixture was stirred at room temperature for 12 hours, then slowly added to ice-water. The reaction mixture was extracted with EtOAc (100 mL×3). The combined organic layers were washed with water, dried over anhydrous Na₂SO₄, filtered and the filtrate was evaporated under reduced pressure. The resulting residue was purified by flash column chromatography on silica gel (PE:EtOAc=5:1) to afford the title compound. MS (ESI) m/e (M+H⁺): 372.1/374.1

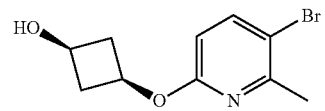

Step C: (1s,3s)-3-((5-bromo-6-methylpyridin-2-yl)oxy)cyclobutanol

To a solution of 3-bromo-6-((1s,3s)-3-((tert-butyldimethylsilyl)oxy)cyclobutoxy)-2-methylpyridine (6.8 g, 18.3 mmol) in THF (10 mL) at 0° C. was added TBAF (36.5 mL, 36.5 mmol, 1M in THF). The reaction mixture was stirred at 16° C. for 5 hours. The volatiles were removed, and the resulting residue was purified by flash column chromatography on silica gel (PE/EtOAc=5/1, Rf=0.4), eluting with 0-20% EtOAc in hexanes, to give the title compound. MS (ESI) m/e (M+H⁺): 258.0/260.0

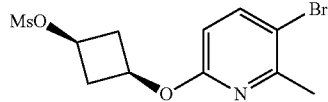 [SMILES: Cc1nc(O[C@H]2C[C@@H](OS(C)(=O)=O)C2)ccc1Br]

Step D: (1s,3s)-3-((5-bromo-6-methylpyridin-2-yl)oxy)cyclobutyl methanesulfonate To a solution of (1s,3s)-3-((5-bromo-6-methylpyridin-2-yl)oxy)cyclobutanol (3.3 g, 12.8 mmol) in CH₂Cl₂ (30 ml) at 0° C. was added Et₃N (3.56 mL, 25.6 mmol), followed by methanesulfonyl chloride (2.19 g, 19.2 mmol). The reaction mixture was stirred at 15° C. for 1 hour. Then brine (4 mL)

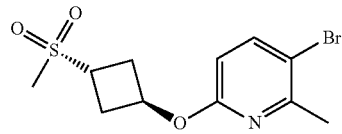

Step F: 3-bromo-2-methyl-6-((1s,3s)-3-(methylsulfonyl)cyclobutoxy)pyridine

To a mixture of 3-Bromo-2-methyl-6-((1r,3r)-3-(methylthio)cyclobutoxy)pyridine (624 mg, 2.16 mmol) in CH₂Cl₂ (3 mL) was added TFA (0.167 ml, 2.16 mmol) at room temperature. The mixture was stirred for 30 min, then mCPBA (1.09 g, 5.41 mmol, 85%) was added. The reaction mixture was stirred at room temperature for 4 hours, followed by the addition of NaHCO₃ (saturated, 5 mL) was added. The organic layer was separated and washed with DCM and water. The aqueous layer was extracted with DCM (30 mL×3). The combined organic layers were concentrated in vacuo. The resulting residue was purified by prep-TLC (PE/EtOAc=2/1, Rf=0.35) to give the title compound. MS (ESI) m/e (M+H⁺): 319.9/321.9

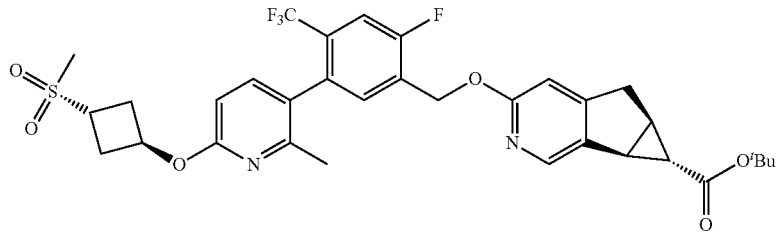

and 5 mL DCM was added to the mixture. The organic layer was separated, washed with brine (10 mL), dried over anhydrous Na₂SO₄, and filtered, and the filtrate was evaporated under reduced pressure. The resulting residue was purified by flash column chromatography on silica gel, eluting with 0-40% then 40% EtOAc in hexanes, to give the title compound. MS (ESI) m/e (M+H⁺): 336.2/338.3

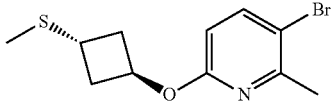

Step E: 3-bromo-2-methyl-6-((1r,3r)-3-(methylthio)cyclobutoxy)pyridine

Sodium methanethiolate (2.1 g, 30 mmol) and (1s,3s)-3-((5-bromo-6-methylpyridin-2-yl)oxy)cyclobutyl methanesulfonate (3.6 g, 10.7 mmol) were dissolved in NMP (6 ml), and then heated in a microwave oven at 100° C. for 30 min under N₂. Then the reaction mixture was cooled to room temperature, diluted with ethyl acetate (20 mL), washed with brine (20 mL), dried over Na₂SO₄, and filtered, and the filtrate was evaporated under reduced pressure. The resulting residue was purified by flash column chromatography on silica gel, eluting with PE/EtOAc=20/1, to give 3-bromo-2-methyl-6-((1r,3r)-3-(methylthio)cyclo-butoxy)pyridine as a white solid. MS (ESI) m/e (M+H⁺): 288.2/290.1

Step G: (5aR,6S,6aS)-tert-butyl 3-((2-fluoro-5-(2-methyl-6-((1s,3s)-3-(methylsulfonyl)-cyclobutoxy)pyridin-3-yl)-4-(trifluoromethyl)benzyl)oxy)-5,5a,6,6a-tetrahydrocyclopropa-[4,5]cyclopenta[1,2-c]pyridine-6-carboxylate A mixture of (5aR,6S,6aS)-tert-butyl 3-((2-fluoro-5-(4,4,5,5-tetramethyl-1,3,2-dioxaborolan-2-yl)-4-(trifluoromethyl)-benzyl)oxy)-5,5a,6,6a-tetrahydrocyclopropa[4,5]cyclopenta[1,2-c]pyridine-6-carboxylate (733 mg, 1.33 mmol), 3-bromo-2-methyl-6-((1r,3r)-3-(methylsulfonyl)-cyclobutoxy)pyridine (356 mg, 1.1 mmol), K₂CO₃ (384.0 mg, 2.78 mmol) and 1, F-bis(di-tert-butylphosphino)ferrocene palladium dichloride (72.5 mg, 0.111 mmol) in a co-solvent of THF (3 mL)/water (1 mL) was irradiated by microwaves at 100° C. for 30 min under a nitrogen atmosphere. After cooling to room temperature, the resulting mixture was filtered. The filtrate was extracted with EtOAc (20 mL×3). The combined EtOAc layers were washed with water, dried and concentrated in vacuo. The resulting residue was purified by pre-TLC (PE:EtOAc=1:1, Rf=0.41) to give the title compound. MS (ESI) m/e (M+H⁺): 663.1.

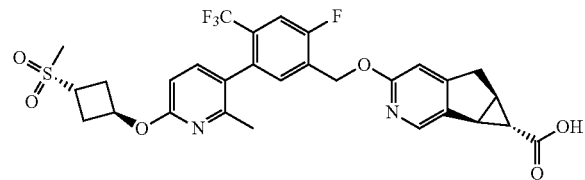

Step I: (5aR,6S,6aS)-3-((2-fluoro-5-(2-methyl-6-((1r,3r)-3-(methylsulfonyl)-cyclobutoxy)pyridin-3-yl)-4-(trifluoromethyl)benzyl)oxy)-5,5a,6,6a-tetrahydrocyclo-propa[4,5]-cyclopenta[1,2-c]pyridine-6-carboxylic acid To a solution of (5aR,6S,6aS)-tert-butyl 3-((2-fluoro-5-(2-methyl-6-((1r,3r)-3-(methylsulfonyl)cyclobutoxy)pyridin-3-yl)-4-(trifluoro-methyl)benzyl)oxy)-5,5a,6,6a-tetrahydrocyclopropa[4,5]cyclopenta[1,2-c]pyridine-6-carboxylate (489 mg, 0.738 mmol) in a co-solvent of MeOH (5 mL), THF (4 mL) and water (3 mL) was added LiOH—$H_2O$ (310 mg, 7.38 mmol). The reaction mixture was stirred at 60° C. for 2 hours. After cooling to room temperature, the resulting mixture was acidified with HCl (2 N) to pH=3, and extracted with ethyl acetate (20 mL×2). The combined organic layers were washed with water, brine, dried over $Na_2SO_4$ and concentrated in vacuo to afford (5aR,6S,6aS)-3-((2-fluoro-5-(2-methyl-6-((1r,3r)-3-(methylsulfonyl)cyclobutoxy)pyridin-3-yl)-4-(trifluoromethyl)benzyl)-oxy)-5,5a,6,6a-tetrahydrocyclopropa[4,5]cyclopenta[1,2-c]pyridine-6-carboxylic acid. The acid was converted to the sodium salt using 0.5 M aqueous NaOH. $^1$H NMR (400 MHz, $CD_3OD$) δ: 7.98 (s, 1H), 7.59 (d, J=10.2 Hz, 1H), 7.44-7.35 (m, 2H), 6.69-6.59 (m, 2H), 5.45 (s, 2H), 5.38 (t, J=6.5 Hz, 1H), 4.02-3.91 (m, 1H), 3.16 (d, J=6.3 Hz, 1H), 3.03-2.92 (m, 6H), 2.79-2.70 (m, 1H), 2.64 (d, J=6.3 Hz, 2H), 2.29 (br. s., 1H), 2.05 (d, J=3.1 Hz, 3H), 1.01 (d, J=2.7 Hz, 1H). MS (ESI) m/e (M+H$^+$): 607.1

Example 20

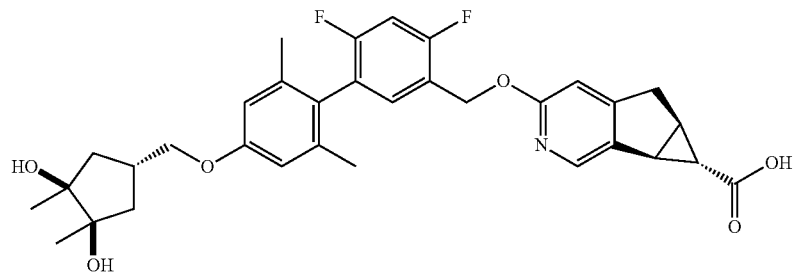 [SMILES: Cc1cc(OC[C@H]2C[C@](C)(O)[C@](C)(O)C2)cc(C)c1-c1cc(COc2cc3c(cn2)[C@H]2[C@@H](C3)[C@@H]2C(=O)O)c(F)cc1F]

(5aR,6S,6aS)-3-((4'-(((1s,3R,4S)-3,4-dihydroxy-3,4-dimethylcyclopentyl)methoxy)-4,6-difluoro-2',6'-dimethyl-[1,1'-biphenyl]-3-yl)methoxy)-5,5a,6,6a-tetrahydrocyclopropa-[4,5]cyclopenta[1,2-c]pyridine-6-carboxylic acid

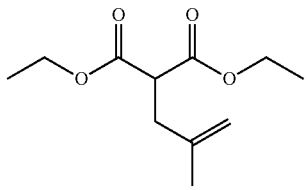

Step A: Diethyl 2-(2-methylallyl)malonate

Sodium hydride (4.00 g, 100 mmol, 60%) was added slowly to a stirred mixture of diethyl malonate (16 g, 100 mmol) in THF (160 mL) at 0° C. The mixture was stirred at 0° C. for 0.5 hour under $N_2$. Then 3-bromo-2-methylprop-1-ene (13.49 g, 100 mmol) was added dropwise into the mixture. The reaction mixture was stirred at 60° C. for 12 hours, then cooled to room temperature. Aqueous ammonium chloride (saturated, 150 mL) was added to the mixture and the mixture was extracted with ethyl acetate (150 mL×2). The combined organic layers were washed with water (50 mL), brine (50 mL), dried ($Na_2SO_4$), and filtered, and the filtrate was evaporated under reduced pressure. The resulting residue was purified by flash column chromatography on silica gel, eluting with (PE/EtOAC=20:1 Rf=0.4) to give the title compound. $^1$H NMR (400 MHz, CDCl$_3$): δ 4.78 (s, 1H), 4.72 (s, 1H), 4.19 (q, J=7.2 Hz, 4H), 3.57 (t, J=7.8 Hz, 1H), 2.61 (d, J=7.8 Hz, 2H), 1.74 (s, 3H), 1.26 (t, J=7.2 Hz, 6H).

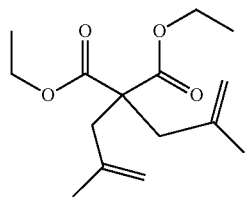 [SMILES: C=C(C)CC(CC(=C)C)(C(=O)OCC)C(=O)OCC]

Step B: Diethyl 2,2-bis(2-methylallyl)malonate

NaH (0.762 g, 19.0 mmol, 60%) was added to a stirred mixture of diethyl 2-(2-methylallyl)malonate (3.4 g, 15.9 mmol) in THF (35 ml) at 0° C. The resulting mixture was stirred at 0° C. for 0.5 hour. Then 3-chloro-2-methylprop-1-ene (1.581 g, 17.46 mmol) was added dropwise into the mixture, and the mixture was stirred at 60° C. for 12 hours. The mixture was then cooled to room temperature, and aqueous ammonium chloride (saturated, 30 mL) was added to quench the reaction. The mixture was then extracted with ethyl acetate (50 mL×2). The combined organic layers were washed with water (50 mL), brine (50 mL), dried ($Na_2SO_4$), filtered and the filtrate was evaporated under reduced pressure. The resulting residue was purified by flash column chromatography on silica gel $SiO_2$, eluting with (PE/EtOAC=20:1 Rf=0.46) to give the title compound. $^1$H NMR (400 MHz, CDCl$_3$): δ 4.78 (s, 2H), 4.67 (s, 2H), 4.10 (q, J=7.3 Hz, 4H), 2.67 (s, 4H), 1.62 (s, 6H), 1.18 (t, J=7.2 Hz, 6H).

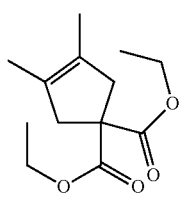 [SMILES: CCOC(=O)C1(C(=O)OCC)CC(C)=C(C)C1]

Step C: Diethyl 3,4-dimethylcyclopent-3-ene-1,1-dicarboxylate

Diethyl 2,2-bis(2-methylallyl)malonate (8.5 g, 31.7 mmol) was dissolved in dry toluene (30 ml) under an atmosphere of nitrogen. 2nd Generation Hoveyda-Grubbs Catalyst (0.198 g, 0.317 mmol) was added into the reaction mixture and the reaction flask was evacuated and back-filled with nitrogen three times. Then the reaction mixture was stirred at 70° C. for 16 hours. After cooling to room temperature, the reaction mixture was filtered through diatomaceous earth. The filtrate was concentrated in vacuo. The resulting residue was purified by reverse phase preparative HPLC (preparative HPLC on a Shimadzu LC-20AP Synergi 250*50 mm*10 um using water and acetonitrile as the eluents. Mobile phase A: water (containing 0.1% TFA, v/v), mobile phase B: acetonitrile. Gradient: 45-75% B, 30 min; 100% B, 10.5-12.5 min; 5% B, 13-15 min Flow rate: 80 ml/min; Detective Wavelength: 205/215) to give the title compound.

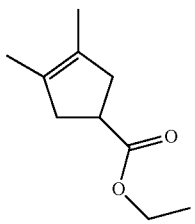

Step D: Ethyl 3,4-dimethylcyclopent-3-enecarboxylate

Lithium chloride (0.353 g, 8.32 mmol) and diethyl 3,4-dimethylcyclopent-3-ene-1,1-dicarboxylate (1.0 g, 4.2 mmol) were dissolved in a co-solvent water (0.5 ml)/DMSO (6 ml). The mixture was radiated by microwave at 200° C. for 50 min under nitrogen atmosphere, then the reaction mixture was extracted with EtOAc (50 ml×3). The organic layer was separated, washed with water (30 mL), dried and concentrated in vacuo to give the title compound, which was used for next step without further purification.

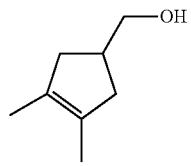

Step E: (3,4-dimethylcyclopent-3-en-1-yl)methanol

LiAlH$_4$ (561 mg, 14.8 mmol) was added to a stirred, cooled mixture of ethyl 3,4-dimethylcyclopent-3-enecarboxylate (829 mg, 4.93 mmol) in THF (15 mL) at 0° C. The mixture was stirred at room temperature for 1 h, then quenched carefully with H$_2$O (5 mL), NaOH (15%, 10 mL) and stirred for 15 min. The mixture was then filtered, and the filtrate was concentrated in vacuo to give the title compound, which was used for next step without further purification. $^1$HNMR (400 MHz, CDCl$_3$) δ 3.71-3.68 (m, 2H), 2.09-2.00 (m, 2H), 1.77-1.71 (m, 1H), 1.71-1.67 (m, 2H), 1.62 (br. s., 6H).

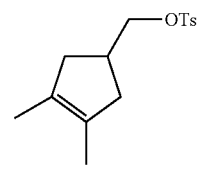 [SMILES: CC1=C(C)CC(COS(=O)(=O)c2ccc(C)cc2)C1]

Step F: (3,4-dimethylcyclopent-3-en-1-yl)methyl 4-methylbenzenesulfonate

A mixture of (3,4-dimethylcyclopent-3-en-1-yl)methanol (1.0 g, 7.92 mmol), TsCl (3.02 g, 15.9 mmol), and Et$_3$N (3.31 ml, 23.8 mmol) in dry DCM (10 ml) was stirred at 0° C. for 0.5 hours. Then the reaction mixture was stirred for 5 hours at room temperature, and extracted with EtOAc (50 mL×3). The combined organic layers were washed with water (50 ml), dried over (Na$_2$SO$_4$) and concentrated in vacuo. The resulting residue was purified by flash chromatography on silica gel (PE:EtOAc=5:1 Rf=0.58) to afford the title compound. $^1$HNMR (400 MHz, CDCl$_3$) δ: 7.77 (d, J=8.2 Hz, 2H), 7.33 (d, J=8.2 Hz, 2H), 3.88 (d, J=7.4 Hz, 2H), 2.54-2.46 (m, 1H), 2.43 (s, 3H), 2.41-2.30 (m, 2H), 1.93 (d, J=17.2 Hz, 2H), 1.51 (s, 6H).

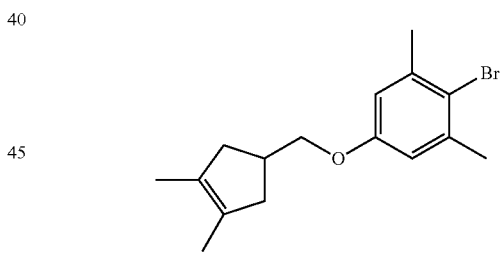

Step G: 2-bromo-5-((3,4-dimethylcyclopent-3-en-1-yl)methoxy)-1,3-dimethylbenzene Cs$_2$CO$_3$ (1.743 g, 5.35 mmol) was added to a stirred mixture of 4-bromo-3,5-dimethylphenol (430 mg, 2.14 mmol) and (3,4-dimethylcyclopent-3-en-1-yl)methyl 4-methylbenzenesulfonate (500 mg, 1.78 mmol) in NMP (10 mL) under N$_2$. The reaction mixture was stirred at 100° C. for 16 hours under N$_2$. After cooling to room temperature, the mixture was filtered through diatomaceous earth. The filtrate was diluted with ethyl acetate (18 mL). The organic layer was washed with water. The water layer was extracted with ethyl acetate (2×30 mL). The combined organic layers were washed with brine, dried over anhydrous Na$_2$SO$_4$, and filtered and the filtrate was concentrated. The resulting residue was purified by flash chromatography on silica gel (PE:EtOAc=40:1) to give the title compound.

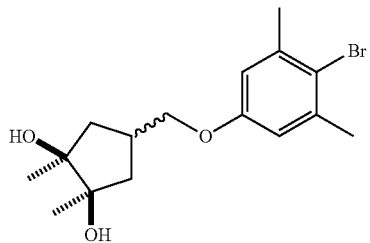 [SMILES: Cc1cc(OCC2C[C@](C)(O)[C@](C)(O)C2)cc(C)c1Br]

Step H: (1R,2S)-4-((4-bromo-3,5-dimethylphenoxy)methyl)-1,2-dimethylcyclo-pentane-1,2-diol A solution of osmium(VIII) oxide (18.5 mg, 0.073 mmol) in a co-solvent of t-BuOH/water (4:1, 0.73 mL) was added to a stirred solution of 2-bromo-5-((3,4-dimethylcyclopent-3-en-1-yl)methoxy)-1,3-dimethylbenzene (450 mg, 1.46 mmol) and 4-methylmorpholine 4-oxide (511 mg, 4.37 mmol) in acetone (10 ml) and water (1 ml) at room temperature. The resulting mixture was stirred at 20° C. for 16 h, then the reaction was quenched via the addition of solid $Na_2SO_3$ (0.3 g). The resulting mixture was stirred at room temperature for 1.5 h, and then diluted with DCM (30 ml). The organic layer was washed with water (2×10 ml), followed by saturated $NaHCO_3$ (20 mL) solution, water (40 ml) and brine (30 mL). The organic phase was separated and dried over anhydrous $Na_2SO_4$. The volatiles were removed in vacuo and the resulting residue was purified by flash chromatography on silica gel $SiO_2$, eluting with PE/EtOAc=10/1 to 1/1 to give the title compound. $^1$HNMR (400 MHz, $CDCl_3$) δ: 11.51 (s, 2H), 8.88 (s, 2H), 8.50 (d, J=7.0 Hz, 2H), 7.25-7.24 (m, 1H), 7.03 (s, 6H), 6.70-6.60 (m, 2H), 6.20-6.10 (m, 2H), 5.80 (s, 6H).

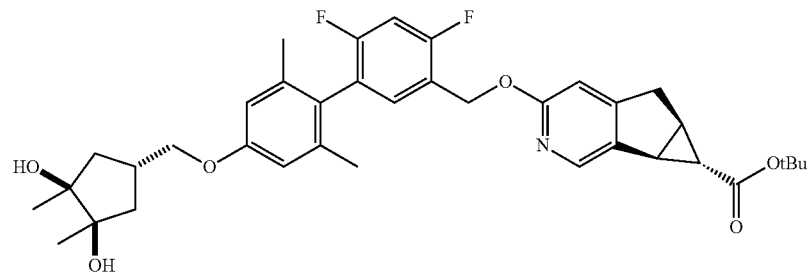

Step I: (5aR,6S,6aS)-tert-butyl 3-((4'-(((1s,3R,4S)-3,4-dihydroxy-3,4-dimethyl-cyclopentyl)methoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate A mixture of 4-((4-bromo-3,5-dimethylphenoxy)methyl)-1,2-dimethylcyclopentane-1,2-diol (93 mg, 0.27 mmol), (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate (162 mg, 0.325 mmol), $K_2CO_3$ (93.4 mg, 0.677 mmol) and 1,1'-bis(di-tert-butylphosphino)-ferrocene palladium dichloride (17.66 mg, 0.027 mmol) in a co-solvent of THF (2 ml)/water (0.5 ml) was irradiated with microwaves at 100° C. for 30 min under a nitrogen atmosphere. After cooling to room temperature, the resulting mixture was filtered. The filtrate was extracted with EtOAc (20 mL×3) and the organic layer was washed with water, and dried over anhydrous $Na_2SO_4$. The mixture was filtered and the filtrate was concentrated in vacuo to give a residue, which was purified by prep-TLC ($SiO_2$, PE:EtOAc=2:1 $R_f$=0.2) to give the title compound. The structure was confirmed by NOE. MS (ESI) m/e (M+H$^+$): 636.1

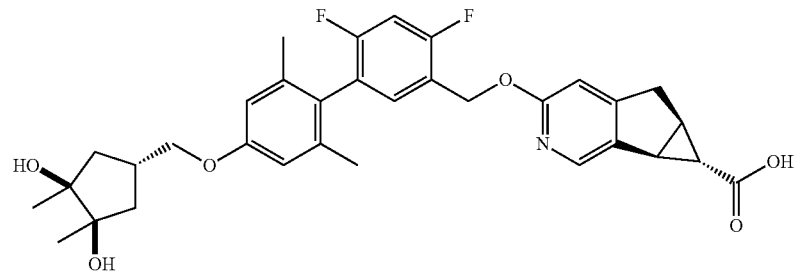 [SMILES: Cc1cc(OC[C@H]2C[C@](C)(O)[C@](C)(O)C2)cc(C)c1-c1cc(COc2cc3c(cn2)[C@H]2[C@@H](C3)[C@@H]2C(=O)O)c(F)cc1F]

Step J: (5 aR,6S,6 aS)-3-((4'-(((1s,3R,4S)-3,4-dihydroxy-3,4-dimethylcyclopentyl)-methoxy)-4,6-difluoro-2',6'-dimethyl-[1,1'-biphenyl]-3-yl)methoxy)-5,5a,6,6a-tetrahydrocyclo-propa[4,5]cyclopenta[1,2-c]pyridine-6-carboxylic acid A mixture of (5aR,6S,6aS)-tert-butyl 3-((4'-(((1s,3R,4S)-3,4-dihydroxy-3,4-dimethylcyclopentyl)methoxy)-4,6-difluoro-2',6'-dimethyl-[1,1'-biphenyl]-3-yl)methoxy)-5,5a,6,6a-tetrahydrocyclo-propa[4,5]cyclopenta[1,2-c]pyridine-6-carboxylate (65 mg, 0.10 mmol) in a co-solvent MeOH (6 ml), THF (3 ml) and water (3 ml) was added LiOH—H$_2$O (64.4 mg, 1.53 mmol). The reaction mixture was stirred at 60° C. for 4 h, then acidified with HCl (2 N) to pH=5, and extracted with ethyl acetate (10 mL×2). The combined organic layers were washed with water, brine, dried over Na$_2$SO$_4$ and concentrated in vacuo to afford the crude product which was purified by prep-HPLC (preparative HPLC on a GILSON 281 instrument fitted with a Phenomenex Gemini C18 250*21.2 mm*4 um using water and acetonitrile as the eluents. Mobile phase A: water (containing 0.01 mol/L TFA, v/v), mobile phase B: acetonitrile. Gradient: 39-69% B, 0-12 min; 100% B, 10.5-12.5 min; 5% B, 13-15 min) to give the title compound. $^1$H NMR (400 MHz, methanol-d$_4$) δ: 8.02-7.93 (m, 1H), 7.27-7.17 (m, 1H), 7.08-6.98 (m, 1H), 6.64 (s, 3H), 5.36-5.31 (m, 2H), 3.87-3.80 (m, 2H), 3.23-3.13 (m, 1H), 3.02-2.92 (m, 1H), 2.83-2.75 (m, 1H), 2.73-2.61 (m, 1H), 2.36-2.27 (m, 1H), 2.12-2.00 (m, 2H), 1.91 (d, J=2.0 Hz, 7H), 1.67-1.55 (m, 2H), 1.21 (s, 6H), 1.07-0.99 (m, 1H). MS (ESI) m/e (M+H$^+$): 580.2

Example 21 & 22

(5aR,6S,6aS)-3-((4'-((1R,3s)-3-((S)-1,2-dihydroxypropan-2-yl)cyclobutoxy)-4,6-difluoro-2',6'-dimethyl-[1,1'-biphenyl]-3-yl)methoxy)-5,5a,6,6a-tetrahydrocyclopropa[4,5]cyclo-penta[1,2-c]pyridine-6-carboxylic acid and (5aR,6S,6aS)-3-((4'-((1S,3s)-3-((R)-1,2-dihydroxypropan-2-yl)cyclobutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

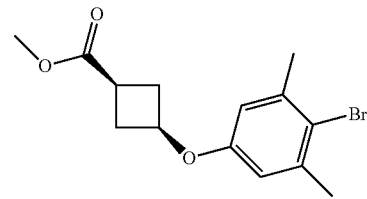 [SMILES: COC(=O)[C@H]1C[C@@H](Oc2cc(C)c(Br)c(C)c2)C1]

Step A: (1s,3s)-methyl 3-(4-bromo-3,5-dimethylphenoxy)cyclobutanecarboxylate

DIAD (3.73 mL, 19.2 mmol) was added to a stirred, cooled mixture of (1r,3r)-methyl 3-hydroxycyclobutanecarboxylate (2.0 g, 15.4 mmol), 4-bromo-3,5-dimethylphenol (3.09 g, 15.4 mmol) and Ph$_3$P (4.84 g, 18.4 mmol) in THF (30 mL) at 0° C. The reaction mixture was stirred at 50° C. for 3 h, then concentrated. The resulting residue was purified by column chromatography on silica gel SiO$_2$, eluting with PE/EtOAC=10/1 to give the title compound. $^1$H NMR (400 MHz, CDCl$_3$) δ: 2.37 (s, 6H), 2.40-2.50 (m, 2H), 2.66-2.89 (m, 3H), 3.71 (s, 3H), 4.47-4.63 (m, 1H), 6.56 (s, 2H).

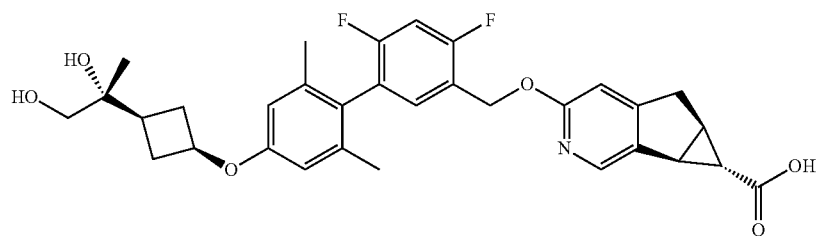

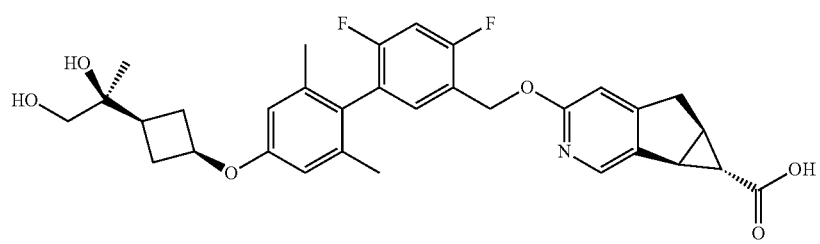

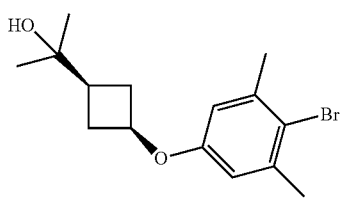 [SMILES: Cc1cc(O[C@H]2C[C@@H](C(C)(C)O)C2)cc(C)c1Br]

Step B: 2-((1s,3s)-3-(4-bromo-3,5-dimethylphenoxy)cyclobutyl)propan-2-ol

Methylmagnesium bromide (13.20 ml, 39.6 mmol) was added to a stirred, cooled mixture of (1s,3s)-methyl 3-(4-bromo-3,5-dimethylphenoxy)cyclobutanecarboxylate (3.1 g, 9.9 mmol) in THF (40 ml) at −78° C. and the mixture was stirred at 22° C. for 2 h. Then the mixture was quenched with NH$_4$Cl (saturated, 50 mL) and extracted with EtOAc (2×50 mL). The combined organic layers were washed with brine (80 mL), dried over anhydrous Na$_2$SO$_4$, filtered and the filtrate was evaporated under reduced pressure to give the title compound, which was used in next step without further purification.

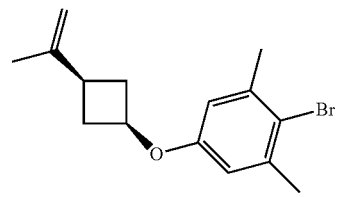 [SMILES: C=C(C)[C@H]1C[C@@H](Oc2cc(C)c(Br)c(C)c2)C1]

Step C: 2-bromo-1,3-dimethyl-5-((1s,3s)-3-(prop-1-en-2-yl)cyclobutoxy)benzene SOCl$_2$ (0.524 ml, 7.18 mmol) was added slowly to a stirred, cooled mixture of 2-((1s,3s)-3-(4-bromo-3,5-dimethylphenoxy)cyclobutyl)propan-2-ol (1.5 g, 4.79 mmol) in toluene (40 mL) at 0° C. and the mixture was stirred at 0° C. for 10 min. Then a solution of DABCO (1.343 g, 11.97 mmol) in toluene (5 mL) was added at 0° C. The resulting mixture was stirred at 25° C. for 16 h, then quenched with NH$_4$Cl (saturated, 20 mL) and extracted with EtOAc (2×50 mL). The combined organic layers were washed with brine (20 mL), dried over anhydrous Na$_2$SO$_4$, filtered and the filtrate was evaporated under reduced pressure. The resulting residue was purified by reverse phase preparative HPLC (preparative HPLC on a GILSON 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 79-97% B, 0-10 min; 100% B, 10.5-12.5 min; 5% B, 13-15 min) to give the title compound. $^1$H NMR (400 MHz, CDCl$_3$) δ: 1.72 (s, 3H), 1.96-2.07 (m, 2H), 2.38 (s, 6H), 2.45-2.57 (m, 1H), 2.58-2.72 (m, 2H), 4.45-4.56 (m, 1H), 4.74 (d, J=26.4 Hz, 2H), 6.59 (s, 2H).

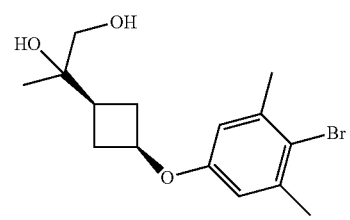 [SMILES: Cc1cc(O[C@H]2C[C@@H](C(C)(O)CO)C2)cc(C)c1Br]

Step D: 2-((1s,3s)-3-(4-bromo-3,5-dimethylphenoxy)cyclobutyl)propane-1,2-diol Osmium(VIII) oxide (0.089 ml, 0.285 mmol, 0.3 M in water/tBuOH (9/1)) was added to a stirred solution of 2-bromo-1,3-dimethyl-5-((1s,3s)-3-(prop-1-en-2-yl)cyclobutoxy)benzene (420 mg, 1.42 mmol) and 4-methylmorpholine 4-oxide (500 mg, 4.27 mmol) in MeCN (15 mL) and water (1.5 mL) at 25° C. The resulting mixture was stirred at 24° C. for 6 h. Then the reaction was quenched by the addition of solid Na$_2$SO$_3$ (2 g) and the resulting mixture was stirred for 1.5 h at room temperature. The mixture was then concentrated in vacuo and the resulting residue was diluted with EtOAc (100 ml). The organic phase was washed with water (2×20 ml), followed by saturated NaHCO$_3$ (40 ml), water (30 ml) and brine (30 ml). The organic layer was dried over anhydrous Na$_2$SO$_4$, filtered and the volatiles were removed under vacuum to give the title compound, which was used in next step without further purification.

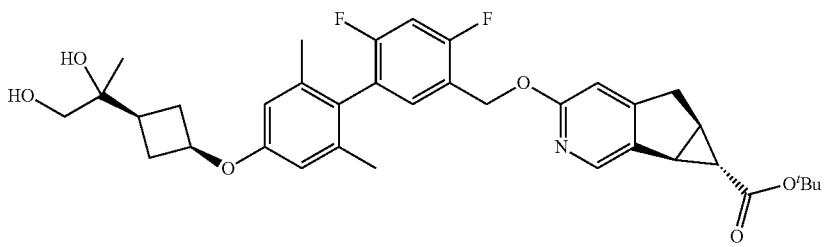 [SMILES: Cc1cc(O[C@H]2C[C@@H](C(C)(O)CO)C2)cc(C)c1-c1cc(COc2cc3c(cn2)[C@H]2[C@@H](C3)[C@@H]2C(=O)OC(C)(C)C)c(F)cc1F]

Step E: (5aR,6S,6aS)-tert-butyl 3-((4'-((1s,3s)-3-(1,2-dihydroxypropan-2-yl)cyclobutoxy)-4,6-difluoro-2',6'-dimethyl-[1,1'-biphenyl]-3-yl)methoxy)-5,5a,6,6a-tetrahydrocyclopropa[4,5]-cyclopenta[1,2-c]pyridine-6-carboxylate A mixture of 2-((1s,3s)-3-(4-bromo-3,5-dimethylphenoxy)cyclobutyl)propane-1,2-diol (200 mg, 0.607 mmol), K$_2$CO$_3$ (210 mg, 1.52 mmol), (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta

[1,2-c]pyridine-6-carboxylate (364 mg, 0.729 mmol) and 2nd Generation XPHOS Pre catalyst (47.8 mg, 0.061 mmol) in THF (3 ml) and water (1 ml) was sealed in a 10 mL vial/autoclave and stirred at 100° C. for 0.5 h under $N_2$ protection under microwave irradiation. After cooling to room temperature, the mixture was filtered through diatomaceous earth and the filtrate was diluted with ethyl acetate (8 mL). The organic layer was washed with water (10 mL). The water layer was extracted with ethyl acetate (5 ml×2). The combined organic layers were washed with brine (5 mL), and dried over anhydrous $Na_2SO_4$. The mixture was filtered and the filtrate was concentrated. The resulting residue was purified by prep-HPLC (preparative HPLC on a GILSON 281 instrument fitted with a Phenomenex Synergi C18 250*21.2 mm*4 um using water and acetonitrile as the eluents. Mobile phase A: water (containing 0.1% TFA, v/v) mobile phase B: acetonitrile. Gradient: 59-89% B, 0-10 min; 100% B, 10.5-12.5 min; 5% B, 13-15 min) to give the title compound. $^1$H NMR (400 MHz, methanol-$d_4$) δ: 1.10 (s, 3H), 1.16 (s, 1H), 1.46 (s, 9H), 1.93 (s, 6H), 2.01-2.21 (m, 3H), 2.32-2.50 (m, 3H), 2.91 (d, J=5.48 Hz, 1H), 3.03-3.17 (m, 1H), 3.24-3.28 (m, 1H), 3.32 (s, 2H), 4.40-4.64 (m, 1H), 5.40 (s, 2H), 6.60 (s, 2H), 6.89 (s, 1H), 7.09 (t, J=9.6 Hz, 1H), 7.27 (t, J=8.0 Hz, 1H), 8.10 (s, 1H). MS (ESI) m/e (M+H$^+$): 622.2

The first peak isomer (74 mg, 0.12 mmol) was added to a stirred mixture of lithium hydroxide-$H_2O$ (74.9 mg, 1.79 mmol) in MeOH (3 ml)/THF (2 ml)/water (1 ml), and the reaction was stirred at 25° C. for 68 h. The mixture was acidified with 2N HCl to pH=3, and extracted with ethyl acetate (2×8 mL). The combined organic layers were washed with brine (8 mL), dried over anhydrous $Na_2SO_4$, filtered and the filtrate was evaporated under reduced pressure. The resulting residue was purified by prep-HPLC (preparative HPLC on a GILSON 281 instrument fitted with a Phenomenex Synergi C18 250*21.2 mm*4 um using water and acetonitrile as the eluents. Mobile phase A: water (containing 0.1% TFA, v/v), mobile phase B: acetonitrile. Gradient: 37-67% B, 0-10 min; 100% B, 10.5-12.5 min; 5% B, 13-15 min) to give isomer I as the carboxylic acid. The acid was converted to its sodium salt using 0.5 M NaOH. $^1$H NMR (400 MHz, methanol-$d_4$) δ: 1.08 (s, 1H), 1.10 (s, 3H), 1.92 (s, 6H), 2.01-2.22 (m, 3H), 2.31-2.50 (m, 3H), 2.79-2.89 (m, 1H), 2.96-3.07 (m, 1H), 3.17-3.26 (m, 1H), 3.32 (s, 2H), 4.46-4.59 (m, 1H), 5.35 (s, 2H), 6.60 (s, 2H), 6.67 (s, 1H), 7.05 (t, J=9.6 Hz, 1H), 7.24 (t, J=8.4 Hz, 1H), 8.03 (s, 1H). MS (ESI) m/e (M+H$^+$): 566.2

The second peak isomer (112 mg, 0.180 mmol) was added to a stirred mixture of lithium hydroxide-$H_2O$ (113 mg, 2.70 mmol) in MeOH (3 ml)/THF (2 ml)/water (1 ml) and the

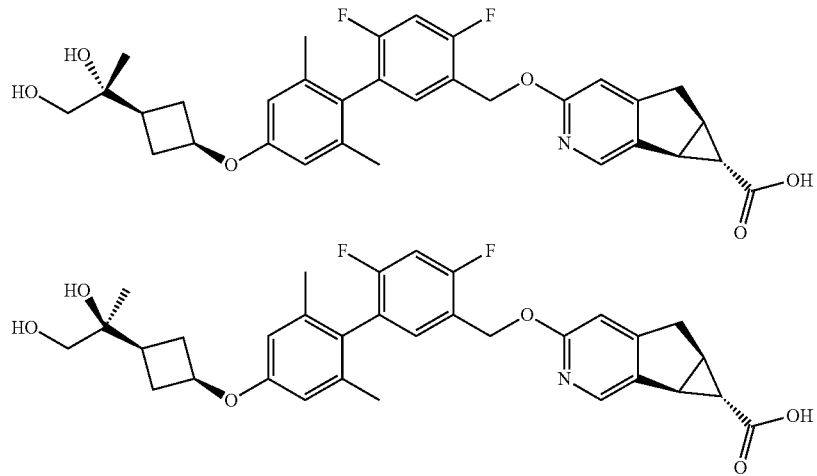

Step F: (5 aR,6S,6aS)-3-((4'-((1R,3s)-3-((S)-1,2-dihydroxypropan-2-yl)cyclobutoxy)-4,6-difluoro-2',6'-dimethyl-[1,1'-biphenyl]-3-yl)methoxy)-5,5a,6,6a-tetrahydrocyclo-propa[4,5]-cyclopenta[1,2-c]pyridine-6-carboxylic acid and (5aR,6S,6aS)-3-((4'-((1S,3s)-3-((R)-1,2-dihydroxypropan-2-yl)cyclobutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (5aR,6S,6aS)-tert-butyl 3-((4'-((1s,3s)-3-(1,2-dihydroxypropan-2-yl)cyclobutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate was resolved by SFC (method: "Column. Chiralpak AD-H 250×4.6 mm I.D., 5 um Mobile phase: 40% of methanol (0.05% DEA) in $CO_2$ Flow rate: 2.5 mL/min Wavelength: 220 nm") to give the first peak isomer with shorter retention time, and the second peak isomer with longer retention time.

reaction was stirred at 25° C. for 68 h. The mixture was acidified with 2N HCl to pH=3, and extracted with ethyl acetate (2×8 mL). The combined organic layers were washed with brine (8 mL), dried over anhydrous $Na_2SO_4$, filtered and the filtrate was evaporated under reduced pressure. The resulting residue was purified by prep-HPLC (preparative HPLC on a GILSON 281 instrument fitted with a Phenomenex Synergi C18 250*21.2 mm*4 um using water and acetonitrile as the eluents. Mobile phase A: water (containing 0.1% TFA, v/v), mobile phase B: acetonitrile. Gradient: 38-68% B, 0-10 min; 100% B, 10.5-12.5 min; 5% B, 13-15 min) to give the isomer II as the carboxylic acid. The acid was converted to its sodium salt using 0.5 M NaOH. $^1$H NMR (400 MHz, methanol-$d_4$) δ: 1.08 (s, 1H), 1.10 (s, 3H), 1.92 (s, 6H), 2.01-2.20 (m, 3H), 2.31-2.50 (m, 3H), 2.81-2.87 (m, 1H), 2.95-3.05 (m, 1H), 3.16-3.26 (m, 1H), 3.32 (s, 2H), 4.46-4.58 (m, 1H), 5.35 (s, 2H), 6.59 (s, 2H), 6.66 (s, 1H), 7.05 (t, J=9.6 Hz, 1H), 7.23 (t, J=8.2 Hz, 1H), 8.02 (s, 1H). MS (ESI) m/e (M+H$^+$): 566.2

Example 23 & 24

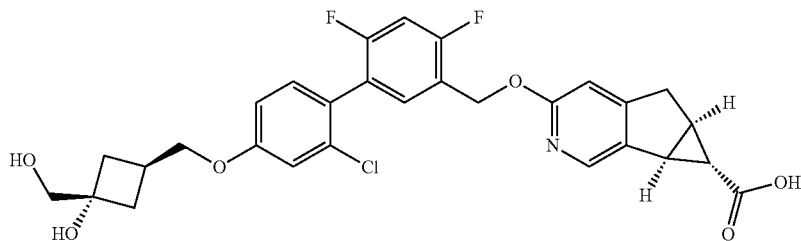 [SMILES: O=C(O)[C@H]1[C@@H]2Cc3cc(OCc4cc(-c5ccc(OC[C@H]6C[C@@](O)(CO)C6)cc5Cl)c(F)cc4F)ncc3[C@@H]21]

(5aR,6S,6aS)-3-((2'-chloro-4,6-difluoro-4'-(((1r,3r)-3-hydroxy-3-(hydroxymethyl)-cyclobutyl)-methoxy)-[1,1'-biphenyl]-3-yl)methoxy)-5,5a,6,6a-tetrahydrocyclo-propa[4,5]cyclopenta-[1,2-c]pyridine-6-carboxylic acid

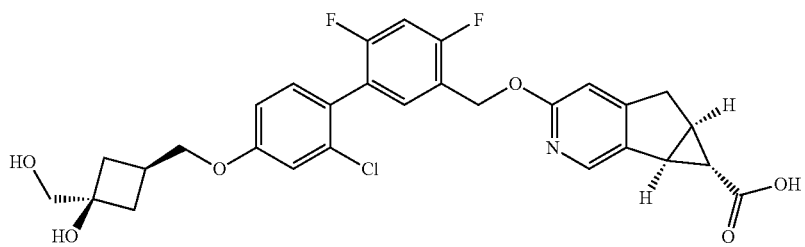 [SMILES: O=C(O)[C@H]1[C@@H]2Cc3cc(OCc4cc(-c5ccc(OC[C@H]6C[C@](O)(CO)C6)cc5Cl)c(F)cc4F)ncc3[C@@H]21]

(5 aR,6S,6aS)-3-((2'-chloro-4,6-difluoro-4'-(((1s,3s)-3-hydroxy-3-(hydroxymethyl)-cyclobutyl)-methoxy)-[1,1'-biphenyl]-3-yl)methoxy)-5,5a,6,6a-tetrahydrocyclo-propa[4,5]cyclopenta[1,2-c]pyridine-6-carboxylic acid

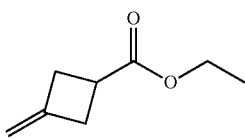

Step A: Ethyl 3-methylenecyclobutanecarboxylate

To the mixture of bromo(methyl)-triphenylphosphorane (18.70 g, 52.3 mmol) in THF (20 ml) was added potassium 2-methylpropan-2-olate (49.1 ml, 49.1 mmol) dropwise. To the resulting suspension was added dropwise a solution of ethyl 3-oxocyclobutanecarboxylate (4.65 g, 32.7 mmol) in 10 mL of THF. Then the mixture was stirred at 20° C. for 15 h; concentrated in vacuo and partitioned with water (20 mL) and EtOAc (20 mL). The aqueous layer was separated and extracted with EtOAc (20 mL×2). The combined organic layers were washed with saturated NaCl solution (10 mL), dried over anhydrous $Na_2SO_4$, filtered and concentrated in vacuo. The resulting residue was purified by normal phase chromatography (ISCO, 40 g SepaFlash® Silica Flash Column, Eluent of 10% EtOAc/PE gradient @ 40 mL/min, 18 min, dry loaded) to give the title compound.

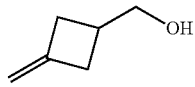

Step B: (3-methylenecyclobutyl)methanol

LAH (1.748 g, 46.1 mmol) was added to a stirred, cooled mixture of ethyl 3-methylenecyclobutanecarboxylate (2.69 g, 11.5 mmol) in THF (20 mL) at 0° C. The mixture was stirred at 25° C. for 5 h, then quenched by the addition of anhydrous $Na_2SO_4$ (18 g), followed by the portionwise addition of EtOAc (50 mL), and the dropwise addition of water until the reaction mixture turned transparent. The mixture was then filtered and the filtrate was concentrated. The residue was purified by normal phase chromatography (ISCO, 20 g SepaFlash® Silica Flash Column, Eluent of 20% EtOAc/PE gradient @ 35 mL/min, 30 min, dry loaded) to give the title compound, which was used in next step without further purification.

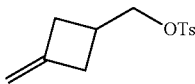 [SMILES: C=C1CC(COS(=O)(=O)c2ccc(C)cc2)C1]

Step C: (3-methylenecyclobutyl) methyl 4-methylbenzenesulfonate

4-Methyl-benzene-1-sulfonyl chloride (2.203 g, 11.55 mmol) was added to a stirred solution of (3-methylenecyclobutyl)methanol (1.89 g, 9.63 mmol) and triethylamine (4.03 ml, 28.9 mmol) in DCM (15 mL). The mixture was stirred at 22° C. for 16 h, then diluted with DCM (15 mL) and water (15 mL). The organic layer was separated, washed with water (15 mL), brine (15 mL) and dried with anhydrous Na$_2$SO$_4$. The mixture was filtered and the filtrate was concentrated. The resulting residue was purified by normal phase chromatography (ISCO, 12 g SepaFlash® Silica Flash Column, Eluent of 5% EtOAc/PE gradient @ 40 mL/min, 30 min, dry loaded) to give the title compound.

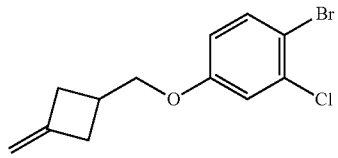

Step D: 1-bromo-2-chloro-4-((3-methylenecyclobutyl)methoxy)benzene

A mixture of (3-methylenecyclobutyl)methyl 4-methylbenzenesulfonate (700 mg, 1.39 mmol), 4-bromo-3-chlorophenol (345 mg, 1.66 mmol) and K$_2$CO$_3$ (575 mg, 4.16 mmol) in DMF (8 ml) was stirred at 100° C. for 15 h. Then the reaction mixture was concentrated in vacuo and partitioned between water (20 mL) and EtOAc (20 mL). The aqueous layer was separated, and extracted with EtOAc (20 mL). The combined organic layers were washed with saturated NaCl solution (10 mL), dried over anhydrous Na$_2$SO$_4$, filtered and concentrated in vacuo. The resulting residue was purified by normal phase chromatography (ISCO, 12 g SepaFlash® Silica Flash Column, Eluent of 5% EtOAc/PE gradient @ 35 mL/min, 25 min, dry loaded) to give the title compound.

Step E: 3-((4-bromo-3-chlorophenoxy)methyl)-1-(hydroxymethyl)-cyclobutanol

To the mixture of 1-bromo-2-chloro-4-((3-methylenecyclobutyl)-methoxy)benzene (405 mg, 1.41 mmol) and NMO (495 mg, 4.22 mmol) in acetone (10 ml) and water (1.0 ml) was added osmium(VIII) oxide (17.90 mg, 0.070 mmol). The resulting mixture was stirred at 22° C. for 18 h, and then quenched by adding Na$_2$S$_2$O$_3$ (20 mL, sat. aqueous solution) and stirred for 1 h. The resulting mixture was diluted with water (10 mL) and EtOAc (30 mL). The aqueous layer was separated and extracted with EtOAc (20 mL×2). The combined organic layers were washed with saturated NaCl solution (10 mL), dried over anhydrous Na$_2$SO$_4$, filtered and concentrated in vacuo. The resulting residue was purified by normal phase chromatography (ISCO, 12 g SepaFlash® Silica Flash Column, Eluent of 50% EtOAc/PE gradient @ 35 mL/min, 30 min, dry loaded) to give the title compound. MS (ESI) m/e (M+H$^+$): 320.7/322.7

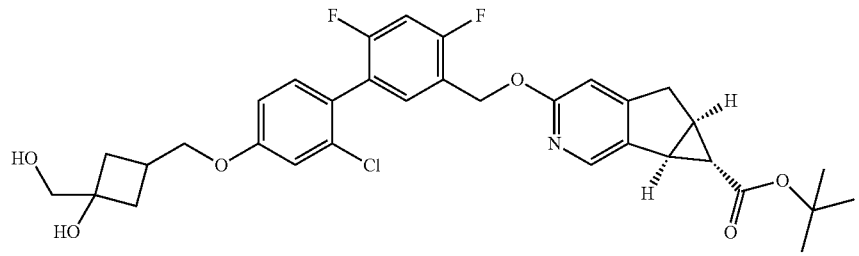

Step F: (5aR,6S,6aS)-tert-butyl 3-((2'-chloro-4,6-difluoro-4'-((3-hydroxy-3-(hydroxyl-methyl)cyclobutyl)methoxy)-[1,1'-biphenyl]-3-yl)methoxy)-5,5a,6,6a-tetrahydrocyclopropa-[4,5]-cyclopenta[1,2-c]pyridine-6-carboxylate To the mixture of 3-((4-bromo-3-chlorophenoxy)-methyl)-1-(hydroxymethyl)cyclobutanol (120 mg, 0.373 mmol), (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydro-cyclopropa[4,5]cyclopenta[1,2-c]pyridine-6-carboxylate (186 mg, 0.373 mmol) and K$_2$CO$_3$ (155 mg, 1.12 mmol) in a solvent mixture of THF (3 ml) and water (1 ml) was added Pd(dtbpf)Cl$_2$ (12.16 mg, 0.019 mmol). The resulting mixture was sealed in a 10 mL vial/autoclave and stirred at 100° C. for 0.5 h under N$_2$. After cooling to room temperature, the mixture was filtered through a pad of diatomaceous earth and the filtrate was diluted with ethyl acetate (8 mL) and water (10 mL). The aqueous layer was separated and extracted with ethyl acetate (10 mL×2). The combined organic layers were washed with saturated NaCl solution (10 mL), dried over anhydrous Na$_2$SO$_4$, filtered and concentrated. The resulting residue was purified by prep-HPLC (preparative HPLC on a GILSON 281 instrument fitted with a YMC-Actus Triart C18 (150*30 mm*5 um) using water and acetonitrile as the eluents. Mobile phase A: water (containing 0.1% TFA, v/v), mobile phase B: acetonitrile. Gradient: 26-79% B, 0-10 min; 100% B, 10.5-12.5 min; 5% B, 13-15 min)) to give the title compound. MS (ESI) m/e (M+H$^+$): 614.2

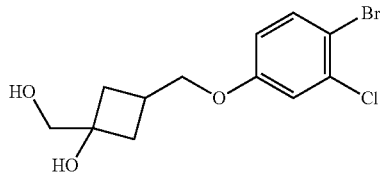 [SMILES: OCC1(O)CC(COc2ccc(Br)c(Cl)c2)C1]

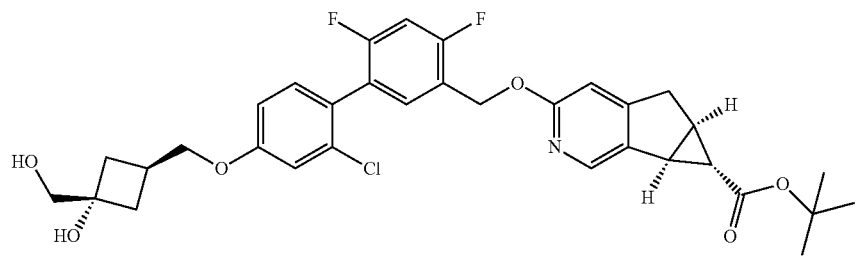

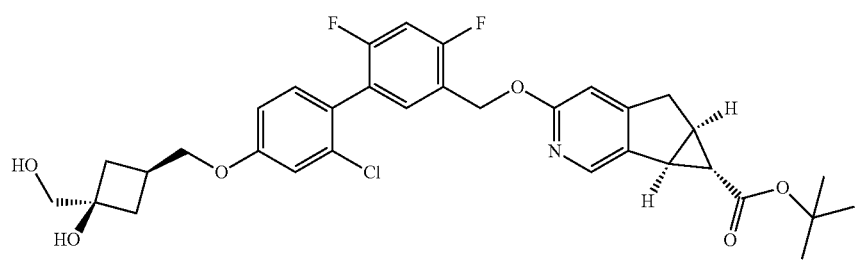

Step G: (5aR,6S,6aS)-tert-butyl 3-((2'-chloro-4,6-difluoro-4'-(((1r,3r)-3-hydroxy-3-(hydroxymethyl)cyclobutyl)methoxy)-[1,1'-biphenyl]-3-yl)methoxy)-5,5a,6,6a-tetrahydro-cyclopropa[4,5]cyclopenta[1,2-c]pyridine-6-carboxylate and (5aR,6S,6aS)-tert-butyl 3-((2'-chloro-4,6-difluoro-4'-(((1s,3s)-3-hydroxy-3-(hydroxymethyl)cyclobutyl)methoxy)-[1,1'-biphenyl]-3-yl)methoxy)-5,5a,6,6a-tetrahydrocyclopropa[4,5]cyclopenta[1,2-c]pyridine-6-carboxylate (5aR,6S,6aS)-tert-butyl 3-((2'-chloro-4,6-difluoro-4'-((3-hydroxy-3-(hydroxymethyl)cyclobutyl)methoxy)-[1,1'-biphenyl]-3-yl)methoxy)-5,5a,6,6a-tetrahydrocyclopropa[4,5]cyclopenta[1,2-c]pyridine-6-carboxylate was separated by SFC (Column: Chiralpak AD-3 50*4.6 mm I.D., 3 um Mobile phase: 60% ethanol (0.05% DEA) in $CO_2$ Flow rate: 3 mL/min Wavelength: 220 nm, retention time $t_{R1}$=0.895 min, retention time $t_{R2}$=2.803 min) to give the first peak isomer with shorter retention time (5aR,6S,6aS)-tert-butyl 3-((2'-chloro-4,6-difluoro-4'-(((1r,3r)-3-hydroxy-3-(hydroxymethyl)cyclobutyl)-methoxy)-[1,1'-biphenyl]-3-yl)methoxy)-5,5a,6,6a-tetrahydrocyclopropa[4,5]cyclopenta[1,2-c]pyridine-6-carboxylate and the second peak isomer with longer retention time (5aR,6S,6aS)-tert-butyl 3-((2'-chloro-4,6-difluoro-4'-(((1s,3s)-3-hydroxy-3-(hydroxymethyl)-cyclobutyl)methoxy)-[1,1'-biphenyl]-3-yl)methoxy)-5,5a,6,6a-tetrahydrocyclopropa[4,5]-cyclopenta[1,2-c]pyridine-6-carboxylate.

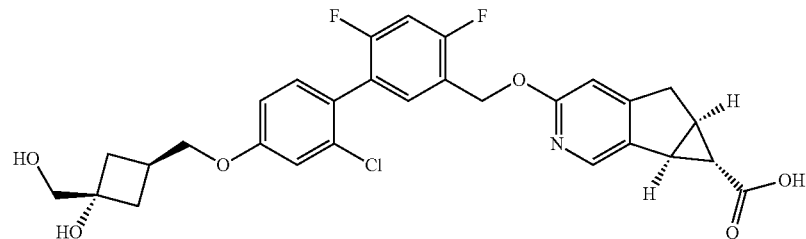

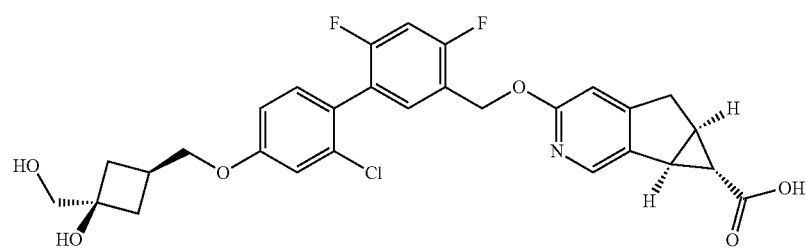 [SMILES: O=C(O)[C@H]1[C@@H]2Cc3cc(OCc4cc(-c5ccc(OC[C@H]6C[C@](O)(CO)C6)cc5Cl)c(F)cc4F)ncc3[C@@H]21]

Step H: (5aR,6S,6aS)-3-((2'-chloro-4,6-difluoro-4'-(((1r,3r)-3-hydroxy-3-(hydroxymethyl)-cyclobutyl)methoxy)-[1,1'-biphenyl]-3-yl)methoxy)-5,5a,6,6a-tetrahydrocyclopropa[4,5]-cyclopenta[1,2-c]pyridine-6-carboxylic acid LiOH.H$_2$O (45.8 mg, 1.09 mmol) was added to a stirred mixture of (5aR,6S,6aS)-tert-butyl 3-((2'-chloro-4,6-difluoro-4'-(((1r,3r)-3-hydroxy-3-(hydroxymethyl)cyclobutyl)methoxy)-[1,1'-biphenyl]-3-yl)methoxy)-5,5a,6,6a-tetrahydrocyclopropa[4,5]cyclopenta[1,2-c]pyridine-6-carboxylate (67 mg, 0.109 mmol) in THF (3 mL), water (1 mL) and MeOH (1 mL). The mixture was stirred at 25° C. for 16 h, then acidified with 1N HCl to pH=3 and extracted with ethyl acetate (10 mL×2). The combined organic layers were washed with brine (8 mL), dried over anhydrous Na$_2$SO$_4$, filtered and concentrate. The resulting crude product was purified by prep-TLC(SiO$_2$, EtOAc) to give (5aR,6S,6aS)-3-((2'-chloro-4,6-difluoro-4'-(((1r,3r)-3-hydroxy-3-(hydroxymethyl)-cyclobutyl)methoxy)-[1,1'-biphenyl]-3-yl)methoxy)-5,5a,6,6a-tetrahydrocyclopropa[4,5]-cyclopenta[1,2-c]pyridine-6-carboxylic acid. The acid was converted to the corresponding sodium salt using 0.5 M aq. NaOH. $^1$H NMR (400 MHz, methanol-d4) δ: 8.02 (s, 1H), 7.44 (t, J=8.4 Hz, 1H), 7.23 (d, J=8.4 Hz, 1H), 7.10-7.02 (m, 2H), 6.96 (dd, J=2.4, 8.4 Hz, 1H), 6.67 (s, 1H), 5.36 (s, 2H), 4.03 (d, J=6.4 Hz, 2H), 3.47 (s, 2H), 3.26-3.16 (m, 1H), 3.04-2.96 (m, 1H), 2.93-2.82 (m, 1H), 2.79 (d, J=5.2 Hz, 1H), 2.37-2.26 (m, 1H), 2.13 (d, J=8.0 Hz, 4H), 1.05 (br. s., 1H). MS (ESI) m/e (M+H$^+$): 558.2

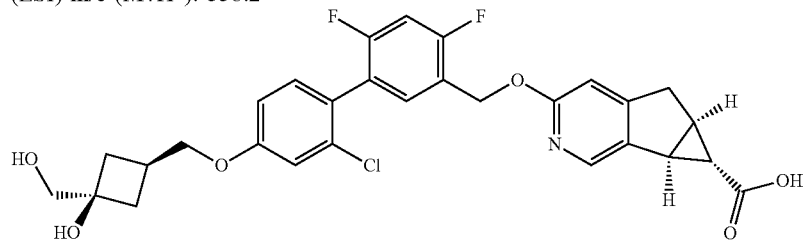

Step I: (5aR,6S,6aS)-3-((2'-chloro-4,6-difluoro-4'-(((1s,3s)-3-hydroxy-3-(hydroxymethyl)-cyclobutyl)methoxy)-[1,1'-biphenyl]-3-yl)methoxy)-5,5a,6,6a-tetrahydrocyclopropa[4,5-]cyclopenta[1,2-c]pyridine-6-carboxylic acid LiOH.H$_2$O (32.8 mg, 0.782 mmol) was added to a stirred mixture of the second peak isomer with longer retention time in chiral HPLC (5aR,6S,6aS)-tert-butyl 3-((2'-chloro-4,6-difluoro-4'-(((1s,3s)-3-hydroxy-3-(hydroxymethyl)cyclobutyl)methoxy)-[1,1'-biphenyl]-3-yl)methoxy)-5,5a,6,6a-tetrahydro-cyclopropa[4,5]cyclopenta[1,2-c]pyridine-6-carboxylate (48 mg, 0.078 mmol) in THF (3 mL), water (1 mL) and MeOH (1 mL). The mixture was stirred at 45° C. for 16 h, then acidified with 1N HCl to pH=3 and extracted with ethyl acetate (10 mL×2). The combined organic layers were washed with brine (8 mL), dried over anhydrous Na$_2$SO$_4$, filtered and concentrated. The resulting crude product which was purified by prep-TLC(SiO$_2$, EtOAc) to give (5aR,6S,6aS)-3-((2'-chloro-4,6-difluoro-4'-(((1s,3s)-3-hydroxy-3-(hydroxymethyl)cyclobutyl)methoxy)-[1,1'-biphenyl]-3-yl)methoxy)-5,5a,6,6a-tetrahydrocyclopropa[4,5]cyclopenta[1,2-c]pyridine-6-carboxylic acid. The acid was converted to the corresponding sodium salt using 0.5 M aq. NaOH. $^1$H NMR (400 MHz, methanol-d4): δ 8.02 (s, 1H), 7.44 (t, J=8.4 Hz, 1H), 7.23 (d, J=8.4 Hz, 1H), 7.13-7.02 (m, 2H), 6.97 (dd, J=2.4, 8.4 Hz, 1H), 6.67 (s, 1H), 5.36 (s, 2H), 4.04 (d, J=5.2 Hz, 2H), 3.56 (s, 2H), 3.26-3.14 (m, 1H), 3.08-2.94 (m, 1H), 2.79 (d, J=6.0 Hz, 1H), 2.41-2.26 (m, 4H), 2.03-1.85 (m, 2H), 1.05 (t, J=2.8 Hz, 1H). MS (ESI) m/e (M+H$^+$): 558.2

Example 25 & 26

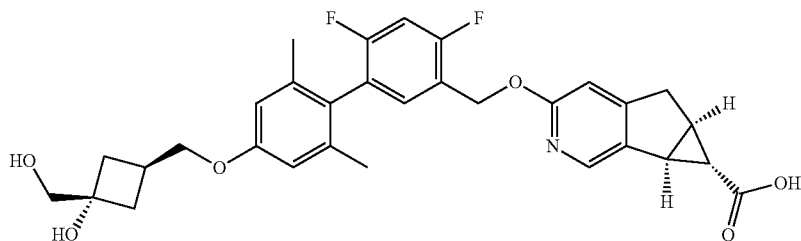 [SMILES: Cc1cc(OC[C@H]2C[C@@](O)(CO)C2)cc(C)c1-c1cc(COc2cc3c(cn2)[C@H]2[C@@H](C3)[C@@H]2C(=O)O)c(F)cc1F]

(5aR,6S,6aS)-3-((4,6-difluoro-4'-(((1r,3r)-3-hydroxy-3-(hydroxymethyl)cyclobutyl)-methoxy)-2',6'-dimethyl-[1,1'-biphenyl]-3-yl)methoxy)-5,5a,6,6a-tetrahydrocyclopropa-[4,5]cyclopenta[1,2-c]pyridine-6-carboxylic acid

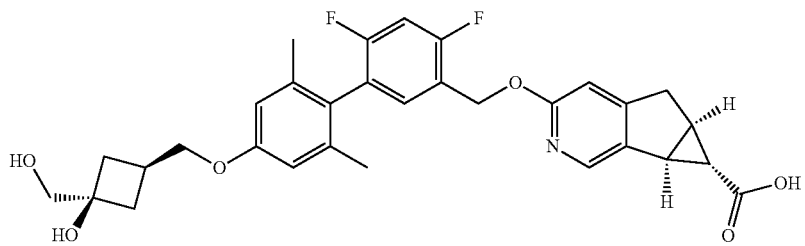 [SMILES: Cc1cc(OC[C@H]2C[C@](O)(CO)C2)cc(C)c1-c1cc(COc2cc3c(cn2)[C@H]2[C@@H](C3)[C@@H]2C(=O)O)c(F)cc1F]

(5aR,6S,6aS)-3-((4,6-difluoro-4'-(((1s,3s)-3-hydroxy-3-(hydroxymethyl)cyclobutyl)-methoxy)-2',6'-dimethyl-[1,1'-biphenyl]-3-yl)methoxy)-5,5a,6,6a-tetrahydrocyclo-propa[4,5]cyclopenta[1,2-c]pyridine-6-carboxylic acid

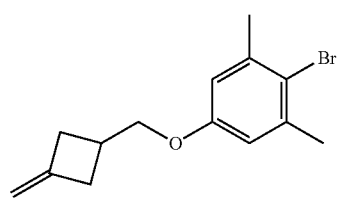 [SMILES: C=C1CC(COc2cc(C)c(Br)c(C)c2)C1]

Step A: 2-bromo-1,3-dimethyl-5-((3-methylenecyclobutyl)methoxy)benzene

The mixture of (3-methylenecyclobutyl) methyl 4-methylbenzenesulfonate (700 mg, 1.39 mmol), 4-bromo-3,5-dimethylphenol (335 mg, 1.66 mmol) and $K_2CO_3$ (575 mg, 4.16 mmol) in DMF (8 ml) was stirred at 100° C. for 15 h. The mixture was then concentrated in vacuo and diluted with water (20 mL) and EtOAc (20 mL). The aqueous layer was extracted with EtOAc (20 mL) and the combined organic layers were washed with saturated NaCl solution (10 mL), dried over anhydrous $Na_2SO_4$, filtered and concentrated in vacuo. The resulting residue was purified by normal phase chromatography (ISCO, 12 g SepaFlash® Silica Flash Column, Eluent of 5% EtOAc/PE gradient @ 35 mL/min, 15 min, dry loaded) to give 2-bromo-1,3-dimethyl-5-((3-methylenecyclobutyl)methoxy)benzene.

Step B: 3-((4-bromo-3,5-dimethylphenoxy)methyl)-1-(hydroxymethyl)-cyclobutanol

To the mixture of 2-bromo-1,3-dimethyl-5-((3-methylenecyclobutyl)-methoxy)benzene (504 mg, 0.896 mmol) and NMO (315 mg, 2.69 mmol) in acetone (10 ml) and water (1.0 ml) was added $OsO_4$ (11.39 mg, 0.045 mmol). The resulting mixture was stirred at 22° C. for 18 h., then quenched by adding $Na_2S_2O_3$ (20 mL) and stirred for 1 h. The resulting mixture was diluted with water (10 mL) and EtOAc (30 mL). The aqueous layer was separated, and extracted with EtOAc (20 mL×2). The combined organic layers were washed with saturated NaCl solution (10 mL), dried over anhydrous $Na_2SO_4$, filtered and concentrated in vacuo. The resulting residue was purified by normal phase chromatography (ISCO, 4 g SepaFlash® Silica Flash Column, Eluent of 60% EtOAc/PE gradient @ 35 mL/min, 20 min, dry loaded) to give 3-((4-bromo-3,5-dimethylphenoxy)methyl)-1-(hydroxymethyl)cyclobutanol. $^1$HNMR (400 MHz, $CDCl_3$) δ: 6.64 (d, J=6.0 Hz, 2H), 3.91 (dd, J=6.0, 17.6 Hz, 2H), 3.63 (d, J=9.6 Hz, 2H), 2.95-2.76 (m, 1H), 2.38 (s, 6H), 2.34-2.27 (m, 1H), 2.25-2.16 (m, 1H), 2.13-2.03 (m, 1H), 2.00-1.88 (m, 1H).

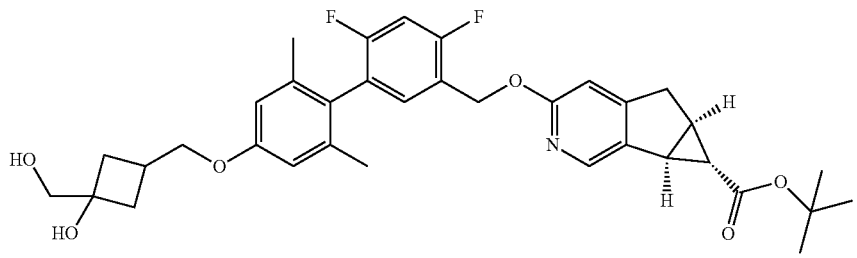 [SMILES: Cc1cc(OCC2CC(O)(CO)C2)cc(C)c1-c1cc(COc2cc3c(cn2)[C@H]2[C@@H](C3)[C@@H]2C(=O)OC(C)(C)C)c(F)cc1F]

Step C: (5aR,6S,6aS)-tert-butyl 3-((4,6-difluoro-4'-((3-hydroxy-3-(hydroxymethyl)-cyclobutyl)methoxy)-2',6'-dimethyl-[1,1'-biphenyl]-3-yl)methoxy)-5,5a,6,6a-tetrahydro-cyclopropa[4,5]cyclopenta[1,2-c]pyridine-6-carboxylate To the mixture of 3-((4-bromo-3,5-dimethylphenoxy)methyl)-1-(hydroxymethyl)cyclobutanol (120 mg, 0.381 mmol), Intermediate 6 (190 mg, 0.381 mmol) and K₂CO₃ (158 mg, 1.14 mmol) in the solvent mixture of THF (3 ml) and water (1 ml) was added Pd(dtbpf)Cl₂ (12.41 mg, 0.019 mmol). The resulting mixture was sealed in a 10 mL vial/autoclave and stirred at 100° C. for 0.5 h under N₂

Step D: (5aR,6S,6aS)-tert-butyl 3-((4,6-difluoro-4'-(((1r,3r)-3-hydroxy-3-(hydroxy-methyl)cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate and (5aR,6S,6aS)-tert-butyl 3-((4,6-difluoro-4'-(((1s,3s)-3-hydroxy-3-(hydroxymethyl)cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate

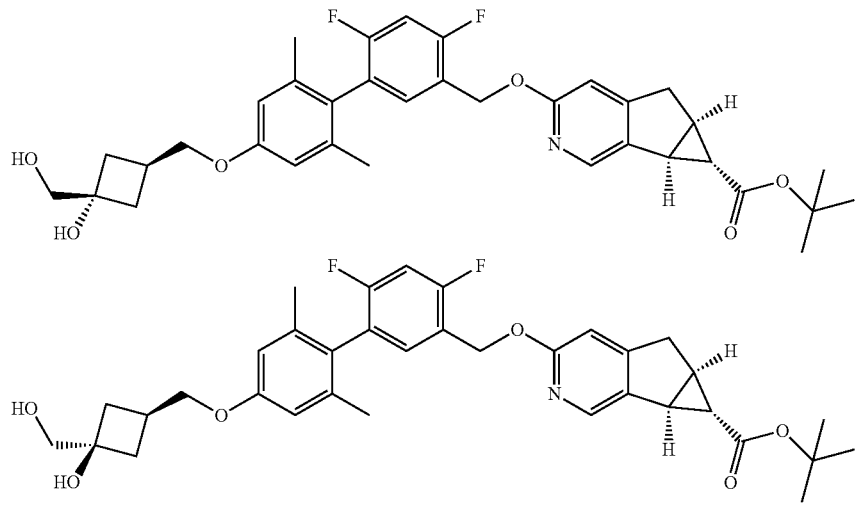

protection. After cooling to room temperature, the mixture was filtered through a pad of diatomaceous earth and the filtrate was diluted with ethyl acetate (8 mL) and water (10 mL). The aqueous layer was separated, and extracted with ethyl acetate (2×10 mL). The combined organic layers were washed with saturated NaCl solution (10 mL), dried over anhydrous Na₂SO₄, filtered and concentrated. The resulting residue was purified by prep-HPLC (preparative HPLC on a GILSON 281 instrument fitted with a YMC-Actus Triart C18 (150*30 mm*5 um) using water and acetonitrile as the eluents. Mobile phase A: water (containing 0.1% TFA, v/v), mobile phase B: acetonitrile. Gradient: 26-67% B, 0-10 min; 100% B, 10.5-12.5 min; 5% B, 13-15 min)) to give (5aR,6S,6aS)-tert-butyl 3-((4,6-difluoro-4'-((3-hydroxy-3-(hydroxymethyl)cyclobutyl)-methoxy)-2',6'-dimethyl-[1,1'-biphenyl]-3-yl)methoxy)-5,5a,6,6a-tetrahydrocyclopropa-[4,5]cyclopenta[1,2-c]pyridine-6-carboxylate. MS (ESI) m/e (M–H⁺): 608.1

(5aR,6S,6aS)-tert-butyl 3-((4,6-difluoro-4'-((3-hydroxy-3-(hydroxymethyl)cyclobutyl)-methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate was separated by SFC (Column: Chiralpak AD-3 50*4.6 mm I.D., 3 um Mobile phase: 40% ethanol (0.05% DEA) in CO₂ Flow rate: 4 mL/min Wavelength: 220 nm, retention time $t_{R1}$=0.413 min, retention time $t_{R2}$=0.799 min) to give the first peak isomer with shorter retention time (5aR,6S,6aS)-tert-butyl 3-((4,6-difluoro-4'-(1r,3r)-3-hydroxy-3-(hydroxymethyl)cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate and the second peak isomer with longer retention time (5aR,6S,6aS)-tert-butyl 3-((4,6-difluoro-4'-(((1s,3s)-3-hydroxy-3-(hydroxymethyl)-cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate.

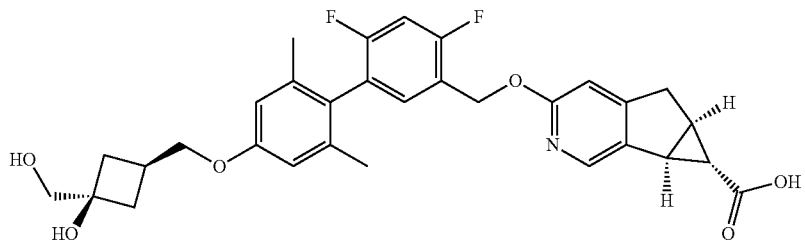 [SMILES: Cc1cc(OC[C@H]2C[C@](O)(CO)C2)cc(C)c1-c1cc(COc2cc3c(cn2)[C@H]2[C@@H](C3)[C@@H]2C(=O)O)c(F)cc1F]

Step E: (5aR,6S,6aS)-3-((4,6-difluoro-4'-(((1r,3r)-3-hydroxy-3-(hydroxymethyl)-cyclobutyl)methoxy)-2',6'-dimethyl-[1,1'-biphenyl]-3-yl)methoxy)-5,5a,6,6a-tetrahydro-cyclopropa[4,5]cyclopenta[1,2-c]pyridine-6-carboxylic acid LiOH.H$_2$O (53.9 mg, 1.28 mmol) was added to a stirred mixture of (5aR,6S,6aS)-tert-butyl 3-((4,6-difluoro-4'-(((1r,3r)-3-hydroxy-3-(hydroxymethyl)cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (65 mg, 0.107 mmol) in THF (2 ml), water (2 ml) and MeOH (2 ml). The mixture was stirred at 45° C. for 16 h, then acidified with 1N HCl to pH=3 and extracted with ethyl acetate (2×10 mL). The combined organic layers were washed with brine (8 mL), dried over anhydrous Na$_2$SO$_4$, filtered and concentrated. The resulting crude product which was purified by prep-TLC (SiO$_2$, EtOAc) to give (5aR,6S,6aS)-3-((4,6-difluoro-4'-(((1r,3r)-3-hydroxy-3-(hydroxymethyl)cyclobutyl)-methoxy)-2',6'-dimethyl-[1,1'-biphenyl]-3-yl)methoxy)-5,5a,6,6a-tetrahydrocyclopropa[4,5]-cyclopenta[1,2-c]pyridine-6-carboxylic acid. The acid was converted to the corresponding sodium salt using 0.5 M aq. NaOH. $^1$HNMR (400 MHz, methanol-d4) δ: 7.97 (s, 1H), 7.22 (t, J=8.0 Hz, 1H), 7.03 (t, J=9.6 Hz, 1H), 6.71-6.56 (m, 3H), 5.33 (s, 2H), 3.93 (d, J=6.8 Hz, 2H), 3.43 (s, 2H), 3.23-3.11 (m, 1H), 3.03-2.90 (m, 1H), 2.88-2.70 (m, 2H), 2.29 (br. s., 1H), 2.08 (d, J=8.0 Hz, 4H), 1.92 (s, 6H), 1.02 (br. s., 1H). MS (ESI) m/e (M−H$^+$): 550.1

16 h, then acidified with 1N HCl to pH=3 and extracted with ethyl acetate (10 mL×2). The combined organic layers were separated, washed with brine (8 mL), dried over anhydrous Na$_2$SO$_4$, filtered and concentrated. The resulting crude product which was purified by prep-TLC(SiO$_2$, EtOAc) to give (5aR,6S,6aS)-3-((4,6-difluoro-4'-(((1s,3s)-3-hydroxy-3-(hydroxymethyl)cyclobutyl)-methoxy)-2',6'-dimethyl-[1,1'-biphenyl]-3-yl)methoxy)-5,5a,6,6a-tetrahydrocyclopropa[4,5]-cyclopenta[1,2-c]pyridine-6-carboxylic acid. The acid was converted to the corresponding sodium salt using 0.5 M aq. NaOH. $^1$H NMR (400 MHz, methanol-d4): δ 7.96 (s, 1H), 7.22 (t, J=8.4 Hz, 1H), 7.03 (t, J=9.6 Hz, 1H), 6.76-6.52 (m, 3H), 5.33 (s, 2H), 3.95 (d, J=4.8 Hz, 2H), 3.52 (s, 2H), 3.21-3.10 (m, 1H), 3.00-2.88 (m, 1H), 2.74 (d, J=4.8 Hz, 1H), 2.35-2.17 (m, 4H), 1.96-1.82 (m, 8H), 1.00 (br. s., 1H). MS (ESI) m/e (M−H$^+$): 520.2

BIOLOGICAL ASSAYS

Generation of GPR40-Expressing Cells

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

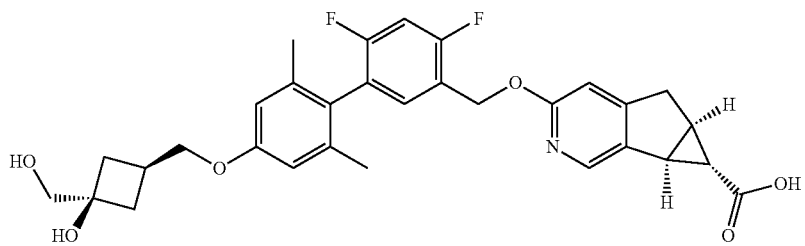 [SMILES: Cc1cc(OC[C@H]2C[C@](O)(CO)C2)cc(C)c1-c1cc(COc2cc3c(cn2)[C@H]2[C@@H](C3)[C@@H]2C(=O)O)c(F)cc1F]

Step F: (5aR,6S,6aS)-3-((4,6-difluoro-4'-(((1s,3s)-3-hydroxy-3-(hydroxymethyl)-cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid LiOH.H$_2$O (52.2 mg, 1.24 mmol) was added to a stirred, mixture of (5aR,6S,6aS)-tert-butyl 3-((4,6-difluoro-4'-(((1s,3s)-3-hydroxy-3-(hydroxymethyl)cyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (63 mg, 0.104 mmol) in THF (2 ml), water (1 ml) and MeOH (2 ml). The mixture was stirred at 45° C. for FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 μL medium/well. The cells were incubated with 20 μl/well of the assay buffer (HBSS, 0.1% BSA, 20 mM HEPES, 2.5 mM probenecid, pH 7.4) containing 8 μM fluo-4, AM, 0.08% pluronic acid at room temperature for 100 minutes. Fluorescence output was measured using FLIPR. Compounds were dissolved in DMSO and diluted to desired concentrations with assay buffer. 13.3 µL/well of compound solution was added.

The compounds of the present invention, including the compounds in Examples 1-13, have $EC_{50}$ values less than 100 nanomolar (nM) in the FLIPR assay described above. The compounds in Examples 1-13 have the $EC_{50}$ values in the FLIPR assay listed in Table I:

Inositol Phosphate Turnover Assay 1:

The assay was performed in 96-well format. HEK cells stably expressing human GPR40 were plated to be 60-80% confluent within 72 h. After 72 h, the plates were aspirated and the cells washed with inositol-free DMEM (ICN). The wash media was replaced with 150 µL of 3H-inositol labeling media (inositol-free media containing 0.4% human albumin or 0.4% mouse albumin, 1× pen/strep antibiotics, glutamine, 25 mM HEPES to which was added 3H-myo-inositol NEN #NET114A 1 mCi/mL, 25 Ci/mmol diluted 1:150 in loading media with a final specific radioactivity of 1 µCi/150 µL). Alternatively, the human and mouse albumin can be added after the overnight labeling step before the addition of LiCl.

The assay was typically run the next day after 18 h labeling. On the day of the assay, 5 µL of 300 mM LiCl was added to all wells and incubated at 37 degrees for 20 min. 0.75 µL of 200× compounds were added and incubated with the cells for 60 min at 37 degrees. The media was then aspirated off and the assay terminated with the addition of 60 µL 10 mM formic acid. The cells were lysed for 60 min at room temperature. 15-30 µL of lysate was mixed with 70 µL/1 mg YSi SPA beads (Amersham) in clear bottom Isoplates. The plates were shaken for 2 h at room temperature. Beads were allowed to settle and the plates were counted in the Wallac Microbeta.

Inositol Phosphate Turnover (IP1) Assay 2:

The assay was performed in 384-well format. HEK cells stably expressing human GPR40 were plated at 15,000 cells per well in growth medium (DMEM/10% fetal calf serum). Cell plates were then incubated 16 hours at 37 degrees in a 5% CO2 incubator.

Measurement of Inositol Phosphate Turnover (IP1) was performed using the CisBio IP-One kit (Part number 62IPA-PEB). After the 16 hour incubation, the cells were washed with HEPES buffer and 10 ul of stimulation buffer (prepared as described in the kit) was added to each well. In a separate plate, compounds were diluted in DMSO (400-fold over the final concentration in the assay well) and 25 nl was acoustically transferred to the appropriate well in the assay cell plate. The plates were then incubated for 60 minutes at 37 degrees. 10 ul of detection buffer (also prepared as described in the IP-One kit) was added to each well and the plates were incubated for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Inositol Phophate Turnover (IP1) Assay $EC_{50}$ values for specific compounds are listed in Table I.

The compounds of the present invention, including the compounds in Examples 1-26, have $EC_{50}$ values less than 6500 nanomolar (nM) in either the Inositol Phophate Turnover (IP1) Assay 1 described above, and/or in the Inositol Phosphate Turnover (IP1) Assay 2 described above. The compounds in Examples 1-26 have the $EC_{50}$ values in the Inositol Phophate Turnover (IP1) Assay 1 and/or Assay 2 listed in Table I.

TABLE I $EC_{50}$ values (nM) for Examples in Human GPR40 FLIPR and IP1 Assays

| Example Number | Human GPR40, FLIPR, $EC_{50}$, nM | Human GPR40 IP1 Assay 1, $EC_{50}$, nM | Human GPR40 IP1 Assay 2, $EC_{50}$, nM |
| --- | --- | --- | --- |
| Compound-1 | 7.0 | 11 | ND |
| Compound-2 | 5.8 | 6.9 | ND |
| Compound-3 | 3.7 | 14 | ND |
| Compound-4 | 10 | 19 | ND |
| Compound-5 | 4.2 | 13 | ND |
| Compound-6 | 4.2 | 47 | ND |
| Compound-7 | 6.7 | 3.4 | ND |
| Compound-8 | 12 | 63 | ND |
| Compound-9 | ND | 8.9 | ND |
| Compound-10 | ND | 2.9 | ND |
| Compound-11 | 5.6 | 6.8 | ND |
| Compound-12 | 6.1 | 20 | ND |
| Compound-13 | 6.7 | 15 | ND |
| Compound-14 | ND | 6.3 | 1.2 |
| Compound-15 | ND | 6.7 | 1.2 |
| Compound-16 | ND | 9.4 | 1.0 |
| Compound-17 | ND | ND | 0.8 |
| Compound-18 | ND | 7.6 | 1.0 |
| Compound-19 | ND | ND | 2.1 |
| Compound-20 | ND | ND | 3.1 |
| Compound-21 | ND | ND | 1.0 |
| Compound-22 | ND | ND | 0.7 |
| Compound-23 | ND | ND | 1.0 |
| Compound-24 | ND | ND | 1.3 |
| Compound-25 | ND | ND | 1.9 |
| Compound-26 | ND | ND | 1.6 |

ND is not determined

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:

1. A compound of structural formula I:

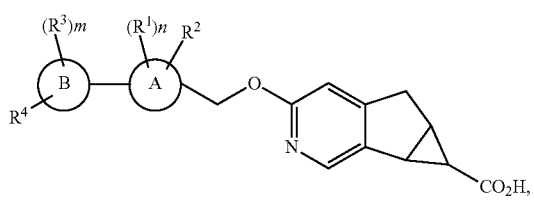

or a pharmaceutically acceptable salt thereof, wherein A is:

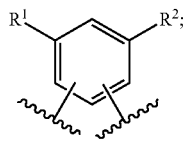

B is selected from the group consisting of:
(1) phenyl, and
(2) pyridyl;
$R^1$ is selected from the group consisting of:
(1) halogen,
(2) —CN,
(3) —$C_{1-6}$alkyl,
(4) —$(CH_2)_r$—$OC_{1-6}$alkyl,
(5) —$(CH_2)_r$—$C_{3-6}$cycloalkyl, and
(6) —$(CH_2)_r$—O—$(CH_2)_r$—$C_{3-6}$cycloalkyl,
wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl;
$R^2$ is halogen;
each $R^3$ when present is independently selected from the group consisting of:
(1) halogen,
(2) —CN,
(3) —$C_{1-6}$alkyl, and
(4) —$(CH_2)_u$—$C_{3-6}$cycloalkyl,
wherein each $CH_2$, $C_{1-6}$alkyl and $C_{3-6}$cycloalkyl is unsubstituted or substituted with one to three substituents selected from halogen;
$R^4$ is selected from the group consisting of:
(1) —O—$CH_2$-cyclobutyl,
(2) —O-cyclohexyl,
(3) 2,6-diazospiro[3.3]heptan-2yl,
(4) piperidinyl, and
(5) phenyl,
wherein $R^4$ is unsubstituted or substituted with one, two, three, four or five substituents selected from $R^5$;

$R^5$ is selected from the group consisting of:
(1) —$(CH_2)_s$halogen,
(2) —$C_{1-6}$alkyl,
(3) —$(CH_2)_s$OH,
(4) —$(CH_2)_s$CN,
(5) —$(CH_2)_s$SO$_2$C$_{1-6}$alkyl, and
(6) —$(CH_2)_s$SO$_2$—$(CH_2)_t$—$C_{3-6}$cycloalkyl,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH;
m is 0, 1, 2 or 3;
n is 1 or 2;
r is 0, 1, 2 or 3;
s is 0, 1, 2 or 3;
t is 0, 1, 2 or 3;
u is 0, 1, 2 or 3;
v is 0, 1, 2 or 3; and
w is 0, 1, 2 or 3.

2. The compound according to claim 1 wherein A is

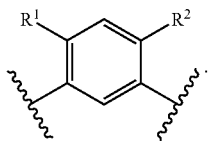

or a pharmaceutically acceptable salt thereof.

3. The compound according to claim 1 wherein B is phenyl, wherein phenyl is unsubstituted or substituted with one, two or three substituents selected from $R^3$;
or a pharmaceutically acceptable salt thereof.

4. The compound according to claim 1 wherein B is pyridyl, wherein pyridyl is unsubstituted or substituted with one, two or three substituents selected from $R^3$; or a pharmaceutically acceptable salt thereof.

5. The compound according to claim 1 wherein $R^1$ is selected from the group consisting of:
(1) halogen,
(2) —CN,
(3) —$C_{1-6}$alkyl, and
(4) —$(CH_2)_r$—$OC_{1-6}$alkyl,
wherein each $CH_2$, —$C_{1-6}$alkyl and —$OC_{1-6}$alkyl is unsubstituted or substituted with one to four substituents selected from halogen, and —$C_{1-6}$alkyl; or a pharmaceutically acceptable salt thereof.

6. The compound according to claim 1 wherein $R^1$ is selected from the group consisting of:
(1) halogen,
(2) —CN, and
(3) —$C_{1-6}$alkyl,
wherein each —$C_{1-6}$alkyl is unsubstituted or substituted with one to four substituents selected from halogen, and —$C_{1-6}$alkyl; or a pharmaceutically acceptable salt thereof.

7. The compound according to claim 1 wherein $R^1$ is selected from the group consisting of:
(1) —CN,
(2) —$C_{1-6}$alkyl, and
(3) —$(CH_2)_r$—$C_{3-6}$cycloalkyl,
wherein each $CH_2$, —$C_{1-6}$alkyl and —$C_{3-6}$cycloalkyl is unsubstituted or substituted with one to four substituents selected from halogen, and —$C_{1-6}$alkyl; or a pharmaceutically acceptable salt thereof.

8. The compound according to claim 1 wherein $R^1$ is halogen, or a pharmaceutically acceptable salt thereof.

9. The compound according to claim 1 wherein $R^2$ is F; or a pharmaceutically acceptable salt thereof.

10. The compound according to claim 1 wherein each $R^3$ when present is independently selected from the group consisting of:
   (1) halogen, and
   (2) —$C_{1-6}$alkyl,
wherein each $C_{1-6}$alkyl is unsubstituted or substituted with one to three substituents selected from halogen; or a pharmaceutically acceptable salt thereof.

11. The compound according to claim 1 wherein $R^5$ is selected from the group consisting of:
   (1) —$(CH_2)_s$halogen,
   (2) —$C_{1-6}$alkyl,
   (3) —$(CH_2)_s$OH,
   (4) —$(CH_2)_s SO_2 C_{1-6}$alkyl, and
   (5) —$(CH_2)_s SO_2$—$(CH_2)_t$—$C_{3-6}$cycloalkyl,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH; or a pharmaceutically acceptable salt thereof.

12. The compound according to claim 1 wherein $R^5$ is selected from the group consisting of:
   (1) halogen,
   (2) —$C_{1-6}$alkyl,
   (3) —OH,
   (4) —$SO_2 C_{1-6}$alkyl, and
   (5) —$SO_2$—$C_{3-6}$cycloalkyl,
wherein each —$C_{1-6}$alkyl and $C_{3-6}$cycloalkyl is unsubstituted or substituted with one to three substituents selected from halogen, $C_{1-6}$alkyl, and —$(CH_2)_w$OH; or a pharmaceutically acceptable salt thereof.

13. The compound according to claim 1 wherein the absolute stereochemistry at the stereogenic carbon centers is indicated below:

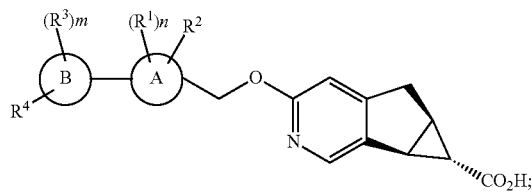

or a pharmaceutically acceptable salt thereof.

14. The compound according to claim 1 wherein:
A is:

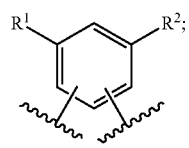

B is phenyl;
$R^1$ is selected from the group consisting of:
   (1) halogen,
   (2) —CN,
   (3) —$C_{1-6}$alkyl, and
   (4) —$(CH_2)_r$—$OC_{1-6}$alkyl,
wherein each $CH_2$, —$C_{1-6}$alkyl and —$OC_{1-6}$alkyl is unsubstituted or substituted with one to four substituents selected from halogen, and —$C_{1-6}$alkyl;

$R^2$ is halogen;
each $R^3$ when present is independently selected from the group consisting of:
   (1) halogen, and
   (2) —$C_{1-6}$alkyl,
wherein each $C_{1-6}$alkyl is unsubstituted or substituted with one to three substituents selected from halogen;
$R^4$ is selected from the group consisting of:
   (1) —O—$CH_2$-cyclobutyl,
   (2) —O-cyclohexyl,
   (3) 2,6-diazospiro[3.3]heptan-2yl,
   (4) piperidinyl, and
   (5) phenyl,
wherein $R^4$ is unsubstituted or substituted with one, two, three, four or five substituents selected from $R^5$;
$R^5$ is selected from the group consisting of:
   (1) —$(CH_2)_s$halogen,
   (2) —$C_{1-6}$alkyl,
   (3) —$(CH_2)_s$OH,
   (4) —$(CH_2)_s$CN,
   (5) —$(CH_2)_s SO_2 C_{1-6}$alkyl, and
   (6) —$(CH_2)_s SO_2$—$(CH_2)_t$—$C_{3-6}$cycloalkyl,
wherein each $CH_2$, $C_{1-6}$alkyl and $C_{3-6}$cycloalkyl is unsubstituted or substituted with one to three substituents selected from halogen, $C_{1-6}$alkyl, and —$(CH_2)_w$OH;
m is 1; and
n is 1;
or a pharmaceutically acceptable salt thereof.

15. The compound according to claim 1 wherein:
A is:

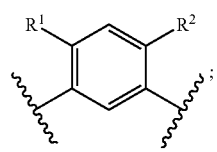

B is phenyl;
$R^1$ is selected from the group consisting of:
   (1) halogen,
   (2) —CN, and
   (3) —$C_{1-6}$alkyl,
wherein each —$C_{1-6}$alkyl is unsubstituted or substituted with one to four substituents selected from halogen, and —$C_{1-6}$alkyl;
$R^2$ is halogen;
each $R^3$ when present is independently selected from the group consisting of:
   (1) halogen, and
   (2) —$C_{1-6}$alkyl,
wherein each $C_{1-6}$alkyl is unsubstituted or substituted with one to three substituents selected from halogen;
$R^4$ is selected from the group consisting of:
   (1) —O—$CH_2$-cyclobutyl,
   (2) —O-cyclohexyl,
   (3) 2,6-diazospiro[3.3]heptan-2yl,
   (4) piperidinyl, and
   (5) phenyl,
wherein $R^4$ is unsubstituted or substituted with one, two, three, four or five substituents selected from $R^5$;
$R^5$ is selected from the group consisting of:
   (1) —$(CH_2)_s$halogen,
   (2) —$C_{1-6}$alkyl, (3) —(CH$_2$)$_s$OH,
(4) —(CH$_2$)$_s$SO$_2$C$_{1-6}$alkyl, and
(5) —(CH$_2$)$_s$SO$_2$—(CH$_2$)$_t$—C$_{3-6}$cycloalkyl,
wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH; and
m is 1;
or a pharmaceutically acceptable salt thereof.

16. The compound according to claim 1 wherein A is

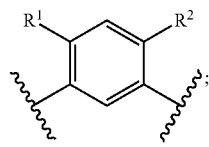

B is phenyl;
R$^1$ is selected from the group consisting of:
(1) halogen,
(2) —CN, and
(3) —C$_{1-6}$alkyl,
wherein each —C$_{1-6}$alkyl is unsubstituted or substituted with one to four substituents selected from halogen, and —C$_{1-6}$alkyl;

R$^2$ is F;
each R$^3$ when present is independently selected from the group consisting of:
(1) halogen, and
(2) —C$_{1-6}$alkyl,
wherein each C$_{1-6}$alkyl is unsubstituted or substituted with one to three substituents selected from halogen;
R$^4$ is selected from the group consisting of:
(1) —O—CH$_2$-cyclobutyl,
(2) —O-cyclohexyl,
(3) 2,6-diazospiro[3,3]heptan-2yl,
(4) piperidine, and
(5) phenyl,
wherein R$^4$ is unsubstituted or substituted with one, two, three, four or five substituents selected from R$^5$;
R$^5$ is selected from the group consisting of:
(1) halogen,
(2) —C$_{1-6}$alkyl,
(3) —OH,
(4) —SO$_2$C$_{1-6}$alkyl, and
(5) —SO$_2$—C$_{3-6}$cycloalkyl,
wherein each CH$_2$, C$_{1-6}$alkyl and C$_{3-6}$cycloalkyl is unsubstituted or substituted with one to three substituents selected from halogen, C$_{1-6}$alkyl, and —(CH$_2$)$_w$OH; and
m is 1;
or a pharmaceutically acceptable salt thereof.

17. A compound selected from:

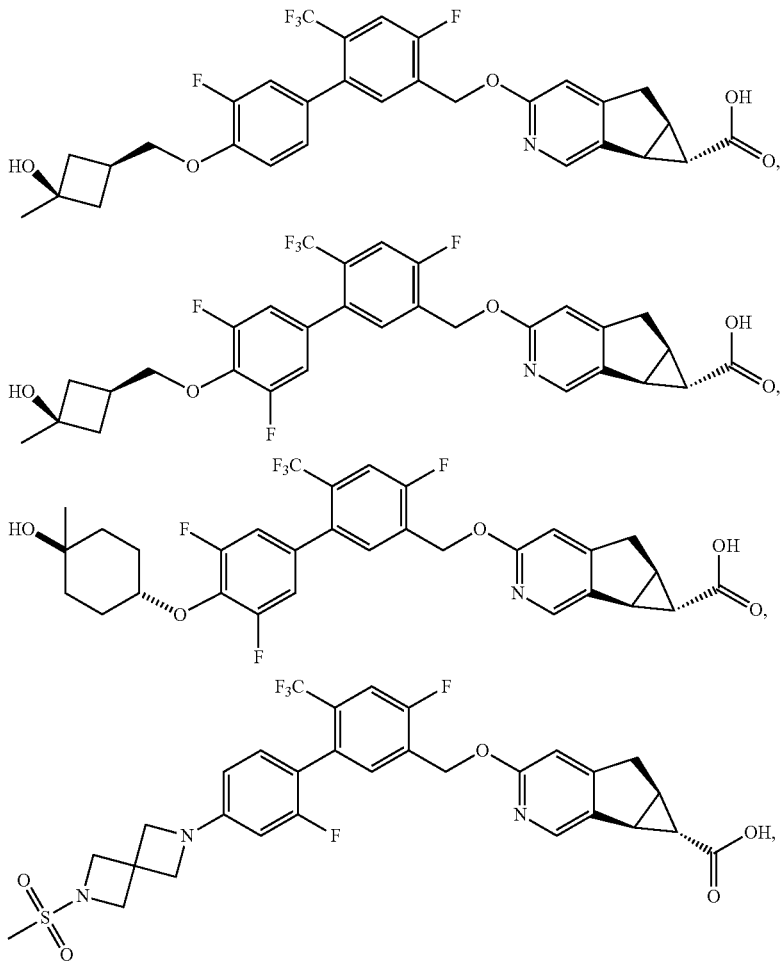

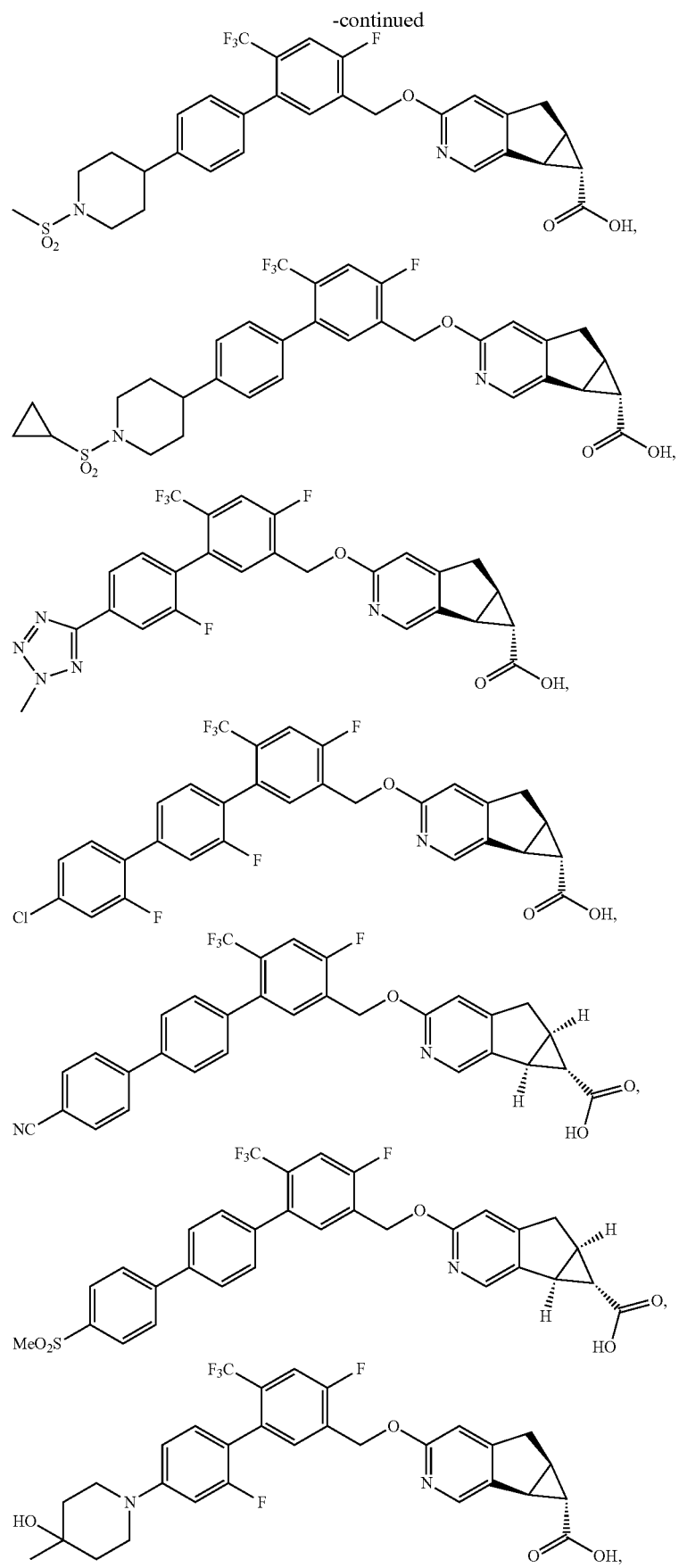

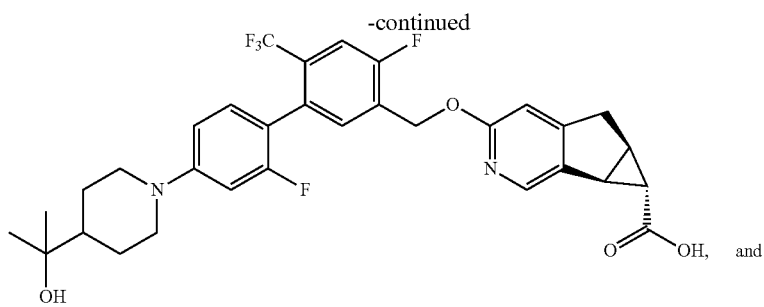

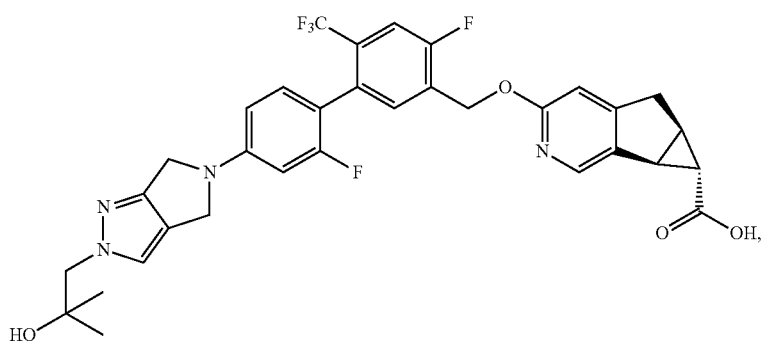

or a pharmaceutically acceptable salt thereof.

18. A pharmaceutical composition comprising a compound of claim 1, or a pharmaceutically acceptable salt thereof, and a pharmaceutically acceptable carrier.

19. A pharmaceutical composition comprising
(1) a compound of claim 1, or a pharmaceutically acceptable salt thereof,
(2) one or more compounds selected from the group consisting of:
(a) PPAR gamma agonists and partial agonists;
(b) biguanides;
(c) protein tyrosine phosphatase-1B (PTP-1B) inhibitors;
(d) dipeptidyl peptidase IV (DP-IV) inhibitors;
(e) insulin or an insulin mimetic;
(f) sulfonylureas;
(g) α-glucosidase inhibitors;
(h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (viii) phenolic anti-oxidants;
(i) PPARα/γ dual agonists,
(j) PPARδ agonists,
(k) antiobesity compounds,
(l) ileal bile acid transporter inhibitors;
(m) anti-inflammatory agents;
(n) glucagon receptor antagonists;
(o) GLP-1;
(p) GIP-1;
(q) GLP-1 analogs;
(r) HSD-1 inhibitors;
(s) SGLT 1 inhibitors; and
(t) SGLT 2 inhibitors; and
(3) a pharmaceutically acceptable carrier.

20. A pharmaceutical composition comprising a compound according to claim 1, or a pharmaceutically acceptable salt thereof, and a compound selected from simvastatin, ezetimibe and sitagliptin; and a pharmaceutically acceptable carrier.

21. A compound selected from:

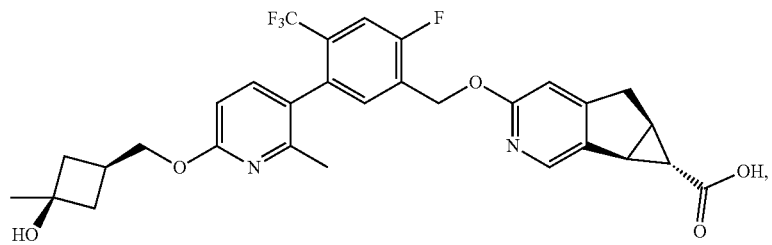

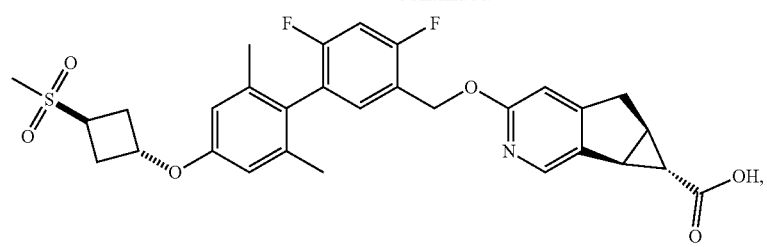
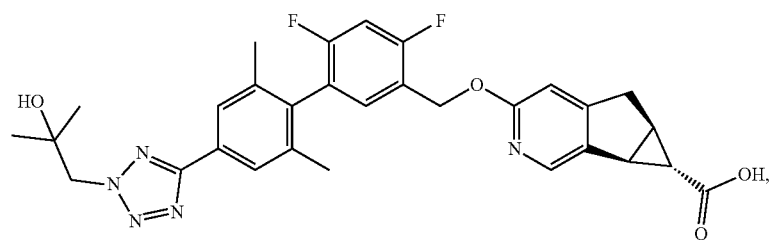
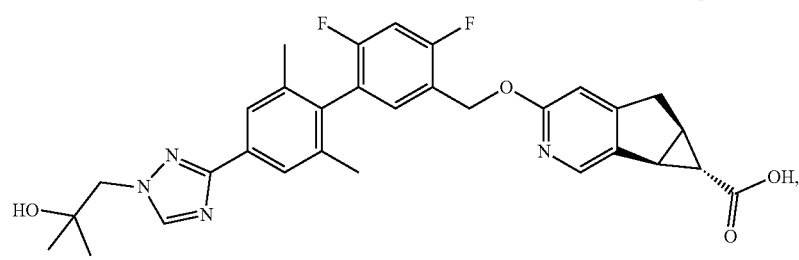
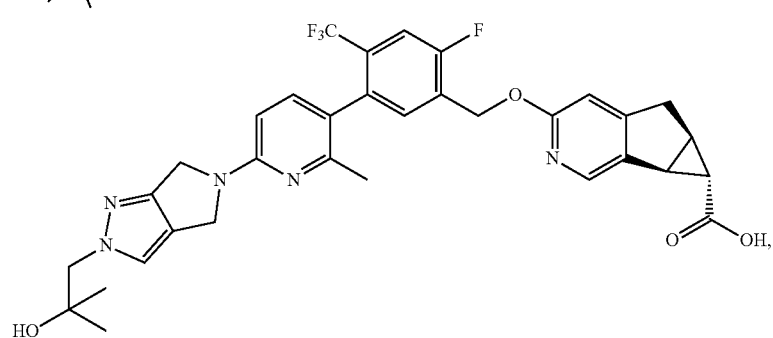
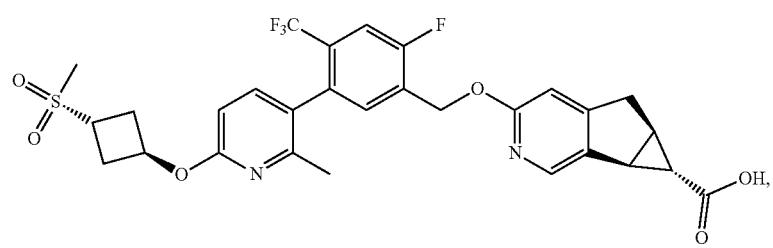
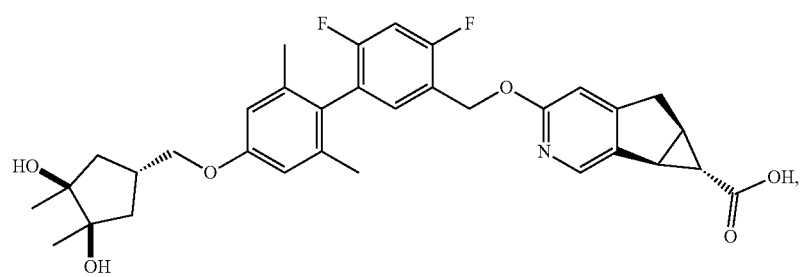

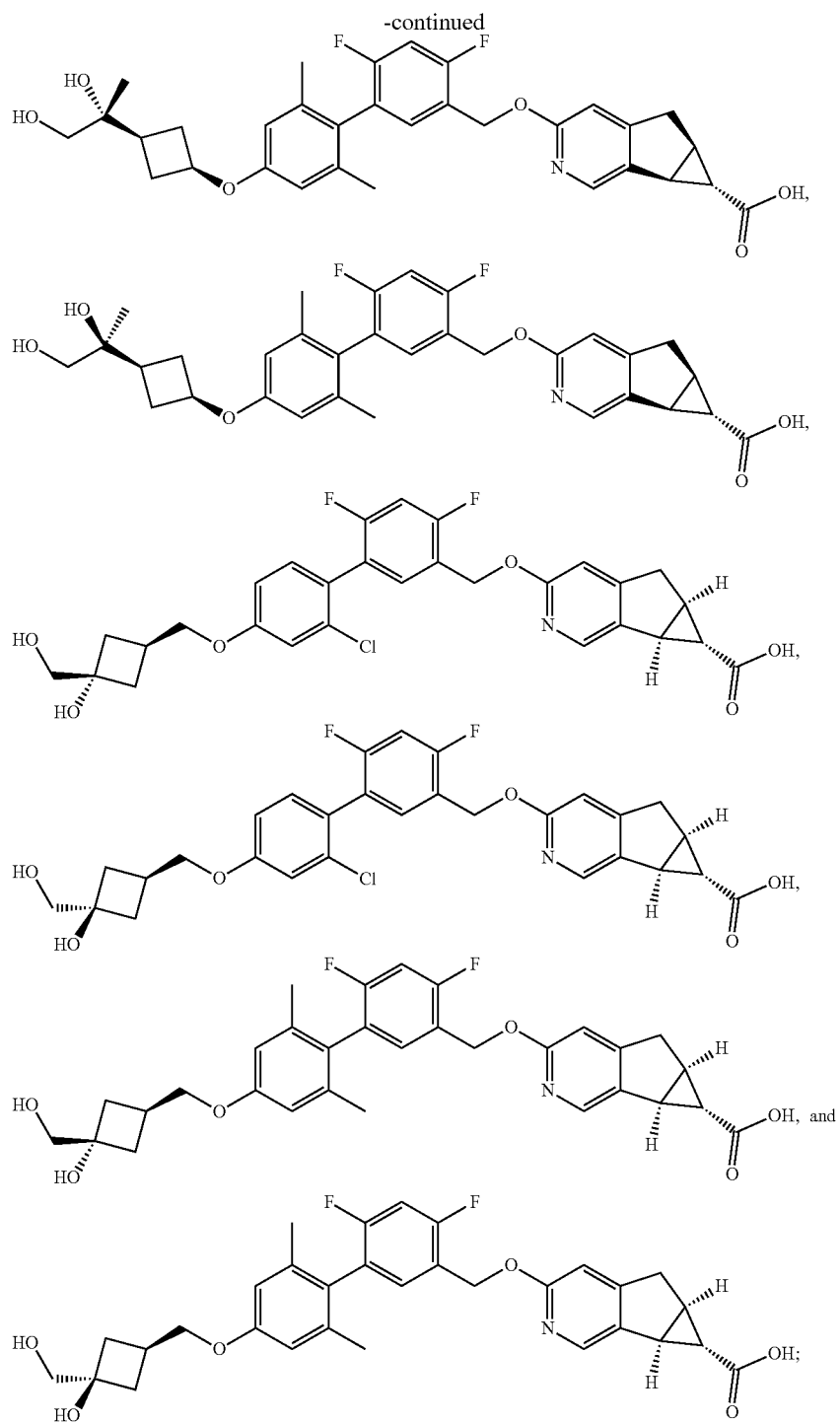
or a pharmaceutically acceptable salt thereof.
* * * * *